(12) United States Patent
Aslanian et al.

(10) Patent No.: US 8,927,559 B2
(45) Date of Patent: Jan. 6, 2015

(54) QUINAZOLINONE-TYPE COMPOUNDS AS CRTH$_2$ ANTAGONISTS

(75) Inventors: Robert G. Aslanian, Rockaway, NJ (US); Christopher W. Boyce, Flemington, NJ (US); Robert D. Mazzola, Jr., Stewartsville, NJ (US); Brian A. McKittrick, New Vernon, NJ (US); Kevin D. McCormick, Basking Ridge, NJ (US); Anandan Palani, Bridgewater, NJ (US); Jun Qin, Somerset, NJ (US); Haiqun Tang, Belle Mead, NJ (US); Dong Xiao, Warren, NJ (US); Younong Yu, East Brunswick, NJ (US); John P. Caldwell, Ringwood, NJ (US); Elizabeth Helen Kelley, Lynnfield, MA (US); Hongjun Zhang, Newton, MA (US); Phieng Siliphaivanh, Newton, MA (US); Rachel N. MacCoss, Oxford (GB); Joey L. Methot, Westwood, MA (US); Jolicia Polivina Gauuan, Schenectady, NY (US); Qin Jiang, Latham, NY (US); Andrew J. Leyhane, Latham, NY (US); Purakkattle Johny Biju, Piscataway, NJ (US); Li Dong, Lawrenceville, NJ (US); Xianhai Huang, Warren, NJ (US); Ning Shao, Watchung, NJ (US); Wei Zhou, Scotch Plains, NJ (US); Pawan K. Dhondi, Elizabeth, NJ (US); Ashwin U. Rao, Morganville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/878,654

(22) PCT Filed: Oct. 6, 2011

(86) PCT No.: PCT/US2011/055054
§ 371 (c)(1),
(2), (4) Date: Apr. 10, 2013

(87) PCT Pub. No.: WO2012/051036
PCT Pub. Date: Apr. 19, 2012

(65) Prior Publication Data
US 2013/0210805 A1   Aug. 15, 2013

Related U.S. Application Data

(60) Provisional application No. 61/391,864, filed on Oct. 11, 2010.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ......... 514/266.3; 544/283; 544/284; 544/287

(58) Field of Classification Search
USPC ............. 544/266.3, 283, 284, 287; 514/266.3
See application file for complete search history.

(56) References Cited

U.S. PATENT DOCUMENTS

| | | | |
|---|---|---|---|
| 4,183,931 A | 1/1980 | Wolfe et al. | |
| 4,358,307 A | 11/1982 | Serban et al. | |
| 6,066,638 A | 5/2000 | Bereznak et al. | |
| 6,245,770 B1 | 6/2001 | Bereznak et al. | |
| 6,255,311 B1 | 7/2001 | Bereznak et al. | |
| 6,518,407 B1 | 2/2003 | Brock et al. | |
| 6,562,831 B1 * | 5/2003 | Finer et al. ................. | 514/266.3 |
| 2005/0038076 A1 | 2/2005 | Garst et al. | |
| 2005/0059687 A1 * | 3/2005 | Makings et al. ........... | 514/266.3 |
| 2009/0012102 A1 | 1/2009 | Ly et al. | |
| 2009/0054468 A1 | 2/2009 | Eriksson et al. | |
| 2013/0296300 A1 | 11/2013 | Boyce et al. | |
| 2013/0303517 A1 | 11/2013 | Boyce et al. | |

FOREIGN PATENT DOCUMENTS

| | | |
|---|---|---|
| EP | 1398032 A1 | 3/2004 |
| WO | 98 26664 A1 | 6/1998 |
| WO | WO0198278 A1 | 12/2001 |

(Continued)

OTHER PUBLICATIONS

Int'l Preliminary Report on Patentability for PCT/US2011/055054, mailed Apr. 25, 2013.

(Continued)

*Primary Examiner* — Paul V. Ward
(74) *Attorney, Agent, or Firm* — Eric A. Meade; Catherine D. Fitch

(57) ABSTRACT

This application provides for compounds of the formula Formula I or a pharmaceutically acceptable salt thereof, wherein the individual variables are defined herein, as well as processes to prepare these compounds, pharmaceutical compositions comprising the same and their use in treating disease state associated with the CRTH$_2$ receptor.

Formula I

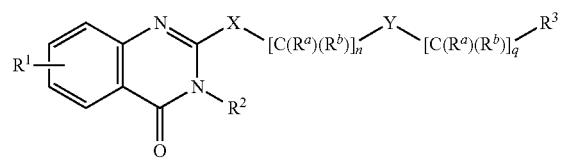

16 Claims, No Drawings

(56) References Cited

FOREIGN PATENT DOCUMENTS

| | | |
|---|---|---|
| WO | 2004 009583 A2 | 1/2004 |
| WO | WO2004111014 A1 | 12/2004 |
| WO | 2005 044260 A1 | 5/2005 |
| WO | 2005 049613 A1 | 6/2005 |
| WO | 2005 079803 A1 | 9/2005 |
| WO | 2006 070325 A2 | 7/2006 |
| WO | 2006 122200 A1 | 11/2006 |
| WO | 2007 107772 A1 | 9/2007 |
| WO | 2008 040820 A2 | 4/2008 |
| WO | 2008 118454 A2 | 10/2008 |
| WO | WO2011060394 A1 | 5/2011 |
| WO | WO2011060395 A1 | 5/2011 |

OTHER PUBLICATIONS

Chem Abstracts, 1977:484933 (1977).

Norman, P., "DP2 Receptor Antagonists in Development", Expert Opin. Investig. Drugs, 2010, pp. 947-961, vol. 19, Issue 8.

Ulven, et al., "Novel CRTH2 antagonists: a review of patents from 2006-2009", Expert Opin. Ther. Patents, 2010, pp. 1505-1530, vol. 20, Issue 11.

Pettipher, R., et al., "Antagonism of the prostaglandin D2 receptors DP1 and CRTH2 as an approach to treat allergic diseases", Nature Reviews/Drug Discovery, Apr. 2007, pp. 313-325, vol. 6, No. 4.

Supplementary European Search Report, corresponding PCT Application No. PCT/US2011/055054, Jul. 23, 2014.

* cited by examiner

QUINAZOLINONE-TYPE COMPOUNDS AS CRTH$_2$ ANTAGONISTS

CROSS REFERENCE TO RELATED APPLICATIONS

This application is a U.S. National Phase application under 35 U.S.C. §371 of PCT Application No. PCT/US2011/55054, filed Oct. 6, 2011, which claims priority under 35 U.S.C. §119(e) from U.S. Provisional Application No. 61/391,864, filed Oct. 11, 2010.

FIELD OF THE INVENTION

This application relates to quinazolinone-type compounds, compositions comprising these compounds, their use as antagonists of the chemoattractant receptor-homologous molecule expressed on T-helper-type-2 cells (CRTH$_2$) and to processes for preparing these compounds.

CRTH$_2$ receptor antagonists are useful in the treatment and prevention of both chronic and acute allergic/immune prostaglandin-mediated disorders and diseases such as, for example, asthma, congestion, allergic rhinitis, atopic dermatitis, chronic obstructive pulmonary disease (COPD), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Other disease states associated with the CRTH$_2$ receptor include respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, these antagonists may inhibit cellular neoplastic transformations and metastic tumor growth and hence can be used in the treatment of cancer. Compounds that antagonize the CRTH$_2$ receptor may also be of use in the treatment and/or prevention prostaglandin-mediated proliferation disorders such as may occur in diabetic retinopathy and tumor angiogenesis. CRTH$_2$ receptor antagonists may also inhibit prostanoid-induced smooth muscle contraction by antagonizing contractile prostanoids or mimicking relaxing prostanoids and hence may be used in the treatment of dysmenorrhea, premature labor and eosinophil related disorders.

BACKGROUND OF THE INVENTION

Prostaglandin D$_2$ (PGD$_2$) is a prostanoid and belongs to a class of chemical mediators that is synthesized by cells in response to stimuli, such as local tissue damage or hormonal stimuli, or by cellular activation pathways. Cells synthesize PGD$_2$ from arachindonic acid by cyclooxygenase and other specific synthases in the pathway.

Upon stimulation, mast cells release PGD$_2$ in major amounts and this release plays a major role in the etiology of respiratory disease, such as asthma and congestion. PGD$_2$ achieves this effect by binding with either of two G-protein coupled receptors; these are designated the D-prostainoid (DP) receptor and the CRTH$_2$ receptor.

PGD$_2$ is known to have a clear role in the allergic inflammatory response. PGD$_2$ is found at high levels in the bronchoalveolar lavage of asthmatics. Inhalation of PGD$_2$ enhances eosinophilic and lymphocytic airway inflammation in allergic animal models and, by using CRTH$_2$ knockout mice, it was demonstrated that PGD$_2$ achieves this role by binding to the CRTH$_2$ receptor. Hence, CRTH$_2$ receptor antagonists would be expected to reduce the allergic inflammatory response caused by PGD$_2$ and these compounds would be useful in the treatment or prevention of allergic/immune disorders.

Current drugs of choice for the treatment of chronic inflammatory airway disease, such as asthma or COPD, are synthetic glucocorticoids; examples of these compounds currently indicated for treatment of these disorders include fluticasone and mometasone. The difficulty with this class of compounds is that it possesses a number of systemic side-effects; these include adrenal suppression, altered bone metabolism and growth suppression in children. These side effects limit the dose that can be administered on a daily basis to the patient. While a non-steroidal class of therapeutics that inhibit bronchoconstriction exists (CysLT$_1$ antagonists), this class of compounds has limited efficacy in achieving the endpoints of reducing inflammatory and improving in lung function when compared to the glucocorticoids. Therefore, a therapeutic that combines the efficacy of inhaled glucocorticoids without the side effects would constitute an advancement in this field.

Ramatroban is a therapeutic that was approved for the treatment of allergic rhinitis in Japan; the compound has the following structure:

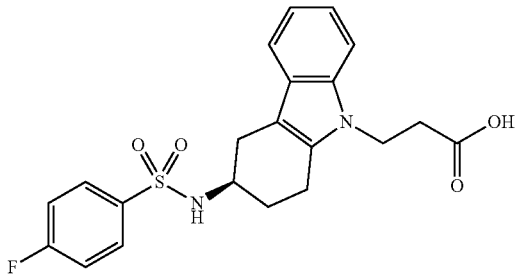 [SMILES: O=C(O)CCn1c2c(c3ccccc31)C[C@H](NS(=O)(=O)c1ccc(F)cc1)CC2]

Ramatroban was originally developed as a thromboxane antagonist. However, it was subsequently discovered that ramatroban also antagonizes to the CRTH$_2$ receptor.

The literature reports other chemical classes of compounds that will antagonize the CRTH$_2$ receptor. US 2009/0012102 to Actimis Pharmaceuticals discloses imidazo[1,2-C]pyrimidinylacetic acid derivatives and indicates that these compounds have excellent activity in antagonizing CRTH$_2$ receptor. Actelion Pharmaceuticals (WO 2006/070325) discloses certain 2,3,4,9-tetrahydro-1H-carbazole derivatives as possessing the ability to antagonize the CRTH$_2$ receptor and indicates that these derivative are useful in the treatment of both chronic and acute allergic/immune disorders. Oxagen (WO 2007/107772) discloses that salts of compounds of the formula:

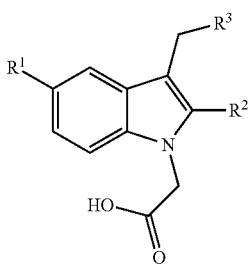

possess CRTH₂ antagonistic activity and indicates that these compounds possess surprising properties over the compounds disclosed in WO 2005/044260.

Quinazolinone derivatives are known in the art, albeit for other indications. WO 1998/26664 to E. I. du Pont de Nemours discloses compounds of the formula:

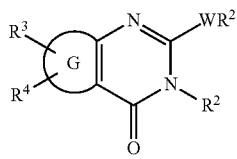

where G may be, inter alia, a fused phenyl ring. This published application teaches that these compounds have fungicidal activity. There are two US patents that issued from this published international application: U.S. Pat. Nos. 6,066,638 and 6,245,770. U.S. Pat. No. 6,255,311 discloses a related series of compounds with the same utility.

U.S. Pat. No. 4,183,931 discloses 2-ketoalkyl-4(3H)-quinazolinones of the formula:

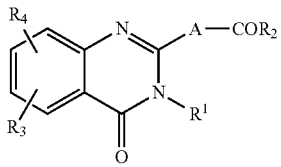

where $R^2$ is an aliphatic, cycloaliphatic, hydrocarbon aromatic or heterocyclic group of 1 to 10 carbons. These compounds are said to possess sedative-hypnotic and/or anticonvulsant activity.

EP 1 398 032 to PheneX Pharmaceuticals discloses 4-oxoquinazolines of the formula:

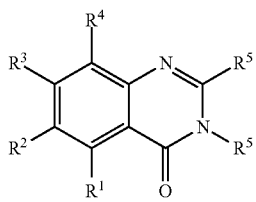

where $R^6$ may be groups such as —S—$R^7$ or —N($R^8$)($R^9$) and $R^7$, $R^8$ and $R^9$ may be groups such as H or substituted alkyl.

WO 2005/049613 to Merck discloses bicyclic pyrimidin-4-(3H)-one derivative of the formula:

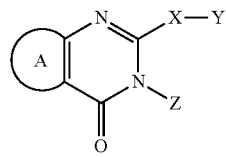

where may be an optionally substituted phenyl ring, X may be oxygen, sulfur or nitrogen and Y is a group of the formula —$(CR^2R^3)_n(CO)_p(NR^4)_q$W. These compounds are said to modulate the vanilloid-1-receptor and are disclosed to be useful in the treatment of pain. Another publication also by Merck that discloses vanilloid-1-receptor modulators is WO 2006/122200.

Talukdar at al., *Indian J. Chem. Sect. B*, pp 41-15 (1977) disclose the following quinazoline derivative:

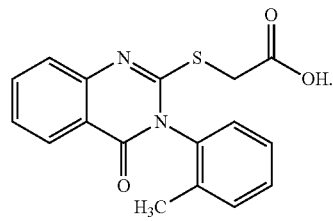 [SMILES: Cc1ccccc1-n1c(SCC(=O)O)nc2ccccc2c1=O]

SUMMARY OF THE INVENTION

In its many embodiments, the present invention provides for a novel class of quinazolinone-type compounds that act as antagonists of CRTH₂, or metabolites, steroisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with CRTH₂ using such compounds or pharmaceutical compositions.

In one aspect, the present application discloses a compound, or pharmaceutically acceptable salts, esters, metabolites, stereoisomers, solvates, prodrugs or polymorphs of said compound, said compound having the general structure shown in Formula I below:

Formula I

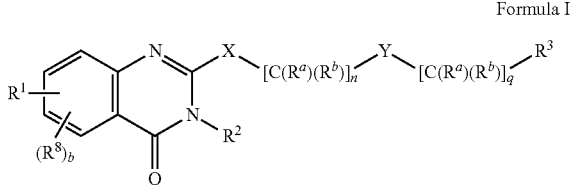

wherein:
X is a bond or —S(O)$_m$—;
Y is selected from the group consisting of:
  a) a bond, —O—, —NH—, —N(R$^9$)— or —N(COR$^9$)—;

b)

c)

d)

; and e)

where
  A is —O—, —S— or N(R)—;
  B is —C— or —N—;
  a is 0, 1, 2, or 3;
  r is 0, 1 or 2;
  s is 0, 1 or 2;
R is H, alkyl or haloalkyl;
R$^a$ is independently H, halo, alkyl or haloalkyl
R$^b$ is independently H, halo, alkyl or haloalkyl;
R$^1$ is heteroaryl, heterocyclyl or heterocyclenyl;
R$^2$ is aryl, heteroaryl, alkyl and heterocyclyl;
R$^3$ is —C(O)OH or —N(H)—SO$_2$—R$^c$;
  where:
    R$^c$ is alkyl, haloalkyl, cycloalkyl, aryl or heteroaryl;
R$^4$ is independently selected from the group consisting of alkyl, —OH, halo, alkoxy, haloalkoxy, —CN and haloalkyl;
R$^8$ is independently selected from the group consisting of —CN, halo, alkyl, haloalkyl, alkoxy, haloalkoxy or cycloalkyl;
R$^9$ is alkyl, haloalkyl, alkoxy, haloalkoxy or cycloalkyl;
and wherein:
  i) the heteroaryl, heterocyclyl or heterocyclenyl group in R$^1$; and
  ii) each of the aryl, heteroaryl, alkyl or heterocyclyl groups of R$^2$; are independently unsubstituted or substituted by 1 to 5 R$^5$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$) and —N(R$^{14}$)C(O)OR$^{16}$;

or when a position is disubstituted by two R$^5$ groups, the two R$^5$ groups can form a cycloalkyl or heterocyclyl ring that is unsubstituted or is substituted by 1 to 5 R$^6$ groups
and wherein:
  each of the alkyl, alkenyl, alkynyl, cycloalkyl, cycloalkenyl, heterocyclyl, heterocyclenyl, aryl, heteroaryl groups in R$^5$ are independently unsubstituted or substituted by 1 to 5 R$^6$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_n$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{16}$)(R$^{16}$), —N(R$^{14}$)C(O)N(R$^{16}$)(R$^{16}$); —N(R$^{14}$)C(O)OR$^{16}$ and —N(R$^{14}$)C(O)R$^{16}$; and wherein each of the alkyl, alkenyl, alkynyl, cycloalkyl, cycloalkenyl, heterocyclyl, heterocyclenyl, aryl, heteroaryl groups in R$^6$ are in independently unsubstituted or substituted by 1 to 5 R$^7$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{16}$, —N(R$^{14}$)(R$^{16}$), —N(R$^{14}$)C(O)R$^{16}$, —N(R$^{14}$)S(O)$_p$R$^{15}$, N(R$^{14}$)S(O)$_p$N(R$^{15}$)(R$^{16}$), —N(R$^{14}$)C(O)N(R$^{15}$)(R$^{16}$); —N(R$^{14}$)C(O)OR$^{16}$ and —N(R$^{14}$)C(O)R$^{16}$:

wherein:
R$^{14}$, R$^{16}$ and R$^{16}$ are independently selected from the group consisting of H, alkyl, alkenyl, alkynyl, cycloalkyl, cycloalkenyl, heterocyclyl, heterocyclenyl, aryl, heteroaryl, R$^{17}$-alkyl, R$^{17}$-alkenyl, R$^{17}$-alkynyl, R$^{17}$-cycloalkyl, R$^{17}$-cycloalkenyl, R$^{17}$-heterocyclyl, R$^{17}$-heterocyclenyl, R$^{17}$-aryl, and R$^{17}$-heteroaryl;
R$^{17}$ is 1-5 substituents independently selected from the group consisting of alkyl, alkenyl, alkynyl, cycloalkyl, cycloalkenyl, heterocyclyl, heterocyclenyl, aryl, halo-substituted aryl, nitrite-substituted aryl, phenyl-substituted aryl, heteroaryl, halo, —CN, —SF$_5$, —OSF$_5$, —NO$_2$, heteroaryl, haloalkyl, —C(O)R$^{18}$, —C(O)OH, —C(O)OR$^{18}$, —C(O)NHR$^{19}$, —C(O)NH$_2$, —C(O)N(R$^{18}$)(R$^{19}$), —S(O)$_m$R$^{18}$, —S(O)$_p$NH$_2$, —S(O)NH$_p$(alkyl), —S(O)$_p$N(alkyl)(alkyl), —S(O)$_p$NH(aryl), —S(O)$_2$NHR$^{19}$, —S(O)$_2$NH(heterocycloalkyl), —S(O)$_2$N(alkyl)(aryl), haloalkoxy, —OH, —OR$^{19}$, —O-heterocycloalkyl, —O-cycloalkylalkyl, —O-heterocyclylalkyl, —NH$_2$, —NHR$^{19}$, —N(alkyl)$_2$: —N(arylalkyl)$_2$, —N(arylalkyl)-(heteroarylalkyl), —NHC(O)R$^{19}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{21}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);
R$^{18}$ is alkyl, cycloalkyl, aryl, arylalkyl or heteroarylalkyl;
R$^{19}$ is alkyl, cycloalkyl, aryl, halo substituted aryl, arylalkyl, heteroaryl or heteroarylalkyl;

$R^{21}$ is alkyl, cycloalkyl, aryl, halo substituted aryl, arylalkyl, heteroaryl or heteroarylalkyl;

b is 0, 1 or 2 n is an integer from 1 to 5;

m is independently an integer from 0 to 2;

p is an integer from 1 to 2; and q is an integer from 0 to 5.

One embodiment of this invention is a compound of Formula I or a pharmaceutically acceptable salt thereof wherein $R^{17}$ is 1-5 substituents independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, heteroaryl, haloalkyl, —C(O)R$^{18}$, —C(O)OH, —C(O)OR$^{18}$, —C(O)NHR$^{19}$, —C(O)NH$_2$, —C(O)N(R$^{18}$)(R$^{19}$), —S(O)$_m$R$^{18}$, —S(O)$_p$NH$_2$, —S(O)NH$_p$(alkyl), —S(O)$_p$N(alkyl)(alkyl), —S(O)$_p$NH(aryl), —S(O)$_2$NHR$^{19}$, —S(O)$_2$NH(heterocycloalkyl), —S(O)$_2$N(alkyl)(aryl), haloalkoxy, —OH, —OR$^{19}$, —O-heterocycloalkyl, —O-cycloalkylalkyl, —O-heterocyclylalkyl, —NH$_2$, —NHR$^{19}$, —N(alkyl)$_2$, —N(arylalkyl)$_2$, —N(arylalkyl)-(heteroarylalkyl), —NHC(O)R$^{19}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{21}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl).

The compounds of Formula I can be useful as antagonists of CRTH$_2$ and, therefore, can be useful in the treatment, prevention or amelioration of the symptoms of disease states associated with antagonizing CRTH$_2$. These disease states include (but not limited to) asthma, congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In an embodiment, the present invention provides a method for the treatment of asthma, congestion, allergic rhinitis and COPD in a mammal in need thereof which comprises administering to a mammal an effective dose of at least one compound having adrenergic activity wherein said compound is an antagonist of CRTH$_2$.

The present invention also provides for the use of the compounds Formula I or a pharmaceutically acceptable salt thereof in the preparation of a medicament for the treatment of asthma, congestion, allergic rhinitis, atopic dermatitis, COPD, dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals.

DETAILED DISCUSSION

In an embodiment, the present invention discloses certain quinazoline-type compounds or Formula I that are represented by those compounds of Formula II or Formula III or their pharmaceutically acceptable salts:

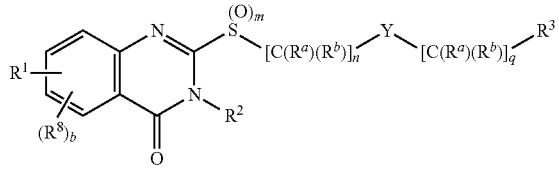

Formula II

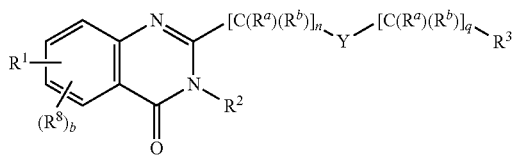

Formula III wherein the variables are those as defined above in the compounds of Formula I.

One embodiment of this invention is a compound of Formula II or Formula III or a pharmaceutically acceptable salt thereof, wherein n is 1 and q is 0.

Another embodiment of this invention is a compound of Formula II Formula III or a pharmaceutically acceptable salt thereof, wherein n is 2 and q is 1.

Another embodiment of this invention is a compound of Formula II or Formula III, or a pharmaceutically acceptable salt thereof wherein n is 4 and q is 0.

Another embodiment of this invention is a compound of Formula II or Formula III where b is 0.

Another embodiment of this invention is a compound of Formula II or III where b is 1 and $R^8$ is halo (e.g., F or Cl) or haloalkyl (e.g., —CF$_3$).

Another embodiment of this invention is a compound of Formula II or Formula III or a pharmaceutically acceptable salt thereof, wherein $R^1$ is heteroaryl (i.e., unsubstituted heteroaryl) or $R^5$-heteroaryl, wherein the heteroaryl ring is a ring selected from the group consisting of thiazole, oxazole, imidazole, 1,2-diazole, triazole, pyridine, pyrimidine, thiophene and furan, isooxazole, isothiazole and oxadiazole.

Another embodiment of this invention is a compound of Formula II or Formula III or a pharmaceutically acceptable salt thereof, wherein $R^1$ is heteroaryl (i.e., unsubstituted heteroaryl) or $R^5$-heteroaryl, wherein the heteroaryl ring is a ring selected from the group consisting of thiazole, oxazole, imidazole, 1,2-diazole, triazole, pyridine, pyrimidine, thiophene and furan, isooxazole, isothiazole, oxadiazole and $R^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), $R^6$-aryl (e.g., $R^6$-phenyl)-C$_1$-C$_5$-alkyl-aryl (e.g., benzyl) and —C$_1$-C$_5$-alkyl-aryl-$R^7$ (e.g., $R^7$-benzyl), where $R^6$ and $R^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —SO$_2$ alkyl.

Another embodiment of this invention is a compound of Formula II or Formula III or a pharmaceutically acceptable salt thereof, wherein $R^1$ is heterocyclyl (i.e., unsubstituted heterocyclyl) or $R^5$-substituted heterocyclyl, wherein the heterocyclyl ring is ring is piperidyl, pyrrolidinyl, piperazinyl, morpholinyl, thiomorpholinyl, thiazolidinyl, 1,4-dioxanyl, tetrahydrofuranyl or tetrahydrothiophenyl and $R^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$haloalkoxy (e.g., —OCF$_3$), aryl (e.g., phenyl), R$^6$-aryl (e.g., R$^6$-phenyl)-C$_1$-C$_5$-alkyl-aryl (e.g., benzyl) and —C$_1$-C$_5$-alkyl-aryl-R$^7$ (e.g., R$^7$-benzyl), where R$^6$ and R$^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —S(O)$_2$alkyl.

Another embodiment of this invention is a compound or Formula II or Formula III or a pharmaceutically acceptable salt thereof wherein R$^1$ is heterocyclenyl (i.e., unsubstituted heterocyclenyl) or R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydro-oxadiazolyl, dihydrothiazolyl, 3,4-dihydro-2H-pyranyl, dihydrofuranyl, fluorodihydrofuranyl, 7-oxabicyclo[2.2.1]heptenyl, 4,5-dihydroisooxazol-3-yl, dihydrothiophenyl, and dihydrothiopyranyl.

Another embodiment of this invention is a compound of Formula II or Formula III or a pharmaceutically acceptable salt thereof wherein R$^1$ is heterocyclenyl (i.e., unsubstituted heterocyclenyl) or R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, 4,5-dihydroisooxazol-3-yl, dihydrothiophenyl, dihydrothiopyranyl and R$^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl)-C$_1$-C$_5$-alkyl-aryl (e.g., benzyl) and —C$_1$-C$_5$-alkyl-aryl-R$^7$ (e.g., R$^7$-benzyl), where R$^6$ and R$^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —S(O)$_2$alkyl.

Another embodiment is a compound of Formula II or Formula III or a pharmaceutically acceptable salt thereof, wherein R$^2$ is unsubstituted aryl (e.g., phenyl).

Another embodiment is a compound of Formula II or Formula III or a pharmaceutically acceptable salt thereof, wherein R$^2$ is R$^5$-aryl-(e.g. R$^5$-phenyl) where R$^5$ is C$_1$-C$_5$-alkyl (e.g., methyl or ethyl), halogen, C$_1$-C$_5$-haloalkyl, (e.g., —CF$_3$), —OH, or —C$_1$-C$_5$-alkoxy (e.g., methoxy or ethoxy).

Another embodiment is a compound of Formula II or Formula III wherein Y is a bond.

Another embodiment is a compound of Formula II or Formula III or a pharmaceutically acceptable salt thereof, wherein Y is a bond, n is 1 and q is 0.

Another embodiment is a compound of Formula II or Formula III or a pharmaceutically acceptable salt thereof, wherein Y is

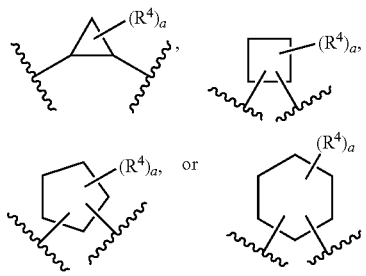

and a is 0 or 1 and R$^4$ is —C$_1$-C$_5$-alkyl.

Another embodiment is a compound of Formula II or Formula III or a pharmaceutically acceptable salt thereof, wherein R$^3$ is —C(O)OH.

Another embodiment is a compound of Formula II or Formula III or a pharmaceutically acceptable salt thereof, wherein R$^1$ is substituted on the 7-position of the quinazolinone moiety.

Another embodiment of this invention is a compound of Formula I that is represented by Formula IV or Formula V or a pharmaceutically acceptable salt thereof that has the formula:

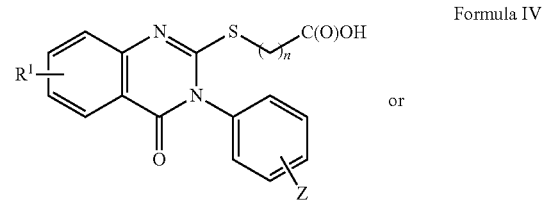

Formula IV or

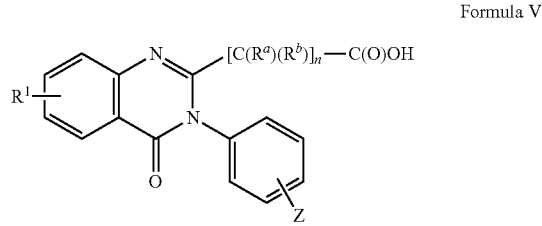

Formula V wherein Z is halogen and the remaining variables are as defined in Formula I above.

Another embodiment of this is invention is a compound of Formula IV or V or a pharmaceutically acceptable salt thereof wherein n is 1 or 2.

Another embodiment of this invention is a compound of Formula IV or V or a pharmaceutically acceptable salt thereof wherein n is 3 or 4.

Another embodiment of this invention is a compound of Formula IV or Formula V or a pharmaceutically acceptable salt thereof, wherein R$^1$ is heteroaryl (i.e., unsubstituted heteroaryl) or R$^5$-heteroaryl, wherein the heteroaryl ring is a ring selected from the group consisting of thiazole, oxazole, imidazole, 1,2-diazole (pyrazole), triazole, pyridine, pyrimidine, thiophene, furan, isooxazole, isothiazole and oxadiazole.

Another embodiment of this invention is a compound of Formula IV or Formula V or a pharmaceutically acceptable salt thereof, wherein R$^1$ is heteroaryl (i.e., unsubstituted heteroaryl) or R$^5$-heteroaryl, wherein the heteroaryl ring is a ring selected from the group consisting of thiazole, oxazole, imidazole, 1,2-diazole, triazole, pyridine, pyrimidine, thiophene and furan, isooxazole, isothiazole, oxadiazole and R$^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl)-C$_1$-C$_5$-alkyl-aryl (e.g., benzyl) and —C$_1$-C$_5$alkyl-aryl-R$^7$ (e.g., R$^7$-benzyl), where R$^6$ and R$^7$ in each occurrence independently are —C$_1$-C$_5$-alkyl (e.g., methyl or ethyl), halogen, —C$_1$-C$_5$-haloalkyl, —CF$_3$), —OH, —C$_1$-C$_5$-alkoxy methoxy or ethoxy) or —S(O)$_2$-alkyl.

Another embodiment of this invention is a compound of Formula IV or Formula V or a pharmaceutically acceptable salt thereof, wherein R$^1$ is heterocyclyl (i.e., unsubstituted heterocyclyl) or R$^5$-substituted heterocyclyl, wherein the heterocyclyl ring is ring is piperidyl, pyrrolidinyl, piperazinyl, morpholinyl, thiomorpholinyl, thiazolidinyl, 1,4-dioxanyl, tetrahydrofuranyl or tetrahydrothiophenyl and R$^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl)-C$_1$-C$_5$-alkyl-aryl (e.g., benzyl) and —C$_1$-C$_5$-alkyl-aryl-R$^7$ (e.g., R$^7$-benzyl), where R$^6$ and R$^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy methoxy or ethoxy) or —S(O)$_2$alkyl.

Another embodiment of this invention is a compound or Formula IV or Formula V or a pharmaceutically acceptable salt thereof wherein R$^1$ is heterocyclenyl (i.e., unsubstituted heterocyclenyl) or R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydro-oxadiazolyl, dihydrothiazolyl, 3,4-dihydro-2H-pyranyl, dihydrofuranyl, fluorodihydrofuranyl, 7-oxabicyclo[2.2.1]heptenyl, 4,5-dihydroisooxazol-3-yl, dihydrothiophenyl, and dihydrothiopyranyl.

Another embodiment of this invention is a compound of Formula IV or Formula V or a pharmaceutically acceptable salt thereof wherein R$^1$ is heterocyclenyl (i.e., unsubstituted heterocyclenyl) or R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl and R$^5$ is selected from the group consisting of —C$_1$-C$_5$-alkyl (e.g., methyl or ethyl), —C$_1$-C$_5$-haloalkyl (e.g., —CF$_3$), —C$_r$C$_5$- alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl), —C$_1$-C$_5$-alkyl-aryl (e.g., benzyl), R$^7$ (e.g., R$^7$-benzyl), heteroaryl (e.g., benzoxazole or benzimidazole) and R$^6$-heteroaryl, where R$^6$ and R$^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —S(O)$_2$alkyl.

Another embodiment is a compound of Formula IV or Formula V or a pharmaceutically acceptable salt thereof, wherein R$^1$ is substituted on the 7-position of the quinazolinone moiety.

Another embodiment of this invention is a compound of Formula IV or Formula V or a pharmaceutically acceptable salt thereof wherein R$^1$ is heterocyclenyl (i.e., unsubstituted heterocyclenyl) or R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyi, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, and dihydrothiopyranyl and R$^5$ is selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl)-C$_1$-C$_5$-alkyl-aryl (e.g., benzyl) and —C$_1$-C$_5$-alkyl-aryl-R$^7$ (e.g., R$^7$-benzyl), where R$^6$ and R$^7$ in each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —S(O)$_2$alkyl.

Another embodiment of the invention of this invention is a compound of Formula I represented by Formula VI or a pharmaceutically acceptable salt thereof that has the formula:

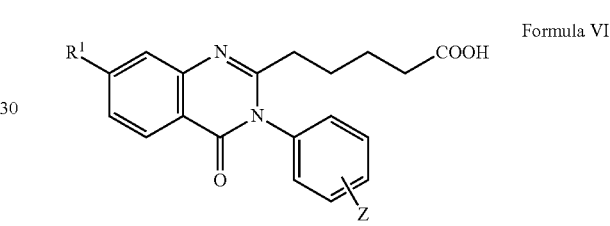

Formula VI wherein Z is a H or a halogen and R$^1$ is as defined in Formula I above.

Another embodiment of the invention of this invention is a compound of Formula VI or a pharmaceutically acceptable salt thereof, wherein R$^1$ is R$^5$-heterocyclenyl, wherein the heterocyclenyl ring is a ring selected from the group consisting of 4,5-dihydro-isoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, 7-oxabicyclo[2.2.1]heptenyl, dihydrothiophenyl, and dihydrothiopyranyl;

R$^5$ is 1 to 2 substituents independently selected from the group consisting of —C$_1$-C$_5$-alkyl (e.g., methyl or ethyl), —C$_1$-C$_5$-haloalkyl (e.g., —CF$_3$), —C$_1$-C$_5$-alkoxy (e.g., methoxy or ethoxy), —C$_1$-C$_5$-haloalkoxy (e.g., —OCF$_3$), aryl (e.g., phenyl), R$^6$-aryl (e.g., R$^6$-phenyl), —C$_1$-C$_5$-alkyl-aryl (e.g., benzyl), —C$_1$-C$_5$-alkyl-aryl-R$^7$ (e.g., R$^7$-benzyl), heteroaryl (e.g., benzoxazole or benzimidazole) and R$^6$-heteroaryl, and where R$^6$ and R$^7$ at each occurrence independently are —C$_1$-C$_5$-alkyl (e.g., methyl or ethyl), halogen, —CN, —C$_1$-C$_5$-haloalkyl, (e.g., —CF$_3$), —OH, —C$_1$-C$_5$-alkoxy (e.g., methoxy or ethoxy) or —S(O)$_2$alkyl.

Another specific embodiment of this invention is a compound of Formula VI or a pharmaceutically acceptable salt thereof, wherein R$^1$ is R$^5$-heterocyclenyl, and the heterocyclenyl of the R$^5$-heterocyclenyl is 4,5-dihydro-isoxazole;

$R^5$ is 1 to 2 substituents independently selected from the group consisting of —$C_1$-$C_5$-alkyl (e.g., methyl or ethyl), aryl (e.g., phenyl), $R^6$-aryl (e.g., $R^6$-phenyl), —$C_1$-$C_5$-alkyl-aryl (e.g., benzyl), —$C_1$-$C_5$-alkyl-aryl-$R^7$ (e.g., $R^7$-benzyl), heteroaryl (e.g., benzoxazole or benzimidazole) and $R^6$-heteroaryl, where the heteroaryl of the $R^6$-heteroaryl is selected from the group consisting of pyridine, benzoxazole, benzothiazole, benzimidazole, imidazo[1,2-a]pyridine, pyrazolo[1,5-a]pyridine, and quinoxaline; and where $R^6$ and $R^7$ at each occurrence independently are —$C_1$-$C_5$-alkyl (e.g., methyl or ethyl), halogen, —CN, —$C_1$-$C_5$-haloalkyl, (e.g., —$CF_3$), —OH, —$C_1$-$C_5$-alkoxy (e.g., methoxy or ethoxy) or —$S(O)_2$alkyl.

Another embodiment of the invention of this invention is a compound of Formula VI or a pharmaceutically acceptable salt thereof, wherein $R^1$ is $R^5$-heteroaryl, wherein the heteroaryl ring is a ring selected from the group consisting of thiazole, oxazole, imidazole, 1,2-diazole, triazole, pyridine, pyrimidine, thiophene, furan, isooxazole, isothiazole, and oxadiazole; and $R^5$ is selected from the group consisting of —$C_1$-$C_5$-alkyl-aryl, —$C_1$-$C_5$-alkyl-aryl-$R^7$, $C_1$-$C_5$-alkyl-heteroaryl, and —$C_1$-$C_5$-alkyl-heteroaryl-$R^7$, —$C_1$-$C_5$-alkyl-N(H)—$S(O)_2$-aryl, —$C_1$-$C_5$-alkyl-O—$CH_2$-aryl, —$C_1$-$C_5$-alkyl-O—$CH_2$-(halo-substituted)aryl, and —$C_1$-$C_5$-alkyl-O—$CH_2$-(phenyl-substituted)aryl; and where $R^7$ is —$C_1$-$C_5$-alkyl (e.g., methyl or ethyl), halogen, —$C_1$-$C_5$-haloalkyl, (e.g., —$CF_3$), —OH, —$C_1$-$C_5$-alkoxy (e.g., methoxy or ethoxy) or —$S(O)_2$-alkyl.

Another embodiment of the invention of this invention is a compound of Formula I represented by Formula VII or a pharmaceutically acceptable salt thereof that has the formula:

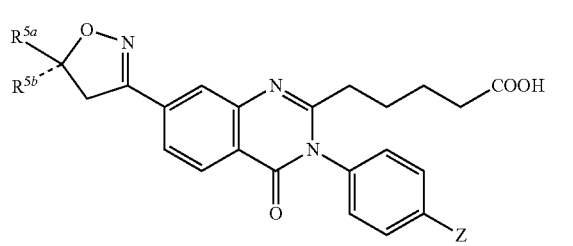

Formula VII wherein Z is H, Cl or F;

$R^{5a}$ is phenyl, benzoxazole, benzothiazole, benzimidazole, imidazo[1,2-a]pyridine, pyrazolo[1,5-a]pyridine, and quinoxaline;

wherein $R^{5a}$ is unsubstituted or substituted by 1 to 2 $R^6$ groups independently selected from the group consisting of $C_1$-$C_3$-alkyl, halo, $CF_3$, and —CN; and wherein $R^{5b}$ is absent or present, and if present, is $CH_3$.

Another embodiment of the invention of this invention is a compound of Formula I represented by Formula VIII or a pharmaceutically acceptable salt thereof that has the formula:

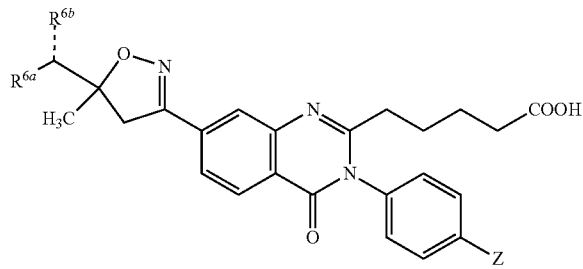

Formula VIII wherein Z is H, Cl or F and $R^{6a}$ is phenyl, wherein the phenyl of $R^{6a}$ is unsubstituted or substituted by 1 to 2 $R^7$ groups independently selected from the group consisting of halo, $C_1$-$C_3$ alkyl, and —CN; and wherein $R^{6b}$ is absent or present, and, if present, is selected from the group consisting of —$CH_3$ and —OH.

Another embodiment of the invention of this invention is a compound of Formula I represented by Formula IX or a pharmaceutically acceptable salt thereof that has the formula:

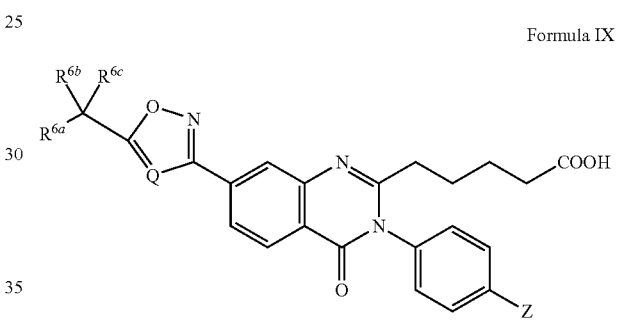

Formula IX wherein Z is H, Cl or F;

Q is C(H) or N;

$R^{6a}$ is selected from the group consisting of:
(a) -M-E; and
(b) -E;

wherein M is selected from the group consisting of —N(H)S(O)—, —N(H)C(O)—, —S—, —S(O)—, —S—, and —$OCH_2$—, E is selected from the group consisting of:
(i) $C_1$-$C_3$-alkyl;
(ii) —O—($C_1$-$C_4$-alkyl);
(iii) an aryl selected from the group consisting of phenyl and napthalene;
(iv) a heteroaryl selected from the group consisting of quinoline, quinoxaline, and benzimidazole;
(v) 2,3-dihydroindole;
wherein said aryl or heteroaryl of E is unsubstituted or substituted by 1 to 3 moieties selected from the group consisting of $C_1$-$C_6$-alkyl, halo, $CF_3$, $OCF_3$, CN, $OCH_3$, and phenyl;

$R^{6b}$ is H, OH, or $OCH_3$; and $R^{6c}$ is H, $C_1$-$C_3$-alkyl, or $CF_3$;

or alternatively, $R^{6b}$ and $R^{6c}$ together with the carbon atom to which they are attached form —C(O)— or —C(=$CH_2$)—.

Another embodiment of the invention of this invention is a compound of Formula IX or a pharmaceutically acceptable salt thereof wherein Q is CH.

Another embodiment of the invention of this invention is a compound of Formula IX or a pharmaceutically acceptable salt thereof wherein Q is N.

Another embodiment of the invention of this invention is a compound of Formula I represented by Formula X or a pharmaceutically acceptable salt thereof that has the formula:

Formula X

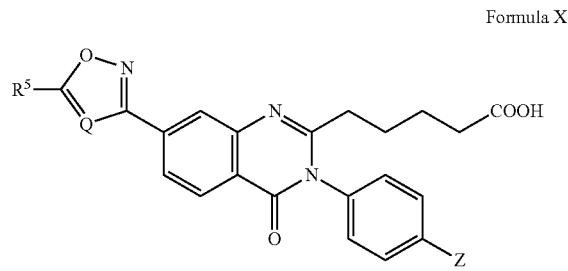

wherein Z is H, Cl or F;
Q is C(H) or N;
R⁵ is selected from the group consisting of:
(a) an aryl selected from the group consisting of phenyl, indane, and tetrahydronapthalene;
(b) a heteroaryl selected from the group consisting of pyridine, quinoline and benzoxazole;
wherein R⁵ is unsubstituted or substituted by 1 to 2 R⁶ groups selected from the group consisting of $C_1$-$C_4$-alkyl, halo, or N-methylpyrazole.

Another embodiment of the invention of this invention is a compound of Formula X or a pharmaceutically acceptable salt thereof wherein Q is CH.

Another embodiment of the invention of this invention is a compound of Formula X or a pharmaceutically acceptable salt thereof wherein Q is N.

Another embodiment are compounds of Example 15, 15F, 15i, 15K, 15L, 15M, 15N, 15o, 15P, 15Q, 15T, 15U, 15V, 15W, 15Z, 19, 19D, 20, 20B, 21, 21D, 24, 24i, 24J, 24M, 24Q, 25, 25C, 25G, 25i, 25J, 25K, 25L, 25M, 26, 26F, 26J, 28E, 29, 32, 35, 35G, 36, 37, 37E, 39K, 39L, 42F, 43, 43D, 44, 101, 105, 111, 119, 121, 124, 125, 136, 140, 141, 158, 160, 161, 162, 163, 166, 167, 171, 172, 174, 175, 176, 178, 180, 182, 184, 186, 189, 191, 193, 194, 195, 196, 197, 198, 201, 203, 205, 206, 208, 209, 213, 217, 219, 220, 222, 224, 229, 231, 235, 242, 244, 250, 256, 261, 263, 264, 268, 273, 282, 283, or 290.

Another embodiment are compounds of Example Numbers 5N, 14, 14C, 15, 15F, 15G, 15H, 15i, 15K, 15L, 15M, 15N, 15o, 15P, 15Q, 15T, 15U, 15V, 15W, 15Z, 19, 19D, 20, 20B, 21, 21D, 24, 24i, 24J, 24M, 25, 25G, 25i, 25J, 25K, 25M, 26, 26J, 28E, 29, 32, 35, 35G, 36, 37, 37E, 44, 101, 105, 111, 178, 180, 184, 207, 242, 263, 273, 283, or 290.

Another embodiment are compounds of Example Numbers 5N, 14, 14C, 15, 15F, 15G, 15H, 15i, 15K, 15L, 15M, 15N, 15o, 15P, 15Q, 15T, 15U, 15V, 15W, 15Z, 19, 19D, 20, 20B, 21, 21D, 101, or 105.

As used above, and throughout this disclosure, the following terms, unless otherwise indicated, shall be understood to have the following meanings:

"Patient" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched, "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)₂, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl. Unless otherwise indicated, an alkyl group is unsubstituted.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl. Unless otherwise indicated, an alkenyl group is unsubstituted.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl. Unless otherwise indicated, an alkynyl group is unsubstituted.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Unless otherwise indicated, an aryl group is unsubstituted.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, (uranyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. Unless otherwise indicated, a heteroaryl group is unsubstituted.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl "Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Unless otherwise indicated, a cycloalkyl group is unsubstituted. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Unless otherwise indicated, a cycloalkenyl group is unsubstituted. Non-limiting examples of suitable monocyclic cycloalkenyls include cyclopentenyl, cyclohexenyl, cyclohepta-1,3-dienyl, and the like. A non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

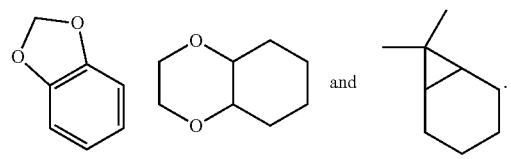

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 12 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. Unless otherwise indicated, a heterocyclyl group is unsubstituted. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Multicyclic rings include multicyclic rings wherein the non-hetero containing ring is aromatic; e.g.,

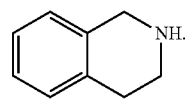

"Heterocyclyl" also includes heterocyclyl rings as described above wherein =O replaces two available hydrogens on the same ring carbon atom. Non-limiting examples are:

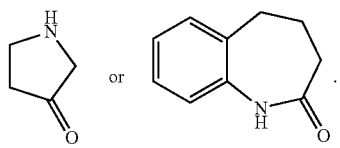 [SMILES: O=C1CCNC1 ; O=C1CCCc2ccccc2N1]

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" or "heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. Unless otherwise indicated, a heterocyclenyl group is unsubstituted. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like.

"Heterocyclenyl" also includes heterocyclenyl rings as described above wherein =O replaces two available hydrogens on the same ring carbon atom. An example of such a moiety is pyrrolidinone:

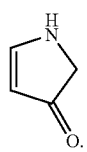

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

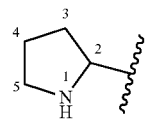

there is no —OH attached directly to carbons marked 2 and 5.

It should also be noted that tautomeric forms such as, for example, the moieties:

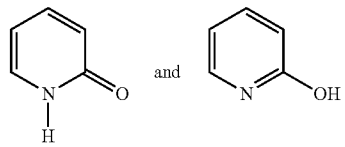 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" it is meant that a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$ etc.) occurs more than one time in any constituent or in Formula I, its definition on each occurrence is independent of its definition at every other occurrence.

In this application, unless otherwise indicated, whenever there is a structural formula provided, such as those of Formulae I to V, this formula is intended to encompass all forms of a compound such as, for example, any solvates, hydrates, stereoisomers, tautomers, etc. in all of its isolated forms. For example, the phrase "a compound of the formula

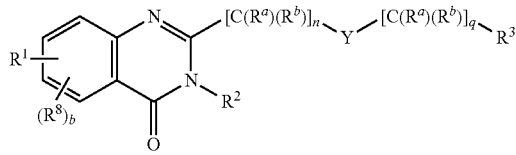

or its pharmaceutically acceptable salts"
would encompass any solvates, hydrates, stereoisomer, tautomers, etc. of compounds falling within the structural formula.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira at al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tender at al, *AAPS PharmSciTech.*, 5(1), article 12 (2004); and A. L. Bingham at al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl at al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g. dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

A preferred dosage is about 0.001 to 100 mg/kg of body weight/day of the compound of Formula I. An especially preferred dosage is about 0.01 to 10 mg/kg of body weight/day of a compound of Formula I, or a pharmaceutically acceptable salt or solvate of said compound.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A.

Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compounds of Formula I or their pharmaceutically acceptable salts may be used in combination, either in a single formulation or co-administered as separate formulations with at least one additional therapeutic agent to treat or prevent the disease state described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adernergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxy¬ loratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula I, optionally co-administered with one or more of such ingredients as listed immediately above.

Another aspect of this invention is a kit comprising a therapeutically effective amount of at least one compound of Formula I or a pharmaceutically acceptable salt or solvate of said compound, optionally at least one therapeutic agent listed above and a pharmaceutically acceptable carrier, vehicle or diluent.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reactions schemes and in the preparations and examples described below.

Where NMR data are presented, $^1$H spectra were obtained on either a Varian VXR-400 (400 MHz, $^1$H), Varian Gemini-300 (300 MHz), Varian Mercury VX-400 (400 MHz), Bruker-Biospin AV-500 (500 MHz) or Bruker Avance DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 µM Zorbax SB-C18 column (10-95% of MeCN—H$_2$O with 0.1% TFA over 2.7 min, 1 mL/min) or with an Applied Biosystems API-150 mass spectrometer and Gemini C18 column (50×4.6 mm, 10-95% CH$_3$CN—H$_2$O with 0.05% TFA over 5 min, 1 mL/min).

The following solvents and reagents may be referred to by their abbreviations in parenthesis:

Me=methyl; Et=ethyl; Pr=propyl; Bu=butyl; t-Bu=tert-butyl; Ph=phenyl, and Ac=acetyl
µl=microliters
Acac=acetylacetone
AcOEt or EtOAc=ethyl acetate
AcOH or HOAc=acetic acid
ACN=acetonitrile
ADDP=azodicarbonyldipiperidine
aq=aqueous
Ar=aryl
atm=atmosphere
9-BBN=9-borabicyclo[3.3.1]nonane
Bn=benzyl
Boc or BOC=tert-butoxycarbonyl
Bz=benzoyl
Boc=tert-butoxycarbonyl
BINAP=2,2'-bis(diphenylphosphino)-1,1"-bisnaphthyl
cat=catalyst or catalytic
Cbz=benyzloxycarbonyl
CELITE=Diatomaceous earth
d=day
DBU=1,8-Diaza-7-bicyclo[5.4.0]undecene
DEAD=diethylazodicarboxylate
DCM or CH$_2$Cl$_2$: dichloromethane:
DMAP=4-Dimethylaminopyridine
DIBAL=diisobutylaluminum hydride
DIPEA or Hünig's Base=N,N-diisopropylethylamine
DME=1,2-dimethoxyethane
DMF=dimethylformamide
DMS=dimethylsulfide
DMSO=dimethyl sulfoxide
Dppf=1,1'-bis(diphenylphosphino)ferrocene
EDCI or DEC=1-(3-dimethylaminopropyl)-3-ethylcarbodiimide
g=grams
h=hour
HATU=O-(7-Azobenzotriazol-1-yl)-1,1,3,3-tetramethyluronium hexafluorophosphate
HBBS=Hanks' balanced salt solution
HetAr=heteroaryl
HMDS=1,1,1,3,3,3-hexamethyldisilazane
HOBt=1-hydroxybenzotriazole
Im=imidazole
LAH=lithium aluminum hydride
LDA=lithium diisopropylamide
LCMS=liquid chromatography mass spectrometry
LG=leaving group
min=minute
mg=milligrams
mL=milliliters
mmol=millimoles
MeOH: methanol
MS=mass spectrometry
NBS=N-bromosuccimide
NMO=N-methylmorpholine N-oxide
NMP=N-Methylpyrrolidone
NMR=nuclear magnetic resonance spectroscopy
PBS=phosphate buffer solution
PG=protecting group
PyBop=benzotriazol-1-yl-oxytripyrrolidinophosphonium hexafluorophosphate
Pyr=pyridine
rac or (±)=racemic mixture or enantiomers
rt or RT=room temperature (ambient, about 25° C.)
sat=saturated
SFC=supercritical fluid chromatography
SM=starting material
TBAF=tetra-n-butylammonium fluoride
TBSCI=t-butyldimethylsilyl chloride
TBS=t-butyldimethyl silyl
TEA=triethylamine (Et$_3$N)
TEMPO=2,2,6,6-Tetramethylpiperidine-1-oxyl
TFA=trifluoroacetic acid
TFAA=Trifluoroacetic anhydride
TPAP=tetrapropylammonium perruthenate
THF=tetrahydrofuran
TLC=thin layer chromatography
TMS=trimethylsilyl
Tos or Ts=p-toluenesulfonyl (tosyl)
Tol=toluene

EXAMPLES

The compounds of this invention can be prepared through the general approach outlined in the following schemes. These schemes are being provided to illustrate the present invention. To assist one in this endeavor the ordinary practitioner would have full knowledge of literature sources such as *Chemical Abstracts, Beilstein, Protective Groups in Organic Synthesis* etc.

Scheme 1 shows an approach in which S1 is treated with an optionally substitute aryl isothiocyanate and base (such as triethylamine) to provide S2, which is then alkylated with an appropriate alkyl ester S4 (with an appropriate linker length such as n=1, 2 or 3) and appropriate base (such as triethylamine, NaH, or KOtBu). Conversion of the right side ester (in which R is an appropriate protecting group, PG, such as alkyl, allyl, benzyl etc) to carboxylic acid S3b (R═H) is accomplished by one of many appropriate synthetic methods known to practitioners in the art (such as TEA treatment of a tBu ester or LiOH treatment of a methyl ester).

Left side transformation, in which A=halogen or activated alcohol, to A=one of the various definitions of $R^1$, such as heteroaryl, heterocyclenyl, or heterocyclyl, occurs by a metal catalyzed or metal-facilitated process (such as Stifle coupling, Suzuki coupling, Negishi coupling or nucleophilic substitution reaction with an appropriately substituted aryl or heteroaryl partner). In an another embodiment, A is an acid, oxime, amide, thioamide, ester, acetylene, olefin, nitrite, azide or other functional group and is transformed into heterocycle by a cycloaddition or other appropriate ring forming process.

SCHEME 1

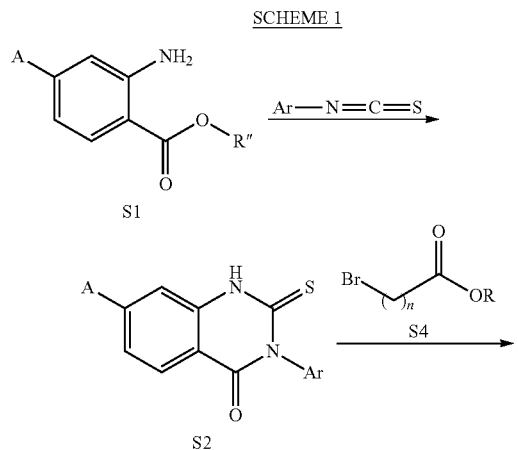

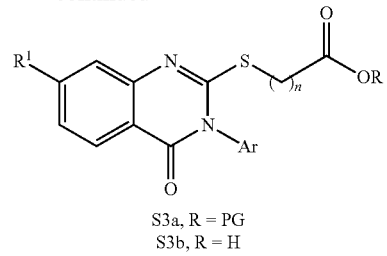

S3a, R = PG
S3b, R = H

Scheme 2 shows an approach in which S1 is treated with an optionally substituted aryl isocyanate (and optional base, such as triethylamine) to provide a quinazolinedione, which is then treated with $POCl_3$, $SOCl_2$, $P_2O_5/Bu_4NCl$, $P_2O_5/Bu_4NBr$ or another appropriate reagent. The resulting quinazolinone S5 is then reacted with an appropriate coupling partner, such as S8a, under suitable conditions (including, but not limited to, Suzuki coupling) to provide S6. Left side transformation, in which A=halogen, ester, or other functional group, to A=R1, is accomplished as previously described for Scheme 1.

Alternatively, compound S5 is reacted with S8b (in which X is a nucleophilic heteroatom such as nitrogen or oxygen) and appropriate base (such as LiOtBu, DIPEA, LDA, NaH, or other appropriate reagent) to provide S7.

SCHEME 2

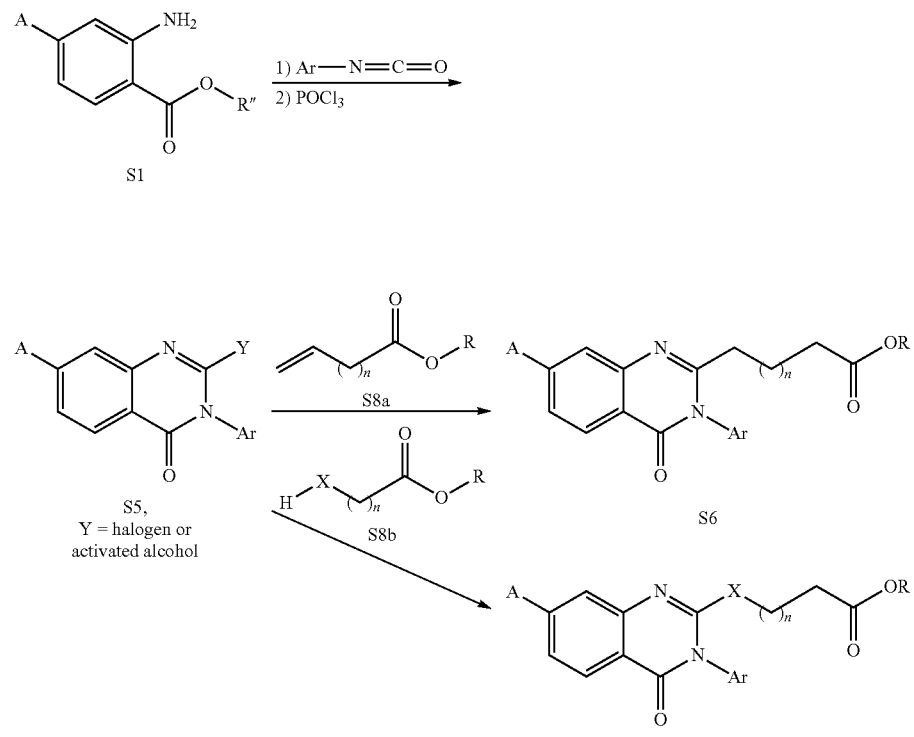

Scheme 3 shows an approach in which S1 is coupled the acid S9 by known amide coupling methods (with reagents such as EDCI, HOBt, PyBop, HATU etc. or with the corresponding acid chloride of S9) and then closed to S11 with an appropriate reagent such as an anhydride (Ac$_2$O, TFAA etc.). Treatment with an amine R'NH$_2$ (in which R' is alkyl, aryl or heteroaryl amine) provides S12.

Compounds, such as those described by formulae S3, S6, S7, and S12, can be prepared by the general methods outlined above. Exemplary compounds were prepared as described in the examples below or from starting materials known in the art. When unavailable from commercial suppliers, starting materials are synthesized according to methods known in the literature. These examples are being provided to further illustrate the present invention. They are for illustrative purposes only; the scope of the invention is not to be considered limited in any way thereby.

Preparative Example 1

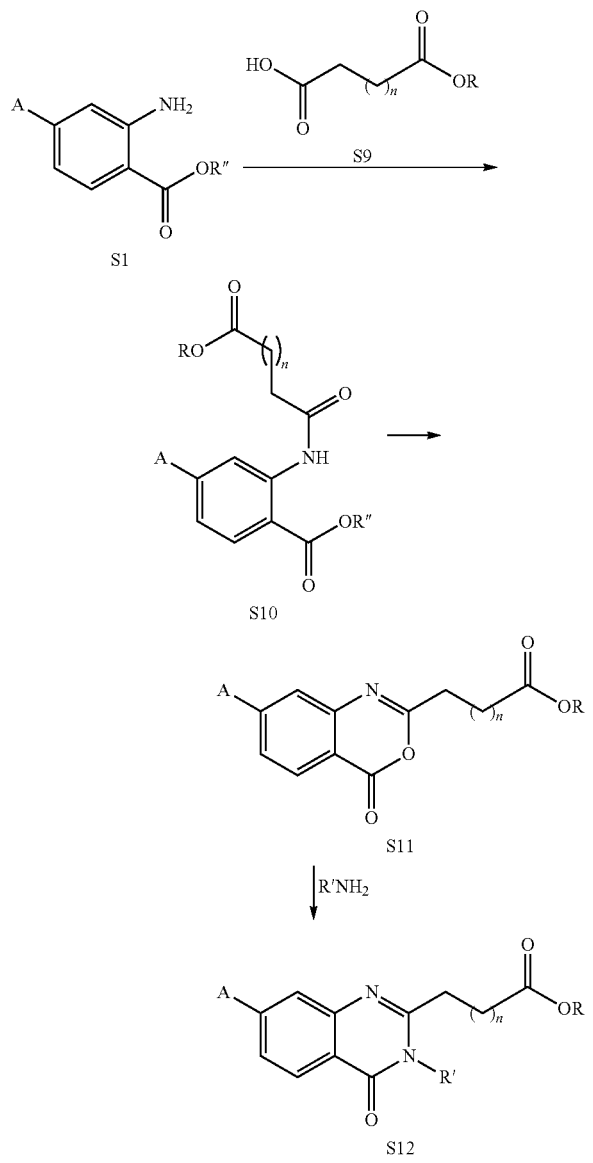

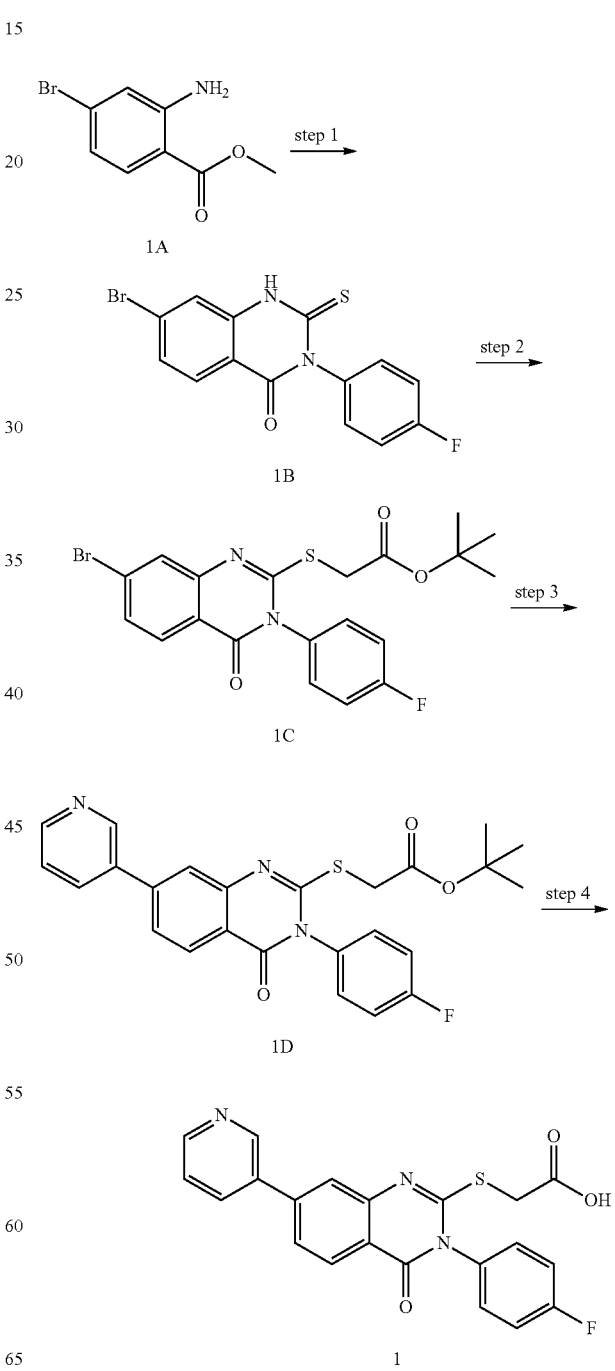

The alkyl linker to the carboxylic acid in compounds such as S3, S6, S7, and S12 may be appropriately substituted by either use of correspondingly substituted starting materials S4, S8a, S8b, and S9 or via corresponding elaboration later in the sequence.

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Step 1

7-Bromo-3(4-fluorophenyl)-2-thioxo-2,3-dihydro-quinazolin-4-(1H)-one

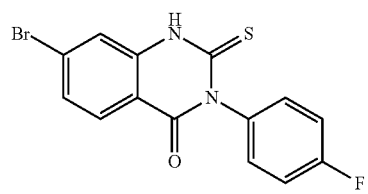

1B

A solution of methyl 2-amino-4-bromobenzoate (1A, 15.1 g, 65.65 mmol), 4-fluorophenyl isothiocyanate (11 g, 71.9 mmol) in 150 mL DMF was heated to 80° C. for 14 h. The reaction mixture was cooled to rt and was treated with 20 mL of water. The white precipitate was filtered and washed with cold i-PrOH (15 mL×3). This white solid was dissolved in 75° C. iPrOH/DMF (1:1) mixture then cooled to 0° C. again. The white precipitate was filtered and washed with cold i-PrOH (15 mL×3) to yield 1B (9.2 g, 40% yield).

Step 2 tert-Butyl 2-(7-bromo-3-(4-fluorophenyl)-4-oxo-3,4-dihydroquinazolin-2-ylthio)acetate

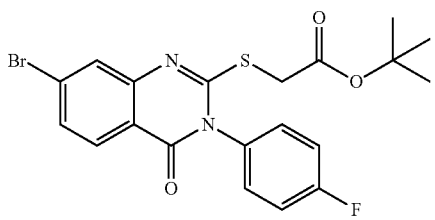

1C

A solution of 1B (0.67 g, 3.41 mmol), tert-butyl 2-bromoacetate (0.67 g, 3.41 mmol), TEA (0.43 g, 4.26 mmol) in 8 mL DMF was heated to 70° C. for 1.5 h. The reaction was cooled to rt and white precipitate was filtered and washed with cold i-PrOH (8 mL×3) to yield 1C (1.2 g, 92% yield).

Step 3 tert-Butyl 2-(3-(4-fluorophenyl)-4-oxo-7-(pyridine-3-O-3,4-dihydroquinazolin-2-ylthio)acetate

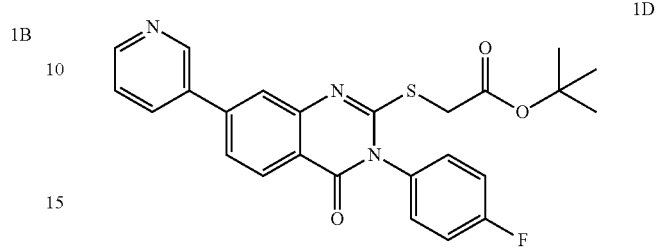

1D

A solution of 1C (40 mg, 0.09 mmol), pyridine-3-ylboronic acid (25 mg, 0.18 mmol), $K_2CO_3$ (24 mg, 0.18 mmol), $Pd(dppf)Cl_2\text{-}CH_2Cl_2$ (6.3 mg, 0.009 mmol) in 1.5 mL of EtOH was microwaved under normal absorption in $N_2$ atmosphere 110° C. for 20 min. The reaction was diluted with EtOAc and washed with water. The organic was concentrated. The residue was purified by prep TLC (40% EtOAc/hexane) to yield 1D (28 mg, Yield=70%).

Step 4

2-(3-(4-Fluoropheny)-4-oxo-7-(pyridine-3-yl)-3,4-dihydroquinazolin-2-ylthio)acetic acid

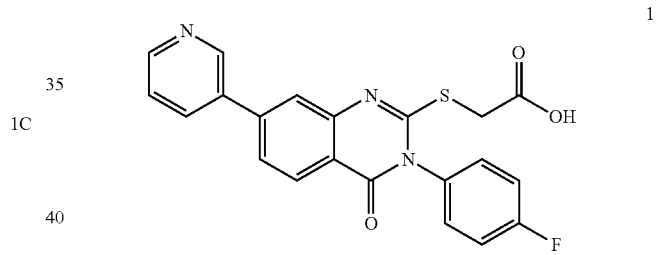

1

To 1D (28 mg, 0.06 mmol) was added 2 mL 20% TFA/DCM. The reaction was kept stirring for 14 h and evaporated to dryness to yield 1 (22 mg, yield=95%), MS (M+H)=408.

In a manner similar to that described above, 1C was reacted with the appropriate coupling partner (e.g. boronic ester or stannane) and then deprotected with TFA to provide the following compounds:

| Compound Number | Coupling Partner | Compound | M + H |
|---|---|---|---|
| 1E | | | 408 |

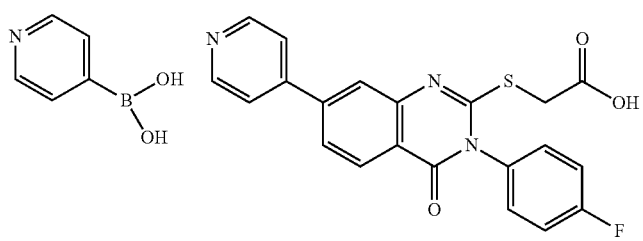

| Compound Number | Coupling Partner | Compound | M + H |
|---|---|---|---|
| 1F | pyrimidin-5-yl boronic acid | 7-(pyrimidin-5-yl)-3-(4-fluorophenyl)-2-(carboxymethylthio)quinazolin-4(3H)-one | 409 |
| 1G | 1H-pyrazol-3-yl boronic acid | 7-(1H-pyrazol-3-yl)-3-(4-fluorophenyl)-2-(carboxymethylthio)quinazolin-4(3H)-one | 397 |
| 1H | 1H-pyrazol-4-yl boronic acid | 7-(1H-pyrazol-4-yl)-3-(4-fluorophenyl)-2-(carboxymethylthio)quinazolin-4(3H)-one | 397 |
| 1i | 1-methyl-1H-pyrazol-4-yl boronic acid | 7-(1-methyl-1H-pyrazol-4-yl)-3-(4-fluorophenyl)-2-(carboxymethylthio)quinazolin-4(3H)-one | 411 |
| 1J | thiazol-5-yl tributylstannane | 7-(thiazol-5-yl)-3-(4-fluorophenyl)-2-(carboxymethylthio)quinazolin-4(3H)-one | 414 |
| 1K | thiazol-4-yl tributylstannane | 7-(thiazol-4-yl)-3-(4-fluorophenyl)-2-(carboxymethylthio)quinazolin-4(3H)-one | 414 |

-continued
| Compound Number | Coupling Partner | Compound | M + H |
|---|---|---|---|
| 1L | 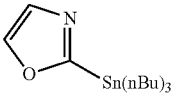 | 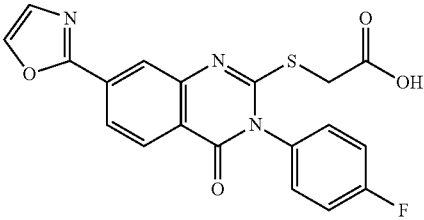 [SMILES: O=C(O)CSc1nc2cc(-c3ncco3)ccc2c(=O)n1-c1ccc(F)cc1] | 398 |
| 1M | 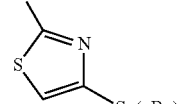 | 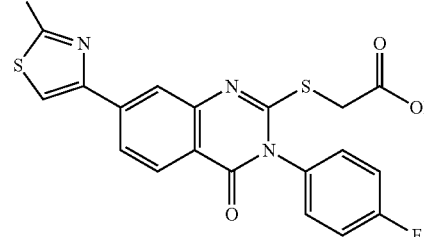 | 444 |
| 1N | 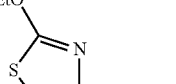 | 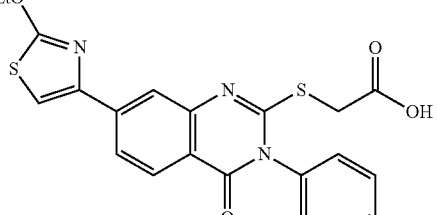 | 458 |
Preparative Example 2
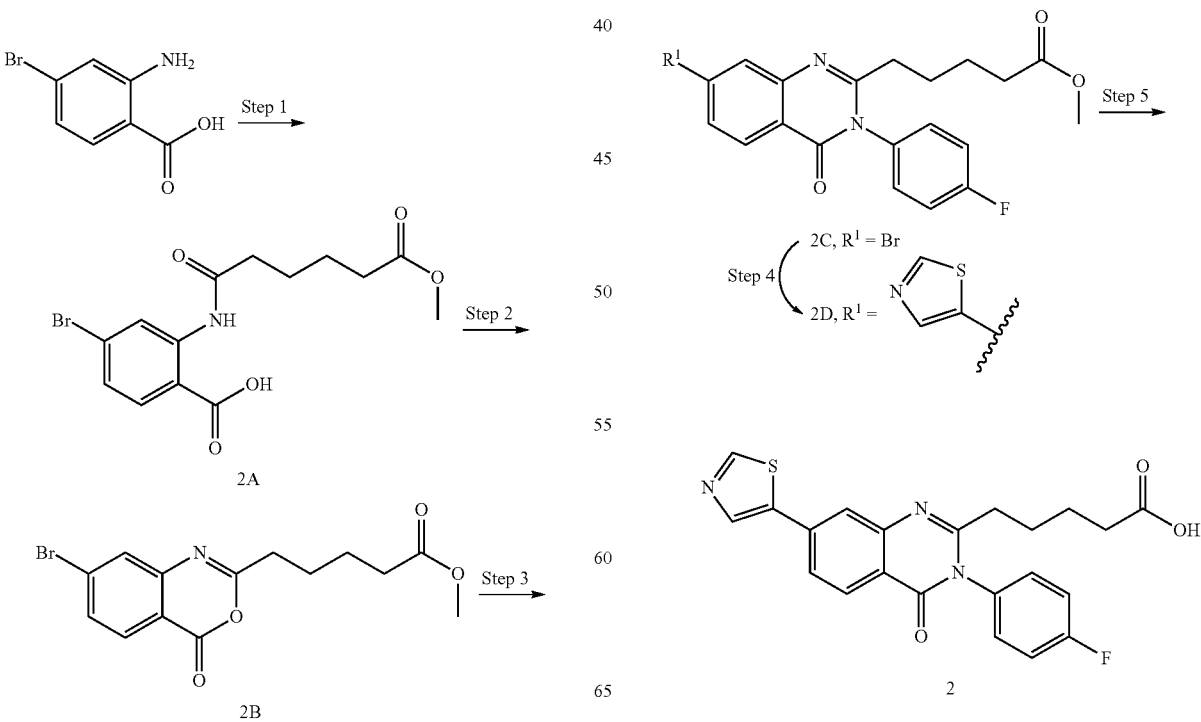

Step 1

4-Bromo-2-(6-methoxy-6-oxohexanamido) benzoic acid

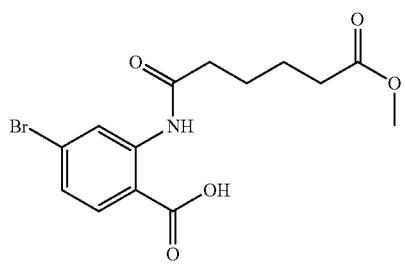

2A

To a solution of 2-amino-4-bromobenzoic acid (20 g, 92.6 mmol), TEA (14 g, 138.9 mmol) in DCM (200 mL) was slowly added methyl 6-chloro-6-oxohexanoate (18.2 g, 101.9 mmol) in 0° C. The reaction was warmed up 40° C. and kept stirring for 4 h. The reaction was cooled to rt and diluted with DCM and extracted with $H_2O$. The organics were dried ($Na_2SO_4$), filtered, and concentrated. The residue was purified by flash chromatography (0% to 60% (65 min) EtOAc/hexanes) to yield 2A (20.5 g; Yield=62%).

Step 2

Methyl 5-(7-bromo-4-oxo-4H-benzo[d][1,3]oxazin-2-yl)pentanoate

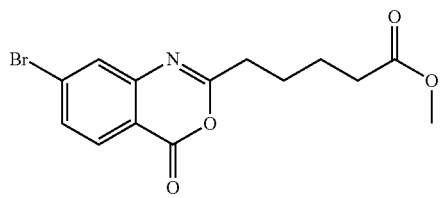

2B

A solution of 2A (8 g, 22.3 mmol) in acetic anhydride (35 mL, 370 mmol) was stirred in 150° C. for 5 h. The reaction was cooled to rt and concentrated to yield 2B (6.8 g; Yield=90%).

Step 3

Methyl 5-(7-bromo-3-(4-fluorophenyl)-4-oxo-3,4-dihydroquinazolin-2-yl)pentanoate

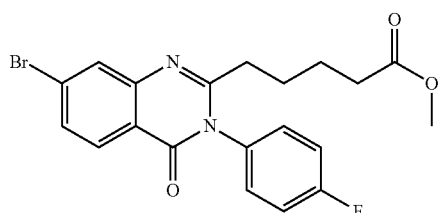

2C

A solution of 2B (6.8 g, 20 mmol), 4-fluoroaniline (3.33 g, 30 mmol) in acetic acid (17 mL, 300 mmol) was stirred in 100° C. for 1 h. The reaction was cooled to rt and diluted with $H_2O$ and EtOAc. The organic layer was removed and the aqueous phase was extracted with EtOAC (3×). The combined organic were concentrated. The residue was purified by flash chromatography (0% to 40% (30 min) EtOAc/hexanes) to yield 2C (4.8 g; Yield=55%).

Step 4

Methyl 5-(3-4-fluorophenyl)-4-oxo-7-(thiazole-5-yl)-3,4-dihydroquinazolin-2-yl)pentanoate

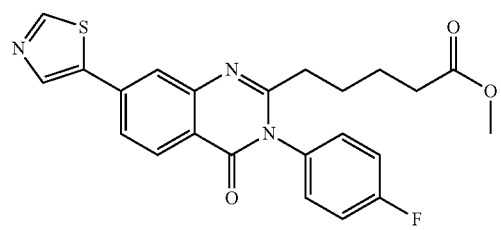

2D

A solution of 2C (50 mg, 0.12 mmol), 5-(tripropylstannyl) thiazole (89.5 mg, 0.24 mmol), CuI (2.2 mg, 0.011 mmol), bis(triphenylphosphino) palladium(II)chloride (16 mg, 0.022 mmol) in 1.5 mL of THF/water (5/1) was microwaved under normal absorption in $N_2$ atmosphere 120° C. for 30 min. The reaction was diluted with EtOAc and washed with water. The organic was concentrated. The residue was purified by prep TLC (40% EtOAc/hexane) to yield 2D (26 mg, Yield=52%), MS (M+H)=438.

Step 5

5-(3-(4-Fluorophenyl)-4-oxo-7-(thiazole-5-yl)-3,4-dihyroquinazolie-2-yl)pentanoic acid

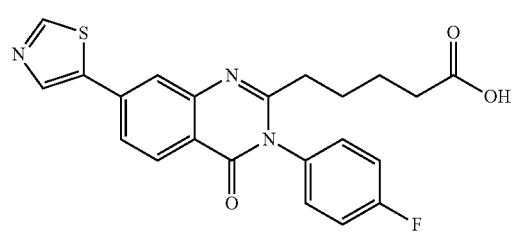

2

To a solution of 2D (26 mg, 0.06 mmol) in 1 mL of THF was added LiOH (3 mg, 0.07 mmol) in 0.5 mL water and stirred for 25 min at rt. The crude material was purified by reverse phase prep LC to yield 2 (22 mg, Yield=84%), MS (M+H)=424.

In a manner similar to that described above, 2C was reacted with the appropriate coupling partner (e.g. stannane) and then deprotected with LiOH to provide the following compounds:

| Compound Number | Coupling Partner | Compound | M + H |
|---|---|---|---|
| 2E | 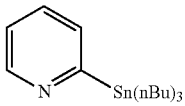 | 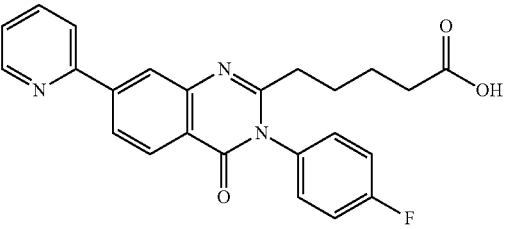 [SMILES: O=C(O)CCCCc1nc2cc(-c3ccccn3)ccc2c(=O)n1-c1ccc(F)cc1] | 418 |
| 2F | 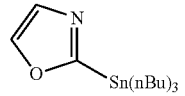 | 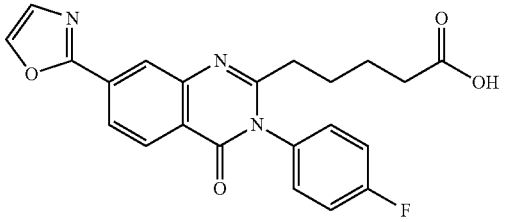 [SMILES: O=C(O)CCCCc1nc2cc(-c3ncco3)ccc2c(=O)n1-c1ccc(F)cc1] | 408 |
| 2G | 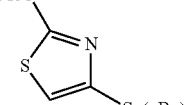 | 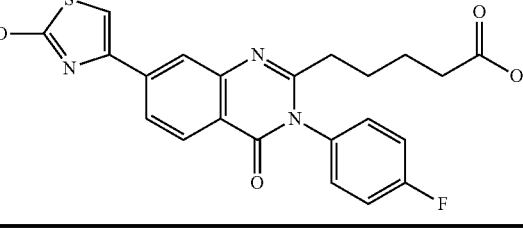 | 454 |

Preparative Example 3

Step 1

Methyl 5-(3-(4-fluorophenyl)-4-oxo-7-(1H-pyrazol-3-yl)-3,4-dihydroquinazolin-2-yl)pentanoate

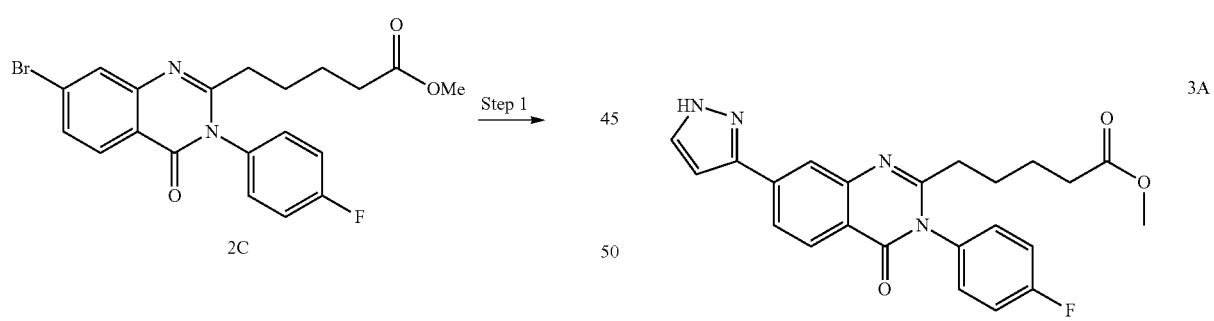

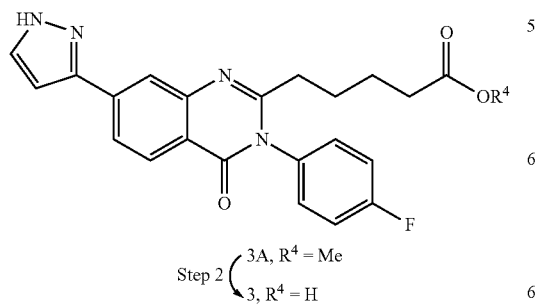

A solution of methyl 5-(7-bromo-3-(4-fluorophenyl)-4-oxo-3,4-dihydroquinazolin-2-yl)pentanoate (2C, 50 mg, 0.12 mmol), 1H-pyrazol-3-ylboronic acid (26 mg, 0.23 mmol), K$_2$CO$_3$ (32 mg, 0.24 mmol), Pd(dppf)Cl$_2$-CH$_2$Cl$_2$ (14 mg, 0.018 mmol) in 1.5 mL of THF/water (5/1) was microwaved under normal absorption in N$_2$ atmosphere 120° C. for 30 min. The reaction was diluted with EtOAc and washed with water. The organic was concentrated. The residue was purified by prep TLC (40% EtOAc/hexane) to yield 3A (28 mg, Yield=60%), MS (M+H)=421.

Step 2

5-(3-(4-Fluorophenyl)-4-oxo-7-(1H-pyrazol-3-yl)-3,4-dihydroquinazolin-2-yl)pentanoic acid

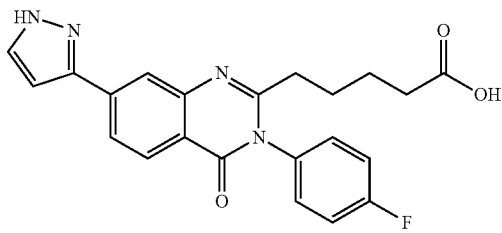

A solution of 3A (28 mg, 0.067 mmol) in 1 mL of THF was added LiOH (3 mg, 0.07 mmol) in 0.5 mL water and stirred for 25 min at rt. The crude material was purified by reverse phase prep LC to yield 3 (25 mg, Yield=84%), MS (M+H)=407.

In a manner similar to that described above, 2C was reacted with the appropriate coupling partner (e.g., boronic acid or boronic ester) and then deprotected with LiOH to provide the following compounds:

| Compound Number | Coupling Partner | Compound | M + H |
|---|---|---|---|
| 3B | | | 407 |
| 3C | | | 419 |
| 3D | | | 448 |
| 3E | | | 418 |
| 3F | | | 407 |

-continued

| Compound Number | Coupling Partner | Compound | M + H |
|---|---|---|---|
| 3G | [benzofuran-2-boronic acid] | [7-(benzofuran-2-yl)-3-(4-fluorophenyl)-4-oxo-quinazoline butanoic acid] | 457 |
| 3H | [3,5-dimethylisoxazole-4-boronic acid] | [7-(3,5-dimethylisoxazol-4-yl)-3-(4-fluorophenyl)-4-oxo-quinazoline butanoic acid] | 436 |
| 3i | [isoxazole-4-boronic acid pinacol ester] | [7-(isoxazol-4-yl)-3-(4-fluorophenyl)-4-oxo-quinazoline butanoic acid] | 408 |

Preparative Example 4

The following compounds were synthesized in a manner similar to that described, substituting methyl 5-chloro-5-oxo-pentanoate in Step 1 of Example 2. The coupling partner used in Step 4 is described in the table.

| Compound Number | Coupling Partner | Compound | M + H |
|---|---|---|---|
| 4A | [thiazol-5-yl tributylstannane] | [7-(thiazol-5-yl)-3-(4-fluorophenyl)-4-oxo-quinazoline butanoic acid] | 410 |
| 4B | [oxazol-2-yl tributylstannane] | [7-(oxazol-2-yl)-3-(4-fluorophenyl)-4-oxo-quinazoline butanoic acid] | 394 |

-continued
| Compound Number | Coupling Partner | Compound | M + H |
|---|---|---|---|
| 4C | thiazole-Sn(nBu)₃ | thiazole-quinazolinone-CO₂H with 4-F phenyl | 410 |
| 4D | pyrazole-Bpin | pyrazole-quinazolinone-CO₂H with 4-F phenyl | 393 |
| 4E | pyrazole-B(OH)₂ | pyrazole-quinazolinone-CO₂H with 4-F phenyl | 393 |
Preparative Example 5
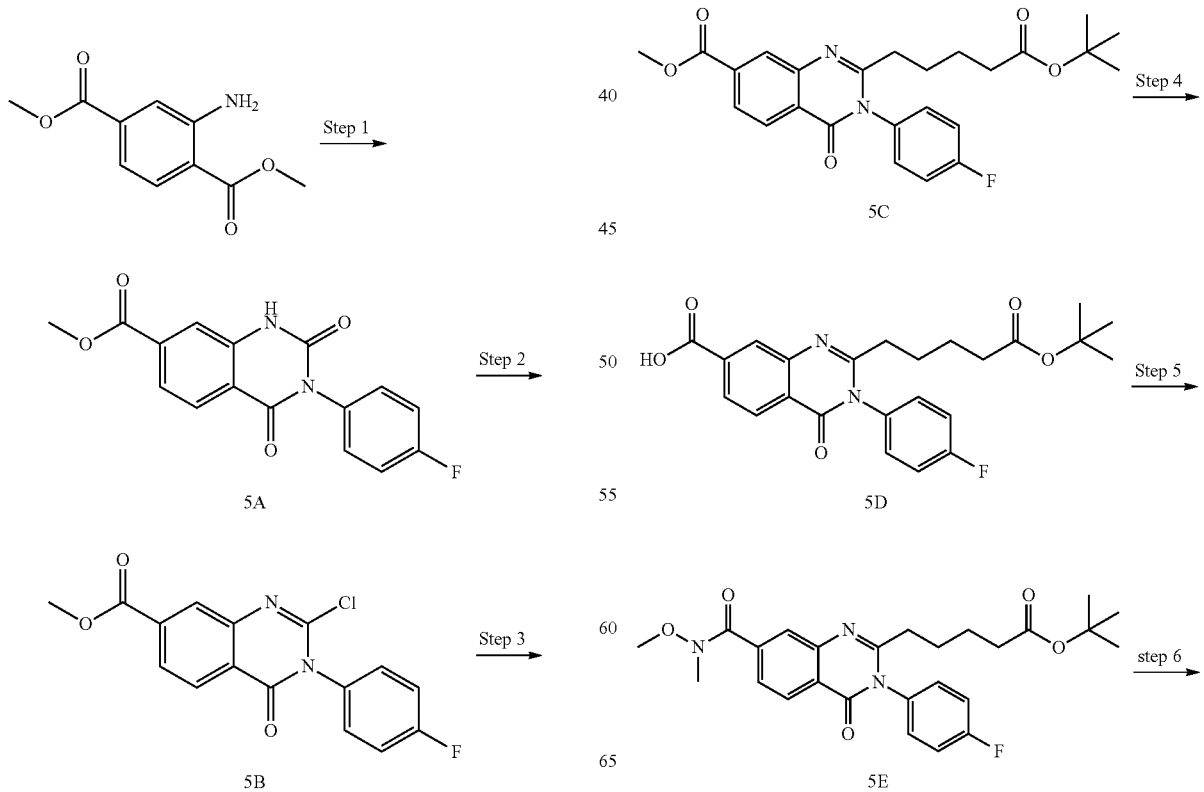

-continued

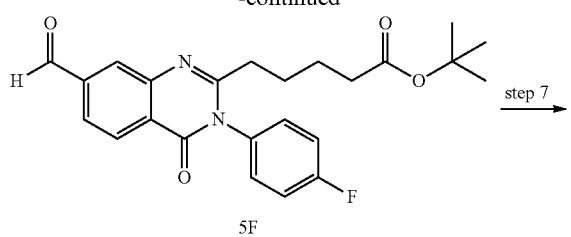
5F

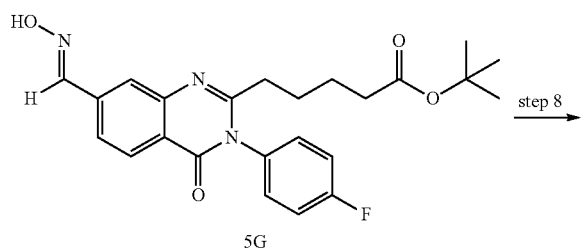
5G

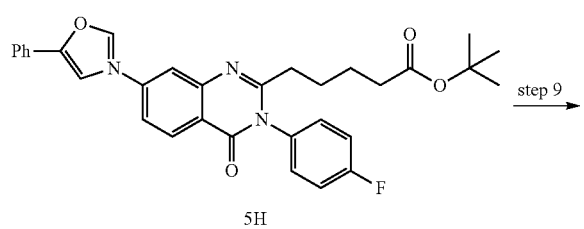
5H

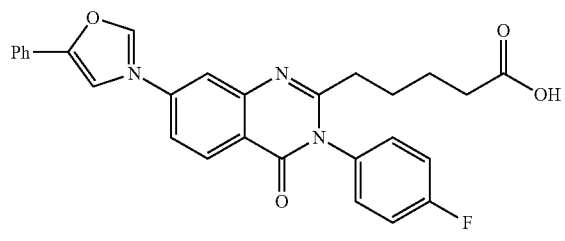
5

Step 1

Methyl 3-(4-fluorophenyl)-2,4-dioxo-1,2,3,4-tetrahydroquinazoline-7-carboxylate

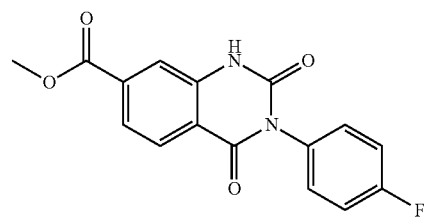
5A

A solution of methyl 2-amino-4-carbomethoxybenzoate (25 g, 120 mmol), TEA (44 mL, 320 mmol), and 4-fluorophenyl isocyanate (15 mL, 130 mmol) in 1,4-dioxane (300 mL) was stirred at 80° C. for 16 h. The reaction was cooled to it and then to 0° C. The solid was filtered and washed with Et₂O to yield 5A (27.96 g; Yield=74%).

Step 2

Methyl 2-chloro-3-(4-fluorophenyl)-4-oxo-3,4-dihydroquinazoline-7-carboxylate

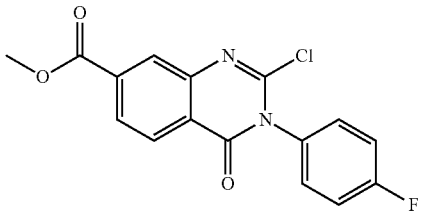
5B

A suspension of 5A (1.5 g, 4.8 mmol), POCl₃ (14 mL, 150 mmol), and N,N-dimethylaniline (6 mL, 40 mmol) was degassed and stirred at 110° C. for 16 h. Additional POCl₃ (6 mL) was added and the reaction was flushed with nitrogen, capped, and heated at 110° C. for 20 h. The reaction was cooled to rt. Some of the excess POCl₃ was concentrated, and then the mixture was cooled to 0° C. The mixture was diluted with DCM and ice was added slowly. This mixture was stirred at 0° C. for 3 h. The organic layer was removed and the aqueous phase was extracted with DCM (3×). The combined organics were dried (Na₂SO₄), filtered, and concentrated. The residue was purified by flash chromatography (0% to 50% (25 min) EtOAc/hexanes) to yield 5B (1.49 g; Yield=94%), MS (M+H)=333.

Step 3

Methyl 245-tert-butoxy-5-oxopentyl)-3-(4-fluorophenyl)-4-oxo-3,4-dihydroquinazoline-7-carboxylate

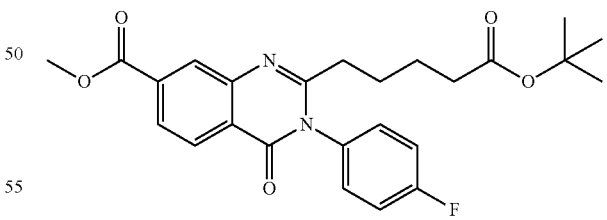
5C

To a solution of tert-butyl pent-4-enoate (1.66 g, 10.6 mmol, prepared from 4-pentenoic acid, trifluoroacetic anhydride and tBuOH) in THF (10 mL, 100 mmol) cooled to 0° C. was added 0.5 M of 9-BBN in THF (21.2 mL). The reaction was stirred at 0° C. for 30 min and at rt for 3 h. To this solution was added methyl 2-chloro-3-(4-fluorophenyl)-4-oxo-3,4-dihydroquinazoline-7-carboxylate (5B, 1.49 g, 4.48 mmol), Pd(dppf)Cl₂—CH₂Cl₂ (440 mg, 0.54 mmol), and K₃PO₄ (2320 mg, 10.9 mmol). The resulting solution was degassed and stirred at 60° C. for 16 h. The filtrate was diluted with DCM and water. The organic layer was removed and the aqueous phase was extracted with DCM (2×). The combined organics were concentrated. The residue was purified by flash chromatography (0% to 20% (15 min) then to 60% (10 min) EtOAc/hexanes) to yield 5C (1.66 g; Yield=80.7%), MS (M+H)=455.

Step 4 tert-Butyl 5-(3-(4-fluorophenyl)-7-(methoxy(methyl) carbamoyl)-4-oxo-3,4-dihydroquinazolin-2-yl)pentanoate

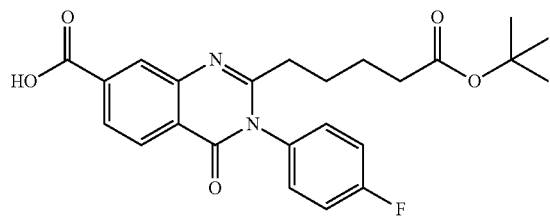

5D

To a solution of 5C (370 mg, 0.81 mmol) in THF (6 mL, 70 mmol) and water (3 mL, 200 mmol) was added LiOH—H$_2$O (70 mg, 2 mmol). The reaction was stirred at it for 45 min and quenched with 0.1N HCl. The reaction was diluted with EtOAc and the organic layer was removed. The aqueous phase was extracted with EtOAc (3×) and the combined organics were dried (Na$_2$SO$_4$), filtered, and concentrated to yield 5D. The material was used without purification.

Step 5 tert-Butyl 5-(3-(4-fluorophenyl)-7-(methoxy(methyl) carbamoyl)-4-oxo-3,4-dihydroquinazolin-2-yl)pentanoate

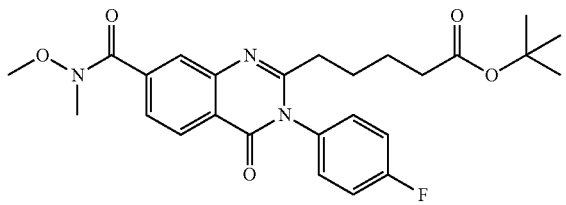

5E

To a solution of 2-(5-tert-butoxy-5-oxopentyl)-3-(4-fluorophenyl)-4-oxo-3,4-dihydroquinazoline-7-carboxylic acid (5D, 99.3 mg, 0.226 mmol), N,O-dimethylhydroxylamine-HCl (28 mg, 0.29 mmol), and DIPEA (0.137 mL, 0.789 mmol) in DCM (2 mL, 30 mmol) was added HOBt (45.7 mg, 0.338 mmol) and EDCI (86.4 mg, 0.451 mmol). The reaction was stirred at it for 68 h. The reaction was concentrated and the residue was purified by flash chromatography (0% to 100% (22 min) EtOAc/hexanes) to 5E (83 mg; Yield=76%), MS (M+H)=484.

Step 6 tert-Butyl-5-(3-(4-fluorophenyl)-7-formyl-4-oxo-3,4-dihydroquinazolin-2-yl)pentanoate

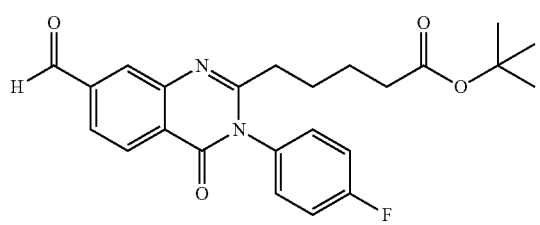

5F

A solution of 5E (425 mg, 0.87 mmol) in 10 mL THF was treated slowly with DIBAL (1N in toluene, 1.3 mL) and then stirred at −78° C. under N$_2$ for 1 h. To the solution was added Na$_2$SO$_4$.10H$_2$O/CELITE (2:1 mixture, 20 g). The mixture was stirred for 1.5 h and filtered. Chromatography (25% EtOAc mix with hexane) provided 5F (325 mg, Yield=89%), MS (M+H)=425.

Step 7 tert-Butyl 5-(3-(4-fluorophenyl)-7-((hydroxyimino) methyl)-4-oxo-3,4-dihydroquinazolin-2-yl)pentanoate

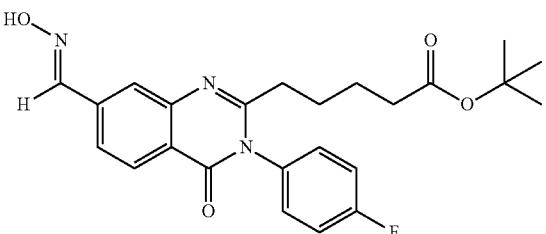

5G

A solution of 5F (325 mg, 0.77 mmol), hydroxylamine hydrochloride (117 mg, 1.68 mol) in 5 mL pyridine was stirred at rt for 2 h. The reaction mixture was evaporated to dryness and diluted with EtOAc and washed with water. The organic layer was removed and the aqueous phase was extracted with EtOAC (3×). The combined organic were concentrated to yield 5G (340 mg, 0.77 mmol) without further purification.

Step 8 tert-Butyl 5-(3-(4-fluorophenyl)-4-oxo-7-(5-phenyl-isoxazol-3-O-3,4-dihydroquinazolin-2-yl)pentanoate

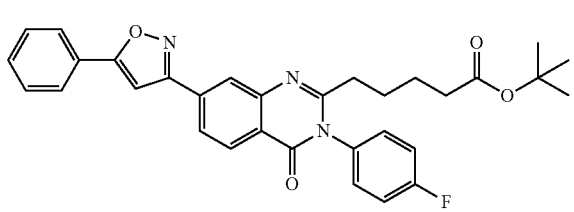

5H

A solution of 5G (85 mg, 0.21 mmol) in 3 mL DCM was treated with NBS (56 mg, 0.31 mmol) and stirred for 1 h. This solution was further treated with phenylacetylene (33 mg, 0.31 mmol) and TEA (26 mg, 0.25 mmol) and then stirred at rt for 14 h. The reaction was diluted with EtOAc and extracted with H$_2$O. The organics were dried (Na$_2$SO$_4$), filtered, and concentrated. The residue was purified by prep TLC (30% EtOAc/hexanes) to yield 5H (70 mg; Yield=62%), MS (M+H)=540.

Step 9

5-(3-(4-Fluorophenyl)-4-oxo-7-(5-phenylisoxazol-3-yl)-3,4-dihydroquinazolin-2-yl)pentanoic acid

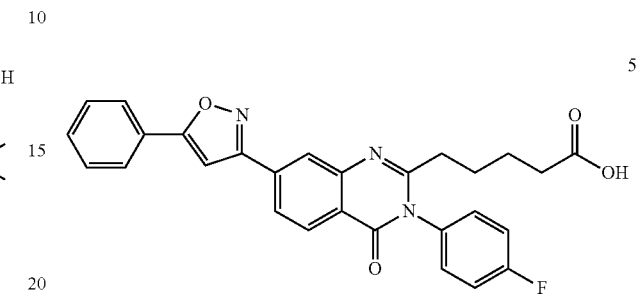

5

To 5H (70 mg, 0.13 mmol) was added 2 mL 20% TFA/DCM. The reaction was kept stirring for 14 h and evaporated to dryness 5 (60 mg, yield=95%), MS (M+H)=484.

In a manner similar to that described above, the following compounds were synthesized by the reaction of 5G with the appropriate acetylene followed by deprotection with TFA:

| Number | Acetylene Reagent | Compound Structure | M + H |
|---|---|---|---|
| 5i | Me—≡—H | 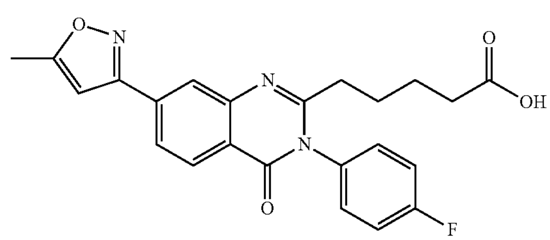 [SMILES: Cc1cc(-c2ccc3c(=O)n(-c4ccc(F)cc4)c(CCCCC(=O)O)nc3c2)no1] | 422 |
| 5J | cyclopropyl—≡—H | 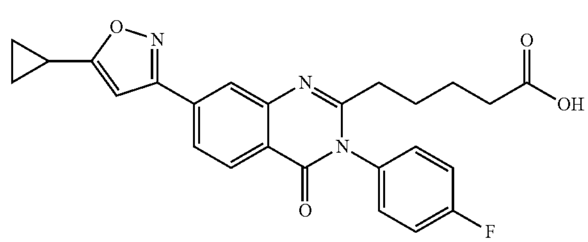 [SMILES: O=C(O)CCCCc1nc2cc(-c3cc(C4CC4)on3)ccc2c(=O)n1-c1ccc(F)cc1] | 448 |
| 5K | TMS—≡—H | 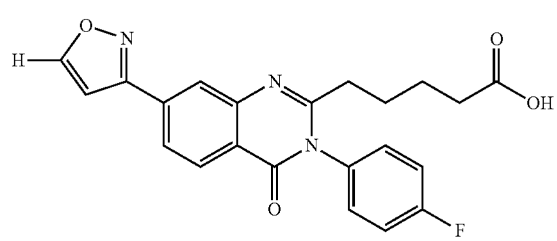 [SMILES: O=C(O)CCCCc1nc2cc(-c3ccon3)ccc2c(=O)n1-c1ccc(F)cc1] | 408 |

-continued

| Number | Acetylene Reagent | Compound Structure | M + H |
|---|---|---|---|
| 5L | | 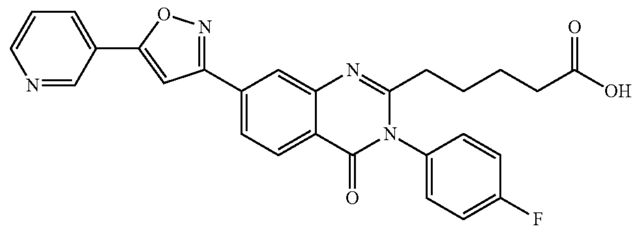 [SMILES: O=C(O)CCCCc1nc2cc(-c3cc(-c4cccnc4)on3)ccc2c(=O)n1-c1ccc(F)cc1] | 485 |
| 5M | F₃C—≡—H | 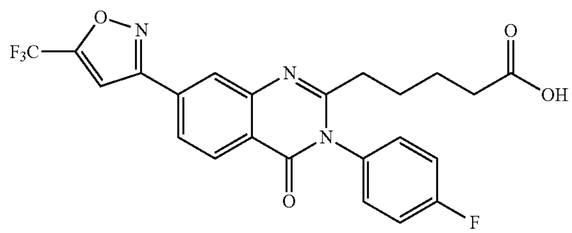 [SMILES: O=C(O)CCCCc1nc2cc(-c3cc(C(F)(F)F)on3)ccc2c(=O)n1-c1ccc(F)cc1] | 476 |
| 5N | | 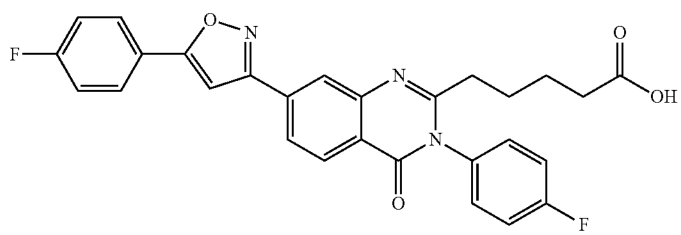 [SMILES: O=C(O)CCCCc1nc2cc(-c3cc(-c4ccc(F)cc4)on3)ccc2c(=O)n1-c1ccc(F)cc1] | 502 |

In a manner similar to that described above, 5G was sequentially treated with NBS and then tributylstannylacetylene-triethylamine to provide 5o.

A mixture of 5o (33 mg, 0.046 mmol), cyclopropanecarbonyl chloride (10 mg, 0.096 mmol), Pd(Ph₃P)₂Cl₂ (4 mg, 0.006 mmol) in toluene were microwaved at 130° C. for 2.5 h. The reaction was diluted with EtOAc, washed with water and brine, and then concentrated. Preparative TLC (1:2 EtOAc: hexanes) followed by deprotection with TFA (as previously described) provided the 5Q. MS (M+H)=476.

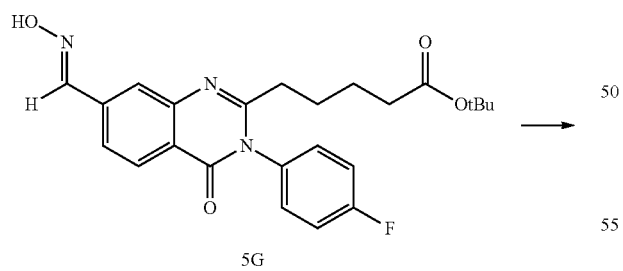

5G

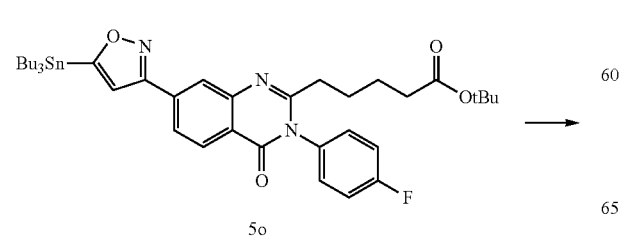

5o

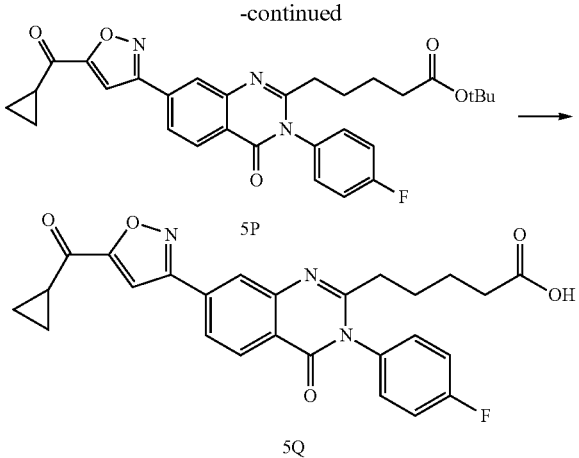

5P

5Q

Preparative Example 6

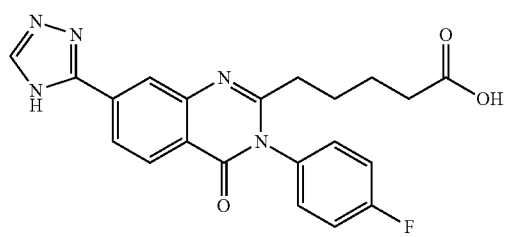

6

Step 1 tert-Butyl 5-(7-carbamoyl-3-(4-fluorophenyl)-4-oxo-3,4-dihydroquinazolin-2-yl)pentanoate

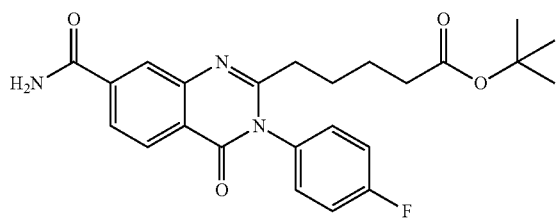

6A

To a solution of 2-(5-tert-butoxy-5-oxopentyl)-3-(4-fluorophenyl)-4-oxo-3,4-dihydroquinazoline-7-carboxylic acid (5D, 253 Mg, 0.574 mmol) and DIPEA (1.00 mL, 5.74 mmol) in DCM (3 mL, 50 mmol) was added NH$_4$Cl (184 mg, 3.45 mmol), HOBt (116 mg, 0.862 mmol), and EDCI (220 mg, 1.15 mmol). The reaction was stirred at rt for 20 h. The reaction was quenched with water and diluted with DCM. The organic layer was removed and the aqueous phase was extracted with DCM (3×). The combined organics were concentrated. The residue was purified by flash chromatography (0% to 100% (15 min) EtOAc/hexanes) to yield 6A (224 mg; Yield=88.7%), MS (M+H)=440.

Step 2 tert-Butyl 5-(3-(4-fluorophenyl)-4-oxo-7-(1H-1,2,4-triazol-5-yl)-3,4-dihydroquinazolin-2-yl)pentanoate

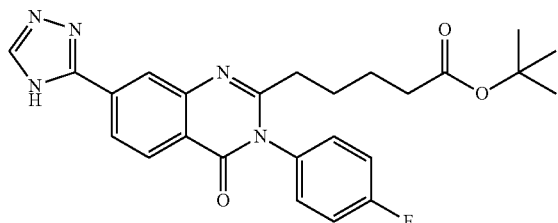

6B

A solution of 6A (30 mg, 0.07 mmol) and 1,1-dimethoxy-N,N-dimethylmethanamine (1 mL, 8 mmol) was heated in the microwave (100° C. for 5 min). The mixture was concentrated and the vessel was charged with AcOH (0.5 mL, 9 mmol) and hydrazine hydrate (0.5 mL, 10 mmol). The resulting mixture was heated in the microwave (100° C. for 7 min). The reaction was diluted with water and EtOAc and the organic layer was removed. The aqueous phase was extracted with EtOAc (3×). The combined organics were dried (Na$_2$SO$_4$), filtered, and concentrated. The residue was purified by reverse phase chromatography (10:90 to 100:00 (10 min) CH$_3$CN/H$_2$O (0.1% formic acid)) to yield 6B (8 mg; Yield=20%), MS (M+H)=464.

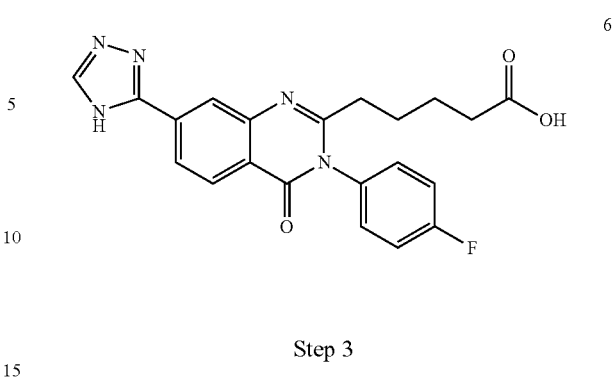

6

Step 3

5-(3-(4-Fluorophenyl)-4-oxo-7-(1H-1,2,4-triazol-5-yl)-3,4-dihydroquinazolin-2-yl)pentanoic acid A solution of 6B (8 mg, 0.02 mmol) and TFA (0.3 mL, 4 mmol) in DCM (0.7 mL, 10 mmol) was stirred at rt for 2 h. The reaction was concentrated and the residue was purified by reverse phase chromatography (10:90 to 100:00 (10 min) CH$_3$CN/H$_2$O (0.1% formic acid)) to yield the title compound 6 (7 mg; Yield=100%).

Preparative Example 7

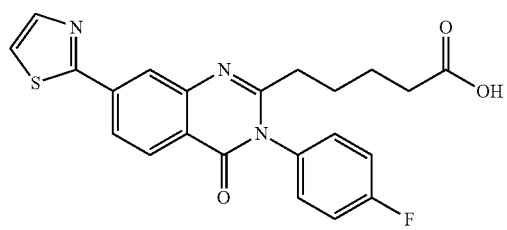

7

Step 1 tert-Butyl 5-(7-carbamothioyl-3-(4-fluorophenyl)-4-oxo-3,4-dihydroquinazolin-2-yl)pentanoate

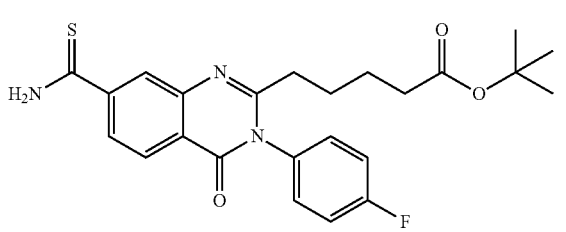

7A

A solution 6A (187 mg, 0.426 mmol) and 2,4-bis(4-methoxyphenyl)-2,4-dithioxo-1,3,2,4-dithiadiphosphetane (245 mg, 0.606 mmol) in toluene (3.5 mL, 33 mmol) was stirred at 110° C. for 1 h. The reaction was cooled to it and was diluted with EtOAc. The organic layer was washed with saturated NaHCO$_3$ (3×), brine (1×), dried (Na$_2$SO$_4$), filtered, and concentrated. The residue was purified by flash chromatography (0% to 100% (15 min) EtOAc/hexanes) to yield 7A (107 mg; Yield=55.2%), MS (M+H)=456.

Step 2 tert-Butyl 5-(3-(4-fluorophenyl)-4-oxo-7-(thiazol-2-yl)-3,4-dihydroquinazolin-2-yl)pentanoate

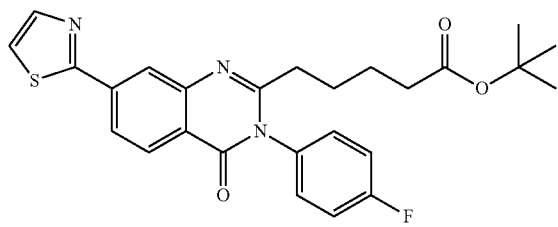

7B

To a suspension of 7A (30.0 mg, 0.0658 mmol) and sodium bicarbonate (30 mg, 0.3 mmol) in THF (0.7 mL, 9 mmol) was added chloroacetaldehyde (0.04 mL, 0.3 mmol). The reaction was stirred at rt for 5 h and at 45° C. for 13 h. The reaction was quenched with water and diluted with DCM. The organic layer was removed and the aqueous phase was extracted with DCM (3×). The combined organics were concentrated. The crude material was taken up in DCM (1.5 mL, 23 mmol) and DIPEA (0.03 mL, 0.2 mmol) was added. The solution was cooled to 0° C. and trifluoroacetic anhydride (0.02 mL, 0.1 mmol) was added. The reaction was warmed to rt where it was stirred for 2 h. The reaction was quenched with MeOH and concentrated. The residue was purified by flash chromatography (0% to 50% (20 min) EtOAc/hexanes) to yield 7B (33 mg; Yield=100%), MS (M+H)=480.

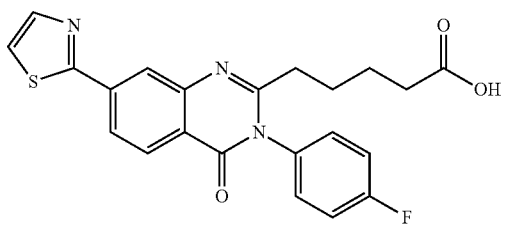

7

Step 3

5-(3-(4-Fluorophenyl)-4-oxo-7-(thiazol-2-yl)-3,4-dihydroquinazolin-2-yl)pentanoic acid A solution of 7B (34 mg, 0.071 mmol) and TFA (0.25 mL, 3.2 mmol) in DCM (0.7 mL, 10 mmol) was stirred for 2 h. The reaction was concentrated and the residue was purified by reverse phase chromatography (10:90 to 100:00 (10 min) CH₃CN/H₂O (0.1% formic acid)) to 7 (21 mg; Yield=70%), MS (M+H)=424.

In a similar manner, compound 7D was prepared:

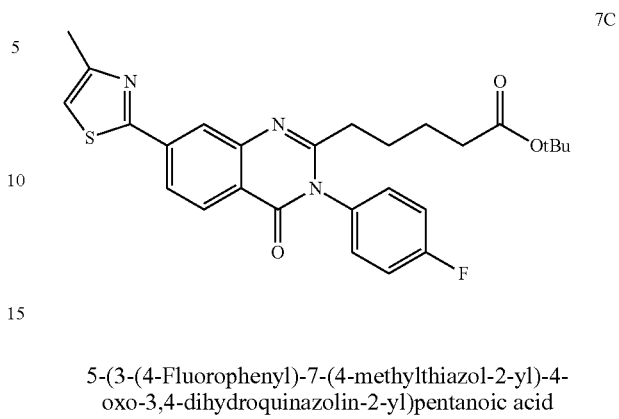

7C 5-(3-(4-Fluorophenyl)-7-(4-methylthiazol-2-yl)-4-oxo-3,4-dihydroquinazolin-2-yl)pentanoic acid To a mixture of 7A (30.0 mg, 0.0658 mmol) and sodium bicarbonate (30 mg, 0.3 mmol) in THF (0.7 mL, 9 mmol) was added chloroacetone (0.03 mL, 0.3 mmol). The reaction was stirred at it for 5 h and at 45° C. for 13 h. The reaction was quenched with water and diluted with DCM. The organic layer was removed and the aqueous phase was extracted with DCM (3×). The combined organics were concentrated. The crude product was taken up in DCM (1.5 mL, 23 mmol) and DIPEA (0.3 mL, 2 mmol) was added. The mixture was cooled to 0° C. and trifluoroacetic anhydride (0.02 mL, 0.1 mmol) was added. The reaction was warmed to it where it was stirred for 2 h. The reaction was quenched with MeOH and concentrated. The residue was purified by flash chromatography (0% to 50% (20 min) EtOAc/hexanes) to yield tert-butyl 5-(3-(4-fluorophenyl)-7-(4-methylthiazol-2-yl)-4-oxo-3,4-dihydroquinazolin-2-yl)pentanoate (7C, 24 mg; Yield=74%), MS (M+H)=494.

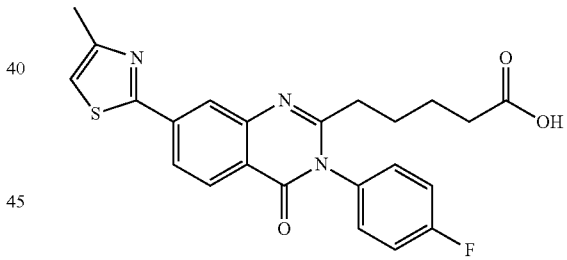

7D

A solution of 7C (24 mg, 0.049 mmol) and TFA (0.25 mL, 3.2 mmol) in DCM (0.7 mL, 10 mmol) was stirred for 2 h at rt. The reaction was concentrated and the residue was purified by reverse phase chromatography (10:90 to 100:00 (10 min) CH₃CN/H₂O (0.1% formic acid)) to yield 7D (16 mg; Yield=75%), MS (M+H)=438.

Preparative Example 8

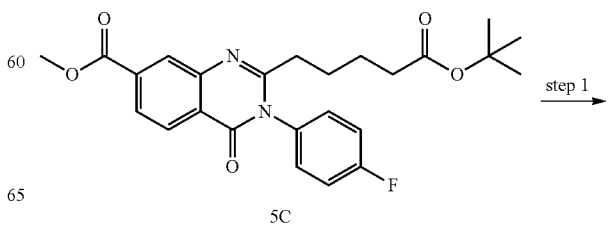

5C

-continued

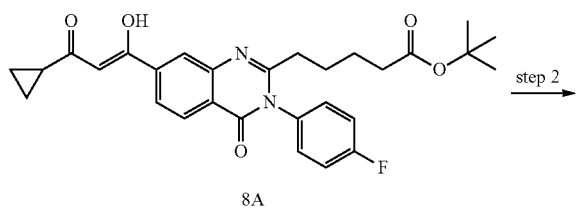

8A

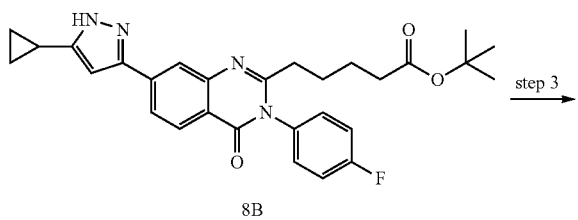

8B

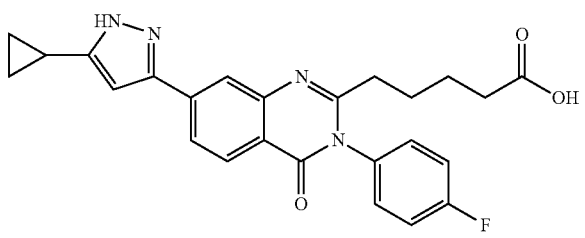

8

Step 1 tert-Butyl 5-(7-(3-cyclopropyl-3-hydroxyacryloyl)-3-(4-fluorophenyl)-4-oxo-3,4-dihydroquinazolin-2-yl)pentanoate

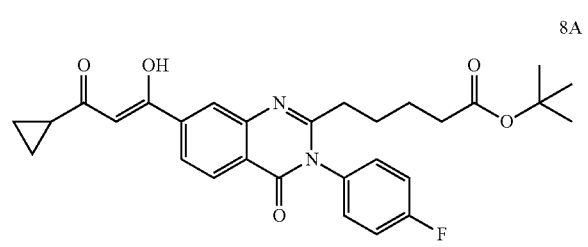 [SMILES: CC(C)(C)OC(=O)CCCCc1nc2cc(/C(O)=C/C(=O)C3CC3)ccc2c(=O)n1-c1ccc(F)cc1]

8A

To a solution of 1.0 M of LiHMDS in hexane (0.44 mL) in THF (0.5 mL, 6 mmol) cooled to −50° C. was added 1-cyclopropylethanone (18 mg, 0.22 mmol) as a solution in THF (0.3 mL). This solution was stirred at −50° C. for 5 min and then treated dropwise with a solution of methyl 2-(5-tert-butoxy-5-oxopentyl)-3-(4-fluorophenyl)-4-oxo-3,4-dihydroquinazoline-7-carboxylate (5C, 100 mg, 0.2 mmol) in THF (0.5 mL). The dark solution was stirred at −50° C. for 1.5 min and then warmed to rt where it remained for 16 h. The reaction was quenched with saturated NH$_4$Cl and diluted with DCM. The organic layer was removed and the aqueous layer was extracted with DCM (3×). The combined organics were dried (Na$_2$SO$_4$), filtered, and concentrated. The material was further purified by reverse phase chromatography (10:90 to 100:00 (10 min) CH$_3$CN/H$_2$O (0.1% formic acid)) to yield 8A (26 mg; Yield=20%), MS (M+H)=507.

Step 2 tert-Butyl 5-(7-(5-cyclopropyl-1H-pyrazol-3-yl)-3-(4-fluorophenyl)-4-oxo-3,4-dihydroquinazolin-2-yl)pentanoate

8B

A solution of 8A (37 mg, 0.073 mmol) and hydrazine monohydrate (0.004 mL, 0.080 mmol) in pyridine (0.6 mL, 7 mmol) was stirred at 60° C. for 16 h. The reaction was concentrated and the residue was purified by flash chromatography (0% to 50% (22 min) EtOAc/hexanes) to yield 8B (28 mg; Yield=76%), MS (M+H)=503.

Step 3

5-(7-(5-Cyclopropyl-1H-pyrazol-3-yl)-3-(4-fluorophenyl)-4-oxo-3,4-dihydroquinazolin-2-yl)pentanoic acid

8

A solution of 8B (25 mg, 0.050 mmol) and TFA (0.3 mL, 4 mmol) in DCM (0.7 mL, 10 mmol) was stirred at rt for 2 h. The reaction was concentrated and the residue was purified by reverse phase chromatography (10:90 to 100:00 (10 min) CH$_3$CN/H$_2$O (0.1% formic acid)) to yield 8 (19 mg; Yield=86%), MS (M+H)=447.

In a manner similar to that described above, compound 8C was prepared:

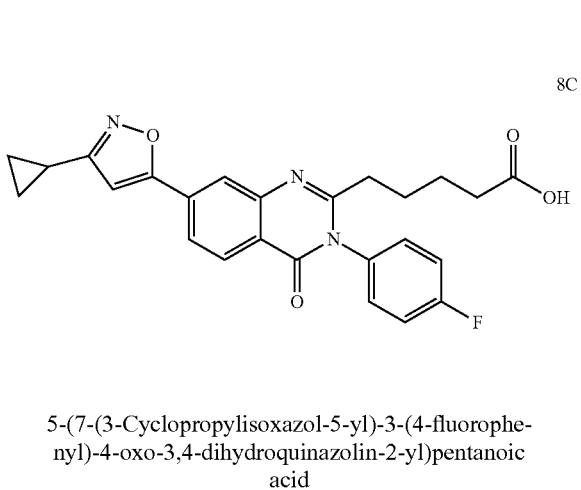

5-(7-(3-Cyclopropylisoxazol-5-yl)-3-(4-fluorophenyl)-4-oxo-3,4-dihydroquinazolin-2-yl)pentanoic acid A solution of 8A (27 mg, 0.053 mmol) and hydroxylamine hydrochloride (4.3 mg, 0.062 mmol) in pyridine (1 mL, 10 mmol) was stirred at 60° C. for 7 h. The reaction was then stirred at at 110° C. for 16 h. The reaction was quenched with 0.1N HCl and diluted with DCM. The organic layer was removed and the aqueous phase was extracted with DCM (3×). The combined organics were concentrated. The residue was purified by flash chromatography (0% to 20% (12 min) to 70% (10 min) EtOAc/hexanes) to yield an inseparable mixture of tert-butyl 5-(7-(3-cyclopropylisoxazol-5-yl)-3-(4-fluorophenyl)-4-oxo-3,4-dihydroquinazolin-2-yl)pentanoate and regioisomer tert-butyl 5-(7-(5-cyclopropylisoxazol-3-yl)-3-(4-fluorophenyl)-4-oxo-3,4-dihydroquinazolin-2-yl)pentanoate (17 mg; Yield=63%), MS (M+H)=504.3.

A solution of the mixture of products (17 mg, 0.034 mmol) and TFA (0.3 mL, 4 mmol) in DCM (0.7 mL, 10 mmol) was stirred at it for 2 h. The reaction was concentrated and the residue was purified by reverse phase chromatography (10:90 to 100:00 (10 min) $CH_3CN/H_2O$ (0.1% formic acid)) to yield an inseparable 70:30 mixture of 8C and 5J (12 mg; Yield=79%), MS (M+H)=448.

In a manner similar to that described above in this example, compound 80 (MS, M+H=422) was synthesized using acetone in step 1:

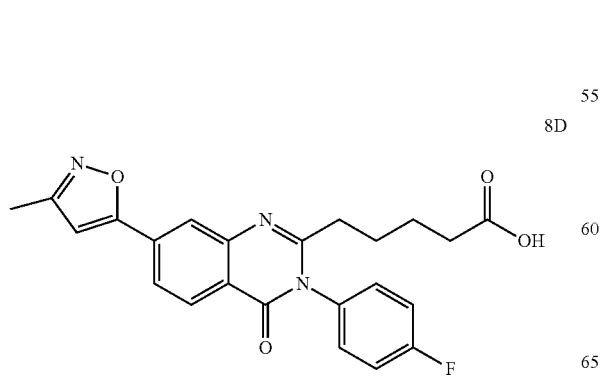

Preparative Example 9

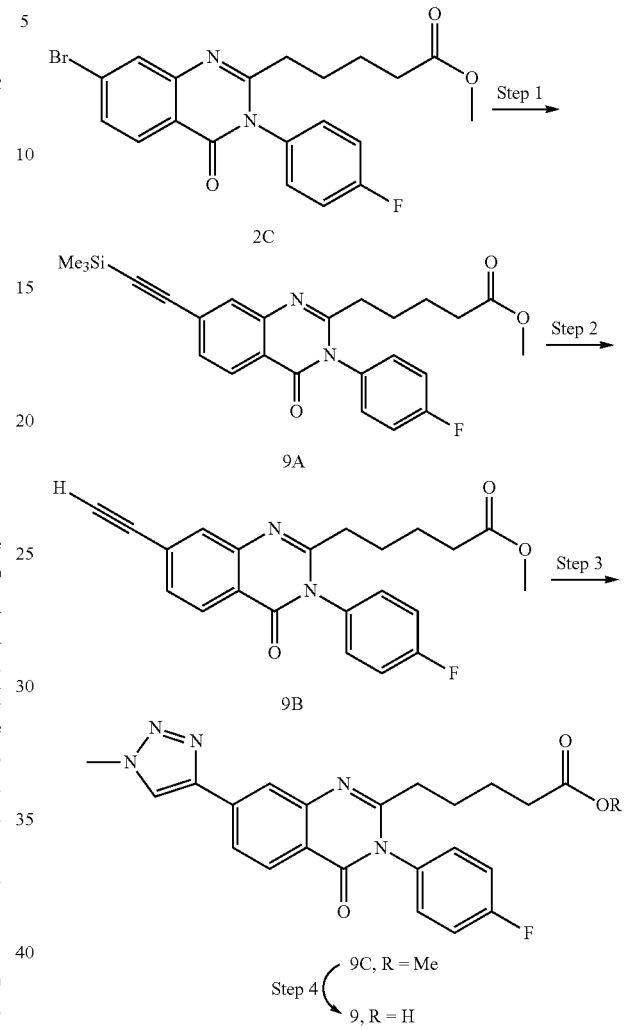

Step 1

Methyl 5-(3-(4-fluorophenyl)-4-oxo-7-((trimethylsilyl)ethynyl)-3,4-dihydroquinazolin-2-yl)pentanoate

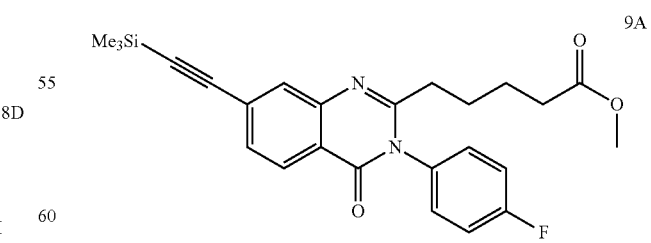

A solution of methyl 5-(7-bromo-3-(4-fluorophenyl)-4-oxo-3,4-dihydroquinazolin-2-yl)pentanoate (2C, 1.2 g, 2.78 mmol), ethynyltrimethylsilane (0.82 g, 8.34 mmol), $Pd(PPh_3)_4$ (0.32 g, 0.278 mmol), CuI (0.16 g, 0.834 mmol), TEA (0.28 g, 2.78 mmol) in 10 mL of DMF was microwaved under high absorption in N₂ atmosphere 60° C. for 10 min. The reaction was diluted with EtOAc and washed with water. The organic was concentrated. The residue was purified by prep TLC (25% EtOAc/hexane) to yield 9A (1.2 g, Yield=95%), MS (M+H)=451.

Step 2

Methyl 5-(7-ethynyl-3-(4-fluorophenyl)-4-oxo-3,4-dihydroquinazolin-20yl)pentanoate

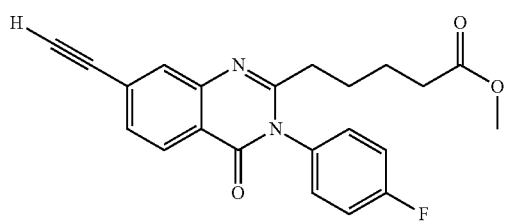

9B

A solution of 9A (170 mg, 0.378 mmol), TBAF (1 N in THF, 0.45 mL, 0.45 mmol) in 1.5 mL THF was stirred in N₂ atmosphere at −30° C. for 40 min. The reaction was diluted with Et₂O and washed with water. The organic was concentrated. The residue was purified by prep TLC (30% EtOAc/hexane) to yield 9B (130 mg, Yield=91%), MS (M+H)=379.

Step 3

Methyl 5-(3-(4-fluorophenyl)-7-(1-methyl-1H-1,2,3-triazol-4-yl)-4-oxo-3,4-dihydroquinzolin-2-yl)pentanoate

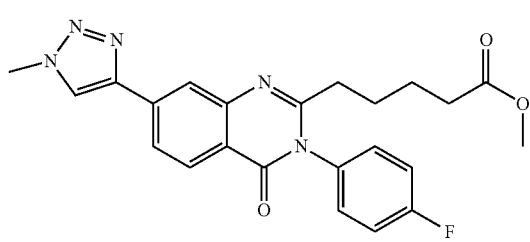

9C

A solution of 9B (100 mg, 0.265 mmol), NaN₃ (43 mg, 0.6625 mmol), MeI (75 mg, 0.53 mmol), CuI (51 mg, 0.265 mmol) in 2 mL of MeCN was stirred under an N₂ atmosphere at 50° C. for 14 h. The reaction was diluted with EtOAc and washed with water. The organic was concentrated. The residue was purified by prep TLC (40% EtOAc/hexane) to yield 9C (70 mg, Yield=60%), MS (M+H)=436.

Step 4

5-(3-(4-Fluorophenyl)-7-(1-methyl-1H-1,2,3-triazol-4-yl)-4-oxo-3,4-dihydroquinazolin-2-yl)pentanoic acid

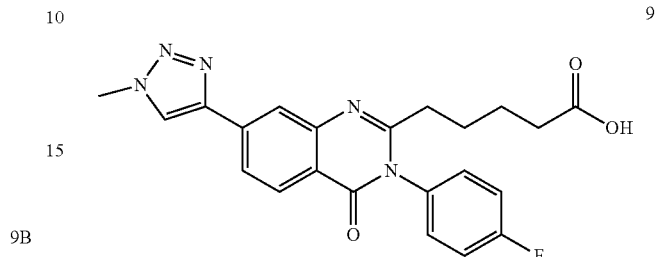

9

A solution of 9C (50 mg, 0.115 mmol) in 1 mL of THF was added LiOH (5 mg, 0.12 mmol) in 0.5 mL aqueous solution and stirred for 2 h at rt. The crude material was purified by reverse phase prep LC to yield 9 (43 mg, Yield=88%), MS (M+H)=422.

Preparative Example 10

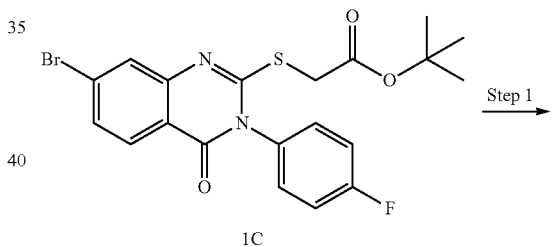

1C

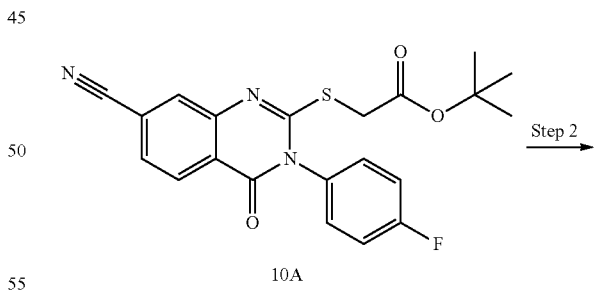

10A

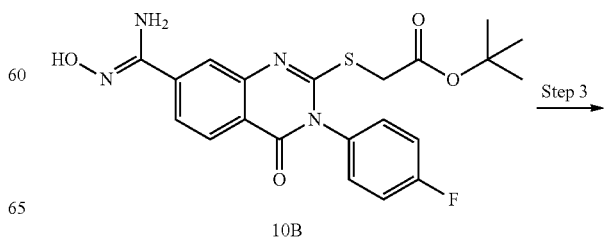

10B

-continued

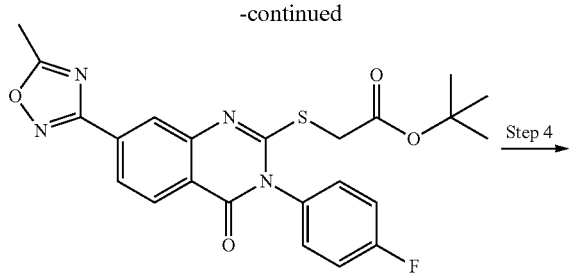

10C

A solution of tert-butyl-2-(7-cyano-3-(4-fluorophenyl)-4-oxo-3,4-dihydroquinazolin-2-ylthio)acetate (10A, 0.05 g, 0.12 mmol) in 50% NH$_2$OH aqueous solution (3 mL) and 20 µL acetic acid was microwaved under high absorption in N$_2$ atmosphere 105° C. for 40 minutes. The reaction was diluted with EtOAc and washed with water. The organic was concentrated to yield tert-butyl 2-(3-(4-fluorophenyl)-7-(N'-hydroxycarbamimidoyl)-4-oxo-3,4-dihydroquinazolin-2-ylthio)acetate (10B), MS (M+H)=445.

Step 3

Tert-butyl 2-(3-(4-fluorophenyl)-7-(5-methyl-1,2,4-oxadiazol-3-yl)-4-oxo-3,4-dihydroquinazolin-2-ylthio)acetate

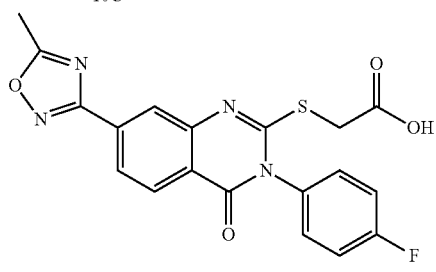

10C

A solution of tert-butyl 2-(3-(4-fluorophenyl)-7-(N'-hydroxycarbamimidoyl)-4-oxo-3,4-dihydroquinazolin-2-ylthio)acetate (10B, 30 mg, 0.0676 mmol) in 3 mL of acetic anhydride was heated in N$_2$ atmosphere 110° C. for 4 hours. The reaction was concentrated to yield tert-butyl 2-(3-(4-fluorophenyl)-7-(5-methyl-1,2,4-oxadiazol-3-yl)-4-oxo-3,4-dihydroquinazolin-2-ylthio)acetate (10C). MS (M+H)=469.

Step 4

2-(3-(4-Fluorophenyl)-7-(5-methyl-1,2,4-oxadiazol-3-yl)4-oxo-3,4-dihydroquinazolin-2-ylthio)acetic acid

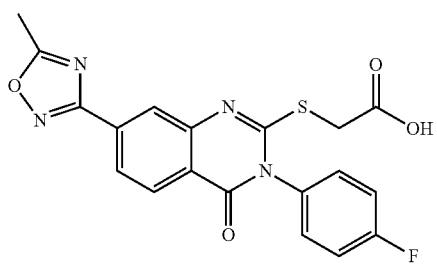

10

A solution of tert-butyl 2-(3-(4-fluorophenyl)-7-(5-methyl-1,2,4-oxadiazol-3-yl)-4-oxo-3,4-dihydroquinazolin-2-ylthio)acetate (10C, 25 mg, 0.0534 mmol), was treated with 5 mL 20% TFA in DCM for 14 hours. The reaction was concentrated and purified by reverse phase prep LC to yield 2-(3-(4-fluorophenyl)-7-(5-methyl-1,2,4-oxadiazol-3-yl)-4-

10

Step 1 tert-Butyl-2-(7-cyano-3-(4-fluorophenyl)-4-oxo-3,4-dihydroquinazolin-2-ylthio)acetate

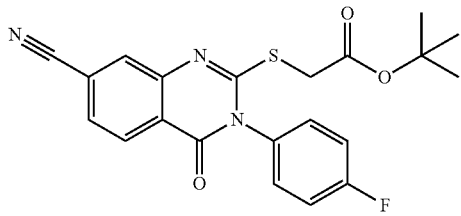

10A

A solution of tert-butyl 2-(7-bromo-3-(4-fluorophenyl)-4-oxo-3,4-dihydroquinaolin-2-ylthio)acetate (1C, 0.4 g, 0.86 mmol), zinc cyanide (0.2 g, 1.71 mmol), tetrakis(triphenylphosphine) palladium (0) (0.1 g, 0.086 mmol) in 5 ml DMF was heated in N$_2$ atmosphere 85° C. for 14 hours. The reaction was diluted with EtOAc and washed with water. The organic was concentrated. The residue was purified by chromotography (25% EtOAc/hexane) to yield tert-butyl-2-(7-cyano-3-(4-fluorophenyl)-4-oxo-3,4-dihydroquinazolin-2-ylthio)acetate (10A, 0.29 g, yield=82%), MS (M+H)=412.

Step 2

Tert-butyl 2-(3-(4-fluorophenyl)-7-(N'-hydroxycarbamimidoyl)-4-oxo-3,4-dihydroquinazolin-2-ylthio)acetate

10B

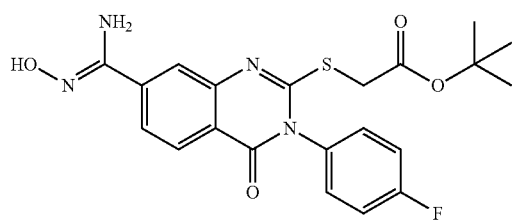

oxo-3,4-dihydroquinazolin-2-ylthio)acetic acid (10, 15.6 mg, 64% yield). MS (M+H)=413.

Preparative Example 11

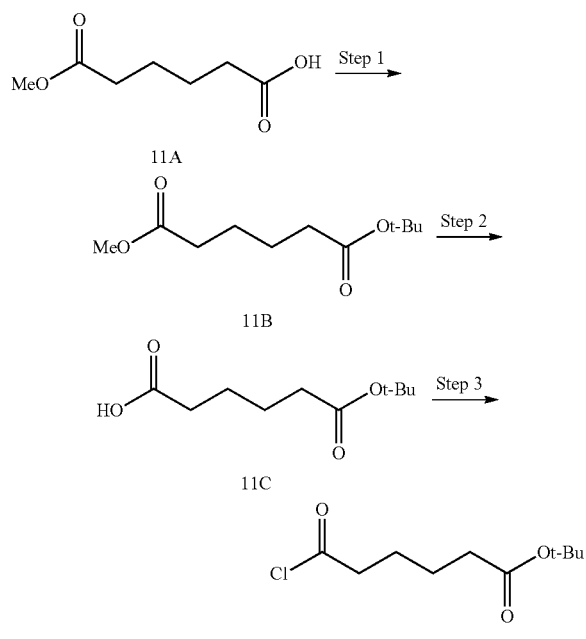

Step 1 tert-Butyl Methyl Adipate

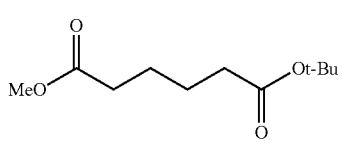
11B

A solution of 6-methoxy-6-oxohexanoic acid (11A) (9.25 mL, 62.4 mmol) and tert-butyl 2,2,2-trichloroacetimidate (27.3 g, 125 mmol) in DCM (100 mL) was cooled to 0° C. $BF_3.Et_2O$ (1.58 mL, 12.5 mmol) was added dropwise. The reaction was warmed to room temperature and stirred for 2 h. The reaction was quenched with 10% aqueous $K_2CO_3$. The organic layer was separated, dried ($Na_2SO_4$), filtered, and concentrated. The residue was triturated in heptane, filtered, and the filtrate was concentrated to yield 11B (10.3 g, yield=76%): $^1$H NMR (300 MHz, $CDCl_3$) δ 3.67 (s, 3H), 2.40-2.10 (m, 4H), 1.80-1.50 (m, 4H), 1.43 (s, 9H).

Step 2

6-tert-Butoxy-6-oxohexanoic Acid

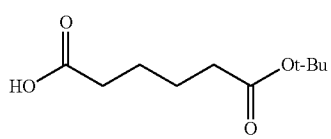
11C

A solution of 11B (10.3 g, 47.6 mmol) and LiOH (1.26 g, 52.8 mmol) in 3:1:1 MeOH/THF/$H_2O$ (50 mL) was stirred at room temperature for 16 h. The reaction was diluted with EtOAc and washed with saturated aqueous $Na_2CO_3$. The aqueous layer was separated and acidified with 1 N HCl, then extracted with EtOAc. The combined organics were washed with brine, dried ($Na_2SO_4$), filtered and concentrated to yield 11C (8.14 g, yield=85%): $^1$H NMR (300 MHz, $CDCl_3$) δ 10.67 (br s, 1H), 2.50-2.10 (m, 4H), 1.65 (m, 4H), 1.44 (s, 9H).

Step 3 tert-Butyl 6-Chloro-6-oxohexanoate

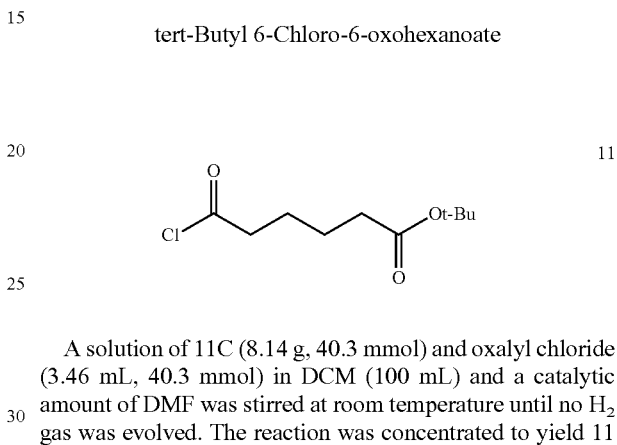

A solution of 11C (8.14 g, 40.3 mmol) and oxalyl chloride (3.46 mL, 40.3 mmol) in DCM (100 mL) and a catalytic amount of DMF was stirred at room temperature until no $H_2$ gas was evolved. The reaction was concentrated to yield 11 (8.01 g, yield=90%).

Preparative Example 12

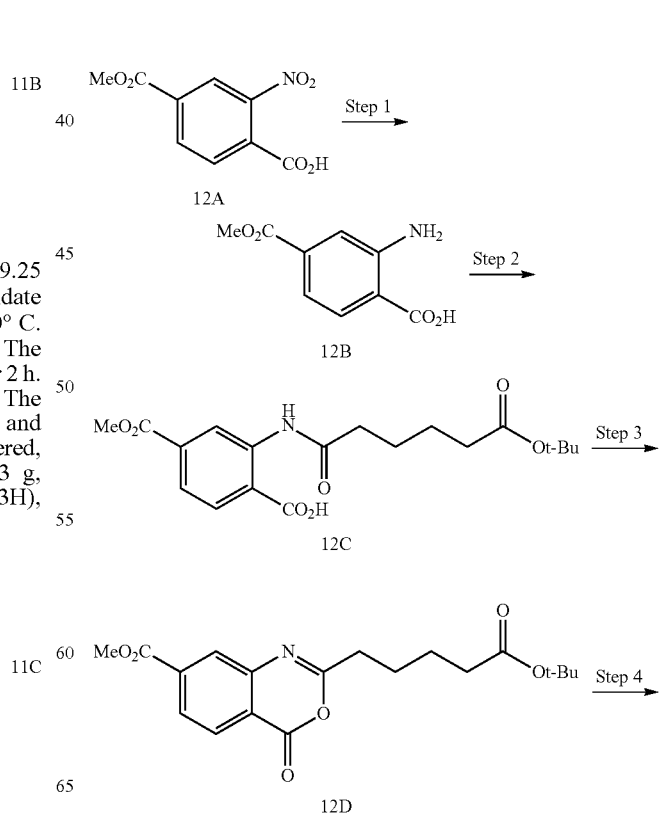

-continued

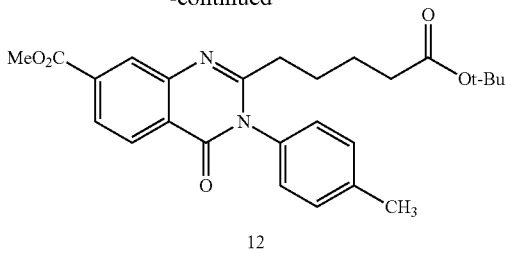

12

Step 1

2-Amino-4-(methoxycarbonyl)benzoic Acid

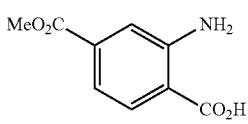
12B

A suspension of 4-(methoxycarbonyl)-2-nitrobenzoic acid (12A) (10.0 g, 44.4 mmol), and 5% Pd/C (4.0 g) in 1:1 MeOH/H$_2$O (50 mL) was subjected to hydrogenation conditions (H$_2$, 50 psi) for 16 h. The reaction was filtered through a pad a CELITE, washed with MeOH, and concentrated to yield 12B (6.51 g, yield=75%): MS (M+H)=196.

Step 2

2-(6-tert-Butoxy-6-oxohexanamido)-4-(methoxycarbonyl)benzoic Acid

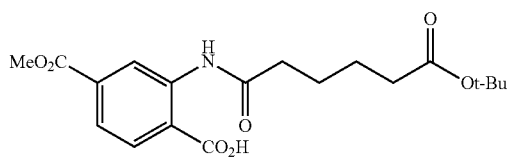
12C

A solution of tert-butyl 6-chloro-6-oxohexanoate (11, 7.71 g, 35.0 mmol) in THF (50 mL) was added to a solution of 12B (6.84 g, 35.0 mmol) and triethylamine (4.86 mL, 35.0 mmol) in THF (100 mL). The reaction was stirred at room temperature for 16 h, and then concentrated. The residue was purified by flash chromatography (0% to 30% EtOAc/heptane) to yield 12C (4.39 g, yield=33%): MS (M+H—C$_4$H$_8$)=324.

Step 3

Methyl 2-(5-tert-Butoxy-5-oxopentyl)-4-oxo-2,4-dihydro-1H-benzo[d][1,3]oxazine-7-carboxylate

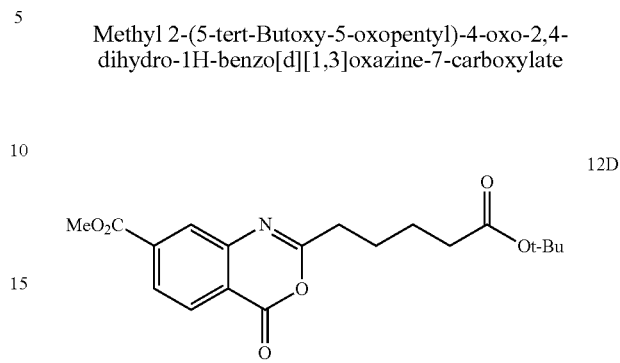
12D

A solution of 12C (4.39 g, 11.6 mmol) in acetic anhydride (19 mL, 197 mmol) was stirred for 16 h at reflux. After this time, the reaction was cooled to room temperature and concentrated. The residue was purified by flash chromatography (0% to 30% EtOAc/heptane) to yield 12D (3.11 g, yield=74%): MS (M+H)=362.

Step 4

Methyl 2-(5-tert-Butoxy-5-oxopentyl)-4-oxo-3-p-tolyl-1,2,3,4-tetrahydroquinazoline-7-carboxylate

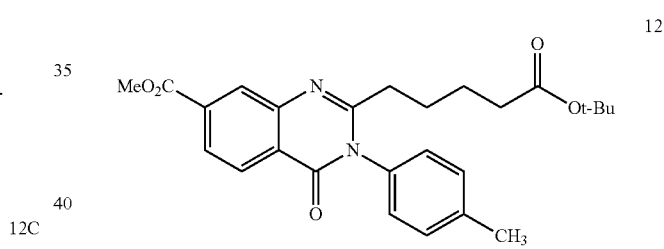
12

A solution of 12D (100 mg, 0.277 mmol) and p-toluidine (35.5 mg, 0.332 mmol) in acetic acid (250 μL, 4.16 mmol) was stirred overnight at 100° C. After this time, the reaction was diluted with EtOAc and H$_2$O. The mixture was poured onto a solid phase extraction tube and washed with DCM. The filtrate was concentrated and the residue was purified by flash chromatography (0% to 20% EtOAc/heptane) to yield 12 (65.6 mg, yield=52%): MS (M+H)=451.

In a manner similar to that described above, 12D was reacted with the appropriate amine to provide the following compounds:

| Compound Number | Amine | Compound | M + H |
|---|---|---|---|
| 12E | | | 505 |

-continued

| Compound Number | Amine | Compound | M + H |
|---|---|---|---|
| 12F | 4-cyanoaniline | MeO2C-quinazolinone with 4-cyanophenyl N-substituent and -(CH2)3CO2tBu | 462 |
| 12G | 3-fluoroaniline | MeO2C-quinazolinone with 3-fluorophenyl N-substituent and -(CH2)3CO2tBu | 455 |
| 12H | 2-fluoroaniline | MeO2C-quinazolinone with 2-fluorophenyl N-substituent and -(CH2)3CO2tBu | 455 |
| 12i | 4-chloroaniline | MeO2C-quinazolinone with 4-chlorophenyl N-substituent and -(CH2)3CO2tBu | 471 |
| 12J | 2,6-dimethylaniline | MeO2C-quinazolinone with 2,6-dimethylphenyl N-substituent and -(CH2)3CO2tBu | 465 |
| 12K | 2-phenylethylamine | MeO2C-quinazolinone with 2-phenylethyl N-substituent and -(CH2)3CO2tBu | 465 |

-continued

| Compound Number | Amine | Compound | M + H |
|---|---|---|---|
| 12L | H2N-CH2-Ph | MeO2C-quinazolinone with N-benzyl, 2-(4-(O-t-Bu ester)butyl) | 451 |
| 12M | 3,5-difluoroaniline | MeO2C-quinazolinone with N-(3,5-difluorophenyl), 2-(4-(O-t-Bu ester)butyl) | 473 |
| 12N | 4-methoxyaniline | MeO2C-quinazolinone with N-(4-methoxyphenyl), 2-(4-(O-t-Bu ester)butyl) | 467 |
| 12o | 3-trifluoromethylaniline | MeO2C-quinazolinone with N-(3-CF3-phenyl), 2-(4-(O-t-Bu ester)butyl) | 505 |
| 12P | 3-chloroaniline | MeO2C-quinazolinone with N-(3-chlorophenyl), 2-(4-(O-t-Bu ester)butyl) | 471 |
| 12Q | 3-methylaniline | MeO2C-quinazolinone with N-(3-methylphenyl), 2-(4-(O-t-Bu ester)butyl) | 451 |

-continued

| Compound Number | Amine | Compound | M + H |
|---|---|---|---|
| 12R | 2-amino-benzonitrile | (structure) | 480 |
| 12S | 4-ethylaniline | (structure) | 465 |
| 12T | 2-methylaniline | (structure) | 451 |
| 12U | 4-isopropylaniline | (structure) | 479 |
| 12V | 2-(trifluoromethyl)aniline | (structure) | 505 |
| 12W | 4-tert-butylaniline | (structure) | 493 |

-continued

| Compound Number | Amine | Compound | M + H |
|---|---|---|---|
| 12X | 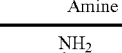 | 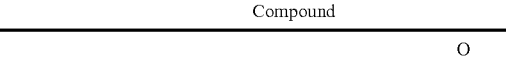 | 462 |

Preparative Example 13

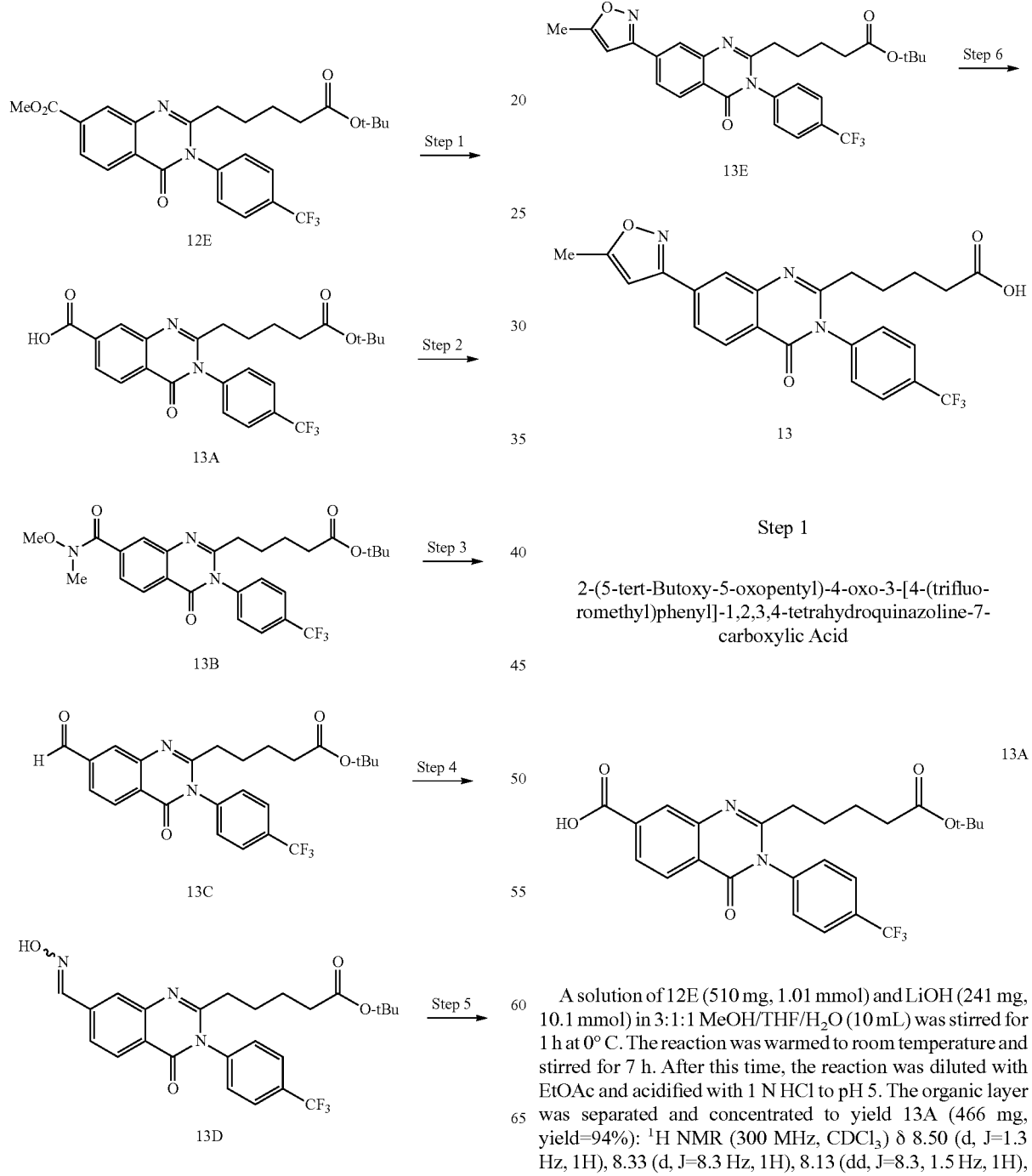

Step 1

2-(5-tert-Butoxy-5-oxopentyl)-4-oxo-3-[4-(trifluoromethyl)phenyl]-1,2,3,4-tetrahydroquinazoline-7-carboxylic Acid A solution of 12E (510 mg, 1.01 mmol) and LiOH (241 mg, 10.1 mmol) in 3:1:1 MeOH/THF/H$_2$O (10 mL) was stirred for 1 h at 0° C. The reaction was warmed to room temperature and stirred for 7 h. After this time, the reaction was diluted with EtOAc and acidified with 1 N HCl to pH 5. The organic layer was separated and concentrated to yield 13A (466 mg, yield=94%): $^1$H NMR (300 MHz, CDCl$_3$) δ 8.50 (d, J=1.3 Hz, 1H), 8.33 (d, J=8.3 Hz, 1H), 8.13 (dd, J=8.3, 1.5 Hz, 1H), 7.86 (d, J=8.3 Hz, 2H), 7.44 (d, J=8.2 Hz, 2H), 2.46 (t, J=7.4 Hz, 2H), 2.20 (t, J=7.3 Hz, 2H), 1.84-1.74 (m, 2H), 1.64-1.53 (m, 2H), 1.43 (s, 9H).

Step 2 tert-Butyl 5-{7-[(Methoxy(methyl)carbamoyl]-4-oxo-3-[4-(trifluoromethyl)phenyl]-1,2,3,4-tetrahydroquinazolin-2-yl}pentanoate

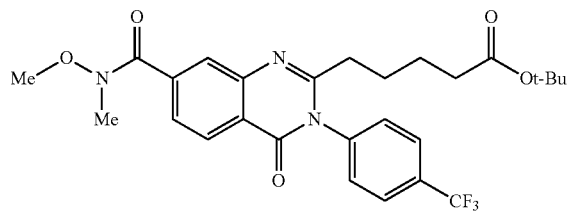

A solution of 13A (50 mg, 0.102 mmol), O,N-dimethylhydroxylamine hydrochloride (25 mg, 0.255 mmol), diisopropyl ethyl amine (147 μL, 2.04 mmol), and BOP-CI (90 mg, 0.306 mmol) in anhydrous THF (100 mL) was stirred for 2 d at room temperature. After this time, the reaction was diluted with EtOAc and washed with 1 N HCl. The organic layer was separated, dried (Na$_2$SO$_4$), filtered, and concentrated. The residue was purified by flash chromatography (0% to 30% EtOAc/heptane) to yield 13B (54.0 mg, yield=99%): MS (M+H)=534.1.

Step 3 tert-Butyl 5-{7-Formyl-4-oxo-3-[4-(trifluoromethyl)phenyl]-3,4-dihydroquinazolin-2-yl}pentanoate

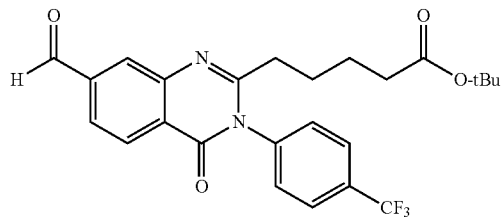

To a stirred solution of 13B (50 mg, 0.094 mmol) in THF (1 mL) was slowly added DIBAL (1M in hexanes, 141 μL, 0.141 mmol) at −78° C. under N$_2$. The reaction was stirred for 1 h. To the solution was added Na$_2$SO$_4$.10H$_2$O/CELITE (2:1 mixture, 3 g). The mixture was stirred for 1.5 h and filtered. The filter cake was washed with EtOAc, and the filtrate was concentrated to yield 13C (39 mg, yield=88%): MS (M+H)=475.1.

Step 4 tert-Butyl 5-{7-[(Hydroxyimino)methyl]-4-oxo-3-[4-(trifluoromethyl)phenyl]-3,4-dihydroquinazolin-2-yl}pentanoate

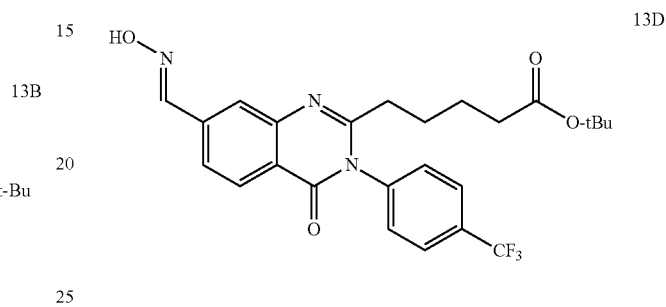

A solution of 13C (139 mg, 0.293 mmol) and hydroxylamine hydrochloride (62 mg, 0.878 mol) in THF (2 mL) was stirred at room temperature for 2 h. The reaction mixture was diluted with EtOAc and washed with water. The organic layer was separated, dried (Na$_2$SO$_4$), filtered, and concentrated to yield 13D (120 mg, yield=84%): MS (M+H)=490.2.

Step 5 tert-Butyl 5-{7-(5-Methylisoxazol-3-yl)-4-oxo-3-[4-(trifluoromethyl)phenyl]-3,4-dihydroquinazolin-2-yl}pentanoate A solution of 13D (120 mg, 0.245 mmol) in DCM (5 mL) was treated with NBS (65 mg, 0.368 mmol) and stirred for 1 h at room temperature. This solution was further treated with triethylamine (41 μL, 0.294 mmol) and then stirred at room temperature under 1-propyne environment (balloon) for 14 h. After this time, the reaction was diluted with EtOAc and water. The aqueous layer was separated and extracted with EtOAc. The combined organics were washed with brine, dried (Na$_2$SO$_4$), filtered, and concentrated. The residue was purified by flash chromatography (0% to 30% EtOAc/heptane) to yield 13E (129 mg, yield=>99%): MS (M+H)=528.2.

Step 6

5-{7-(5-Methylisoxazol-3-yl)-4-oxo-3-[4-(trifluoromethyl)phenyl]-3,4-dihydroquinazolin-2-yl}pentanoic acid

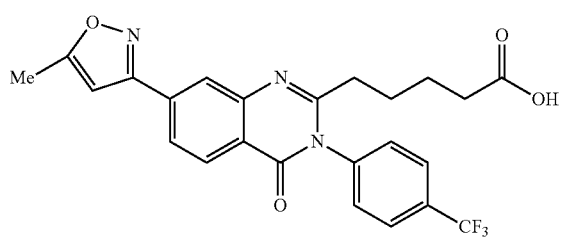

13

To a solution of 13E (129 mg, 0.245 mmol) in DCM (5 mL) was added TFA (1 mL) and the solution stirred for 1 h at room temperature. After this time, the reaction was concentrated and the residue was purified by preparative HPLC [10:90 to 100:0 (18 min) $CH_3CN$/water (0.1% TFA)]. The desired fractions were combined and partitioned between EtOAc and 1 N HCl. The organic layer was separated, dried ($Na_2SO_4$), filtered, and concentrated. The residue was dissolved in 2:1:1 $CH_3CN/H_2O/NH_4OH$ (4 mL) and lyophilized to yield 13 (29.8 mg, yield=25%): MS (M+H)=472.1.

Preparative Example 14

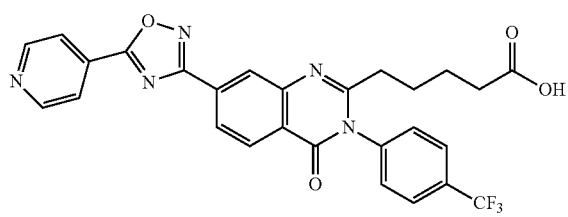

14

Step 1

Methyl 5-[7-cyano-3-(4-fluorophenyl)-4-oxo-3,4-dihydroquinazolin-2-yl]pentanoate

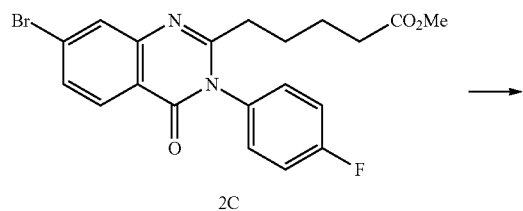

2C

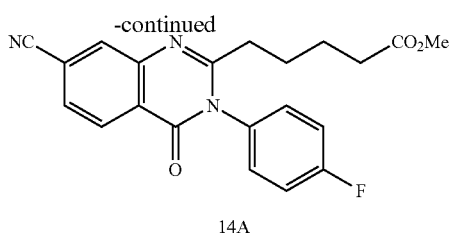

14A

To a microwave reaction vial was added methyl 5-[7-bromo-3-(4-fluorophenyl)-4-oxo-3,4-dihydroquinazolin-2-yl]pentanoate (2C) in DMF (0.2 M) was added $Zn(CN)_2$ (1.05 eq), and $Pd(Ph_3P)_4$ (0.1 eq), and the mixture was heated at 100° C. for 45 min. The reaction mixture was diluted with EtOAc and aq. $NaHCO_3$. The organic layer was separated, washed with $H_2O$ and brine, dried over $MgSO_4$, and concentrated. The residue was purified by flash chromatography (EtOAc/hexanes) to afford 14A.

Step 2

Methyl 5-[3-(4-fluorophenyl)-7-(M-hydroxycarbamimidoyl)-4-oxo-3,4-dihydroquinazolin-2-yl]pentanoate

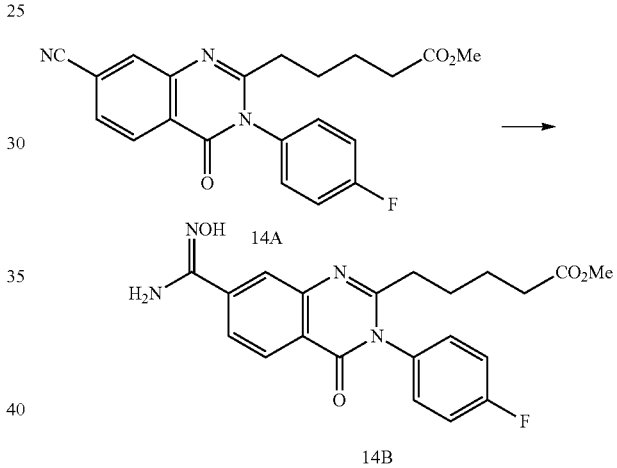

14A

14B

To a microwave reaction vial containing methyl 5-[7-cyano-3-(4-fluorophenyl)-4-oxo-3,4-dihydroquinazolin-2-yl]pentanoate (14A) in MeOH (0.2 M) was added hydroxylamine hydrochloride (1.05 eq) and $Et_3N$ (3 eq). The mixture was heated at reflux overnight, concentrated, and the residue was taken up in DMF and used for next step without purification.

Steps 3-4

5-{3-(4-fluorophenyl)-4-oxo-7-[5-(pyridin-4-0)-1,2,4-oxadiazol-3-yl]-3,4-dihydroquinazolin-2-yl}pentanoic acid

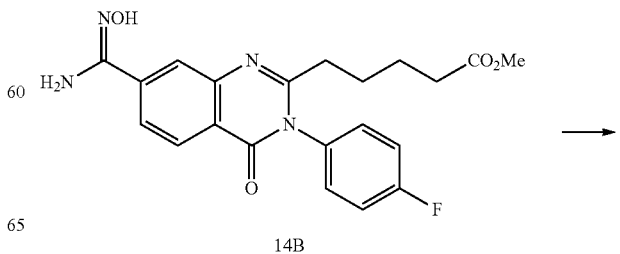

14B

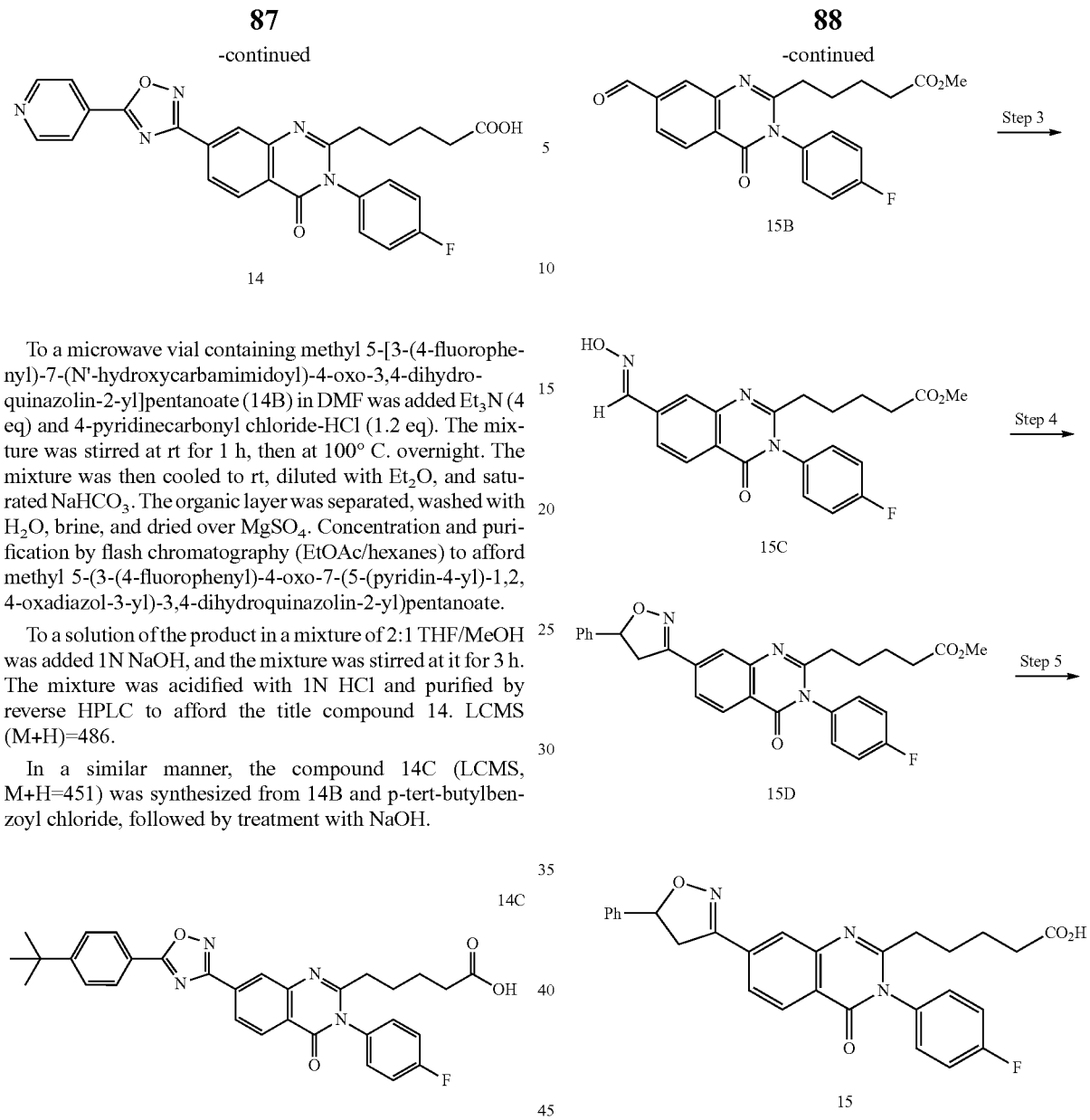

To a microwave vial containing methyl 5-[3-(4-fluorophenyl)-7-(N'-hydroxycarbamimidoyl)-4-oxo-3,4-dihydroquinazolin-2-yl]pentanoate (14B) in DMF was added Et$_3$N (4 eq) and 4-pyridinecarbonyl chloride-HCl (1.2 eq). The mixture was stirred at rt for 1 h, then at 100° C. overnight. The mixture was then cooled to rt, diluted with Et$_2$O, and saturated NaHCO$_3$. The organic layer was separated, washed with H$_2$O, brine, and dried over MgSO$_4$. Concentration and purification by flash chromatography (EtOAc/hexanes) to afford methyl 5-(3-(4-fluorophenyl)-4-oxo-7-(5-(pyridin-4-yl)-1,2,4-oxadiazol-3-yl)-3,4-dihydroquinazolin-2-yl)pentanoate.

To a solution of the product in a mixture of 2:1 THF/MeOH was added 1N NaOH, and the mixture was stirred at it for 3 h. The mixture was acidified with 1N HCl and purified by reverse HPLC to afford the title compound 14. LCMS (M+H)=486.

In a similar manner, the compound 14C (LCMS, M+H=451) was synthesized from 14B and p-tert-butylbenzoyl chloride, followed by treatment with NaOH.

Preparative Example 15

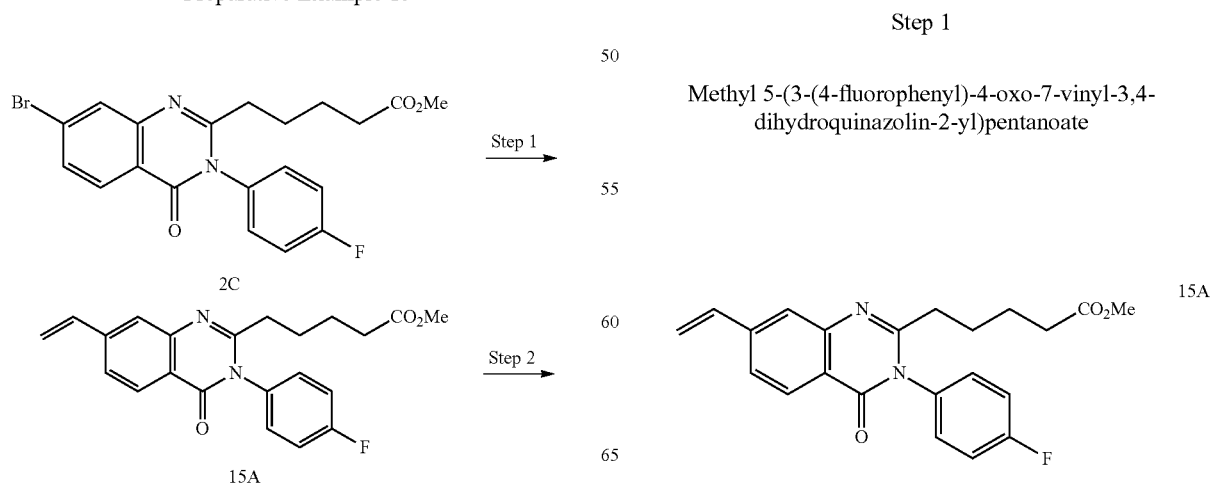

Step 1

Methyl 5-(3-(4-fluorophenyl)-4-oxo-7-vinyl-3,4-dihydroquinazolin-2-yl)pentanoate To the suspension of compound 2C (7.4 g, 17 mmol) in 75 ml of DME/H$_2$O (4:1) was added vinylboronic acid pinacol ester (5.8 mL, 34 mmol), PdCl$_2$(PPh$_3$)$_2$ (1.2 g, 1.7 mmol), and Na$_2$CO$_3$ (5.4 g, 51 mmol). The mixture was heated at 70° C. overnight, diluted with H$_2$O and then extracted with EtOAc. The organic layer was collected, dried over Na$_2$SO$_4$, concentrated and purified (30% EtOAc/Hexane) to give 5.6 g of compound 15A. Yield: 86%.

Step 2

Methyl 5-(3-(4-fluorophenyl)-7-formyl-4-oxo-3,4-dihydroquinazolin-2-yl)pentanoate

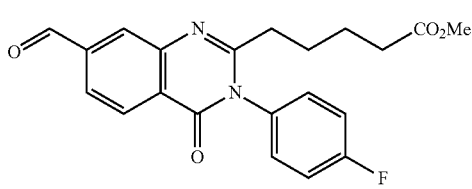

15B

The solution of compound 15A (5.6 g, 14.7 mmol) was cooled to −78° C. with a dry-ice bath, and then ozonolyzed for 40 minutes. The reaction was quenched by addition of Ph$_3$P (3.9 g, 14.7 mmol). The mixture was concentrated and purified (40% EtOAc/Hexane) to give 4.5 g of compound 15B. Yield: 80%.

Step 3

Methyl 5-(3-(4-fluorophenyl)-7-((hydroxyimino)methyl)-4-oxo-3,4-dihydroquinazolin-2-yl)pentanoate

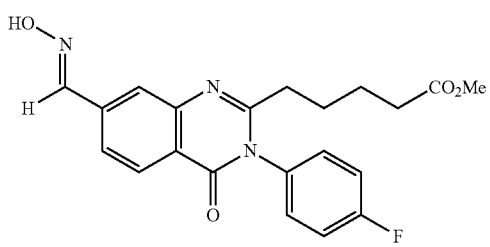

15C

To the suspension of compound 15B (4.5 g, 11.8 mmol) in 20 mL of pyridine was added NH$_2$OH. HCl (2.2 g, 31.7 mmol). After heating at 60° C. for 2 h, the solvent was removed, and the residue was taken up in EtOAc and H$_2$O. The organic layer was collected, concentrated to give 5 g of compound 15C as pale yellow solid.

Step 4 methyl 5-(3-(4-fluorophenyl)-4-oxo-7-(5-phenyl-4,5-dihydroisoxazol-3-yl)-3,4-dihydroquinazolin-2-yl)pentanoate

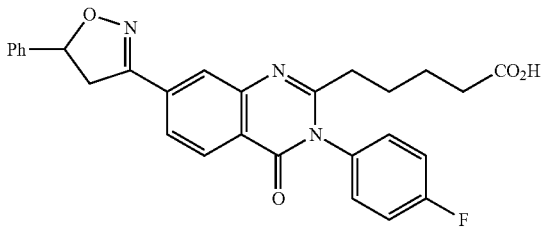 [SMILES: O=C(O)CCCCc1nc2cc(C3=NOC(c4ccccc4)C3)ccc2c(=O)n1-c1ccc(Cl)cc1]

15D

To the suspension of compound 15C (0.05 g, 0.13 mmol) in 5 mL of CH$_2$Cl$_2$ was added styrene (0.027 g, 0.26 mmol), and NaOCl (0.86 mL, 0.52 mmol). After stirring at it overnight, the mixture was diluted with CH$_2$Cl$_2$ and H$_2$O. The organic layer was collected, dried over Na$_2$SO$_4$, concentrated and purified (40% EtOAc/Hexane) to give 0.047 g of compound 15D. Yield: 75%.

Step 5

5-(3-(4-fluorophenyl)-4-oxo-7-(5-phenyl-4,5-dihydroisoxazol-3-yl)-3,4-dihydroquinazolin-2-yl)pentanoic acid

15

To the suspension of compound 15O (0.047 g, 0.094 mmol) in 6 mL of MeOH/H$_2$O (1:1) was added LiOH. H$_2$O (0.016 g, 0.376 mmol). After heating at 50° C. for 2 h, the solvent was removed. The product was acidified to pH 5 by adding 1N HCl (aq), concentrated and purified by prep-TLC (10% CH$_2$Cl$_2$/MeOH) to give 0.025 g of the title compound 15. Yield: 55%. LCMS (M+H)=486.

In a manner similar to that described above for 15, the following compounds were prepared:

| Compound Number | Compound | M + H |
|---|---|---|
| 15E | 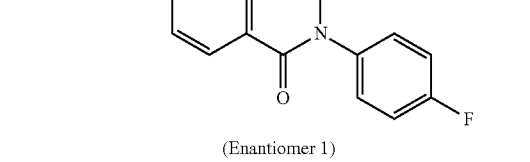 (Enantiomer 1) | 500 |
| 15F | 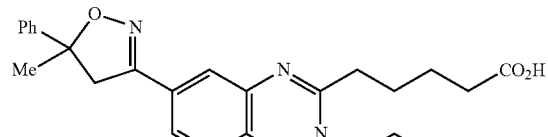 (Enantiomer 2) | 500 |
| 15G | 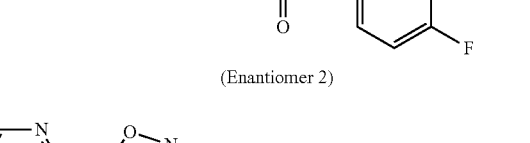 | 487 |
| 15H | 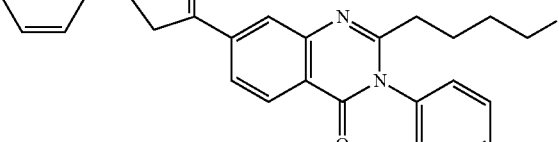 | 487 |
| 15i | 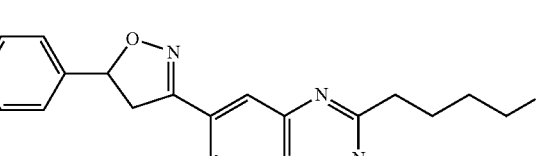 (Enantiomer 1) | 516 |
| 15J | 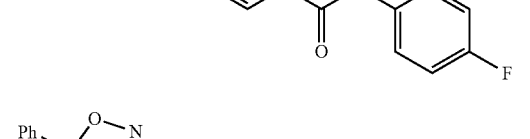 (Enantiomer 2) | 516 |

-continued

| Compound Number | Compound | M + H |
|---|---|---|
| 15K | | 502 |
| 15L | | 503 |
| 15M | | 503 |
| 15N | | 516 |
| 15o | | 532 |
| 15P | | 520 |

-continued

| Compound Number | Compound | M + H |
|---|---|---|
| 15Q | | 511 |
| 15R | | 579 |
| 15S | | 521 |
| 15T | | 595 |
| 15U | | 537 |
| 15V | | 530 |

-continued
| Compound Number | Compound | M + H |
|---|---|---|
| 15W | | 546 |
| 15X | | 478 |
| 15Y | | 494 |
| 15Z | | 491 |
Preparative Example 16
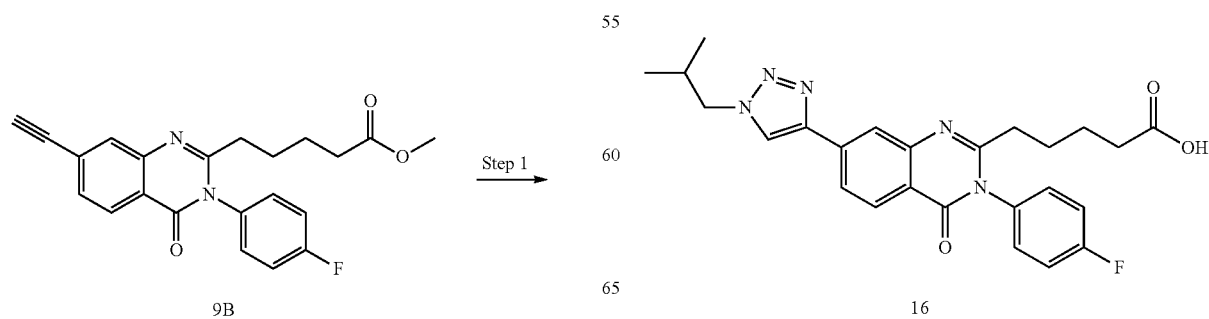

Step 1

5-{3-(4-fluorophenyl)-7-[1-(2-methylpropyl)-1H-1,2,3-triazol-4-yl]-4-oxo-3,4-dihydroquinazolin-2-yl}pentanoic acid

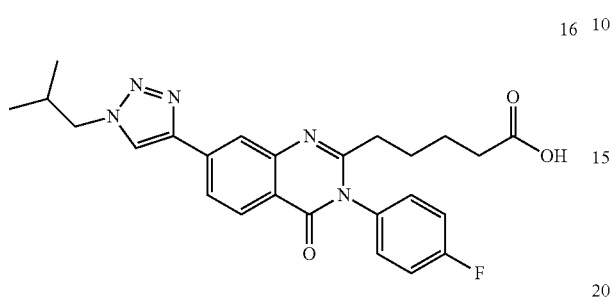

16

Sodium azide (7 mg, 0.108 mmol) was added to a solution of 1-bromo-2-methylpropane (14 µL, 0.127 mmol) in a 1:1 mixture of tert-butanol (1 mL) and water (1 mL) and heated to 70° C. for 48 hours. Reaction was cooled to 25° C., copper (5.37 mg, 0.085 mmol) and methyl 5-(7-ethynyl-3-(4-fluorophenyl)-4-oxo-3,4-dihydroquinazolin-20yl)pentanoate (9B, 40 mg, 0.106 mmol) were added and mixture was heated to 125° C. in the microwave for 20 minutes. After the reaction was stirred at 25° C. for 48 h, THF (1 mL) and 1 N NaOH (0.317 mL) were added. The reaction was heated to 45° C. and stirred for 20 minutes. The reaction mixture was partitioned between EtOAc and 1 N HCl. The organic layer was concentrated and purified via reverse phase HPLC over a gradient of 35-80% ACN in water with 0.1% TFA to yield 16 (1.8 mg, Yield=3.67%), MS (M+H)=464.

Preparative Example 17

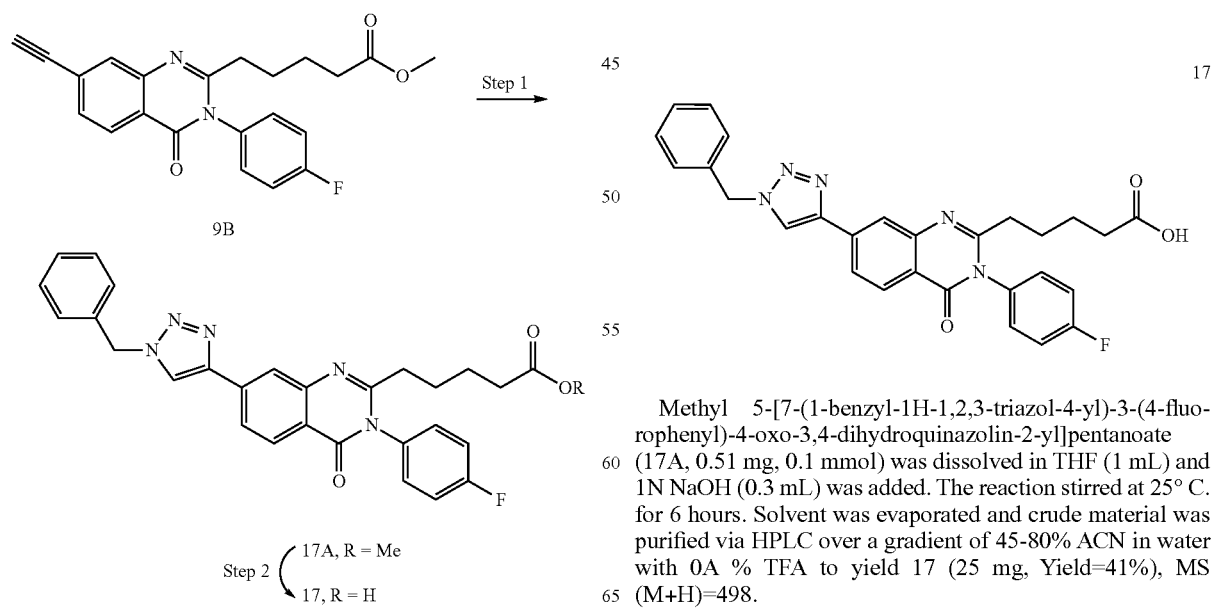

Step 1

Methyl 5-[7-(1-benzyl-1H-1,2,3-triazol-4-yl)-3-(4-fluorophenyl)-4-oxo-3,4-dihydroquinazolin-2-yl]pentanoate

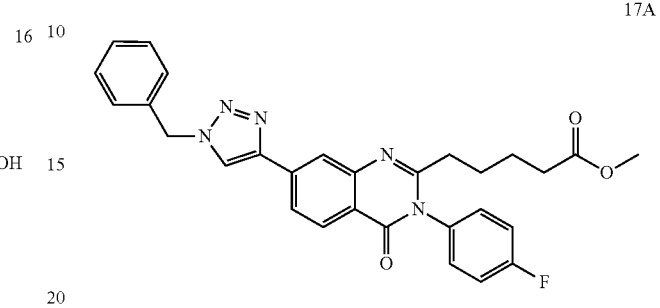

17A

Methyl 5-(7-ethynyl-3-(4-fluorophenyl)-4-oxo-3,4-dihydroquinazolin-20yl)pentanoate (9B, 40 mg, 0.106 mmol) and sodium ascorbate (8.38 mg, 0.042 mmol) were dissolved in a 1:1 mixture of EtOH (0.5 mL) and DMF (0.5 mL). Benzyl azide (0.013 mL, 0106 mmol), followed by a solution of copper (II) sulfate pentahydrate (5.28 mg, 0.021 mmol) in water (0.1 mL) were added and the reaction stirred at 25° C. for 16 hours. The reaction was partitioned between dilute ammonium hydroxide and EtOAc. The organic layer was extracted with EtOAc (3×). Combined organic layers washed with dilute ammonium hydroxide and brine and were dried over magnesium sulfate. Solvent was evaporated to yield the title compound 17A which was carried on without further purification (0.54 g, MS (M+H)=512).

Step 2

5-[7-(1-benzyl-1H-1,2,3-triazol-4-yl)-3-(4-fluorophenyl)-4-oxo-3,4-dihydroquinazolin-2-yl]pentanoic acid Methyl 5-[7-(1-benzyl-1H-1,2,3-triazol-4-yl)-3-(4-fluorophenyl)-4-oxo-3,4-dihydroquinazolin-2-yl]pentanoate (17A, 0.51 mg, 0.1 mmol) was dissolved in THF (1 mL) and 1N NaOH (0.3 mL) was added. The reaction stirred at 25° C. for 6 hours. Solvent was evaporated and crude material was purified via HPLC over a gradient of 45-80% ACN in water with 0A % TFA to yield 17 (25 mg, Yield=41%), MS (M+H)=498.

The following compound was made following the procedure described above:

| Compound Number | Compound | M + H |
|---|---|---|
| 17B | 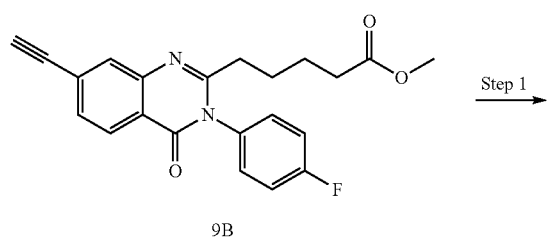 | 567 |

Preparative Example 18

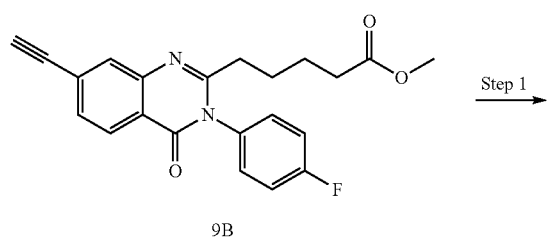

9B

L-proline (2.45 mg, 0.022 mmol), 4-bromochlorobenzene (21 mg, 0.108 mmol), sodium azide (8.45 mg, 0.130 mmol), copper (II) sulfate pentahydrate (1.35 mg, 5.42 μmol), sodium ascorbate (2.1 mg, 10.84 μmol), $Na_2CO_3$ (2.2 mg, 0.22 mmol) and methyl 5-(7-ethynyl-3-(4-fluorophenyl)-4-oxo-3,4-dihydroquinazolin-2-yl)pentanoate (9B, 41 mg, 0.108 mmol) were dissolved in a 9:1 mixture of DMSO (1 mL) and water (0.11 mL). The reaction was heated to 100° C. for 5 hours and then stirred at 65° C. for 48 hours. Upon cooling to 25° C., 1N NaOH (0.433 mL) and EtOAc were added and the reaction stirred for 2 hours. Solvent was evaporated and material was purified via reverse phase HPLC over a gradient of 25-60% ACN in water with 0.1% TFA to yield 18 (8.8 mg, Yield=16%), MS (M+H)=408.

Preparative Example 19

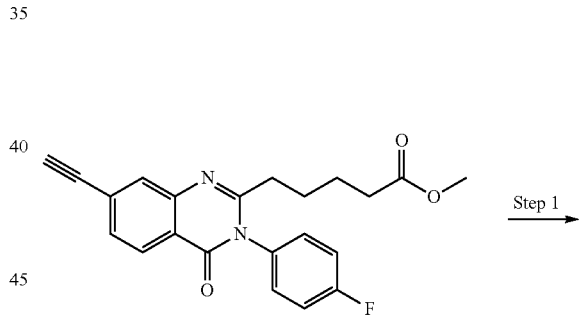

Step 1

5-[3-(4-fluorophenyl)-4-oxo-7-(1H-1,2,3-triazol-4-yl)-3,4-dihydroquinazolin-2-yl]pentanoic acid

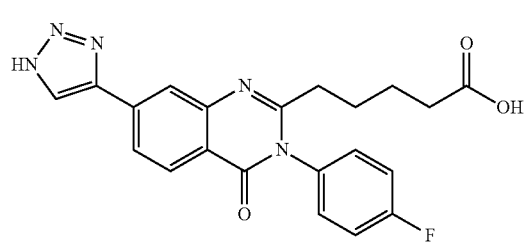

18

Step 1

Methyl 5-{7-[1-(4-fluorobenzyl)-1H-1,2,3-triazol-4-yl]-3-(4-fluorophenyl)-4-oxo-3,4-dihydroquinazolin-2-yl}pentanoate Step 2

5-{7-[1-(4-fluorobenzyl)-1H-1,2,3-triazol-4-yl]-3-(4-fluorophenyl)-4-oxo-3,4-dihydroquinazolin-2-yl}pentanoic acid

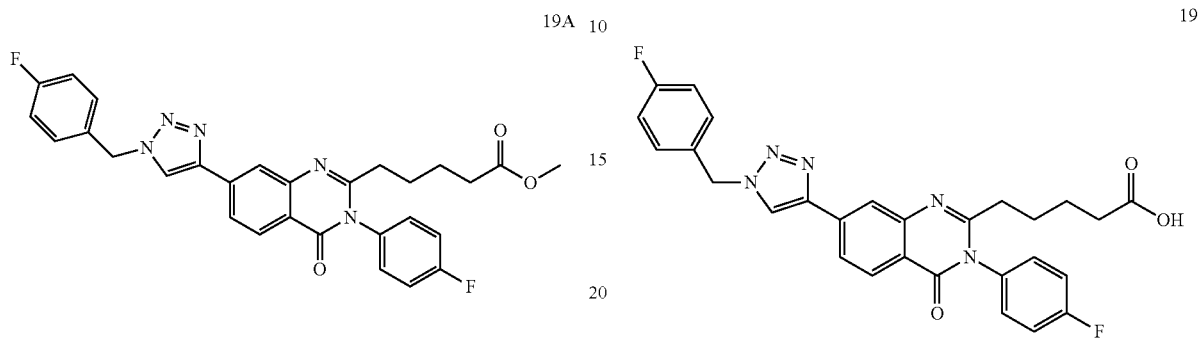

To a solution of 4-fluorobenzyl bromide (17 mg, 0.092 mmol) in a 9:1 mixture of DMSO (1 mL) and water (0.11 mL) was added L-proline (2.1 mg, 0.018 mmol), $Na_2CO_3$ (1.9 mg, 0.018 mmol), sodium azide (7.2 mg, 0.11 mmol), sodium ascorbate (1.8 mg, 9.3 µmol) and methyl 5-(7-ethynyl-3-(4-fluorophenyl)-4-oxo-3,4-dihydroquinazolin-20yl)pentanoate (9B, 35 mg, 0.092 mmol). Copper (II) sulfate pentahydrate (1.1 mg, 4.6 µmol) in water (0.1 mL) was next added and the reaction was heated to 65° C. for 16 hours. The reaction was cooled to 25° C., partitioned between ammonium hydroxide and EtOAc, and the organic layer was extracted with EtOAc (3×). Combined organic layers were washed with brine, dried over sodium sulfate and solvent was evaporated to yield 19A, which was carried on to the next step without further purification (58 mg, MS (M+H)=530).

Methyl 5-{7-[1-(4-fluorobenzyl)-1H-1,2,3-triazol-4-yl]-3-(4-fluorophenyl)-4-oxo-3,4-dihydroquinazolin-2-yl}pentanoate (19A, 49 mg, 0.093 mmol) was dissolved in THF (1 mL) and potassium trimethylsilanolate (47 mg, 0.37 mmol) was added. The reaction stirred at 25° C. for 3 hours. The mixture was then partitioned between 1N HCl and EtOAc. The organic layer was extracted with EtOAc (3×) and solvent was evaporated. Crude material was purified via reverse phase HPLC over a gradient of 45-80% ACN in water with 0.1% TFA to yield 19 (25 mg, Yield=43%), MS (M+H)=516.

The following compounds were made following the procedure described above:

| Compound Number | Compound | M + H |
|---|---|---|
| 19B | | 499 |
| 19C | | 532 |

| Compound Number | Compound | M + H |
|---|---|---|
| 19D | 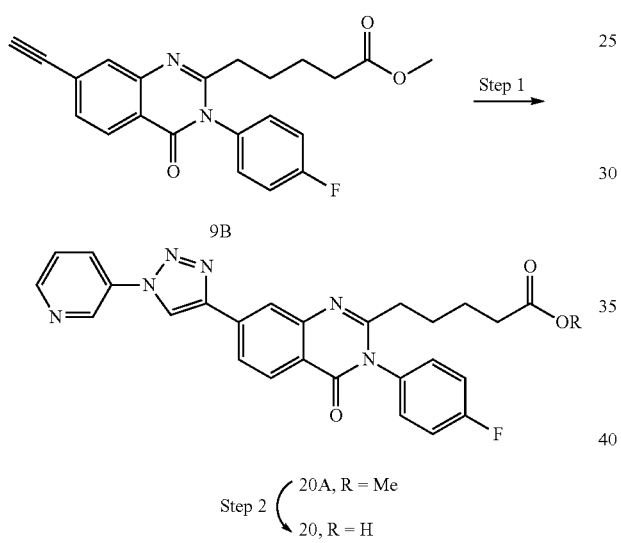 | 576 |

Preparative Example 20

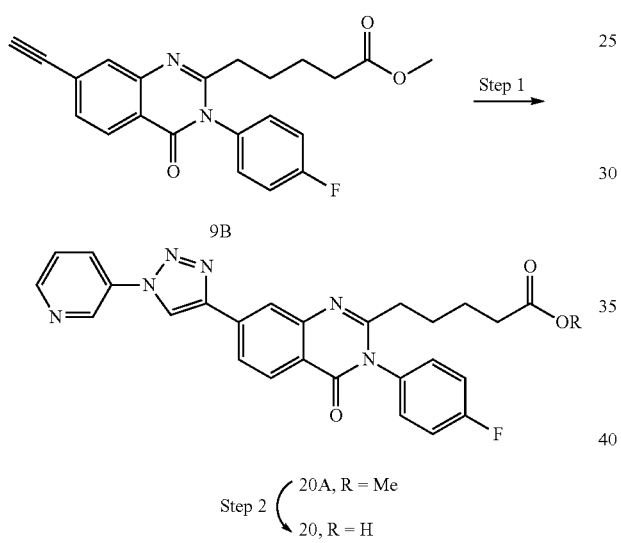

Step 1

Methyl 5-{3-(4-fluorophenyl)-4-oxo-7-[1,2,3-triazol-4-yl]-3,4-dihydroquinazolin-2-yl}pentanoate

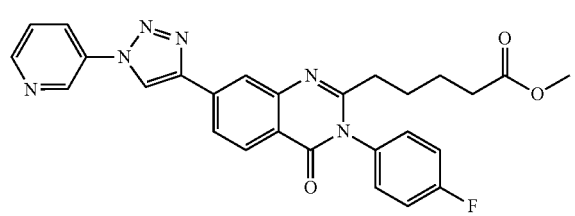

To a solution of 3-Iodopyridine (19 mg, 0.094 mmol) in a 9:1 mixture of DMSO (1 mL) and water (0.11 mL) was added L-proline (2.1 mg, 0.018 mmol), Na$_2$CO$_3$ (1.9 mg, 0.018 mmol), sodium azide (7.3 mg, 0.11 mmol), sodium ascorbate (1.8 mg, 9.3 µmol) and methyl 5-(7-ethynyl-3-(4-fluorophenyl)-4-oxo-3,4-dihydroquinazolin-20yl)pentanoate (9B, 35 mg, 0.092 mmol). Copper (II) sulfate pentahydrate (1.1 mg, 4.6 µmol) in water (0.1 mL) was then added and the reaction was heated to 65° C. for 16 hours. The reaction was cooled to 25° C., partitioned between ammonium hydroxide and EtOAc, and the organic layer was extracted with EtOAc (3×). Combined organic layers were washed with ammonium hydroxide and brine, dried over sodium sulfate and solvent was evaporated. Crude material was purified on a silica column over a gradient of 0-100% EtOAc in hexanes to yield 20A (28.3 mg, Yield=61%), MS (M+H)=499.

Step 2

5-{3-(4-fluorophenyl)-4-oxo-7-[1-(pyridin-3-yl)-1H-1,2,3-triazol-4-yl]-3,4-dihydroquinazolin-2-yl}pentanoic acid Methyl 5-{3-(4-fluorophenyl)-4-oxo-7-[1-(pyridin-3-yl)-1H-1,2,3-triazol-4-yl]-3,4-dihydroquinazolin-2-yl}pentanoate (20A, 28 mg, 0.056 mmol) was dissolved in THF (1 mL) and 1N NaOH (0.225 mL) was added. The reaction stirred at 25° C. for 7 hours. Solvent was evaporated and material was purified via reverse phase HPLC over a gradient of 35-70% ACN in water with 0.1% TFA to yield 20 (16 mg, Yield=48%), MS (M+H)=485.

The following compound was made following the procedure described above:

| Compound Number | Compound | M + H |
|---|---|---|
| 20B | 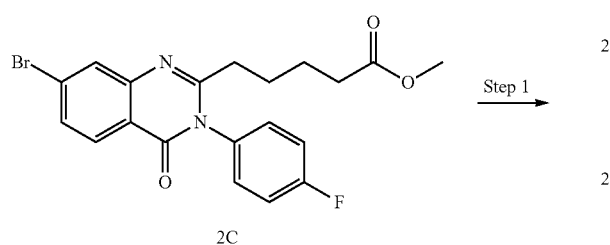 | 485 |

Preparative Example 21

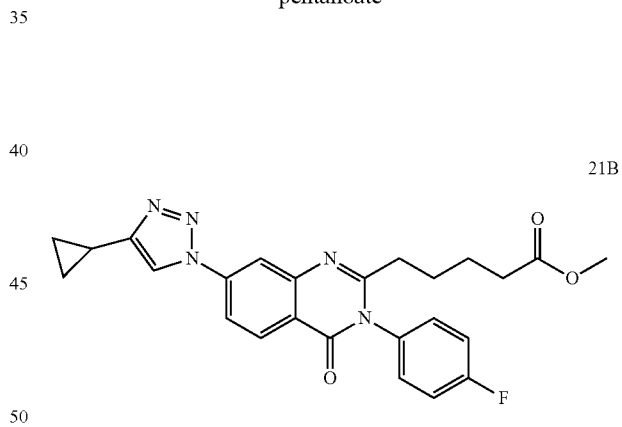

Step 1

Methyl 5-[7-azido-3-(4-fluorophenyl)-4-oxo-3,4-dihydroquinazolin-2-yl]pentanoate

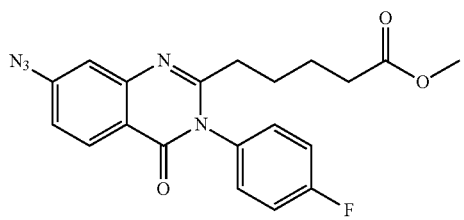

21A

Sodium azide (180 mg, 2.77 mmol) was added to a solution of methyl 5-(7-bromo-3-(4-fluorophenyl)-4-oxo-3,4-dihydroquinazolin-2-yl)pentanoate (2C, 200 mg, 0.46 mmol) in a 9:1 NMP (3 mL):water (0.33 mL) solvent system. The reaction was heated to 130° C. in the microwave for 5 hours. After the reaction cooled to 25° C., the mixture was partitioned between EtOAc and water. The organic layer was extracted with EtOAc (3×). Combined organic layers were washed with brine, dried over sodium sulfate and solvent was evaporated to yield 21A, which was used in the next step without further purification (200 mg, MS (M+H)=396).

Step 2

Methyl 5-[7-(4-cyclopropyl-1H-1,2,3-triazol-1-yl)-3-(4-fluorophenyl)-4-oxo-3,4-dihydroquinazolin-2-yl]pentanoate Methyl 5-[7-azido-3-(4-fluorophenyl)-4-oxo-3,4-dihydroquinazolin-2-yl]pentanoate (21A, 100 mg, 0.126 mmol) was dissolved in a 10:1 mixture of DMF (2 mL) and EtOH (0.2 mL). Sodium ascorbate (10 mg, 0.051 mmol) and cyclopropylacetylene (0.017 mL, 0.201 mmol) were added to the reaction, followed by copper (II) sulfate pentahydrate (6.3 mg, 0.025 mmol) in water (0.125 mL). Reaction stirred at 25° C. for 48 hours. A second batch of all reagents was added and reaction stirred again at 25° C. for 16 hours. Dilute ammonium hydroxide was added and the reaction was partitioned in a separatory funnel. The organic layer was extracted with EtOAc (3×), combined organic layers were washed with brine, dilute ammonium hydroxide, dried over sodium sulfate and solvent was evaporated. Material purified on a silica column (over a gradient of 0-50% EtOAc in hexanes to yield 21B (16.4 mg, Yield=28%), MS (M+H)=462.

Step 3

5-[7-(4-cyclopropyl-1H-1,2,3-triazol-1-yl)-3-(4-fluorophenyl)-4-oxo-3,4-dihydroquinazolin-2-yl]pentanoic acid In a manner similar to Example 18 (Step 2), compound 21B was treated with potassium trimethylsilanolate to provide 21. Yield=16%. MS (M+H)=448.

The following compounds were made following the procedure described above:

Preparative Example 22

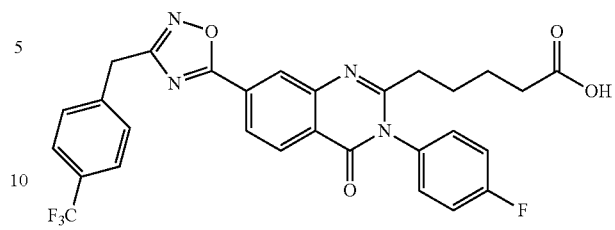

Step 1

N'-hydroxy-2-(4-(trifluoromethyl)phenyl)acetimidamide

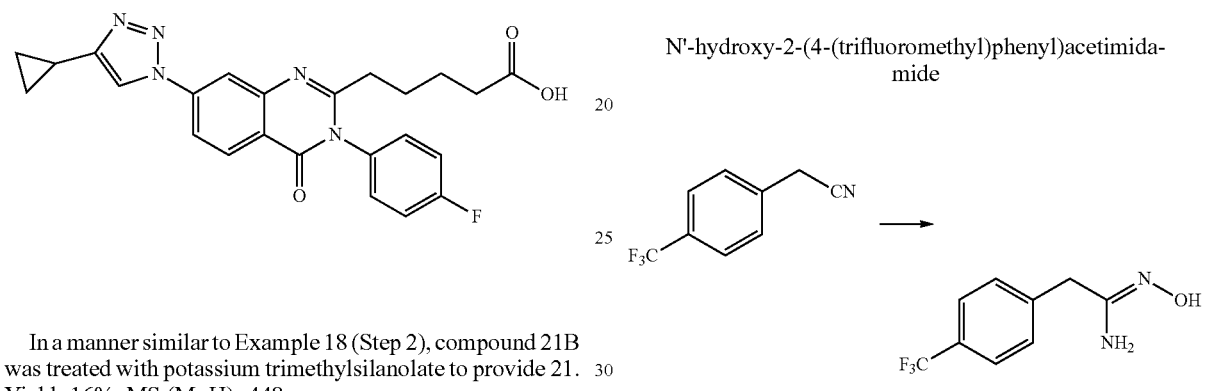

| Compound Number | Compound | M + H |
|---|---|---|
| 21C | | 466 |
| 21D | | 484 |
| 21E | | 498 |

Hydroxylamine hydrochloride (1.126 g, 16.20 mmol) was added at room temperature to a mixture of 4-trifluorobenzyl nitrile (1 g, 5.4 mmol) and potassium carbonate (4.48 g, 32.4 mmol) in MeOH (25 mL) and the mixture was stirred at room temperature overnight. TLC showed that a small amount starting material was left. The mixture was diluted with dichloromethane (100 mL), washed with water (2×20 mL), dried (MgSO$_4$), filtered and the solvent was evaporated under reduced pressure to give 22A as a brown yellow syrup.

Step 2 tert-butyl 5-(3-(4-fluorophenyl)-4-oxo-7-(3-(4-(trifluoromethyl)benzyl)-1,2,4-oxadiazol-5-yl)-3,4-dihydroquinazolin-2-yl)pentanoate

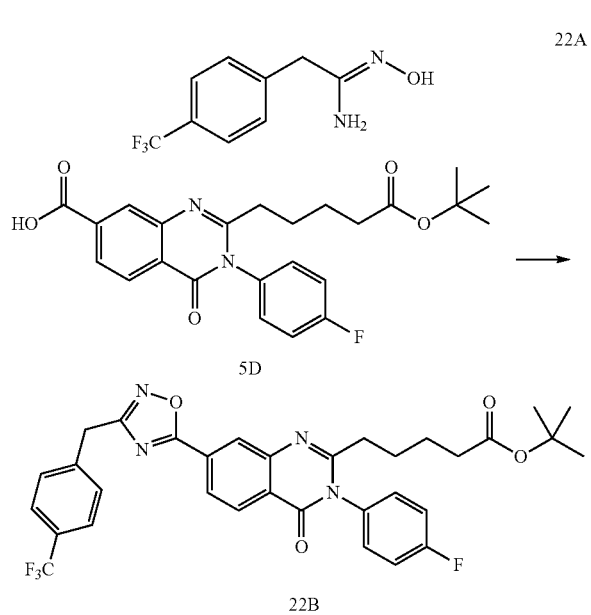

CDI (30.4 mg, 0.187 mmol) was added to a stirred, room temperature mixture of 5D (75 mg, 0.170 mmol) in DMF (1 mL) and the mixture was stirred at room temperature for 2 h. Reactant 22A (44.6 mg, 0.204 mmol) in DMF (0.5 mL) was added to the mixture and the resultant mixture was kept stirring at 80° C. for overnight. The mixture was cooled and was purified by column chromatography to provide 22B (94 mg).

Step 3

5-(3-(4-fluorophenyl)-4-oxo-7-(3-(4-(trifluoromethyl)benzyl)-1,2,4-oxadiazol-5-yl)-3,4-dihydroquinazolin-2-yl)pentanoic acid

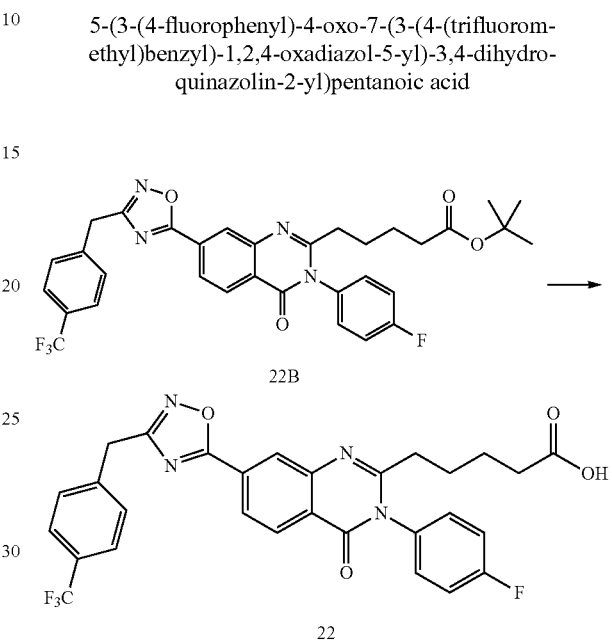

Compound 22B (90 mg, 0.145 mmol) was added to a stirred mixture of DCM (1.5 mL) and TFA (1.0 mL). The reaction was done in 2.5 hours as judged by LCMS. Solvent was removed and the crude was purified by column chromatography eluting with DCM/EtOAc to give compound 22 (82 mg). MS (M+H)=567.

The following compounds were made following the procedure described above:

| Compound Number | Compound | M + H |
|---|---|---|
| 22C | | 517 |
| 22D | | 529 |

| Compound Number | Compound | M + H |
|---|---|---|
| 22E | 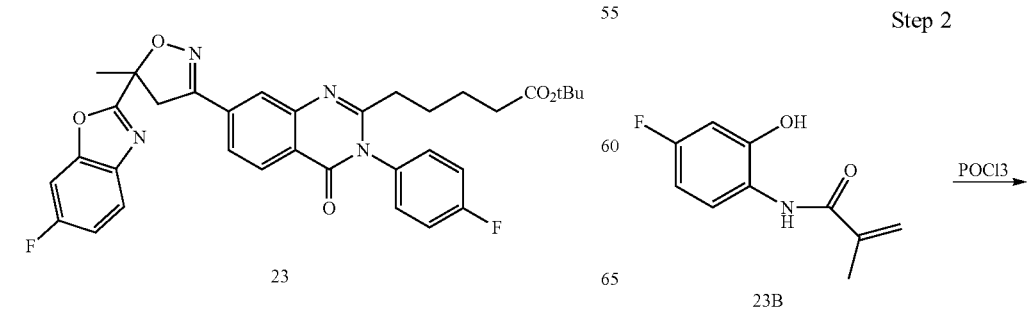 | 513 |

Preparative Example 23

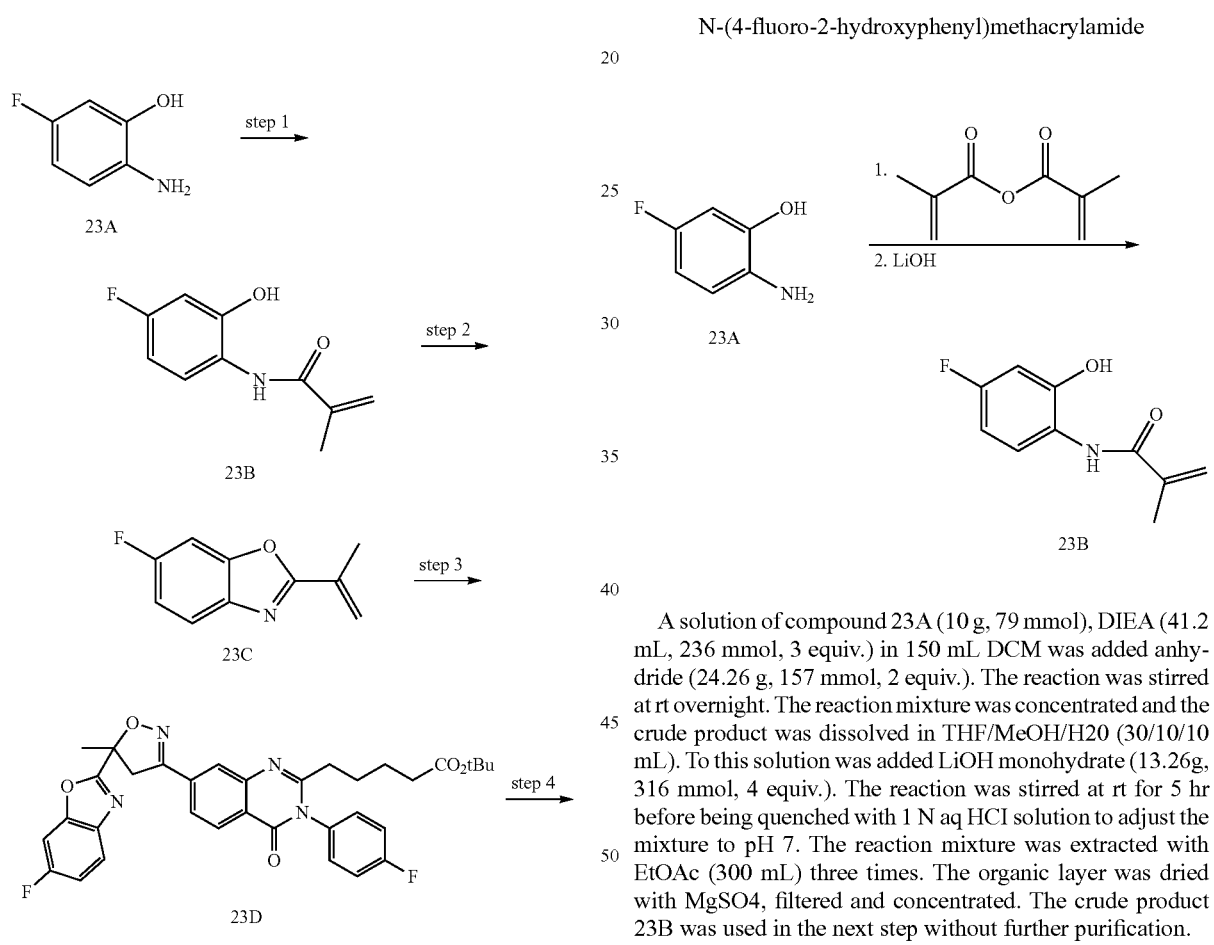

Step 1

N-(4-fluoro-2-hydroxyphenyl)methacrylamide

A solution of compound 23A (10 g, 79 mmol), DIEA (41.2 mL, 236 mmol, 3 equiv.) in 150 mL DCM was added anhydride (24.26 g, 157 mmol, 2 equiv.). The reaction was stirred at rt overnight. The reaction mixture was concentrated and the crude product was dissolved in THF/MeOH/H20 (30/10/10 mL). To this solution was added LiOH monohydrate (13.26g, 316 mmol, 4 equiv.). The reaction was stirred at rt for 5 hr before being quenched with 1 N aq HCl solution to adjust the mixture to pH 7. The reaction mixture was extracted with EtOAc (300 mL) three times. The organic layer was dried with MgSO4, filtered and concentrated. The crude product 23B was used in the next step without further purification.

Step 2

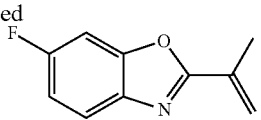

23C

A solution of 23B (7 g, 35.9 mmol) was heated in neat POCl₃ (20 mL) at 100° C. for 2 hr. The reaction was cooled to rt and concentrated to remove POCl₃. The residue was diluted with EtOAc and washed with 1 N aq. NaOH solution and then brine. The organic layer was dried with MgSO₄, filtered and concentrated. Column chromatography provided 23C as a brown solid (4 g, 63% yield).

Step 3

6-fluoro-2-(prop-1-en-2-yl)benzo[d]oxazole

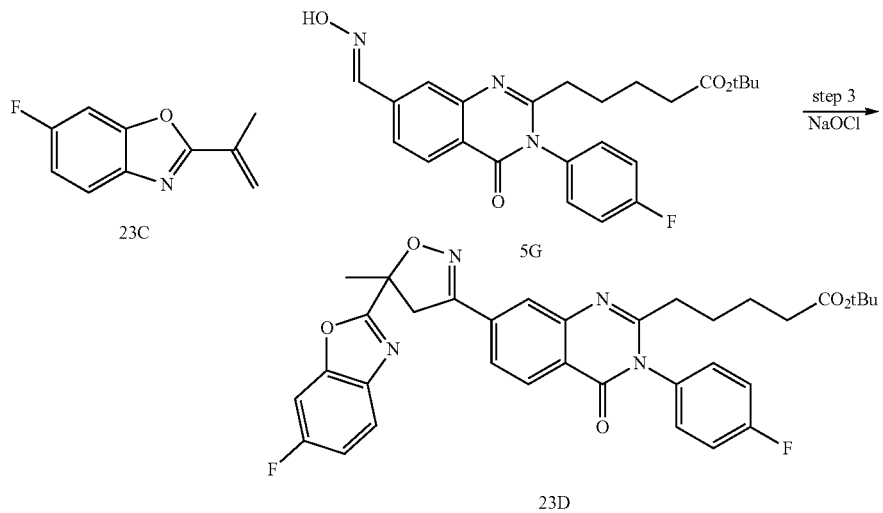

To a solution of 23C (3.14 g, 17.7 mmol) and 5G (5.28 g, 13.3 mmol) in DCM (100 mL) was added 4% NaOCl aq. solution 200 mL (4 equiv.). The reaction was stirred at rt overnight. The reaction was diluted with EtOAc and washed with water. The organic layer was concentrated. The residue was purified by silica gel column to yield 23D (8.63 g, 85%).

Step 4

5-(7-(5-(6-fluorobenzo [d]oxazol-2-yl)-5-methyl-4,5-dihydroisoxazol-3-yl)-3-(4-fluoropheny)-4-oxo-3,4-dihydroquinazolin-2-yl) pentanoic acid

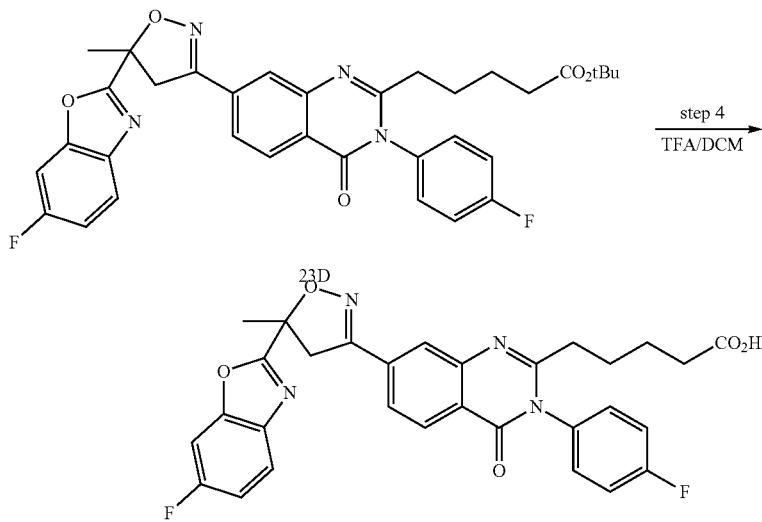

To 23D (1.05 g, 1.71 mmol) was added 10 mL 20% TFA DCM. The reaction was kept stirring for 12 h and evaporated to dryness. Silica gel column purification gave 23 (900 mg, 94%). $^1$H NMR (500 MHz, CD$_3$OD) δ 8.22 (d, J=8.0 Hz, 1H), 8.00-7.94 (m, 2H), 7.74 (dd, J=5.0, 9.0 Hz, 1H), 7.51-7.44 (m, 3H), 7.38-7.34 (m, 2H), 7.23-7.19 (m, 1H), 4.40 (d, J=17 Hz, 1H), 3.77 (d, J=17 Hz, 1H), 2.51 (t, J=7.5 Hz, 1H), 2.20 (t, J=7.0 Hz,), 1.78 (m, 2H), 1.59 (m, 2H). MS (M+H)=559.

Preparative Example 24

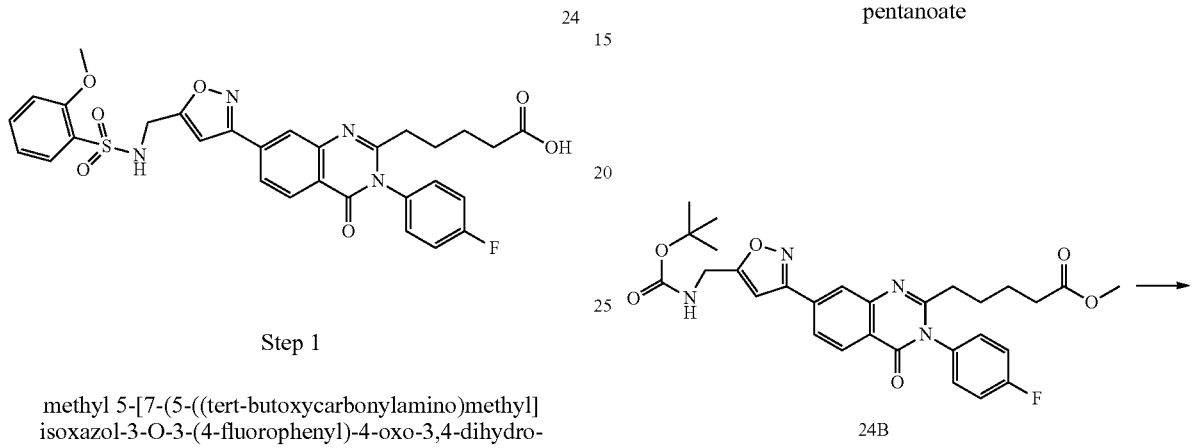

24

Step 1 methyl 5-[7-(5-((tert-butoxycarbonylamino)methyl] isoxazol-3-O-3-(4-fluorophenyl)-4-oxo-3,4-dihydro-quinazolin-2-yl)pentanoate A mixture of 15C (2.0 g, 5.03 mmol), 24A (2.34 g, 15.10 mmol) and NaOCl (14.99 g, 20.13 mmol) in CH$_2$Cl$_2$ (30 mL) was stirred at room temperature overnight. It was then diluted with CH$_2$Cl$_2$, washed with water, brine, dried over Na$_2$SO$_4$, filtered, concentrated and purified by flash column chromatography to give the product 24B (2.3 g, 4.18 mmol, 83%) as colorless oil.

Step 2 methyl 5-(7-(5-(aminomethyl)isoxazol-3-yl)-3-(4-fluorophenyl)-4-oxo-3,4-dihydroquinazolin-2-yl) pentanoate

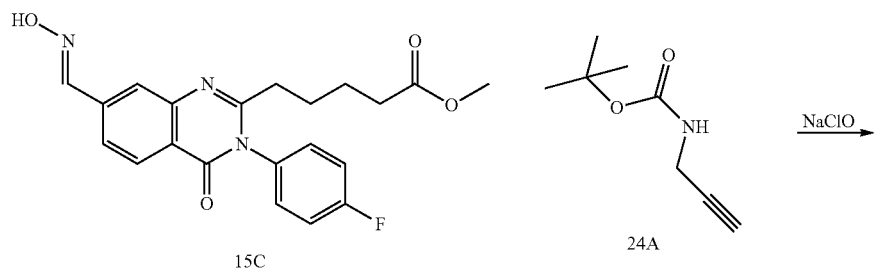

15C     24A

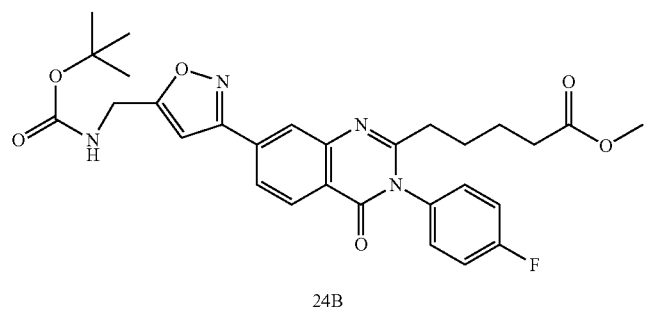

24B

-continued

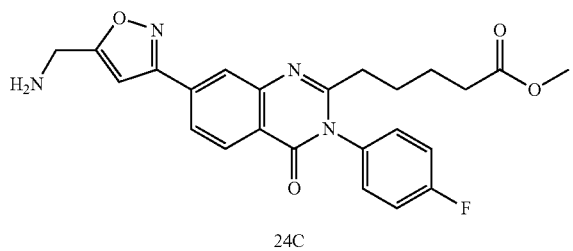

24C

A solution of 24B (140 mg, 0.25 mmol) in TFA (2 mL)/CH$_2$Cl$_2$ (2 mL) was stirred at room temperature for 3 h. Then the solvent was removed under vacuum and the residue product 24C was used in the next step without purification (110 mg, 96%).

Step 3 methyl 5-(3-(4-fluorophenyl)-7-(5-((2-methoxyphenylsulfonamido) methyl)isoxazol-3-yl)-4-oxo-3,4-dihydroquinazolin-2-yl)pentanoate

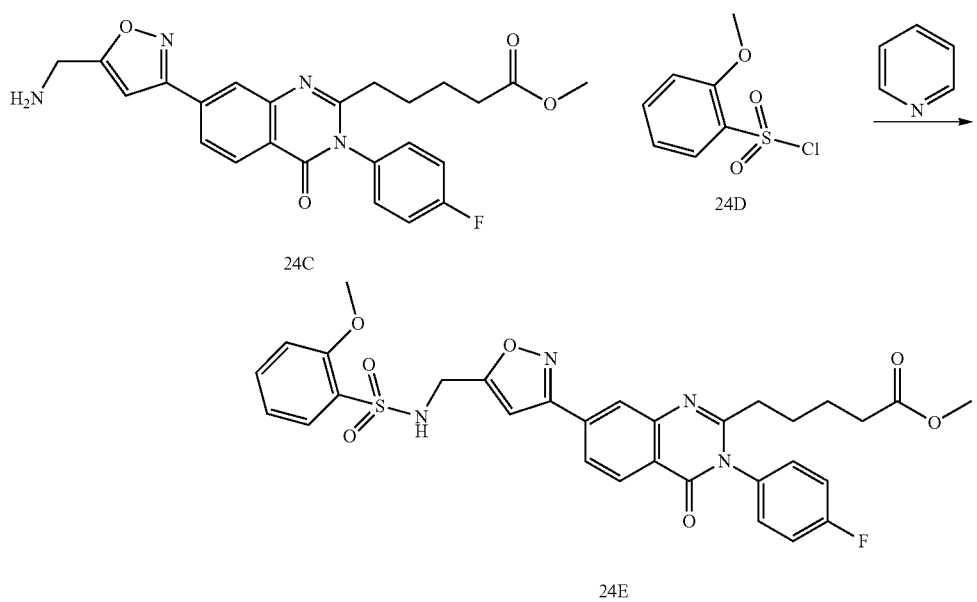

A mixture of 24C (56 mg, 0.124 mmol), 24D (38.5 mg, 0.186 mmol) and pyridine (0.050 mL, 0.622 mmol) in CH$_2$Cl$_2$ (2 mL) was stirred at room temperature overnight. It was then concentrated and the residue was purified by flash column to give the product 24E (65 mg, 0.105 mmol, 84%) as white powder.

Step 4

5-(3-(4-fluorophenyl)-7-(5-((2-methoxyphenylsulfonamido)methyl)isoxazol-3-yl)-4-oxo-3,4-dihydroquinazolin-2-yl)pentanoic acid

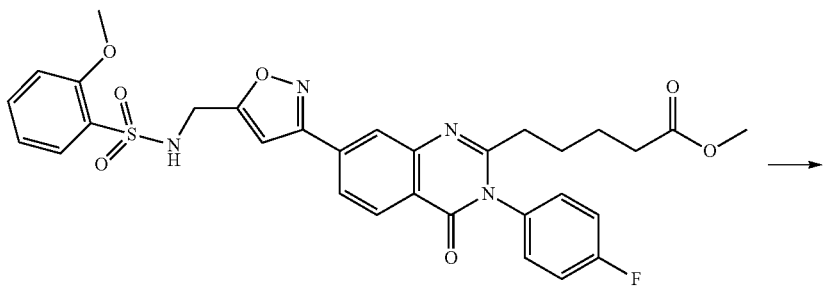

24E

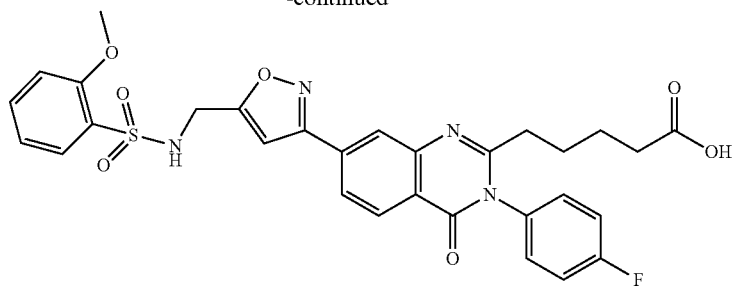
24
A solution of 24E (65 mg, 0.105 mmol) and LiOH (56%, 6.72 mg, 0.157 mmo) in THF (3 mL) and 1H$_2$O (1 mL) was stirred at room temperature overnight. It was then purified by reverse phase HPLC to give the product 24 (44 mg, 0.073 mmol, 69.3%) as white solid. MS (M−H)=607.
The following compounds were made in a similar manner to that described above:
| Cpd | Structure | MS (M + H$^+$) |
|---|---|---|
| 24F | 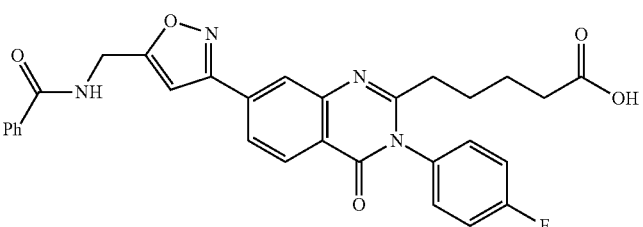 | 541 |
| 24G | 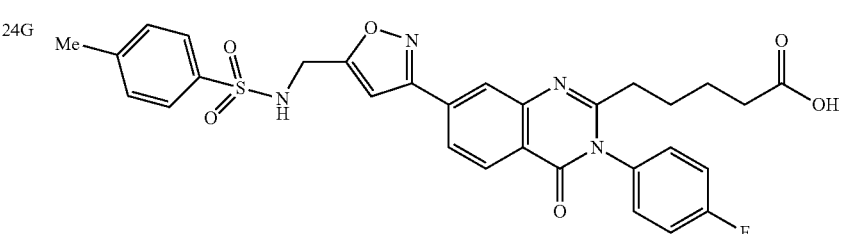 | 591 |
| 24H | 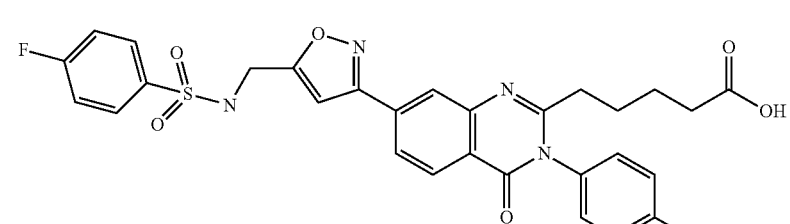 | 595 |
| 24i | 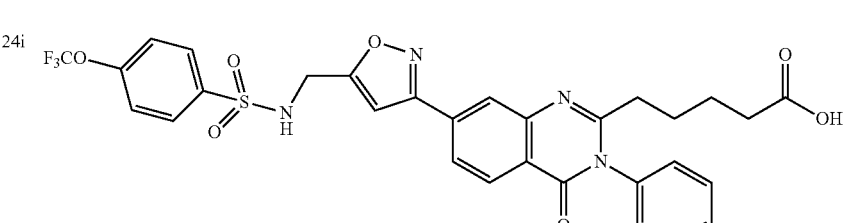 | 661 |

-continued

| Cpd | Structure | MS (M + H⁺) |
|---|---|---|
| 24J | 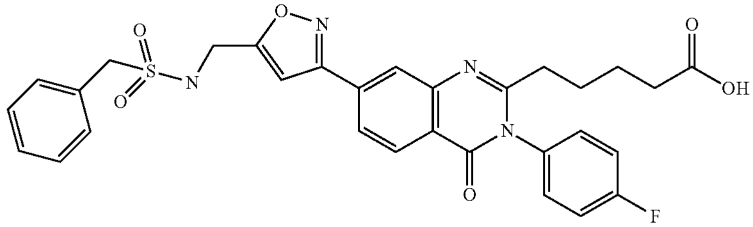 [SMILES: O=C(O)CCCCc1nc2cc(-c3cc(CNS(=O)(=O)Cc4ccccc4)on3)ccc2c(=O)n1-c1ccc(F)cc1] | 591 |
| 24K | 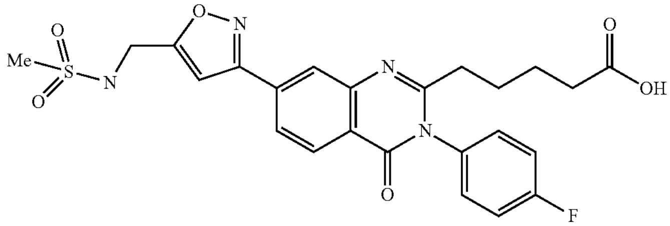 [SMILES: CS(=O)(=O)NCc1cc(-c2ccc3c(=O)n(-c4ccc(F)cc4)c(CCCCC(=O)O)nc3c2)no1] | 515 |
| 24L | 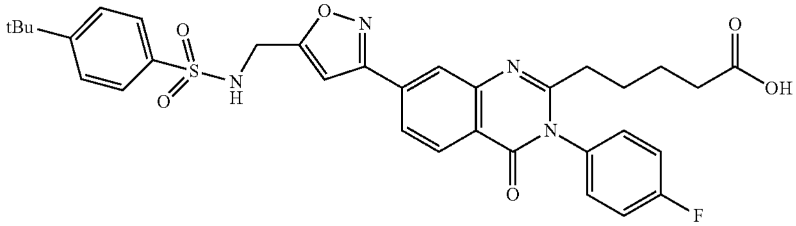 | 633 |
| 24M | 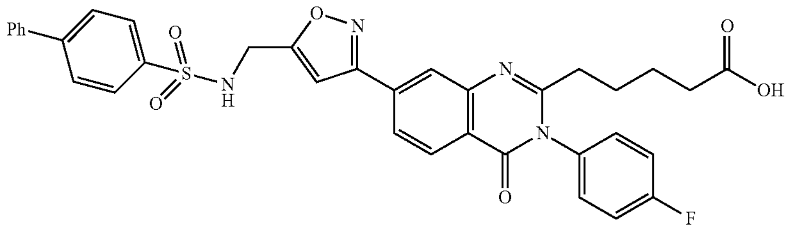 | 653 |
| 24N | 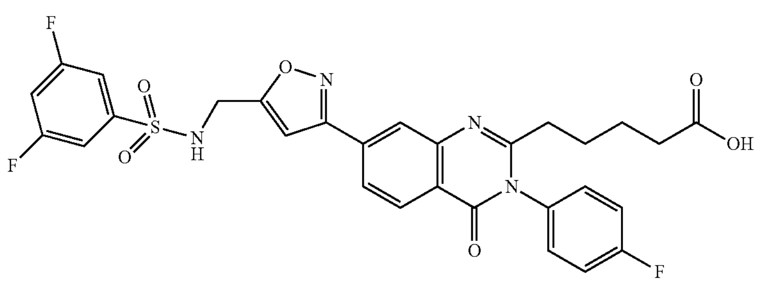 [SMILES: O=C(O)CCCCc1nc2cc(-c3cc(CNS(=O)(=O)c4cc(F)cc(F)c4)on3)ccc2c(=O)n1-c1ccc(F)cc1] | 613 |
| 24o | 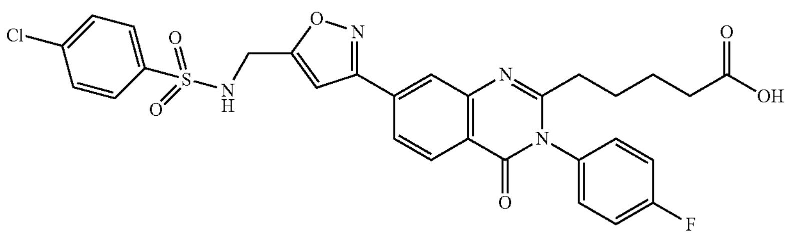 [SMILES: O=C(O)CCCCc1nc2cc(-c3cc(CNS(=O)(=O)c4ccc(Cl)cc4)on3)ccc2c(=O)n1-c1ccc(F)cc1] | 611 |

125 126
-continued

| Cpd | Structure | MS (M + H⁺) |
|---|---|---|
| 24P | 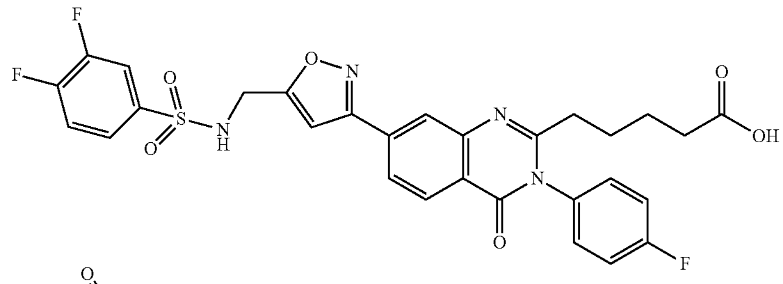 | 613 |
| 24Q | 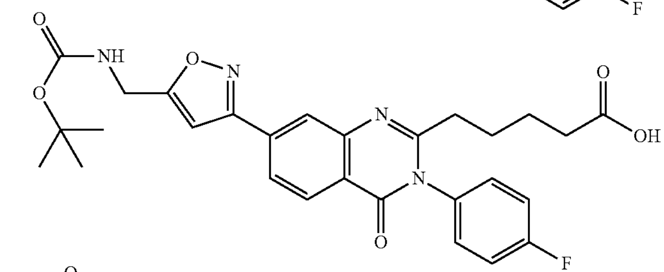 | 537 |
| 24R | 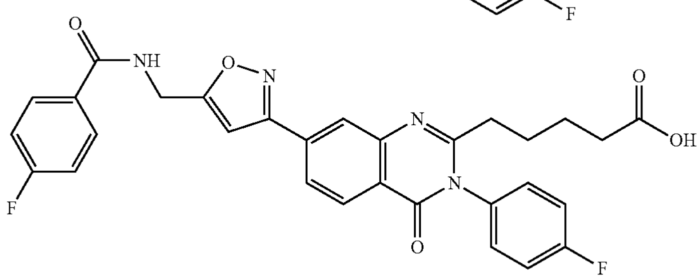 | 559 |

Preparative Example 25

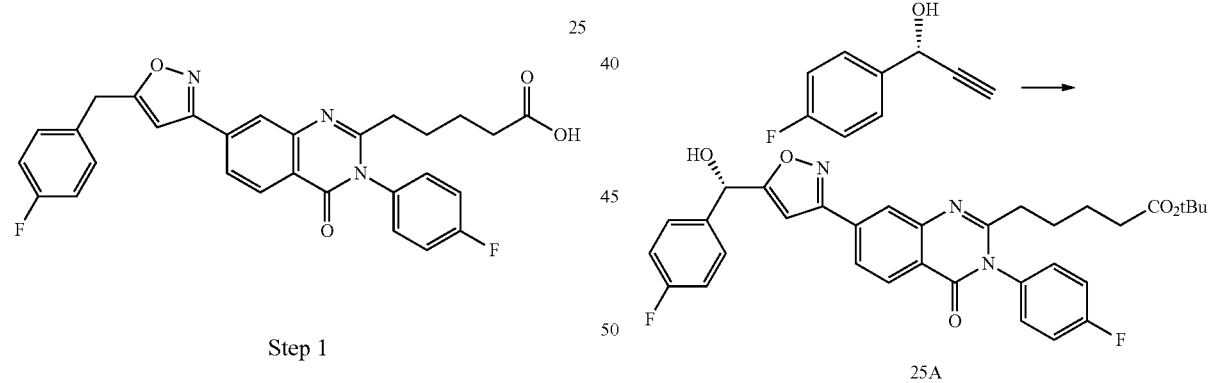

Step 1

(S)-tert-butyl 5-(3-(4-fluorophenyl)-7-(5-((4-fluorophenyl)(hydroxy)methyl)isoxazol-3-yl)-4-oxo-3,4-dihydroquinazolin-2-yl)pentanoate

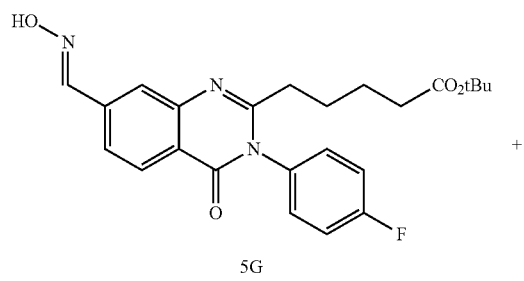

1-(4-Fluorophenyl)-prop-2-yn-1-ol was prepared from 4-fluorobenzaldehyde and ethynylmagesium bromide (−78° C. to room temperature overnight) in a manner similar to that described in the literature (i.e., Tetrahedron 2009, 65, 6320-6324). The enantiomers were separated by chiral SFC chromatography (Regis Technologies (S,S) Whelk-01 column, $CO_2$ with 10% iPA-hexane cosolvent).

A mixture of the oxime 5G (8.25 g, 18.77 mmol), (R)-1-(4-fluorophenyl)-prop-2-yn-1-ol (5.64 g, 37.5 mmol, second eluting peak from chiral SFC separation described above) and sodium hypochlorite (130 mL, 4% w/v, 75 mmol) was stirred at it in a sealed tube overnight. The reaction was diluted with EtOAc, washed with brine and water, dried over $Na_2SO_4$, filtered and concentrated. Chromatography (330 g silica, 0 to 40% EtOAc/Hexanes) provided 25A (4.6 g).

Step 2

5-(7-(5-(4-fluorobenzyl)isoxazol-3-yl)-3-(4-fluorophenyl)-4-oxo-3,4-dihydroquinazolin-2-yl)pentanoic acid

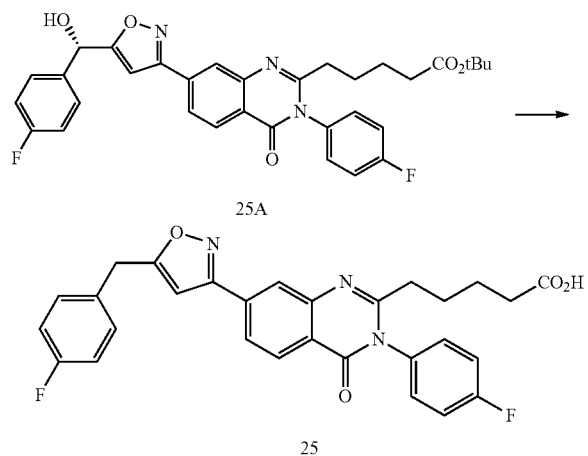

A mixture of 25A (4.6 g, 7.83 mmol) in 500 mL $CH_3CN$ was treated with NaI (11.73 g, 78 mmol) followed by TMSCl (10.01 ml, 78 mmol, via syringe) and stirred at 60° C. overnight. The reaction was diluted with EtOAc, washed with water and 10% aqueous $Na_2S_2O_3$, dried over $Na_2SO_4$, filtered and concentrated. Chromatography (330 g silica, 0 to 5% MeOH/$CH_2Cl_2$ 0 to 40% EtOAc/Hexanes) provided 25 (4.11 g). The free acid was converted to the sodium salt (MeOH, 1M NaOH). MS (M+H)=516. HNMR (500 MHz, DMSO): 8.2 (2H, m), 8.0 (1H, d), 7.05 (2H, m), 7.4 (4H, m), 7.2 (2H, t), 7.1 (1H, s), 4.25 (2H, s), 2.35 (2H, t), 1.75 (2H, t), 1.6 (2H, m), 1.3 (2H, m)

Alternatively, compound 25A was converted to compound 25B by treatment with TFA as previously described. MS (M+H)=532.

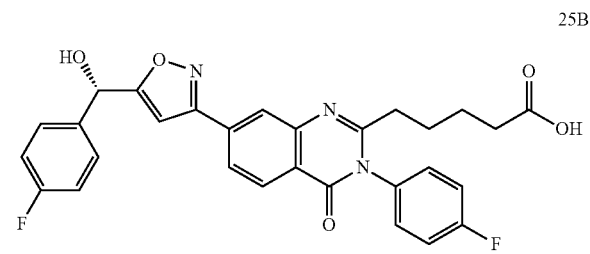 [SMILES: O=C(O)CCCCc1nc2cc(-c3cc([C@@H](O)c4ccc(F)cc4)on3)ccc2c(=O)n1-c1ccc(F)cc1]

In a manner similar to that described above, the following compounds were also prepared.

| Cpd | Structure | MS (M + H+) |
|---|---|---|
| 25C | <img> | 532 |
| 25D | <img> | 514 |
| 25E | <img> | 514 |

| Cpd | Structure | MS (M + H+) |
|---|---|---|
| 25F | 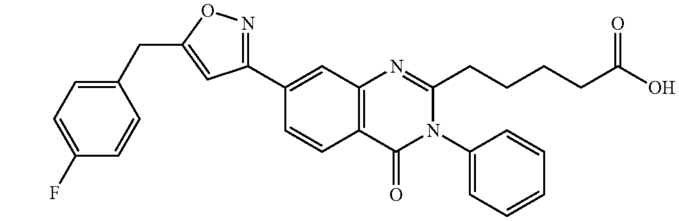 [SMILES: O=C(O)CCCCc1nc2cc(-c3cc(Cc4ccc(F)cc4)on3)ccc2c(=O)n1-c1ccccc1] | 498 |
| 25G | Enantiomer 1 | 565 |
| 25H | Enantiomer 2 | 565 |
| 25i | 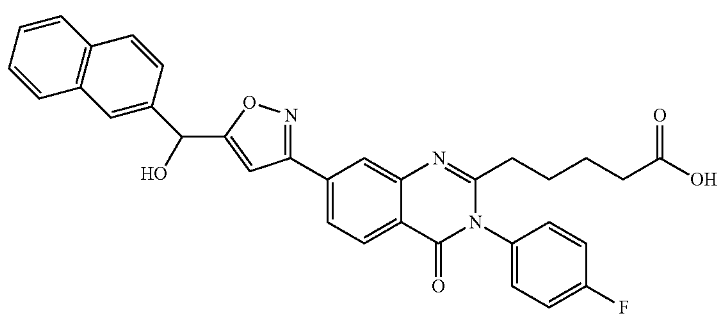 [SMILES: O=C(O)CCCCc1nc2cc(-c3cc(C(O)c4ccc5ccccc5c4)on3)ccc2c(=O)n1-c1ccc(F)cc1] | 564 |
| 25J | 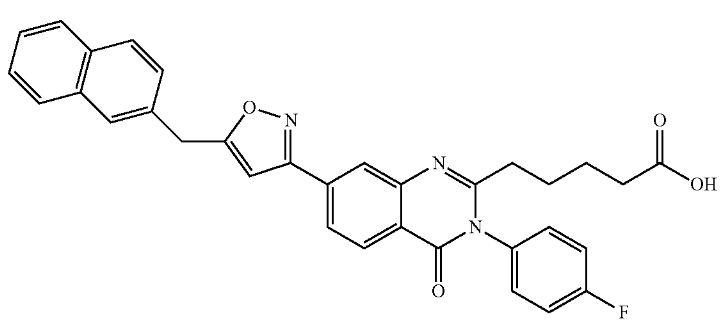 [SMILES: O=C(O)CCCCc1nc2cc(-c3cc(Cc4ccc5ccccc5c4)on3)ccc2c(=O)n1-c1ccc(F)cc1] | 548 |

| Cpd | Structure | MS (M + H+) |
|---|---|---|
| 25K | 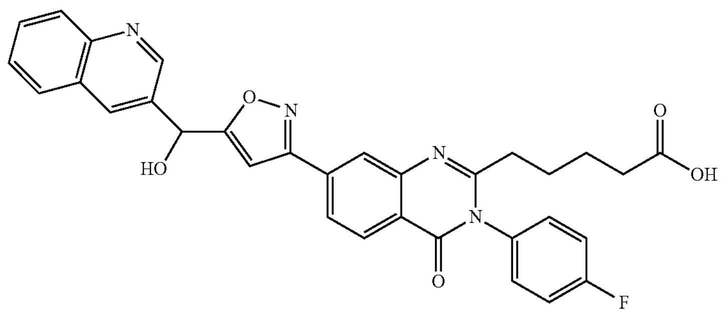 [SMILES: O=C(O)CCCCc1nc2cc(-c3cc(C(O)c4cnc5ccccc5c4)on3)ccc2c(=O)n1-c1ccc(F)cc1] | 564 |
| 25L | 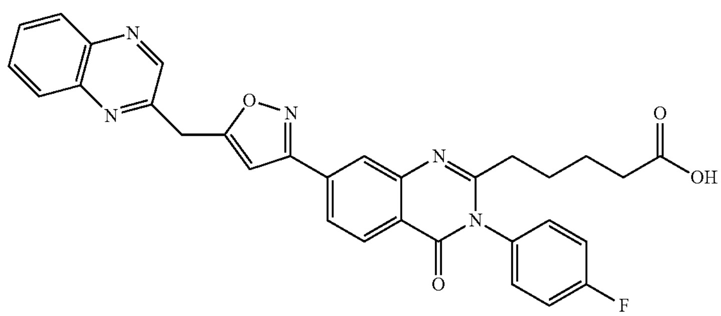 [SMILES: O=C(O)CCCCc1nc2cc(-c3cc(Cc4cnc5ccccc5n4)on3)ccc2c(=O)n1-c1ccc(F)cc1] | 550 |
| 25M | 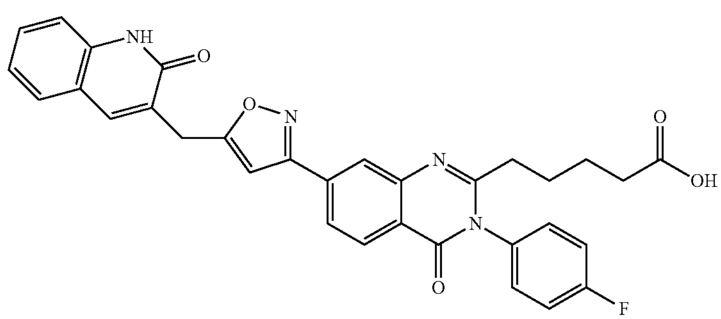 [SMILES: O=C(O)CCCCc1nc2cc(-c3cc(Cc4cc5ccccc5[nH]c4=O)on3)ccc2c(=O)n1-c1ccc(F)cc1] | 564 |
Preparative Example 26
Step 1
tert-butyl 5-(3-(4-fluorophenyl)-7-OR)-5-((S)-hydroxy(phenyl)methyl)-5-methyl-4,5-dihydroisoxazol-3-yl)-4-oxo-3,4-dihydroquinazolin-2-yl) pentanoate
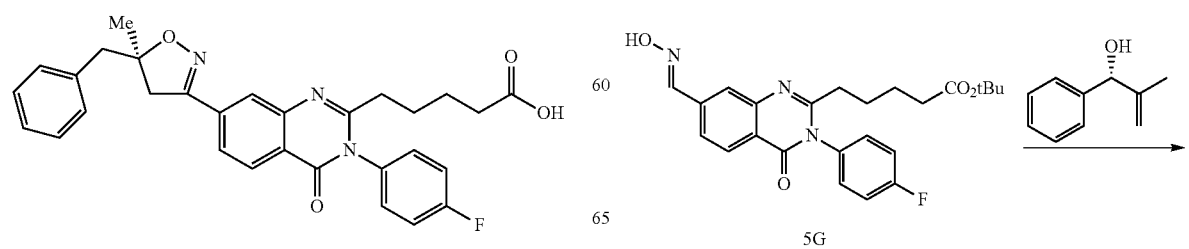

-continued

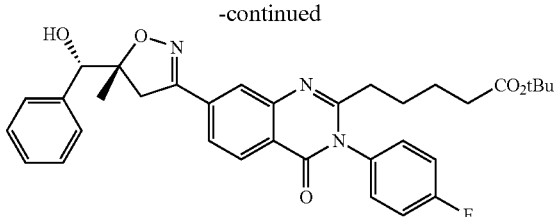

26A

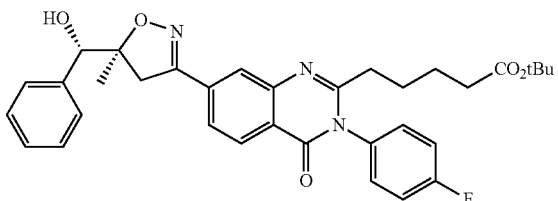

26B

Commercially available 2-methyl-1-phenylprop-2-en-1-ol was subjected to chiral SFC chromatography (Chiral Technologies Chiracel OD-H column, $CO_2$ with 10% cosolvent comprising 50% EtOH-hexanes) to provide the pure enantiomers.

A mixture of the oxime 5G (1.5 g, 3.41 mmol), (R)-2-methyl-1-phenylprop-2-en-1-ol (1st eluting peak from chiral SFC chromatography described above, 1.01 g, 6.83 mmol) and sodium hypochlorite (4% w/v, 23.6 mL, 13.65 mmol) was stirred at it overnight. The reaction was diluted with EtOAc, washed with brine and water, dried over $Na_2SO_4$, filtered and concentrated. Chromatography (330 g silica, 0 to 50% EtOAc/Hexanes) provided 26B (630 mg) and 26A.

Step 2

5-(3-(4-fluorophenyl)-7-(S)-5-((S)-hydroxy(phenyl)methyl)-5-methyl-4,5-dihydroisoxazol-3-yl)-4-oxo-3,4-dihydroquinazolin-2-yl)pentanoic acid

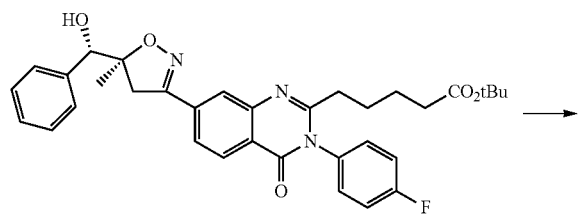

26B

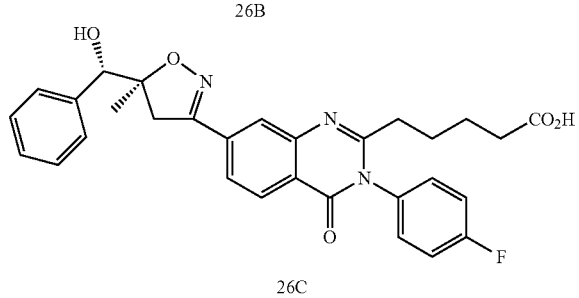

26C

A solution of 26B (630 mg, 1.08 mmol) and TFA (10 mL) was stirred at it for 3 h. The reaction was concentrated and the concentrate was purified by column chromatography (0-5% MeOH/$CH_2Cl_2$) to give 26C as a white solid (460 mg). MS (M+H)=530.

Step 3

(R)-5-(7-(5-benzyl-5-methyl-4,5-dihydroisoxazol-3-yl)-3-(4-fluorophenyl)-4-oxo-3,4-dihydroquinazolin-2-yl)pentanoic acid

26C

26

A mixture of compound 26C (450 mg, 0.850 mmol), red phosphorous (526 mg, 17.0 mmol) and iodine (1.294 g, 5.10 mmol) in AcOH/$H_2O$(8 mL/0.8 mL) in a sealed tube was heated at 120° C. for 3 hrs. The reaction was cooled to rt, diluted with EtOAc and 50 mL of 10% $Na_2S_2O_3$, and filtered. The precipitate was washed with EtOAc. The organic filtrate was washed once with water $H_2O$, dried over $Na_2SO_4$, filtered and concentrated. Chromatography (0-5% MeOH/$CH_2Cl_2$) gave 26 as a white solid (240 mg). MS (M+H)=514. HNMR (500 MHz, $CDCl_3$): 8.2 (1H, d), 7.9 (1H, d), 7.7 (1H, s), 7.2-7.3 (9H, m), 3.35 (1H, d), 3.1-3.2 (1H, d), 3.0-3.1 (2H, d), 2.45 (2H, t), 2.35 (2H, t), 1.8 (2H, m), 1.65 (2H, m), 1.55 (3H, s).

In a manner similar to that described above, the following compounds were also prepared.

| Cpd | Structure | MS (M + H+) |
|---|---|---|
| 26D | 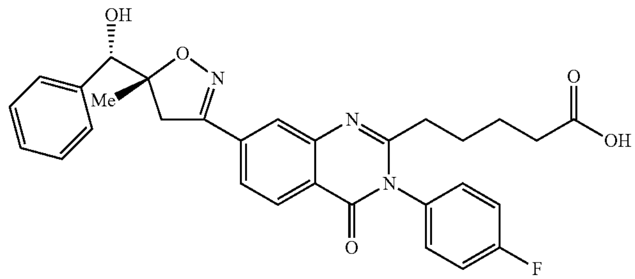 [SMILES: C[C@]1([C@@H](O)c2ccccc2)CC(c2ccc3c(=O)n(-c4ccc(F)cc4)c(CCCCC(=O)O)nc3c2)=NO1] | 530 |
| 26E | 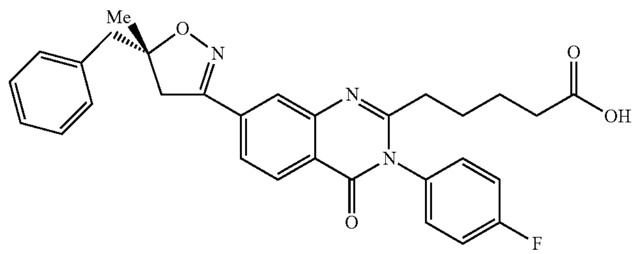 [SMILES: C[C@]1(Cc2ccccc2)CC(c2ccc3c(=O)n(-c4ccc(F)cc4)c(CCCCC(=O)O)nc3c2)=NO1] | 514 |
| 26F | 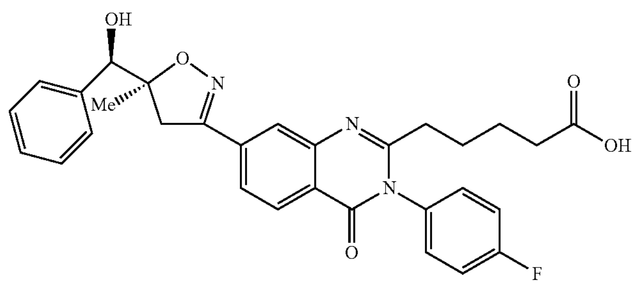 [SMILES: C[C@@]1([C@H](O)c2ccccc2)CC(c2ccc3c(=O)n(-c4ccc(F)cc4)c(CCCCC(=O)O)nc3c2)=NO1] | 530 |
| 26G | 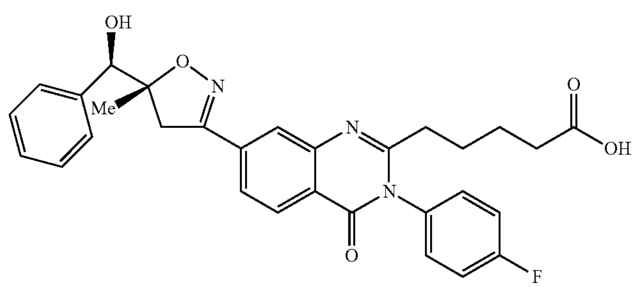 [SMILES: C[C@]1([C@H](O)c2ccccc2)CC(c2ccc3c(=O)n(-c4ccc(F)cc4)c(CCCCC(=O)O)nc3c2)=NO1] | 530 |
| 26H | 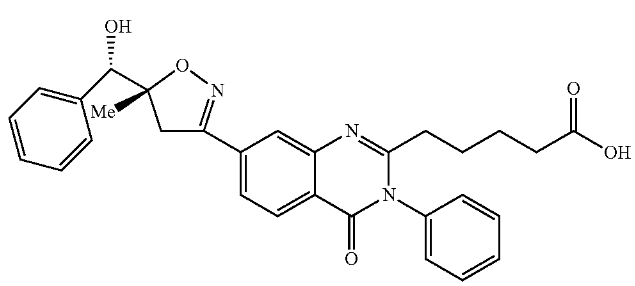 [SMILES: C[C@]1([C@@H](O)c2ccccc2)CC(c2ccc3c(=O)n(-c4ccccc4)c(CCCCC(=O)O)nc3c2)=NO1] | 512 |

-continued

| Cpd | Structure | MS (M + H⁺) |
|---|---|---|
| 26i | 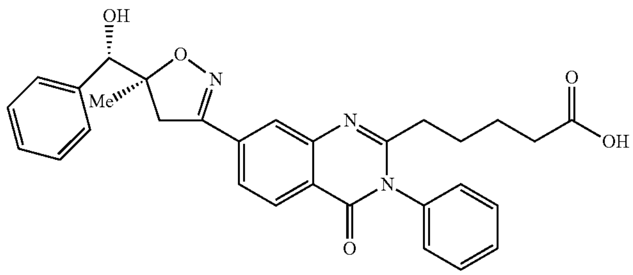 [SMILES: C[C@@]1([C@@H](O)c2ccccc2)CC(c2ccc3c(=O)n(-c4ccccc4)c(CCCCC(=O)O)nc3c2)=NO1] | 512 |
| 26J | 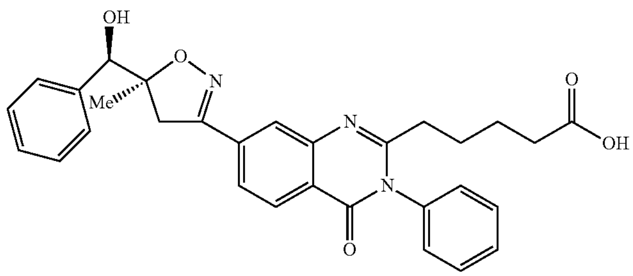 [SMILES: C[C@@]1([C@H](O)c2ccccc2)CC(c2ccc3c(=O)n(-c4ccccc4)c(CCCCC(=O)O)nc3c2)=NO1] | 512 |
| 26K | 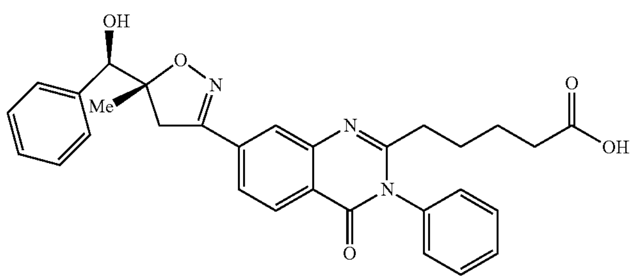 [SMILES: C[C@]1([C@H](O)c2ccccc2)CC(c2ccc3c(=O)n(-c4ccccc4)c(CCCCC(=O)O)nc3c2)=NO1] | 512 |
| 26L | 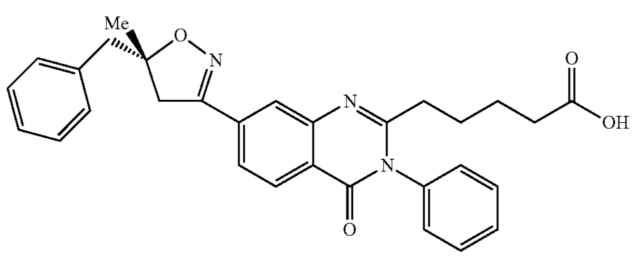 [SMILES: C[C@]1(Cc2ccccc2)CC(c2ccc3c(=O)n(-c4ccccc4)c(CCCCC(=O)O)nc3c2)=NO1] | 496 |
| 26M | 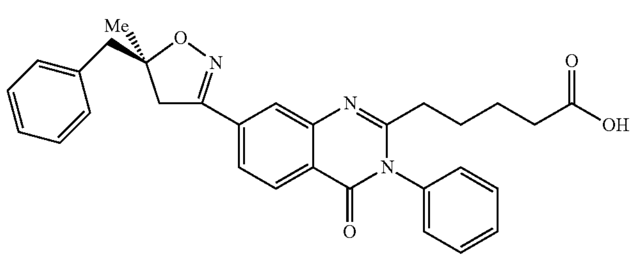 [SMILES: C[C@@]1(Cc2ccccc2)CC(c2ccc3c(=O)n(-c4ccccc4)c(CCCCC(=O)O)nc3c2)=NO1] | 496 |

Preparative Example 27

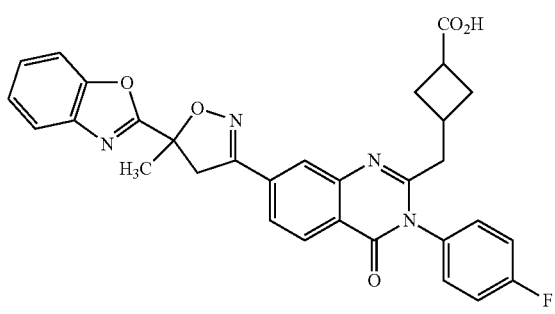

Step 1 methyl 2-((3-(tert-butoxycarbonyl)cyclobutyl)methyl)-3-(4-fluorophenyl)3-(4-oxo-3,4-dihydro-quinazoline-7-carboxylate

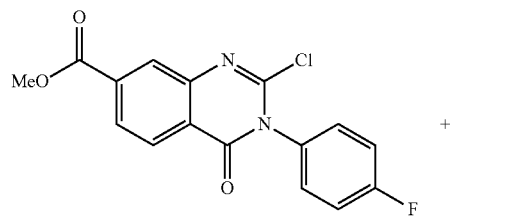

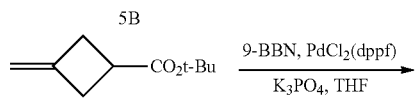

A stirred solution of tert-butyl 3-methylenecyclobutanecarboxylate 27A (0.254 g, 1.51 mmol, 1.5 equiv, prepared from 3-methylidenecyclobutane-carboxylic acid, TFAA, and tBuOH) in THF (1 mL) under nitrogen was cooled to 0° C. 9-BBN (0.5 N in THF, 3.60 mL, 1.81 mmol, 1.8 equiv) was added and the solution was heated to 60° C. for 3 h. After this time, the reaction mixture was cooled to room temperature and methyl 2-chloro-3-(4-fluorophenyl)-4-oxo-3,4-dihydro-quinazoline-7-carboxylate 5B (300 mg, 1.00 mmol), Pd(dppf)Cl$_2$.CH$_2$Cl$_2$ (163 mg, 0.20 mmol, 20 mol %) and K$_3$PO$_4$ (637 mg, 3.00 mmol, 3.0 equiv) were added. The reaction mixture was degassed and heated at 60° C. under nitrogen for 12 h. After this time, the reaction was cooled to room temperature and diluted with water and CH$_2$Cl$_2$. The aqueous layer was separated and extracted with CH$_2$Cl$_2$ (2×15 mL), dried over Na$_2$SO$_4$, filtered and concentrated. The residue was purified by flash chromatography (10-15% EtOAc/hexanes) to yield 200 mg of the desired product 27B.

Step 2 tert-butyl 3-((3-(4-fluorophenyl)-7-formyl-4-oxo-3,4-dihydroquinazolin-2-yl)methyl)cyclobutanecarboxylate

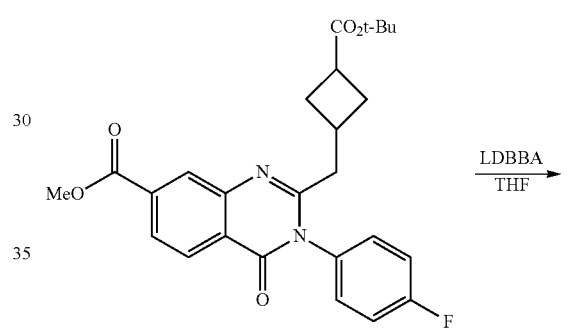

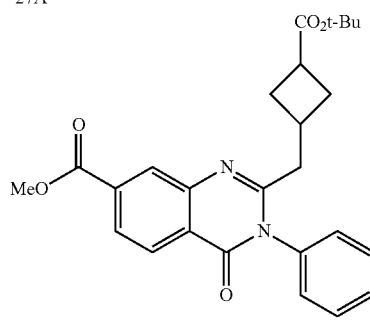

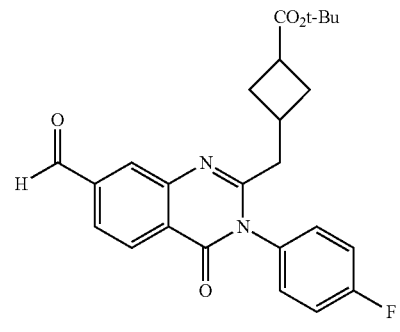

To a mixture of compound 27B (0.714 g, 1.53 mmol) in THF (5 mL) at 0° C. was added lithium diisobutyl-t-butoxyaluminum hydride (LDBBA, 0.25 N in THF/hex, 7.35 mL, 1.84 mmol, 1.2 equiv). After stirring at that temperature for 3 h, a saturated solution of Na$_2$SO$_4$ (2 mL) and CELITE were added and allowed to stir overnight. The reaction mixture was filtered and extracted with CH$_2$Cl$_2$ (2×10 mL), washed with brine, dried over Na$_2$SO$_4$, filtered and evaporated to dryness.

The residue was purified by flash chromatography (10-30% EtOAc/hexanes) to yield 0.5 g of compound 27C as an off-white solid.

Step 3 tert-butyl 3-((3-(4-fluorophenyl)-7-((hydroxyimino)methyl)-4-oxo-3,4-dihydroquinazolin-2-yl)methyl)cyclobutanecarboxylate

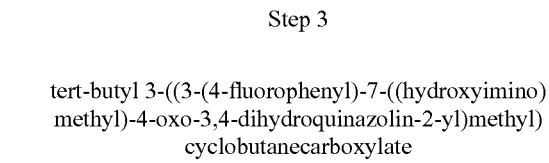

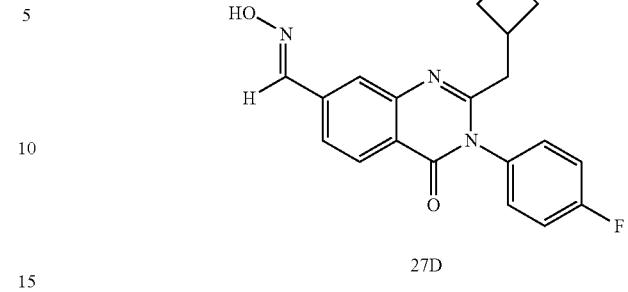

Hydroxylamine hydrochloride (159 mg, 2.291 mmol) was added to a stirred mixture of Compound 27C (200 mg, 0.458 mmol) and Hunig's base (DIPEA, 800 µl, 4.58 mmol) in THF (2 mL) and the mixture was stirred at room temperature overnight. After the reaction was complete, 0.1 N HCl solution (5 mL) was added the reaction mixture was extracted with $CH_2Cl_2$ (2×10 mL), washed with brine, dried over $Na_2SO_4$, filtered and evaporated to dryness to yield 200 mg of the desired product 27D. The product was used as such without any further purification.

Step 4 tert-butyl 3-((7-(5-(benzo[d]oxazol-2-yl)-5-methyl-4,5-dihydroisoxazol-3-yl)-3-(4-fluorophenyl)-4-oxo-3,4-dihydroquinazolin-2-yl)methyl)cyclobutanecarboxylate

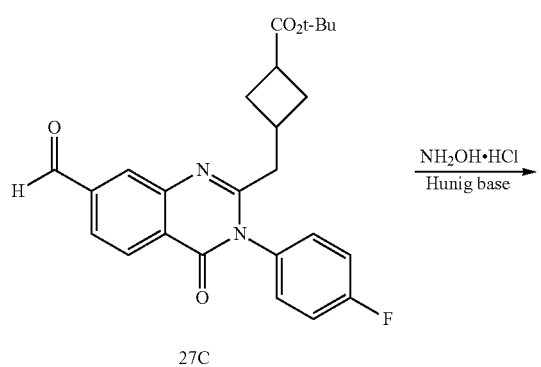

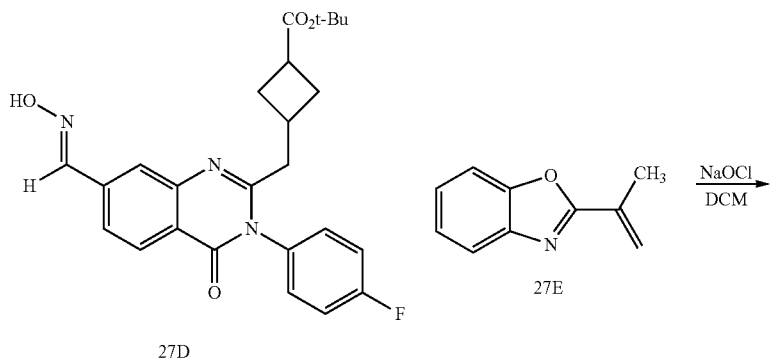

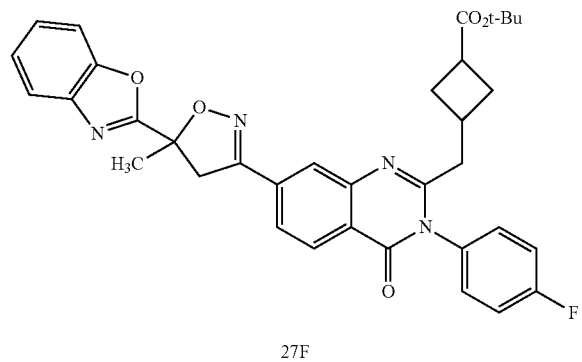

Sodium hypochlorite (2.0 mL, 1.36 mmol, 4.0 equiv) was added to a stirred mixture of oxime 27D (158 mg, 0.34 mmol) and 2-isopropenylbenzoxazole 27E (84 mg, 0.52 mmol, 1.5 equiv) in CH₂Cl₂ and the mixture was vigorously stirred at room temperature overnight. After the reaction was complete, water (5 mL) was added the reaction mixture was extracted with CH₂Cl₂ (2×10 mL), washed with brine, dried over Na₂SO₄, filtered and evaporated to dryness. The residue was purified by flash chromatography (10-40% EtOAc/hexanes) to yield 113 mg of compound 27F as a yellow oil.

Step 5

3-((7-(5-(benzo[d]oxazol-2-yl)-5-methyl-4,5-dihydroisoxazol-3-yl)-3-(4-fluorophenyl)-4-oxo-3,4-dihydroquinazolin-2-yl)methyl)cyclobutanecarboxylic acid

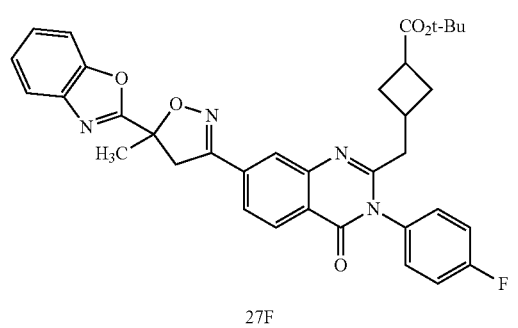

To a mixture of Compound 27F (50 mg, 0.08 mmol) in 2 mL CH₂Cl₂ was added TFA (54 µL, 0.8 mmol, 10.0 equiv). The reaction mixture was stirred at room temperature for 2 h after which the excess TFA was evaporated. Purification by preparative TLC (10% MeOH/DCM) yielded 25 mg of the desired product 27 as a white solid. MS (M+H)=553.

Preparative Example 28

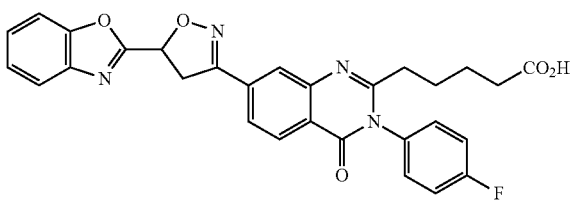

Step 1

2-Vinylbenzoxazole

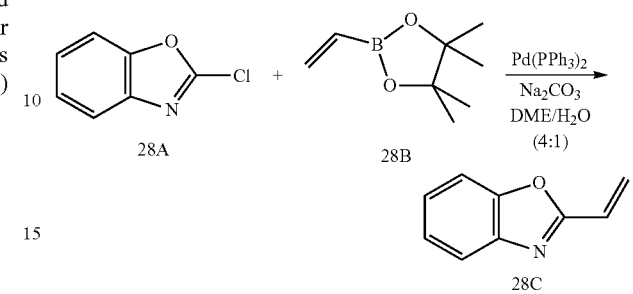

A mixture of 2-chlorobenzo[d]oxazole 28A (1 g, 6.51 mmol), 4,4,5,5-tetramethyl-2-vinyl-1,3,2-dioxaborolane 28B (2.006 g, 13.02 mmol), tetrakis (0.752 g, 0.651 mmol) and Na₂CO₃ (2.071 g, 19.54 mmol) in DME (10 mL) and water (2.500 mL) was heated at 80° C. for 5 h. After cooling to room temperature, the crude was purified by flash chromatography eluting with 0-4% EtOAc/hexanes to yield compound 28C as a brown oil.

Steps 2-3

5-(7-(5-(benzo[d]oxazol-2-yl)-4,5-dihydroisoxazol-3-yl)-3-(4-fluorophenyl)-4-oxo-3,4-dihydroquinazolin-2-yl)pentanoic acid

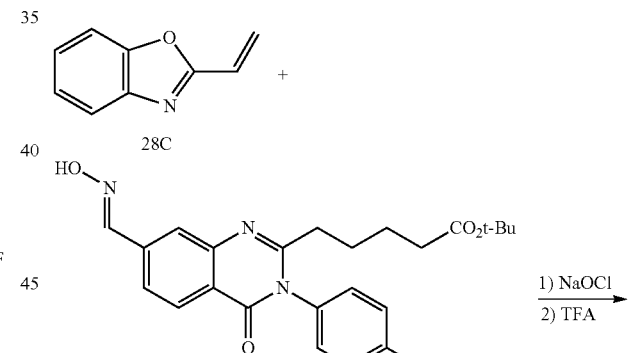

In a manner similar to that previously described, 28C was converted to compound 28 (MS (M+H)=527) which was subsequently subjected to chiral SFC chromatography (Chiral Technologies Chiralpak OJ-H column, CO₂ with 50% EtOH cosolvent) to provide the pure enantiomers 28D (second eluting fraction, MS (M+H)=527) and 28E (first eluting fraction, MS (M+H)=527).

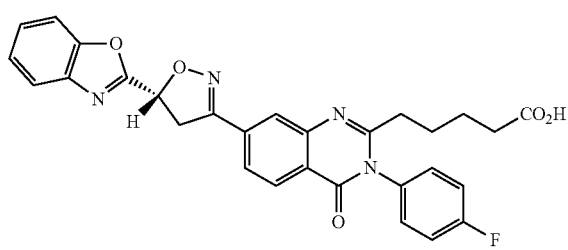

28D

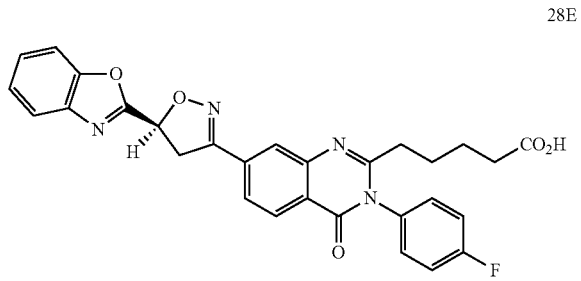

28E

Preparative Example 29

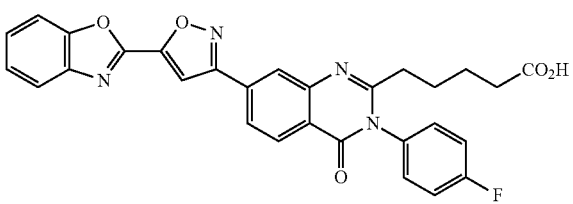

29

Step 1

2-((trimethylsilyl)ethynyl)benzo[d]oxazole

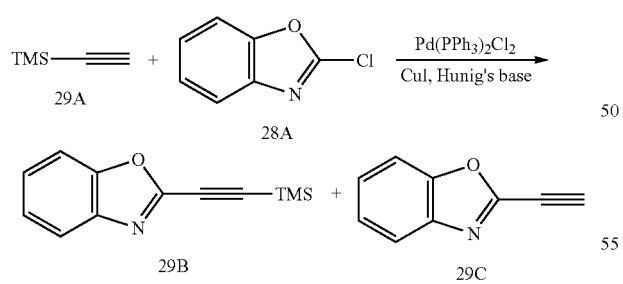

A mixture of bis(triphenylphosphine)palladium(II) chloride (0.229 g, 0.326 mmol), triethylamine (1.815 mL, 13.02 mmol), copper(I) iodide (0.124 g, 0.651 mmol), trimethylsilylacetylene (29A, 1.645 mL, 11.72 mmol) and compound 28A (1.0 g, 6.51 mmol) in dichloroethane (10 mL) under an inert atmosphere was heated at 80° C. overnight. After the reaction was complete, the mixture was cooled, diluted with dichloromethane (10 mL), washed with aq. NaHCO$_3$, dried (Na$_2$SO$_4$), filtered and the solvent was evaporated under reduced pressure. The residue was purified by column chromatography on silica gel eluting with 0-5% EtOAc/hexanes to give a mixture of Compound 29B (575 mg) and Compound 29C (200 mg).

Steps 2-3

In a manner similar to that previously described, 29B was converted to compound 29 (MS (M+H)=525

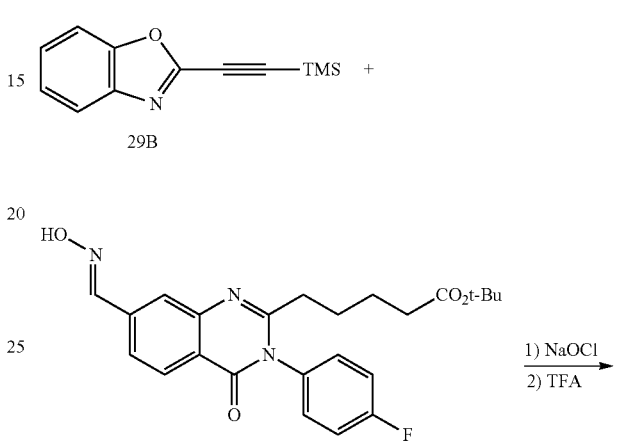

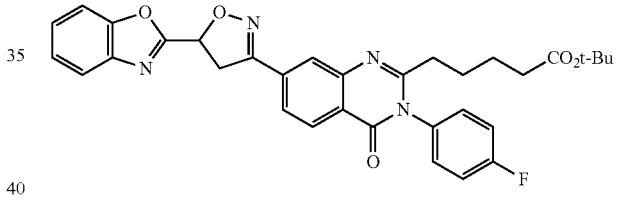

29

Preparative Example 30

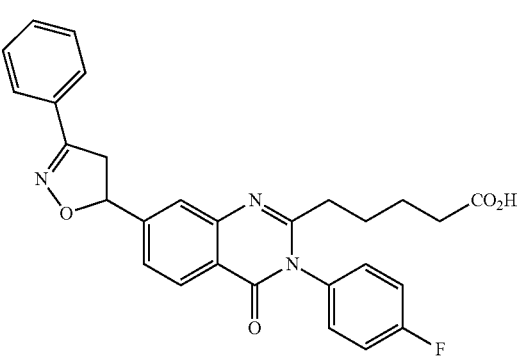

30

Step 1 methyl 5-(3-(4-fluorophenyl)-4-oxo-7-(3-phenyl-4,5-dihydroisoxazol-5-yl)-3,4-dihydroquinazolin-2-yl)pentanoate

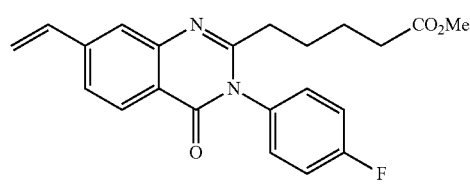

15A

+

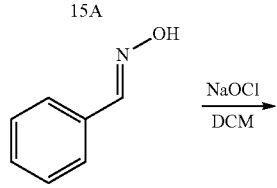

30A

NaOCl / DCM

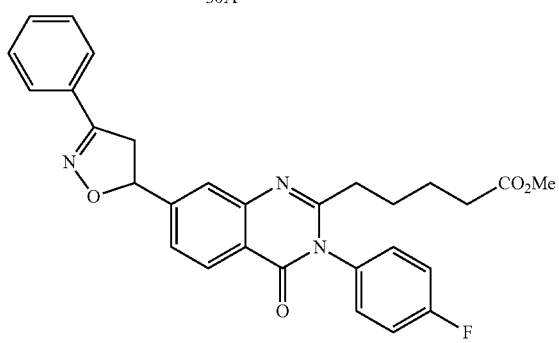

30B

In a manner similar to that previously described, compound 15A was reacted with benzoxime 30A and NaOCl to provide 30B.

Step 2

5-(3-(4-fluorophenyl)-4-oxo-7-(3-phenyl-4,5-dihydroisoxazol-5-yl)-3,4-dihydroquinazolin-2-yl)pentanoic acid

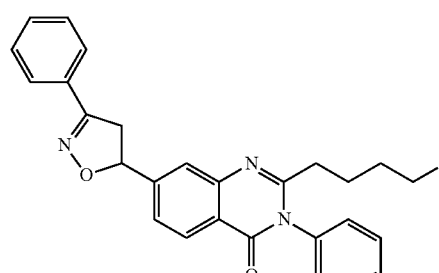

30B

LiOH →

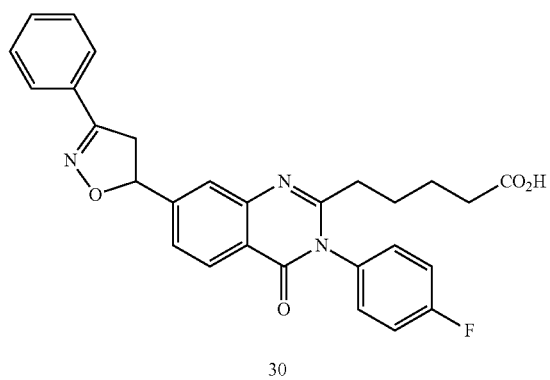

30

To a mixture of 30B (163 mg, 0.33 mmol) in 4 mL THF was added LiOH.H₂O (55 mg, 1.31 mmol, 4.0 equiv) in 1 mL water. The reaction mixture was stirred at room temperature for 3 h. Upon completion, the reaction mixture was neutralized with 1 N HCl, extracted with CH₂Cl₂ (2×5 mL), dried over Na₂SO₄, filtered and concentrated to dryness. The product was purified by reverse phase chromatography to yield 72 mg of the desired product 30 as an off white solid. MS (M+H)=486.

Preparative Example 31

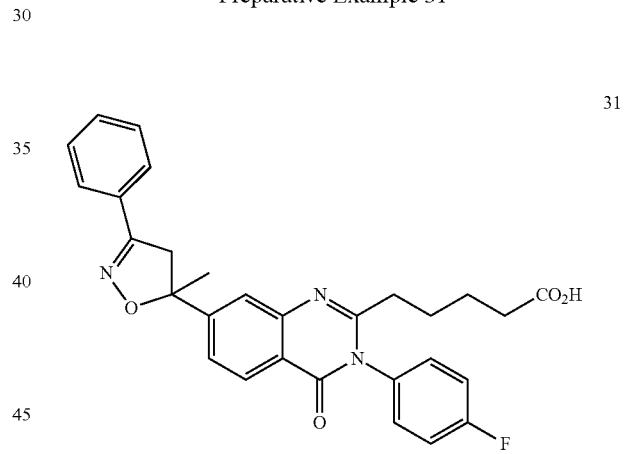

31

Step 1 methyl 5-(3-(4-fluorophenyl)-4-oxo-7-(prop-1-en-2-yl)-3,4-dihydroquinazolin-2-yl)pentanoate

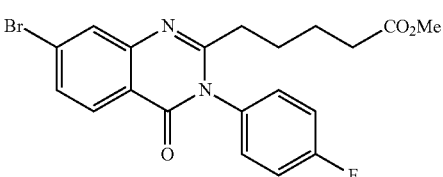

2C

+

149
-continued

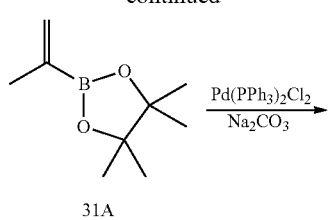
31A

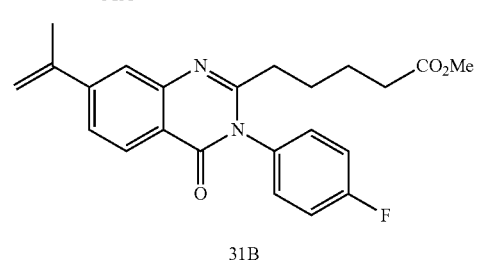
31B

In a manner similar to that described for compound 15A, compound 2C was reacted with 31A to provide 31B.

Steps 2-3

5-(3-(4-fluorophenyl)-7-(5-methyl-3-phenyl-4,5-dihydroisoxazol-5-yl)-4-oxo-3,4-dihydroquinazolin-2-yl)pentanoic acid

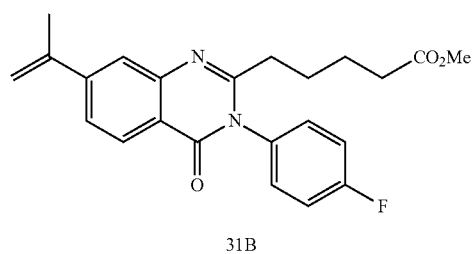

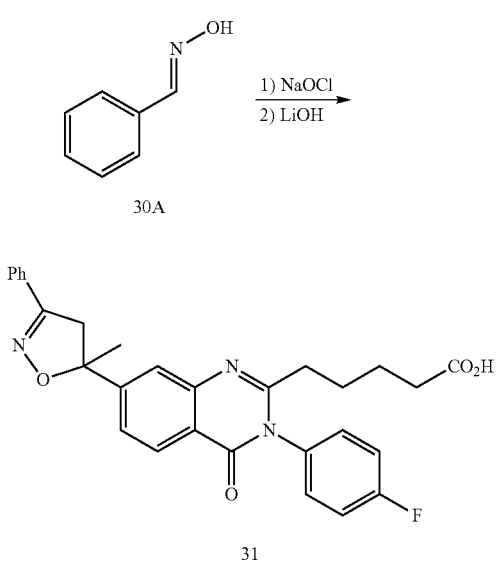

150

In a manner similar to that described previously, compound 31B was sequentially reacted with benzoxime 30A/NaOCl and then hydrolyzed with LiOH to provide the title compound 31. MS (M+H)=500.

Preparative Example 32

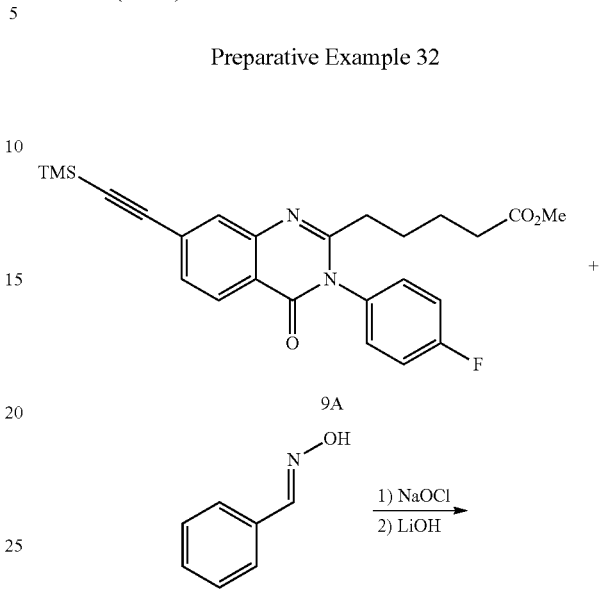

In a manner similar to that previously described, compound 9A was sequentially reacted with 30A/NaOCl and then LiOH to provide 32. MS (M+H)=484.

Preparative Example 33

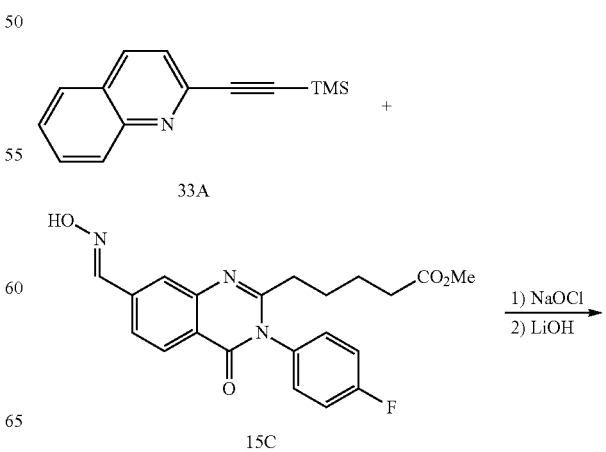

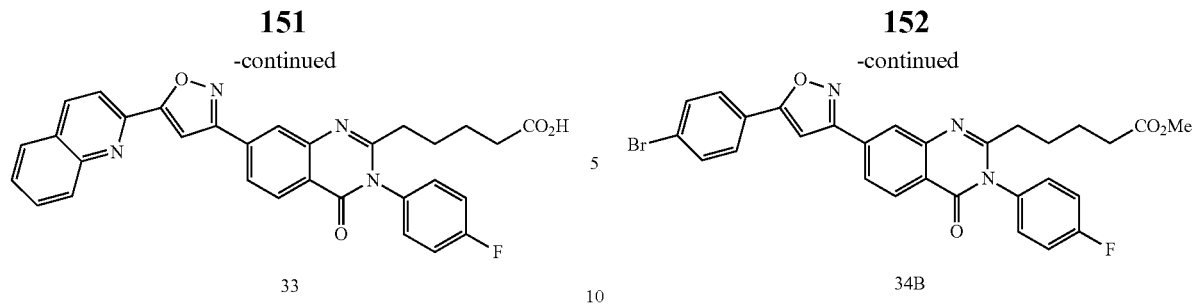

In a manner similar to that described in Example 29, compound 33A (prepared from 2-chloroquinoline and trimethylsilylacetylene) was sequentially reacted with compound 15C/NaOCl and then LiOH to provide compound 33. MS (M+H)=535.

Preparative Example 34

In a manner similar to that described previously, 4-bromophenylacetylene 34A was reacted with compound 15C/NaOCl to provide 34B.

Steps 2-3

5-(3-(4-fluorophenyl)-7-(5-(4-(1-methyl-1H-pyrazol-4-yl)phenyl)isoxazol-3-yl)-4-oxo-3,4-dihydro-quinazolin-2-yl)pentanoic acid

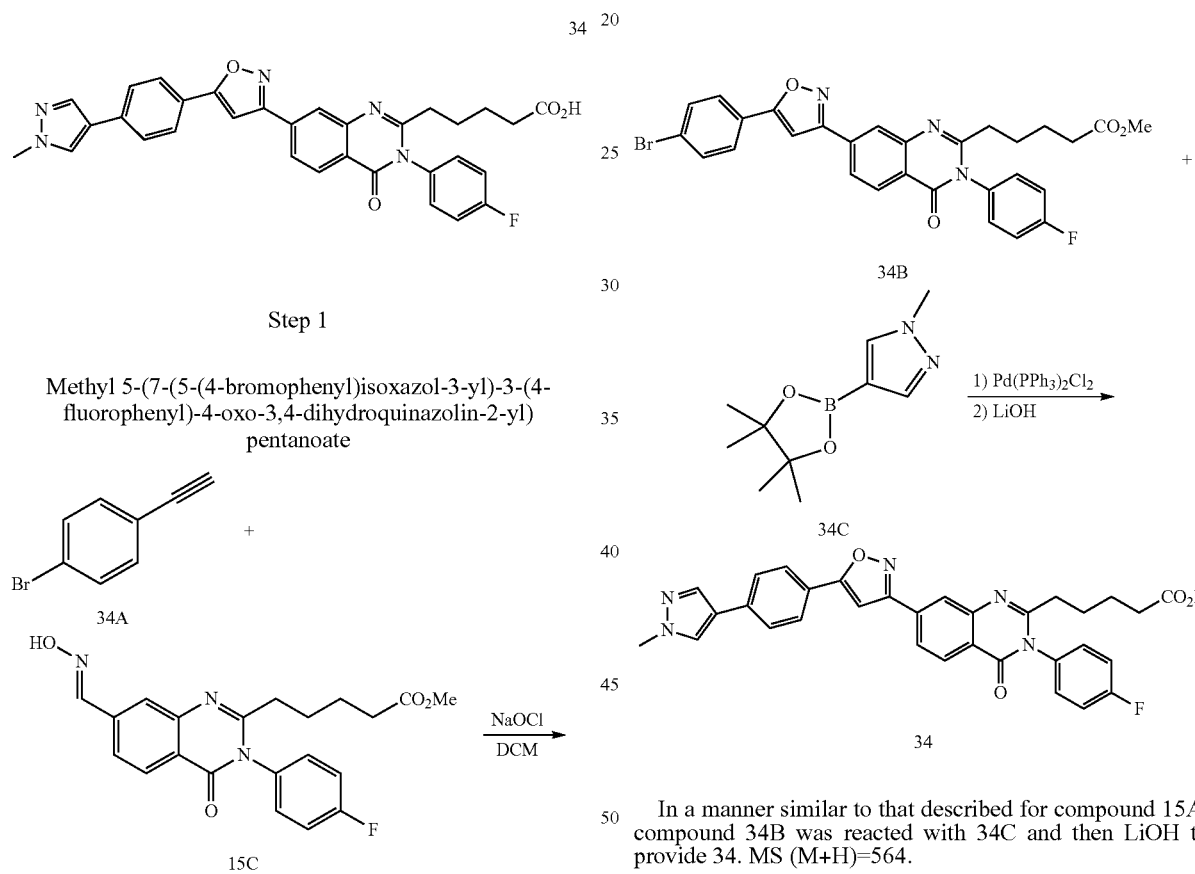

Step 1

Methyl 5-(7-(5-(4-bromophenyl)isoxazol-3-yl)-3-(4-fluorophenyl)-4-oxo-3,4-dihydroquinazolin-2-yl)pentanoate In a manner similar to that described for compound 15A, compound 34B was reacted with 34C and then LiOH to provide 34. MS (M+H)=564.

Preparative Example 35

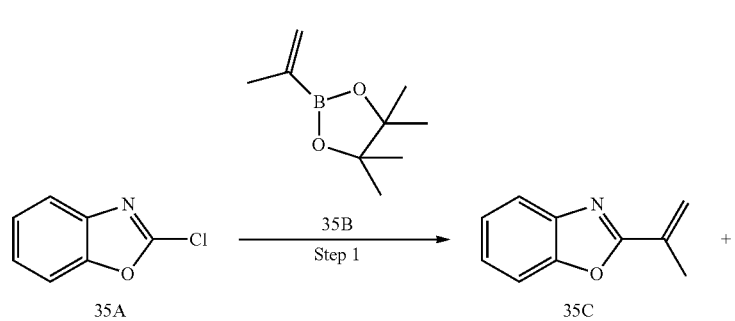

-continued

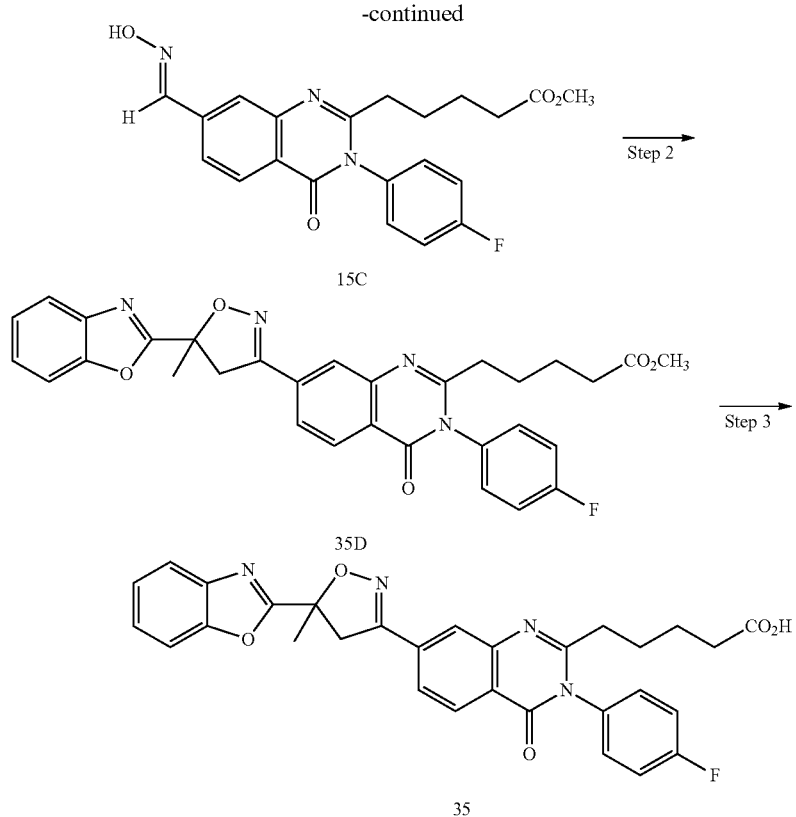

Step 1

2-(prop-1-en-2-yl)benzo[d]oxazole

To a solution of 2-chlorobenzo[d]oxazole (35A, 2.2 g, 14.3 mmol) and 35B (3.5 g, 20.8 mmol) in 75 mL of DME/H$_2$O (4:1) was added PdCl$_2$(PPh$_3$)$_2$ (1.0 g, 1.43 mmol) and Na$_2$CO$_3$ (4.5 g, 42.9 mmol). After heating at 80° C. for 20 h, the mixture was extracted with ether and water, dried over Na$_2$SO$_4$, filtered, concentrated and chromatographed (15% EtOAc/Hexane) to give 1.9 g of 35C, yield: 83%.

Step 2 methyl 5-(7-(5-(benzo[d]oxazol-2-yl)-5-methyl-4,5-dihydroisoxazol-3-yl)-3-(4-fluorophenyl)-4-oxo-3,4-dihydroquinazolin-2-yl)pentanoate To the suspension of compound 15C (0.20 g, 0.50 mmol) in 20 mL of CH$_2$Cl$_2$ was added 35C (0.16 g, 1.0 mmol), and NaOCl (3.3 mL, 2.0 mmol). After stirring at it overnight, the mixture was extracted with CH$_2$Cl$_2$ and H$_2$O. The organic layer was collected, dried over Na$_2$SO$_4$, concentrated and the residue was purified by column chromatography (40% EtOAc/Hexane) to give 0.246 g of compound 35D. Yield: 88%. MS (M+H)=555.

The enantiomers of 35D (100 mg) were separated by chiral HPLC (Chiral Technologies AD semi-prep column using 70% Hexane/iPA) to give 36 mg of 35E (enantiomer 1, 1st eluting peak from SFC chromatography) and 36 mg of 35F (enantiomer 2, 2nd eluting peak).

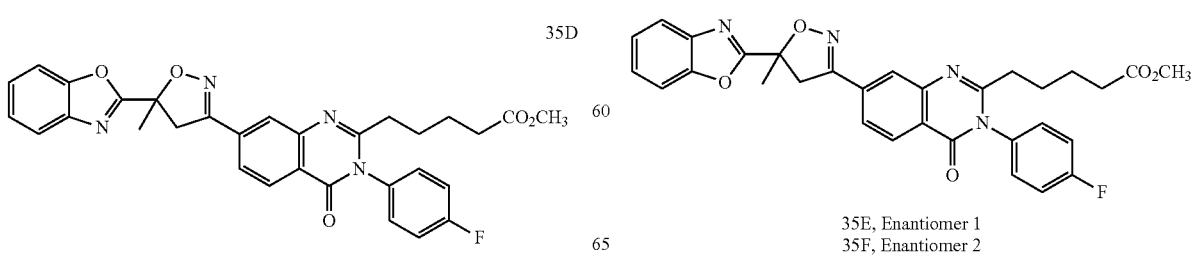

35E, Enantiomer 1
35F, Enantiomer 2

Step 3

5-(7-(5-(benzo[d]oxazol-2-yl)-5-methyl-4,5-dihydroisoxazol-3-yl)-3-(4-fluorophenyl)-4-oxo-3,4-dihydroquinazolin-2-yl)pentanoic acid (Enantiomer 1)

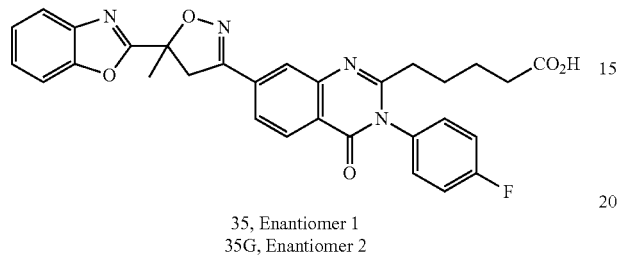

35, Enantiomer 1
35G, Enantiomer 2

To the suspension of 35E (Enantiomer I, 0.036 g, 0.065 mmol) in 4 mL of THF/H₂O (1:1) was added LiOH—H₂O (0.011 g, 0.26 mmol). After heating at 50° C. for 0.5 h, the reaction was concentrated, adjusted to pH=5 by adding a few drops of 1N HCl (aq), again concentrated and then purified by prep-TLC (10% MeOH/CH₂Cl₂) to give 0.015 g of compound 35 (Enantiomer 1). Yield: 43 MS (M+H)=541. ¹H NMR (500 MHz, CDCl₃) δ 8.28 (d, 1 H, J=8.5 Hz), 7.98 (d, 1 H, J=8.5 Hz), 7.9 (s, 1H), 7.75 (d, 1 H, J=7.5 Hz), 7.58 (d, 1 H, J=7.0 Hz), 7.39 (m, 2 H), 7.28 (s, 4 H), 4.43 (d, 1 H, J=17 Hz), 3.58 (d, 1 H, J=17 Hz), 2.45 (m, 2 H), 2.35 (m, 2 H), 2.10 (s, 3 H), 1.80 (m, 2 H), 1.64 (m, 2 H).

In a similar manner, compound 35F (Enantiomer 2) was converted to 35G (Enantiomer 2). MS (M+H)=541.

Preparative Example 36

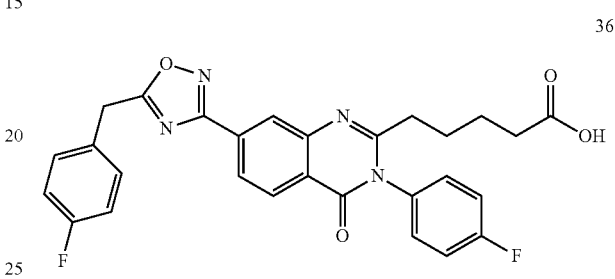

36

Step 1 methyl 5-(7-(5-(4-fluorobenzyl)-1,2,4-oxadiazol-3-yl)-3-(4-fluorophenyl)-4-oxo-3,4-dihydroquinazolin-2-yl)pentanoate

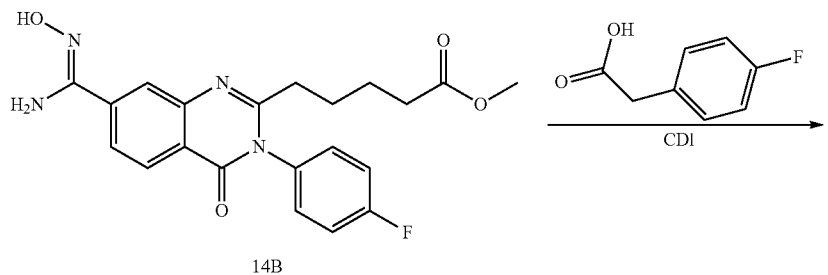

14B

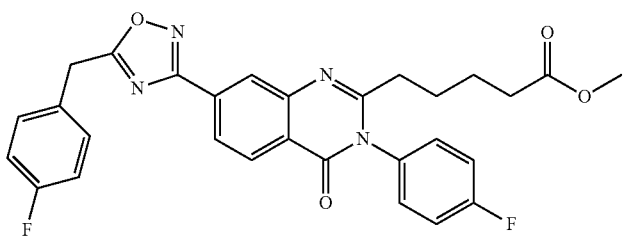

36A 1,1'-Carbonyldiimidazole (15.14 mg, 0.093 mmol) was added to a stirred, room temperature mixture of 4-fluoroacetic acid (13.74 mg, 0.089 mmol) in N,N-dimethylformamide (2 mL) and the mixture was stirred at room temperature for 1 h. Compound 14B (35 mg, 0.085 mmol) was added to the mixture and the resultant mixture was kept stirring at 80° C. for 16 h. The mixture was cooled, diluted with ethyl acetate (10 mL), washed with aqueous sodium hydrogen carbonate (saturated, 1×5 mL), dried (MgSO$_4$), filtered and the solvent was evaporated under reduced pressure to give 36A (40 mg, 0.075 mmol, 89% yield) as a yellow oil. MS (M+H)=531.

Step 2

5-(7-(5-(4-fluorobenzyl)-1,2,4-oxadiazol-3-yl)-3-(4-fluorophenyl)-4-oxo-3,4-dihydroquinazolin-2-yl) pentanoic acid

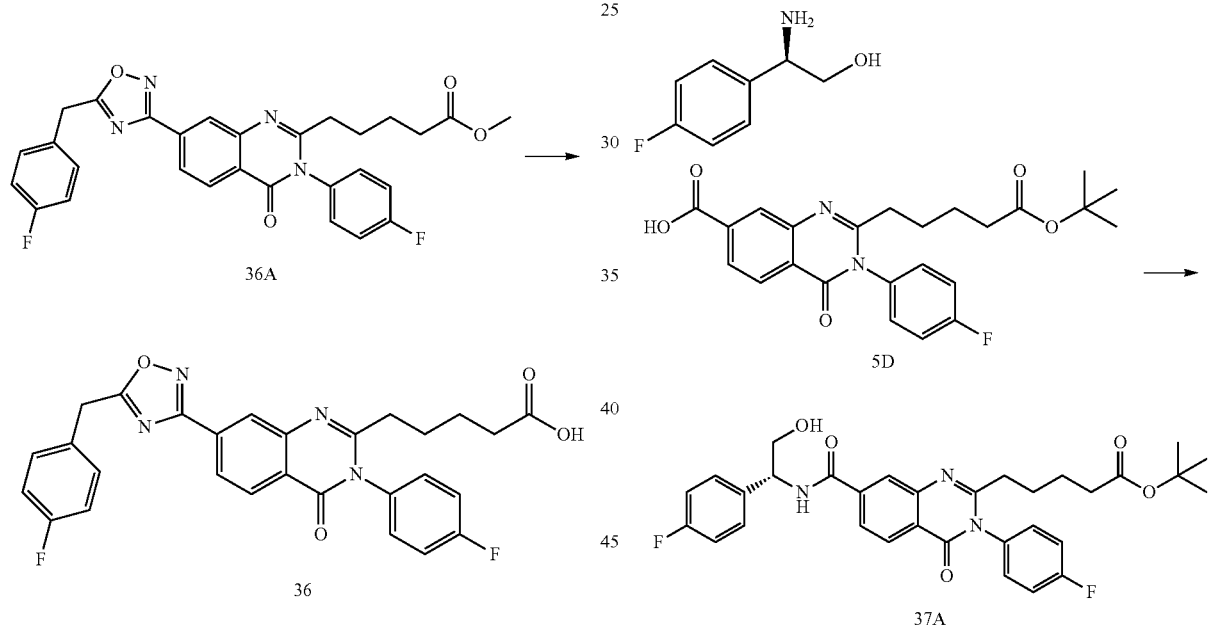

LiOH (3.61 mg, 0.151 mmol) was added to a stirred, room temperature mixture of 36A (40 mg, 0.075 mmol) in MeOH (1 mL)-tetrahydrofuran (0.5 mL) and water (1.000 mL), and the mixture was stirred at room temperature for 2 h. The reaction mixture was diluted with diethyl ether (1 water (2 mL) was added, the aqueous layer was separated, acidified with to pH 2~3, extracted with dichloromethane (2×3 mL), the combined organic was dried MgSO$_4$, filtered and concentrated. The residue was purified by preparative HPLC Reverse phase (C-18, eluting with Acetonitrile/Water+0.1% TFA) to give 36 (8.0 mg, 0.015 mmol, 21% yield) as an off white solid. MS (M−H)=517. HNMR (500 MHz, CDCl$_3$) 8.457 (d, J=2 Hz, 1H), 8.361 (d, J=8 Hz, 1H), 8.156 (dd, J$_1$=8.2 Hz, J$_2$=2 Hz, 1H), 7.411 (m, 2H), 7.275 (m, 4H), 7.100 (m, 2H), 4.331 (s, 2H), 2.248 (m, 2H), 2.380 (m, 2H), 1.838 (m, 2H), 1.665 (m, 2H).

Preparative Example 37

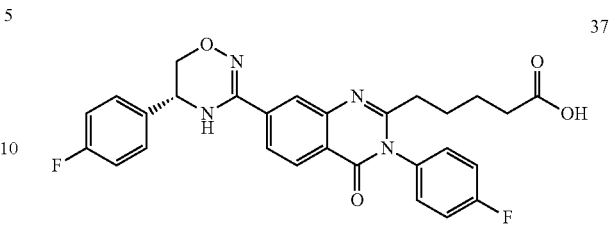

Step 1

(R)-tert-butyl 5-(3-(4-fluorophenyl)-7-(1-(4-fluorophenyl)-2-hydroxyethyl-carbamoyl)-4-oxo-3,4-dihydroquinazolin-2-yl)pentanoate (R)-2-amino-2-(4-fluorophenyl)ethanol (85 mg, 0.545 mmol, available from commercial sources or via reduction of (R)-2-amino-2-(4-fluorophenyl)acetic acid with 2 eq NaBH$_4$ and 4 eq BF$_3$—OEt$_2$, THF, 0° C. to RT overnight), 5D (200 mg, 0.454 mmol), HOBT (174 mg, 1.135 mmol), EDC (218 mg, 1.135 mmol) and Hunig's base (0.238 mL, 1.362 mmol) were mixed in dichloromethane (5 mL), and the mixture was stirred at room temperature overnight. The mixture was diluted with dichloromethane (10 mL), washed with aqueous sodium hydrogen carbonate (saturated, 1×5 mL), and brine (5 mL) dried (MgSO$_4$), filtered and the solvent was evaporated under reduced pressure. The residue was purified by column chromatography (24 g silica, 80% EtOAc/hexane) to give 37A (207 mg, 0.358 mmol, 79% yield) as a white foam; MS (M+H)=578.

Step 2

(R)-tert-butyl 5-(7-(2-(1,3-dioxoisoindolin-2-yloxy)-1-(4-fluorophenyl)ethyl carbamoyl)-3-(4-fluorophenyl)-4-oxo-3,4-dihydroquinazolin-2-yl)pentanoate was stirred at 80° C. for 48 h and then cooled. The white precipitate was filtered off. The filtrate was concentrated and the residue was purified by column chromatography on 24 g silica (25% to 80% EtOAc/hexane) to give 37B (140 mg, 0.194 mmol, 55.9% yield) as a yellow foam. MS (M+H)=723.

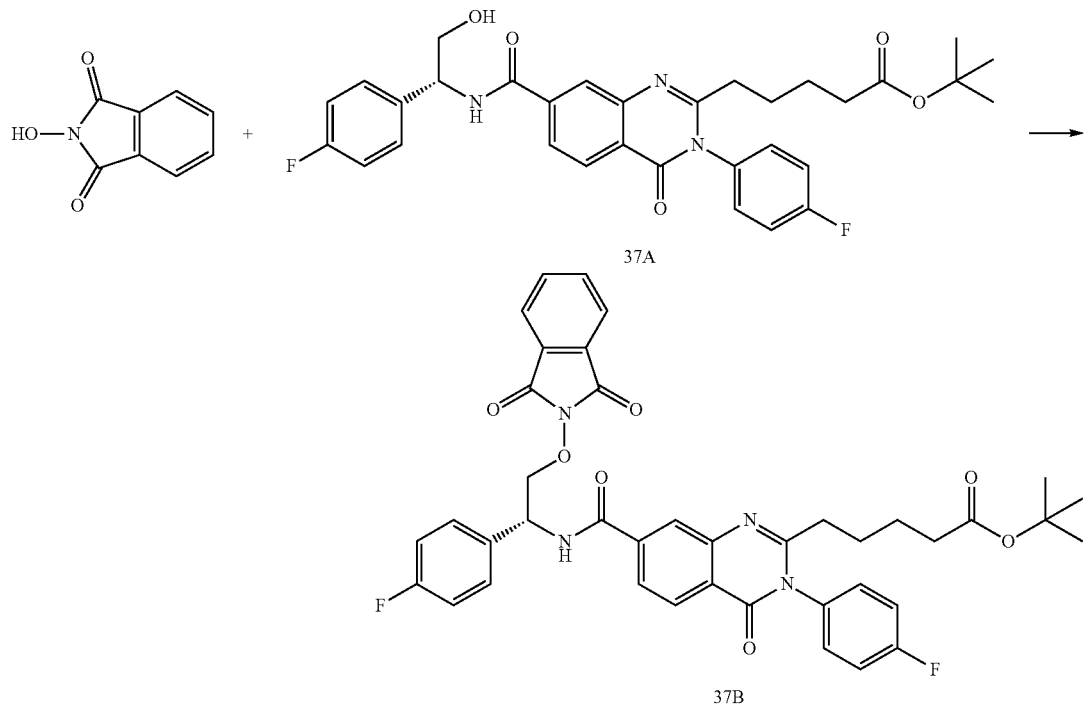

Tri-n-butylphosphine (105 mg, 0.519 mmol) was added to a stirred, room temperature mixture of 37A (200 mg, 0.346 mmol), N-hydroxyphthalimide (79 mg, 0.485 mmol) and 1,1'-(Azodicarbonyl)dipiperidine (131 mg, 0.519 mmol) in tetrahydrofuran (5 mL) to give a red solution. The mixture

Step 3

(R)-tert-butyl 5-(7-(2-(aminooxy)-1-(4-fluorophenyl) ethylcarbamoyl)-3-(4-fluorophenyl)-4-oxo-3,4-dihydroquinazolin-2-yl)pentanoate

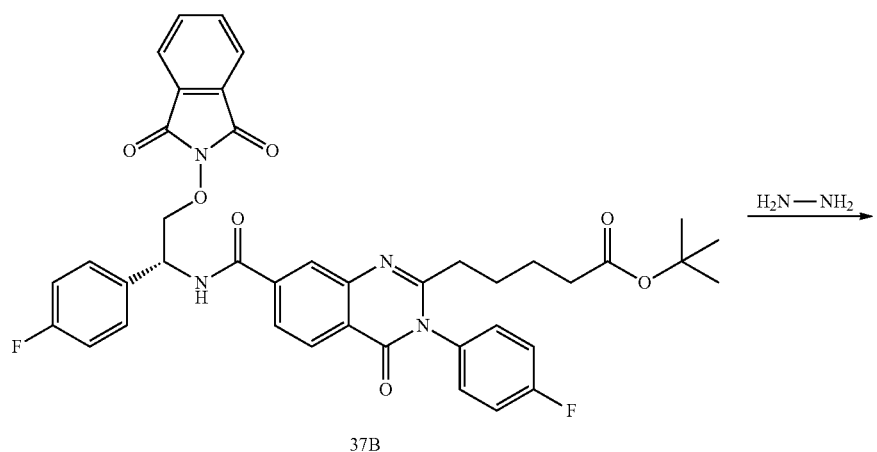

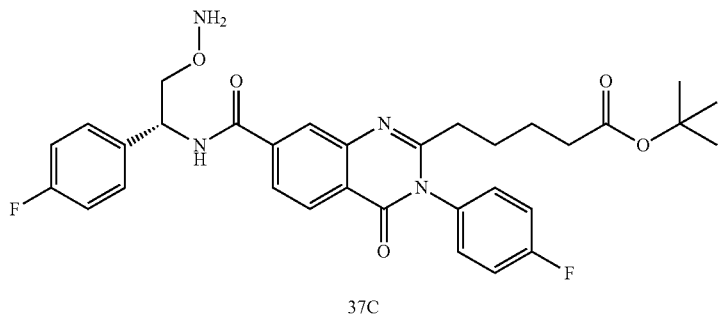

37C

Hydrazine monohydrate (0.028 mL, 0.581 mmol) was added to a stirred, room temperature mixture of 37B (140 mg, 0.194 mmol) in dichloromethane (2 mL) and methanol (2.000 mL), and the mixture was stirred at room temperature for 1 h.

The mixture was diluted with dichloromethane (10 mL), washed with aqueous sodium hydrogen carbonate (saturated, 2×8 mL), dried (MgSO$_4$), filtered and the solvent was evaporated under reduced pressure to give 37C (100 mg, 0.169 mmol, 87% yield) as a light yellow solid. MS (M+H)=593.

Step 4

Phosphorus pentoxide (240 mg, 1.687 mmol) was added to a stirred, room temperature mixture of 37C (100 mg, 0.169 mmol) in ethanol (2 mL) and the mixture was stirred at 80° C. for 48 h. Water (5 mL), aqueous sodium hydrogen carbonate (saturated, 5 mL) and ethyl acetate (10 mL) were added. The aqueous was extracted once more with ethyl acetate (5 mL) and the combined organic was dried MgSO$_4$, and concentrated. The residue was purified by column chromatography (24 g silica, eluting with 30% to 100% EtOAc/hexane) to give 37D (25 mg, 0.046 mmol, 27.1% yield) as a colorless gum. MS (M+H)=547.

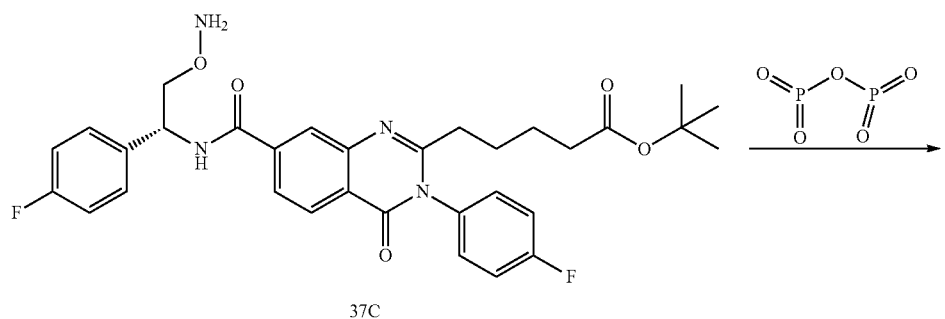

37C

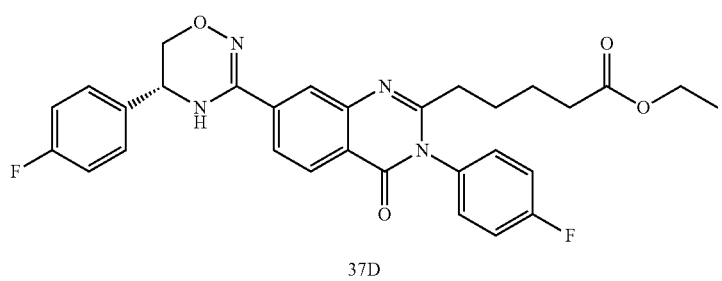

37D

Step 5

(R)-5-(3-(4-fluorophenyl)-7-(5-(4-fluorophenyl)-5,6-dihydro-4H-1,2,4-oxadiazin-3-yl)-4-oxo-3,4-dihydroquinazolin-2-yl)pentanoic acid

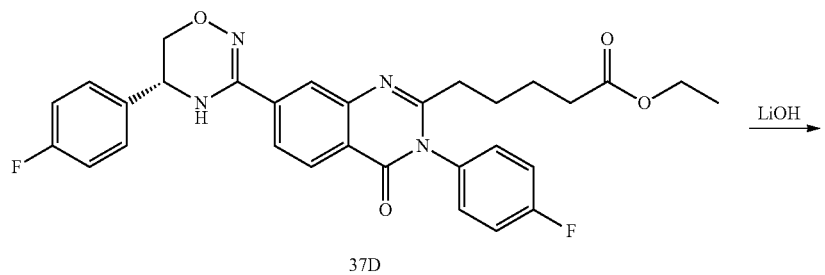

37D

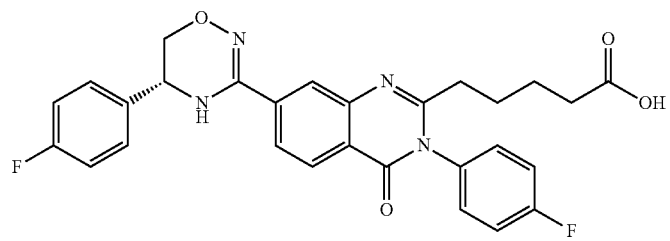

37

Lithium hydroxide (1.095 mg, 0.046 mmol) was added to a stirred mixture of 37D (25 mg, 0.046 mmol) in tetrahydrofuran (0.500 mL), water (0.500 mL) and methanol (0.5 mL), and the mixture was stirred at room temperature for 2 h. The reaction mixture was diluted with water (1 mL) and dichloromethane (5 mL) and then acidified with 2N HCl to pH 2-3 and extracted with dichloromethane (2×3 mL). The combined organic was dried MgSO$_4$, filtered, concentrated, and purified via PTLC (Emerck 0.5 mm, eluting with CH$_2$Cl$_2$/hexane/MeOH/AcOH (1%)=2:1:0.3). The residue was further purified by SFC to obtain the desired product 37. MS (M+H)=519.

Compound 37E was synthesized in a similar manner using (S)-2-amino-2-(4-fluorophenyl)ethanol in Step 1. MS (M+H)=519.

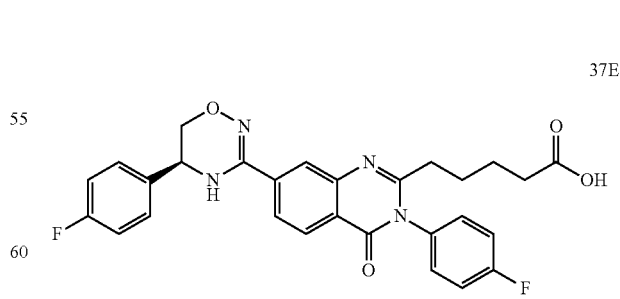

37E

Preparative Example 39

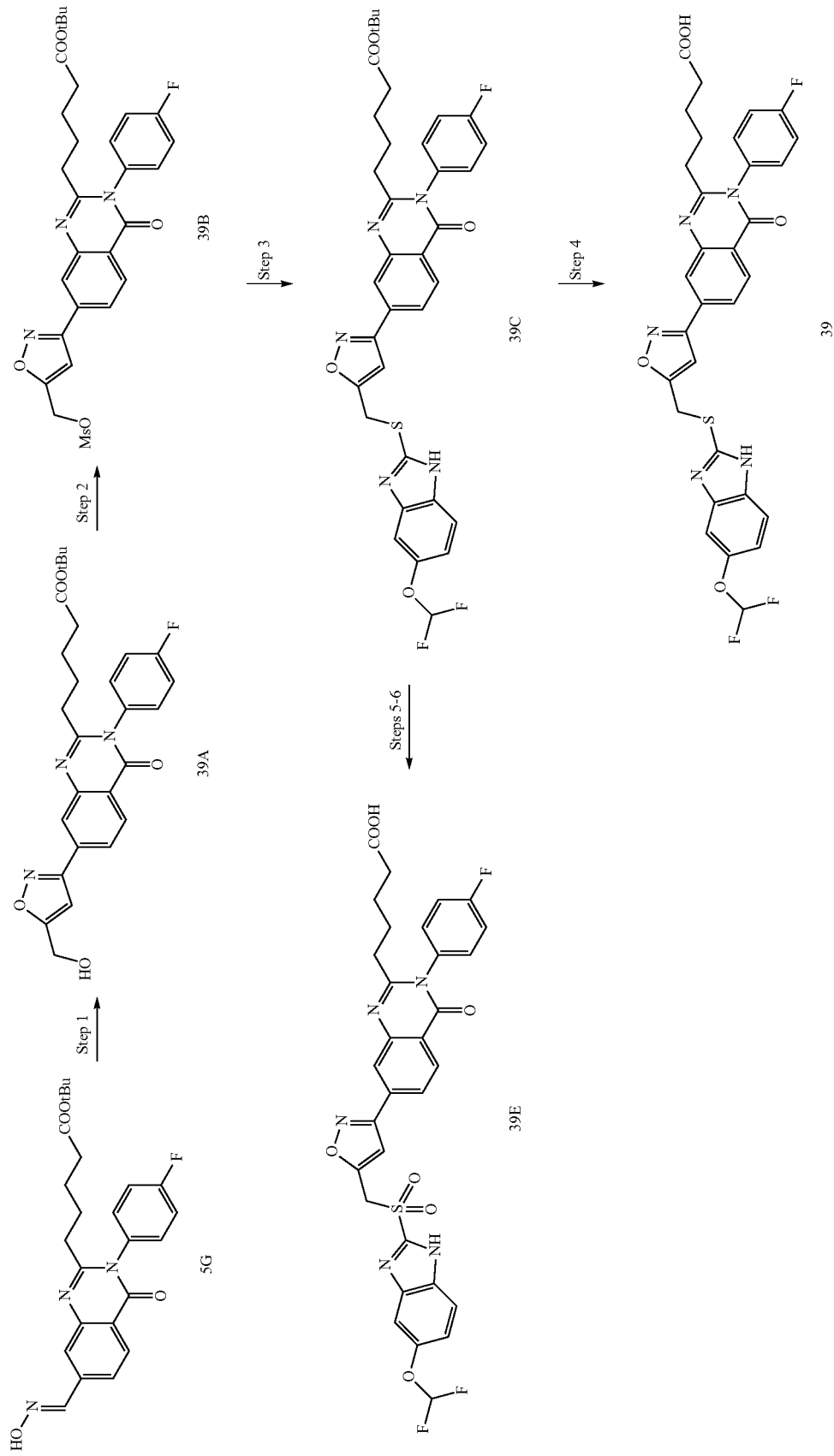

Step 1 tert-butyl 5-(3-(4-fluorophenyl)-7-(5-(hydroxymethyl)isoxazol-3-yl)-4-oxo-3,4-dihydroquinazolin-2-yl)pentanoate

Step 2 tert-butyl 5-(3-(4-fluorophenyl)-7-(5-((methylsulfonyloxy)methyl)isoxazol-3-yl)-4-oxo-3,4-dihydroquinazolin-2-yl)pentanoate

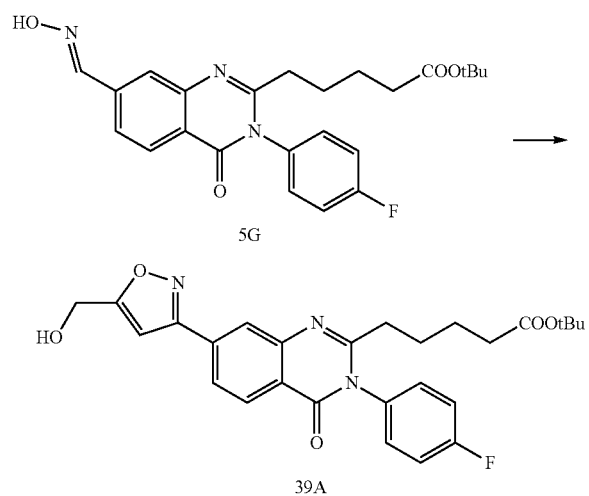

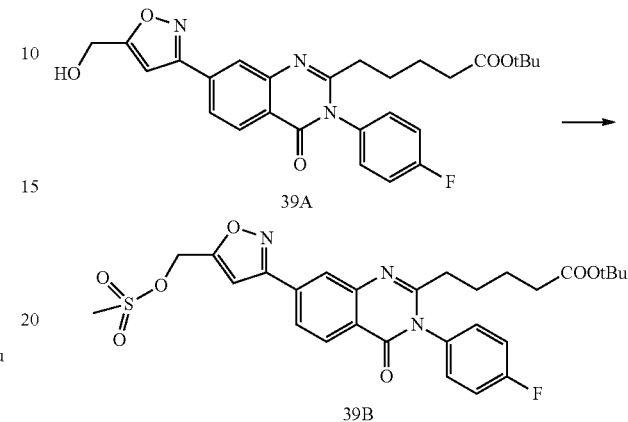

A solution of 5G (2.0 g, 4.55 mmol) in DCM (25 mL) was treated with propargyl alcohol (0.53 mL, 9.10 mmol) and sodium hypochlorite (30.9 mL, 18.20 mmol) and stirred for 24 h at room temperature. After this time, the reaction was diluted with EtOAc and organic layer extracted. The aqueous layer was separated and extracted with EtOAc once more. The combined organics were washed with brine, dried (Na$_2$SO$_4$), filtered, and concentrated. The residue was purified by flash chromatography (0% to 80% EtOAc/hexane) to yield 39A (980 mg, yield=43%). MS (M+H)=494.

A solution of 39A (980 mg, 1.986 mmol) in DCM (10 mL) was treated with N,N-diisopropylethylamine (1.04 mL, 5.96 mmol) followed by methanesulfonyl chloride (0.231 mL, 2.98 mmol), both added dropwise at 0° C. The reaction was stirred for 3 hours (0° C. to room temperature) and then was diluted with DCM and washed with water. The organic layer was separated, dried (Na$_2$SO$_4$), filtered, and concentrated to yield 39B (1.13 g, yield=100%). MS (M±H)=572.

Step 3 tert-butyl 5-(7-(5-((5-(difluoromethoxy)-1H-benzo[d]imidazol-2-ylthio)methyl) isoxazol-3-yl)-3-(4-fluorophenyl)-4-oxo-3,4-dihydroquinazolin-2-yl)pentanoate

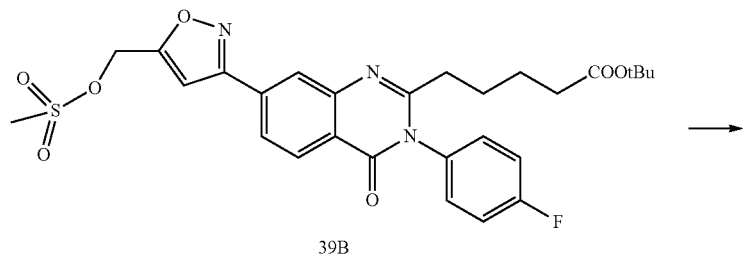

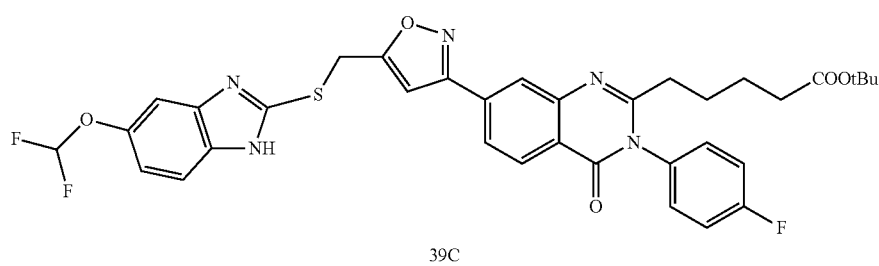

Compound 39B (75 mg, 0.131 mmol), 5-difluoromethoxy-2-mercapto-1H-benzimidazole (0.043 g, 0.197 mmol) and potassium carbonate (0.054 g, 0.394 mmol) were combined in acetone (5 mL) and stirred at 70° C. for 3 hours. The reaction was filtered, washed with DCM and concentrated to yield 39C (91 mg, yield=100%). MS (M+H)=692.

Step 4

5-(7-(5-((5-(difluoromethoxy)-1H-benzo[d]imidazol-2-ylthio)methyl)isoxazol-3-yl)-3-(4-fluorophenyl)-4-oxo-3,4-dihydroquinazolin-2-yl)pentanoic acid

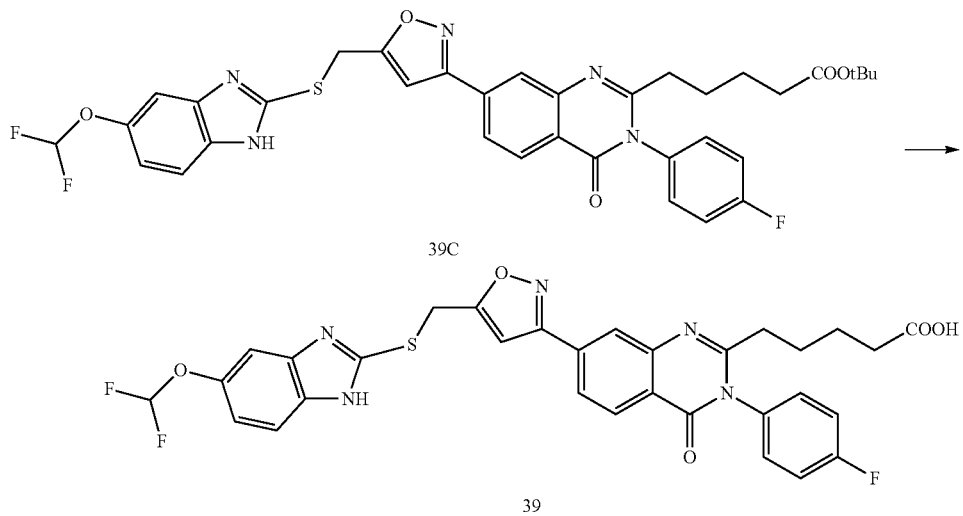

A solution of 39C (45 mg, 0.065 mmol) in DCM (1 mL) was treated with trifluoroacetic acid (2 mL, 0.065 mmol) and stirred at room temperature for 1 hour. After this time, the reaction was concentrated and purified via reverse phase HPLC (C18, 10-90% ACN in water with 0.1% TFA) to yield 39 (25 mg, yield=60%). MS (M+H)=636.

Step 5 tert-butyl 5-(7-(5-((5-(difluoromethoxy)-1H-benzo[d]imidazol-2-ylsulfonyl) methyl)isoxazol-3-yl)-3-(4-fluorophenyl)-4-oxo-3,4-dihydroquinazolin-2-yl) pentanoate

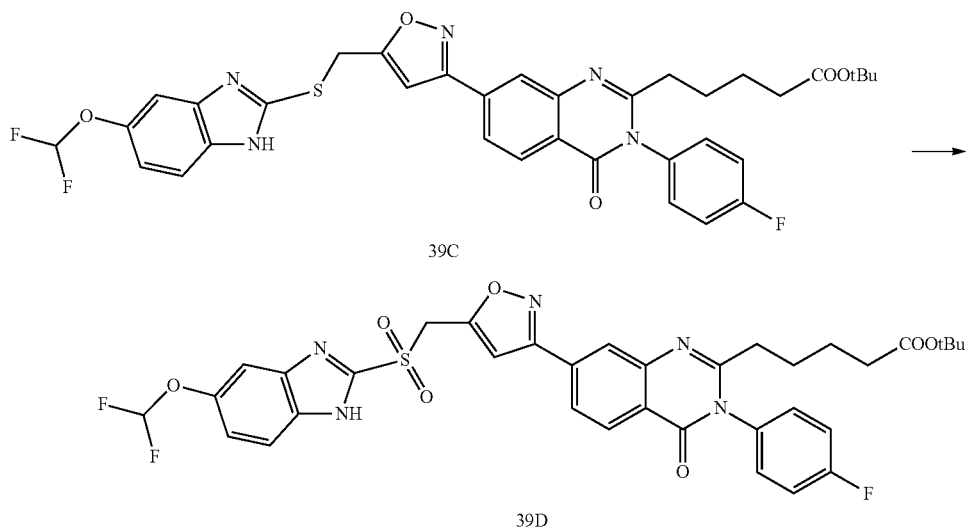

A solution of 39C (40 mg, 0.058 mmol) in DCM (1 mL) was treated with 3-chloroperoxybenzoic Acid (0.022 g, 0.127 mmol) and stirred at room temperature for 2 hours. After this time, the reaction was concentrated and purified (C18 reverse phase HPLC, 10-90% ACN in water with 0.1% TFA) to yield 39D (30 mg, yield=72%). MS (M+H)=724

Step 6

5-(7-(5-((5-(difluoromethoxy)-1H-benzo[d]imidazol-2-ylsulfonyl) methyl)isoxazol-3-yl)-3-(4-fluorophenyl)-4-oxo-3,4-dihydroquinazolin-2-yl)pentanoic acid

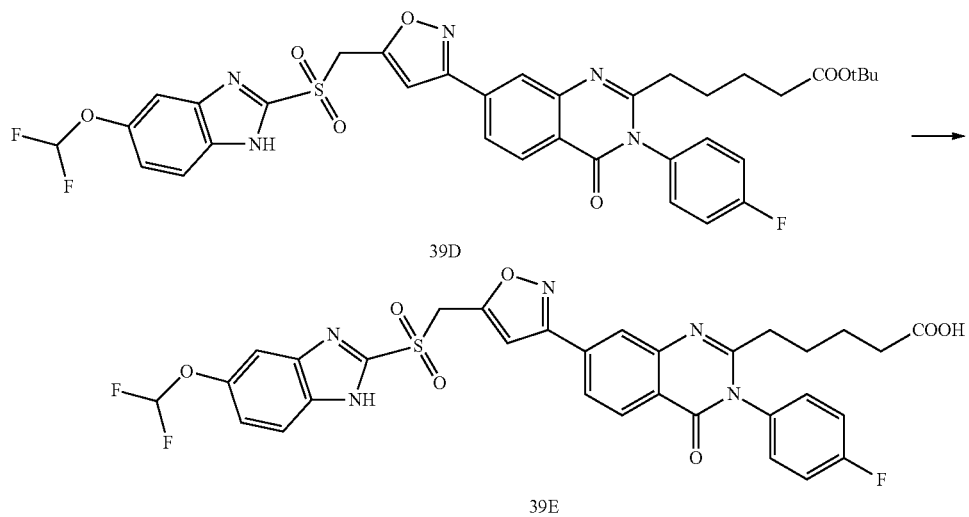

A solution of 39D (30 mg, 0.041 mmol) in DCM (1 mL) was treated with trifluoroacetic acid (2 mL, 0.041 mmol) and stirred at room temperature for 1 hour. After this time, the reaction was concentrated and purified (C18 reverse phase HPLC, 10-90% ACN in water with 0.1% TFA) to yield 39E (15.5 mg, yield=56%). MS (M+H)=668.

The following compounds were synthesized in a similar manner to that described above.

| Cpd | Structure | MS (M + H⁺) |
|---|---|---|
| 39F | 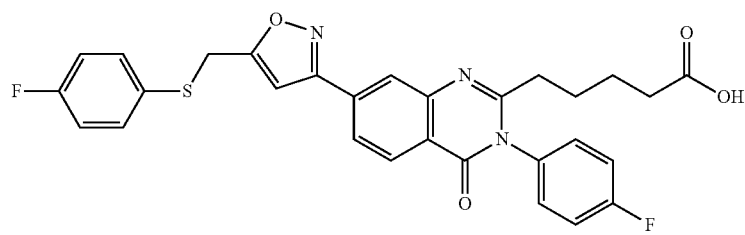 [SMILES: O=C(O)CCCCc1nc2cc(-c3cc(CSc4ccc(F)cc4)on3)ccc2c(=O)n1-c1ccc(F)cc1] | 548 |
| 39G | 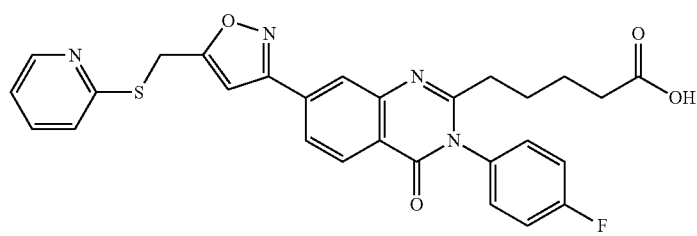 [SMILES: O=C(O)CCCCc1nc2cc(-c3cc(CSc4ccccn4)on3)ccc2c(=O)n1-c1ccc(F)cc1] | 531 |

-continued

| Cpd | Structure | MS (M + H⁺) |
|---|---|---|
| 39H | 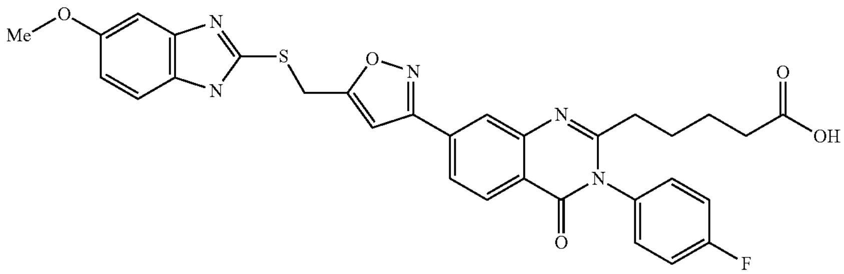 [SMILES: COc1ccc2[nH]c(SCc3cc(-c4ccc5c(=O)n(-c6ccc(F)cc6)c(CCCCC(=O)O)nc5c4)no3)nc2c1] | 600 |
| 39i | 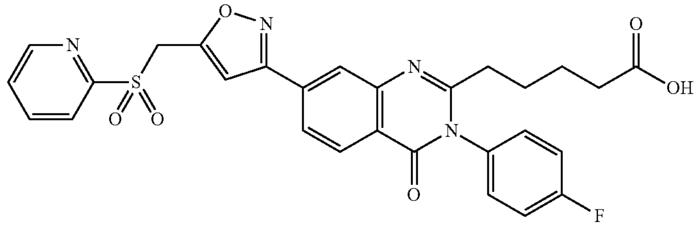 [SMILES: O=C(O)CCCCc1nc2cc(-c3cc(CS(=O)(=O)c4ccccn4)on3)ccc2c(=O)n1-c1ccc(F)cc1] | 563 |
| 39J | 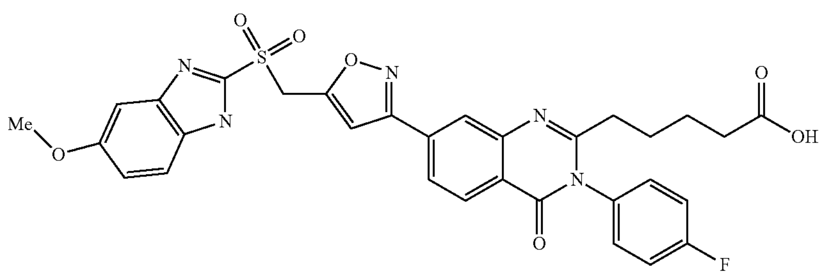 [SMILES: COc1ccc2[nH]c(S(=O)(=O)Cc3cc(-c4ccc5c(=O)n(-c6ccc(F)cc6)c(CCCCC(=O)O)nc5c4)no3)nc2c1] | 632 |
| 39K | 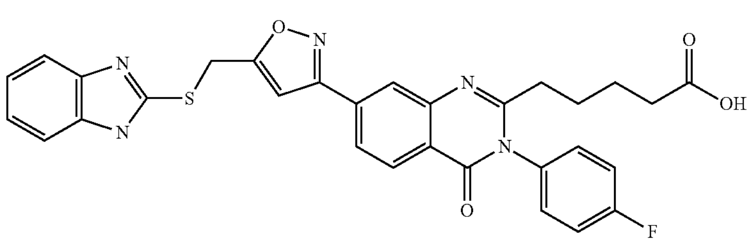 [SMILES: O=C(O)CCCCc1nc2cc(-c3cc(CSc4nc5ccccc5[nH]4)on3)ccc2c(=O)n1-c1ccc(F)cc1] | 570 |
| 39L | 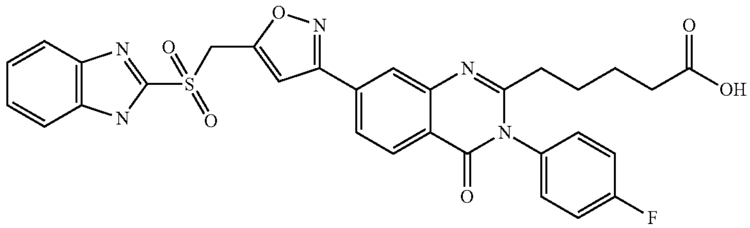 [SMILES: O=C(O)CCCCc1nc2cc(-c3cc(CS(=O)(=O)c4nc5ccccc5[nH]4)on3)ccc2c(=O)n1-c1ccc(F)cc1] | 602 |

Preparative Example 40

5-(7-(5-((1H-benzo[d]imidazol-2-ylsulfinyl)methyl)isoxazol-3-yl)-3-(4-fluorophenyl)-4-oxo-3,4-dihydroquinazolin-2-yl)pentanoic acid

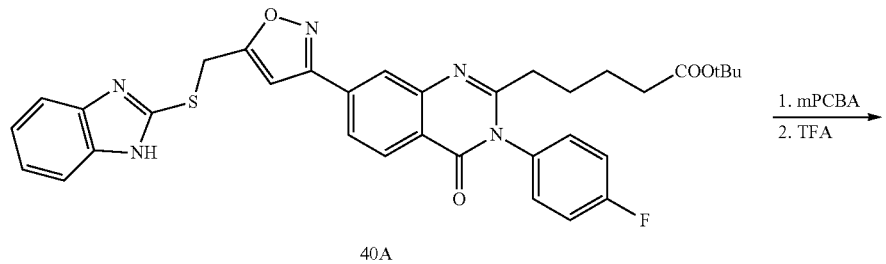

40A

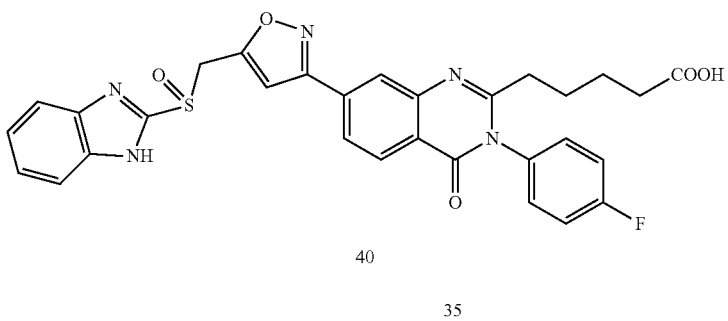

40

A solution of the thioether 40A (50 mg, 0.08 mmol, synthesized from 39B and 2-mercapto-1H-benzimidazole in a manner similar to that described in Example 39, Step 3) in DCM (1 mL) was treated with 3-chloroperoxybenzoic acid (19 mg, 0.08 mmol) and stirred at room temperature for 2 hours. The reaction mixture was then treated with TFA (1 mL) and stirred for one hour. The reaction was concentrated and purified (C18 reverse phase HPLC, 10-90% ACN in water with 0.1% TFA) to yield the sulfoxide 40 (28 mg). MS (M+H)=586.

Preparative Example 41

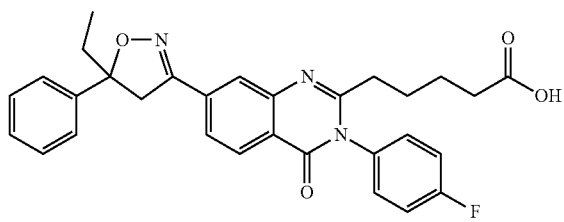

41

Steps 1-3

2-Phenyl-1-butene

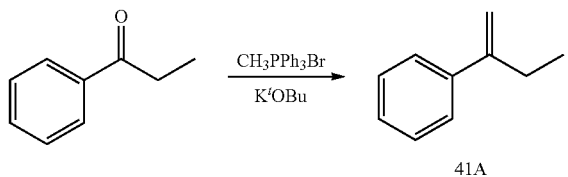

41A

A solution of methyltriphenylphosphonium bromide (10.98 g, 30.1 mmol) in 140 mL of tetrahydrofuran at −78° C. was treated with KOtBu (3.28 g, 28.6 mmol) and stirred for 40 minutes. Ethyl phenyl ketone (2.02 g, 15 mmol) was then added at −78° C. and the reaction mixture was allowed to warm up to room temperature and stirred overnight. The reaction mixture was cooled to 0° C. and quenched with aqueous ammonium chloride solution. The mixture was extracted thrice with ethyl acetate and the combined organic layer was dried with anhydrous sodium sulfate, filtered, concentrated, and purified (0-10% ethyl acetate/hexanes) to obtain 41A.

In a manner similar to that described earlier, compound 41A was reacted with 5G/NaOCl and then TFA to provide 41. MS (M+H)=514.

Preparative Example 42

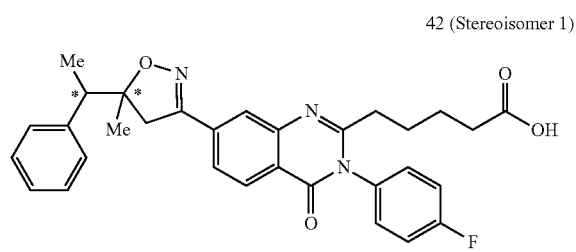 [SMILES: CC(c1ccccc1)C1(C)CC(c2ccc3c(=O)n(-c4ccc(F)cc4)c(CCCCC(=O)O)nc3c2)=NO1]

42 (Stereoisomer 1)

Steps 1-3

2-phenyl-3-methylbut-3-ene

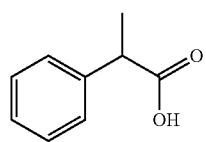

42A

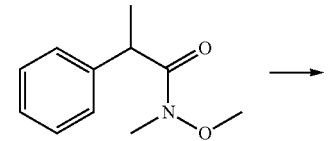

42B

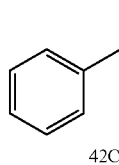

42C  42D

To a 0.2 M solution of 42A (1 equiv.) in dichloromethane at room temperature was added. N,O-dimethylhydroxylamine hydrochloride (1.5 equiv.), HATU (1.5 equiv.), N,N-diisopropylethylamine (3 equiv.) and stirred overnight. The reaction mixture was quenched with 1 N HCl. The filtrate was extracted thrice with dichloromethane. The combined organic layer was dried with anhydrous sodium sulfate, filtered, and purified (0-20% ethyl acetate/hexanes to obtain 42B.

To a 0.8 M solution of 42B (1 equiv.) in tetrahydrofuran at 0° C. was added methylmagnesiumbromide (1.2 equiv.) and stirred for 30 minutes at 0° C. The reaction mixture was quenched with aqueous ammonium chloride solution and then extracted thrice with ethyl acetate. The combined organic layer was dried with anhydrous sodium sulfate, filtered, concentrated, and purified (0-7% ethyl acetate/hexanes to obtain 42C (92% yield).

In a manner similar to that described in Example 41, compound 42C was then treated with methyltriphenylphosphoniumbromide and potassium-tert-butoxide to provide 42D (63% yield).

Steps 4-5

5-(3-(4-fluorophenyl)-7-(5-methyl-5-(1-phenylethyl)-4,5-dihydroisoxazol-3-yl)-4-oxo-3,4-dihydroquinazolin-2-yl)pentanoic acid In a manner similar to that described earlier (e.g., Example 15), the above described olefin 42D was reacted with 5G and NaOCl. The four resulting stereoisomers were separated by chiral SFC chromatography (Chiral Technologies Chiralpak AD-H column, CO$_2$ with 45% EtOH) and then deprotected with TFA to provide 42 (Stereoisomer 1, derived from 1st eluting SFC peak, MS M+H=528), 42E (Stereoisomer 2, from 2nd eluting SFC peak, MS M+H=528), 42F (Stereoisomer 3, from 3rd eluting SFC peak, MS M+H=528), and 42G (Stereoisomer 4, from 4th eluting SFC peak, MS M+H=528).

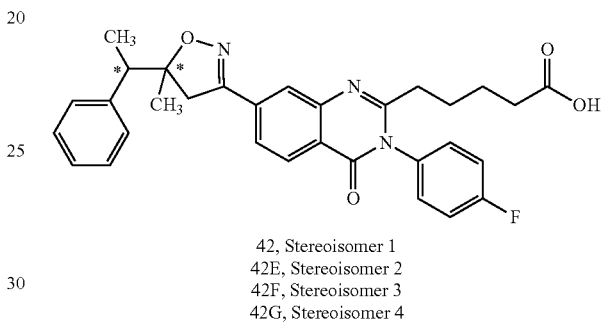

42, Stereoisomer 1
42E, Stereoisomer 2
42F, Stereoisomer 3
42G, Stereoisomer 4

Preparative Example 43

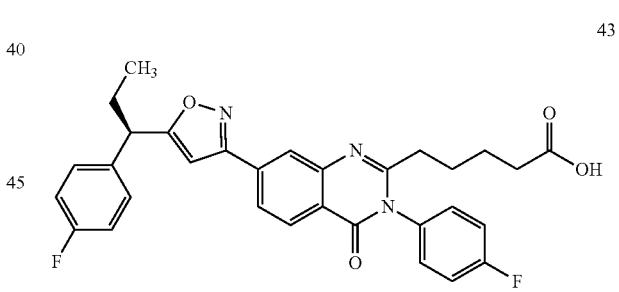

43

Step 1

1-fluoro-4-(pent-1-yn-3-yl)benzene

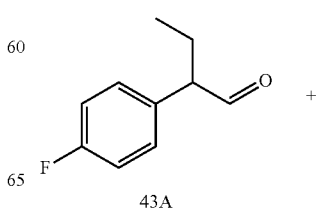

43A

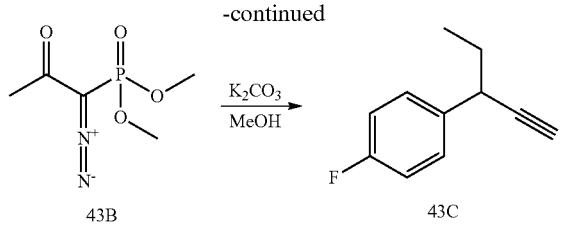

A stirred solution of 2-(p-fluorophenyl)butyraldehyde (43A, 2 g, 12.03 mmol) and dimethyl (acetyldiazomethyl) phosphonate (43B, 2.77 g, 14.44 mmol) in 45 mL of methanol at 0° C. was treated with potassium carbonate (3.99 g, 28.9 mmol) and stirred overnight at room temperature. The mixture was diluted with water and extracted with ethyl acetate. The combined organic layer was washed with brine, dried with anhydrous sodium sulfate, filtered, concentrated, and purified (40 g silica, eluting with 0-3% ethyl acetate/hexane) to give 43C (1.65 g, 10.19 mmol, 85% yield).

Steps 2-3

(R)-5-(3-(4-fluorophenyl)-7-(5-(1-(4-fluorophenyl) propyl)isoxazol-3-yl)-4-oxo-3,4-dihydroquinazolin-2-yl)pentanoic acid In a manner similar to that described earlier, compound 43C was sequentially reacted with 5G/NaOCl and TFA. The enantiomers were separated by chiral SFC chromatography (Chiral Technologies Chiralpak AD-H column, CO$_2$ with 50% cosolvent comprising 1:1 MeOH/MeCN) to provide 43 (1st eluting peak from SFC, MS M+H=544) and 43D (2nd eluting peak from SFC, MS M+H=544).

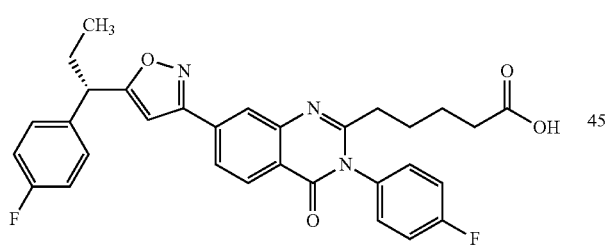

Preparative Example 44

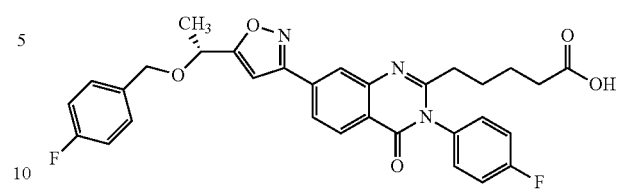

Step 1

(R)-methyl 5-(3-(4-fluorophenyl)-7-(5-(1-hydroxyethyl)isoxazol-3-yl)-4-oxo-3,4-dihydroquinazolin-2-yl)pentanoate

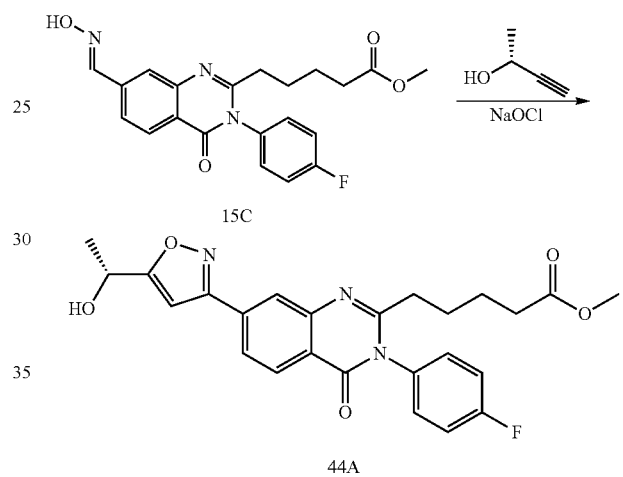

In a manner similar to that described earlier (such as in Example 5), the oxime 15C was reacted with (R)-but-3-yn-2-ol and NaOCl to provide 44A. MS (M+H)=466.

Steps 2-3

(R)-methyl 5-(7-(5-(1-(4-fluorobenzyloxy)ethyl) isoxazol-3-yl)-3-(4-fluorophenyl)-4-oxo-3,4-dihydroquinazolin-2-yl)pentanoate

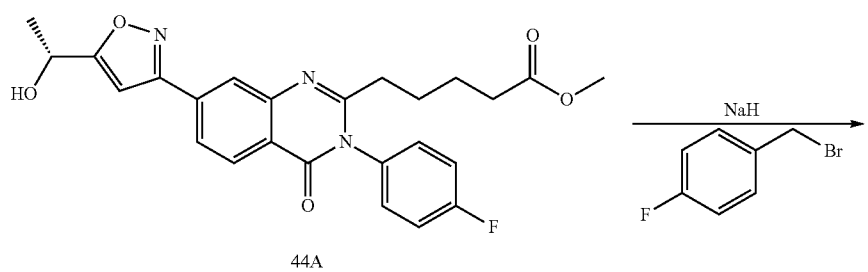

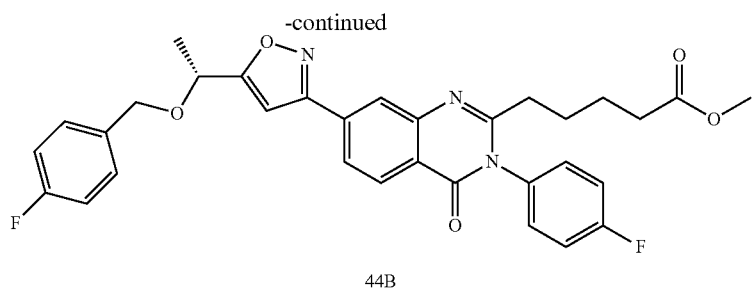

44B

Sodium hydride (6.87 mg, 0.172 mmol) was added to the solution of 44A (50 mg, 0.107 mmol) in 3 mL of N,N-dimethylformamide at 0° C. and stirred for 10 minutes. 4-Fluorobenzylbromide (30.5 mg, 0.161 mmol) was added and the reaction was warmed up to room temperature and stirred overnight. The mixture was quenched with aqueous ammonium chloride and the mixture was extracted with ethyl acetate. The combined organic layer was dried with anhydrous sodium sulfate, filtered, concentrated, and purified (24 g silica, eluting with 0-40% ethyl acetate/hexane) to give 44B (20.7 mg, 0.036 mmol, 33.6% yield). MS (M+H)=574.

Compound 44B was converted to the title compound 44 by treatment with LION as previously described (such as in Example 15, Step 5). MS (M+H)=560.

Preparative Example 45

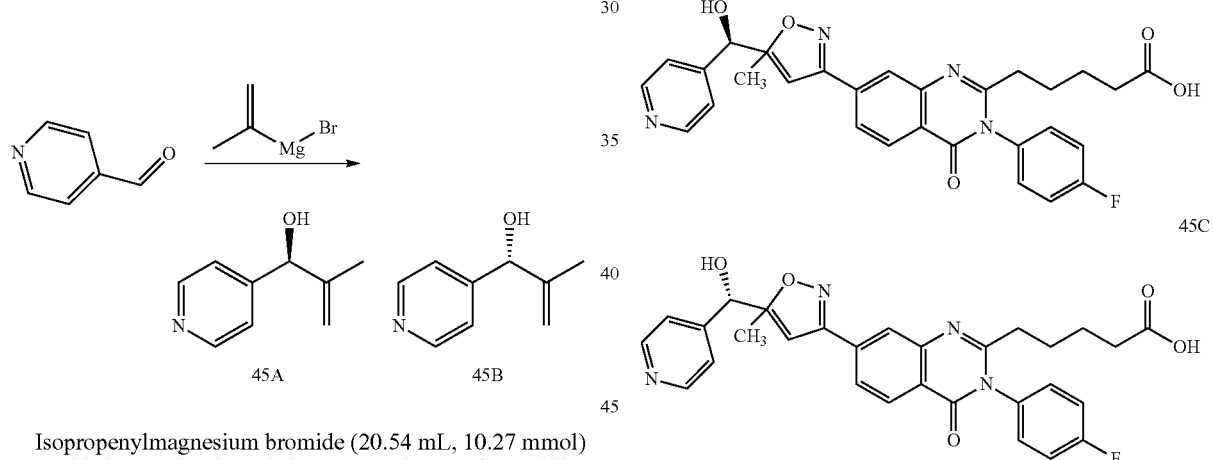

Isopropenylmagnesium bromide (20.54 mL, 10.27 mmol) was added to a stirred, cooled −78° C. mixture of 4-pyridinecarboxaldehyde (0.880 mL, 9.34 mmol) in tetrahydrofuran (25 mL) and the mixture was stirred at room temperature for 45 min. Aqueous NH$_4$Cl solution was added to the suspension at room temperature. The mixture was diluted with ethyl acetate (20 mL), washed with brine (1×10 mL), dried (Na$_2$SO$_4$), filtered and the solvent was evaporated under reduced pressure. The crude material was purified by column chromatography (65% EtOAc/Hexanes) to give a racemic white solid (903 mg, 65%). The enantiomers were separated by SFC chiral chromatography (Chiral Technologies AD-H column, CO$_2$ with 5% EtOH to provide 45A (1st eluting peak) and 45B (2nd eluting peak), which were individually reacted with 15C/NaOCl and then LiOH to provide 45 (derived from SFC 1st peak, MS M+H=531) and 45C (derived from SFC 2nd peak, MS M+H=531), respectively.

The following compounds were prepared following procedures similar to those exemplified in the examples above.

| Cpd | Structure | MS (M + H⁺) |
|---|---|---|
| 100 | 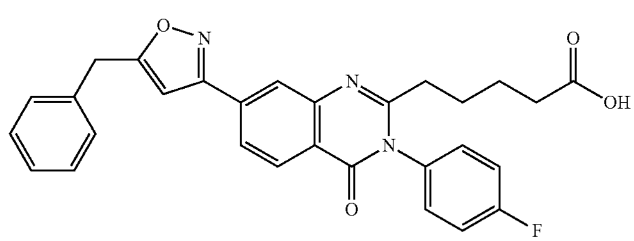 [SMILES: O=C(O)CCCCc1nc2cc(-c3cc(Cc4ccccc4)on3)ccc2c(=O)n1-c1ccc(F)cc1] | 498 |

-continued

| Cpd | Structure | MS (M + H⁺) |
|---|---|---|
| 101 | 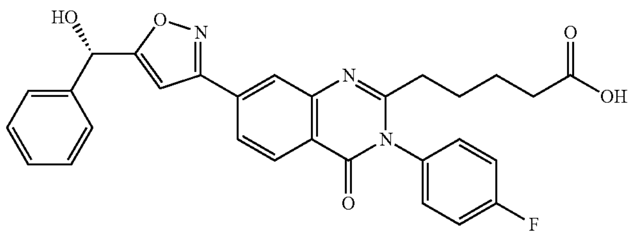 [SMILES: O=C(O)CCCCc1nc2cc(-c3cc([C@@H](O)c4ccccc4)on3)ccc2c(=O)n1-c1ccc(F)cc1] | 514 |
| 102 | 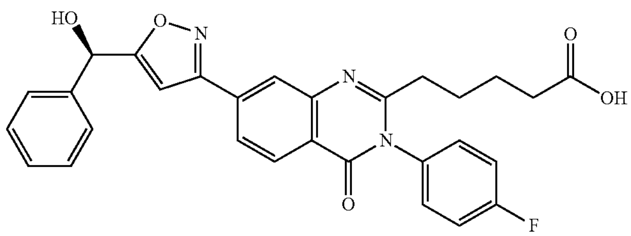 [SMILES: O=C(O)CCCCc1nc2cc(-c3cc([C@H](O)c4ccccc4)on3)ccc2c(=O)n1-c1ccc(F)cc1] | 514 |
| 103 | 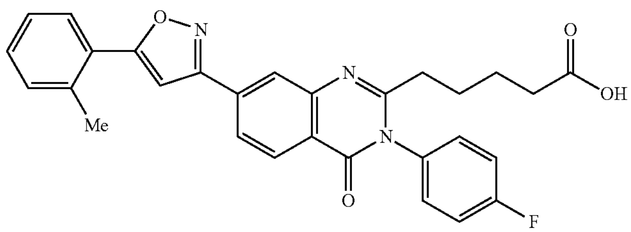 [SMILES: Cc1ccccc1-c1cc(-c2ccc3c(=O)n(-c4ccc(F)cc4)c(CCCCC(=O)O)nc3c2)no1] | 498 |
| 104 | 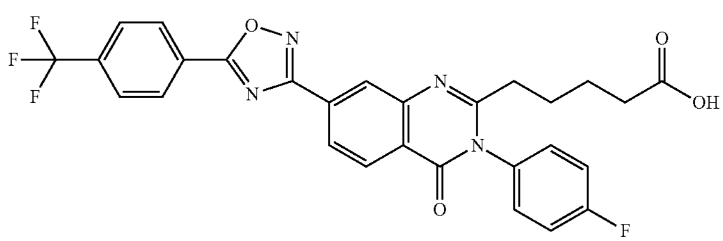 [SMILES: O=C(O)CCCCc1nc2cc(-c3noc(-c4ccc(C(F)(F)F)cc4)n3)ccc2c(=O)n1-c1ccc(F)cc1] | 553 |
| 105 | 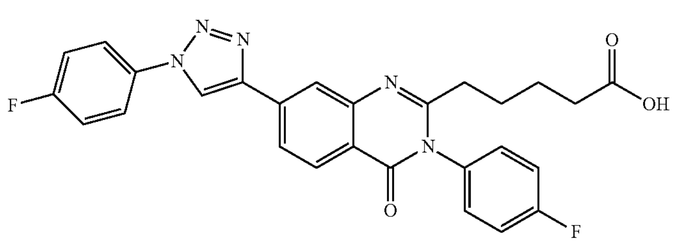 [SMILES: O=C(O)CCCCc1nc2cc(-c3cn(-c4ccc(F)cc4)nn3)ccc2c(=O)n1-c1ccc(F)cc1] | 502 |
| 106 | 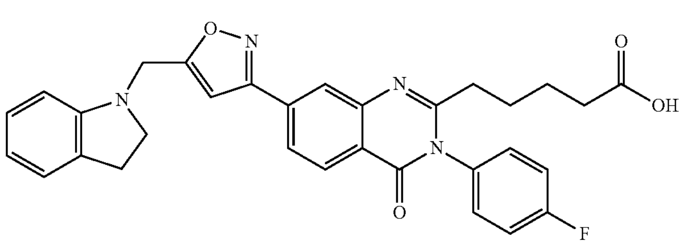 [SMILES: O=C(O)CCCCc1nc2cc(-c3cc(CN4CCc5ccccc54)on3)ccc2c(=O)n1-c1ccc(F)cc1] | 539 |

-continued

| Cpd | Structure | MS (M + H⁺) |
|---|---|---|
| 107 | 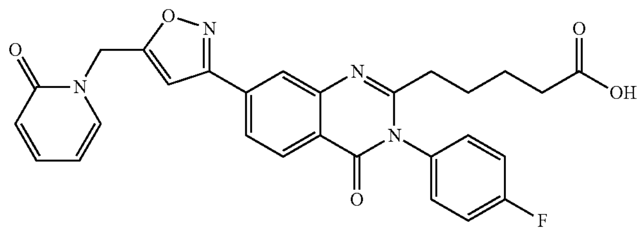 [SMILES: O=C(O)CCCCc1nc2cc(-c3cc(Cn4ccccc4=O)on3)ccc2c(=O)n1-c1ccc(F)cc1] | 515 |
| 108 | 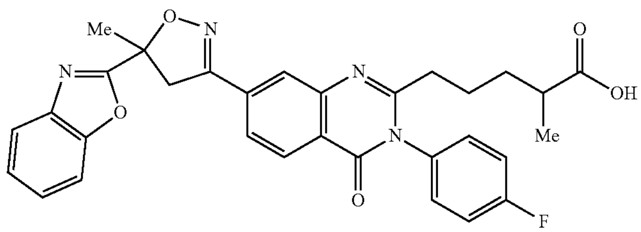 [SMILES: CC(CCCc1nc2cc(C3=NOC(C)(c4nc5ccccc5o4)C3)ccc2c(=O)n1-c1ccc(F)cc1)C(=O)O] | 555 |
| 109 | 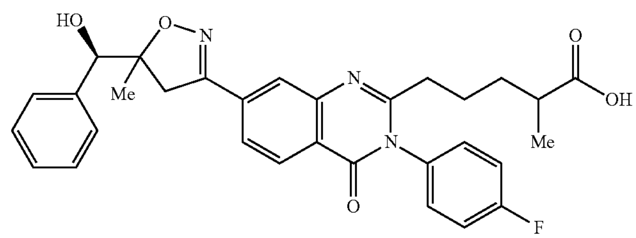 [SMILES: CC(CCCc1nc2cc(C3=NOC(C)([C@H](O)c4ccccc4)C3)ccc2c(=O)n1-c1ccc(F)cc1)C(=O)O] | 544 |
| 110 | 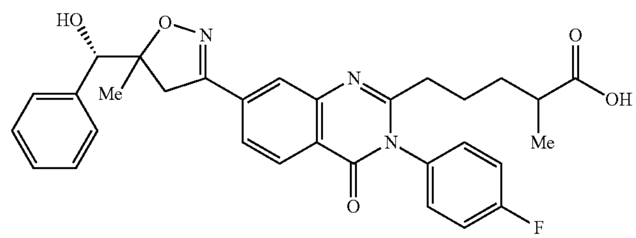 [SMILES: CC(CCCc1nc2cc(C3=NOC(C)([C@@H](O)c4ccccc4)C3)ccc2c(=O)n1-c1ccc(F)cc1)C(=O)O] | 544 |
| 111 | 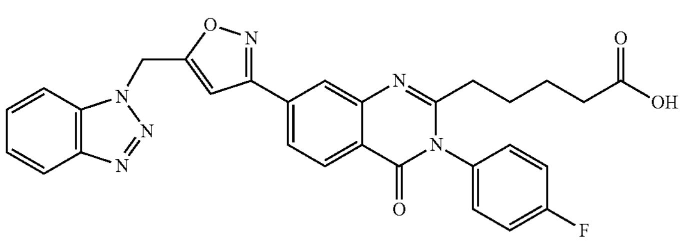 [SMILES: O=C(O)CCCCc1nc2cc(-c3cc(Cn4nnc5ccccc54)on3)ccc2c(=O)n1-c1ccc(F)cc1] | 539 |
| 112 | 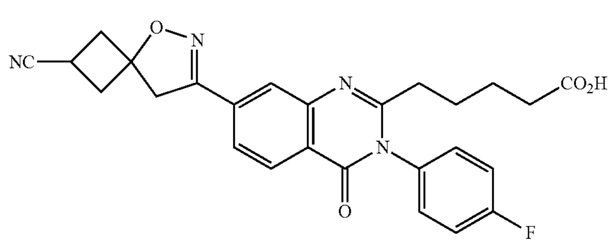 [SMILES: N#CC1CC2(CC(c3ccc4c(=O)n(-c5ccc(F)cc5)c(CCCCC(=O)O)nc4c3)=NO2)C1] | 475 |

-continued

| Cpd | Structure | MS (M + H⁺) |
|---|---|---|
| 113 | 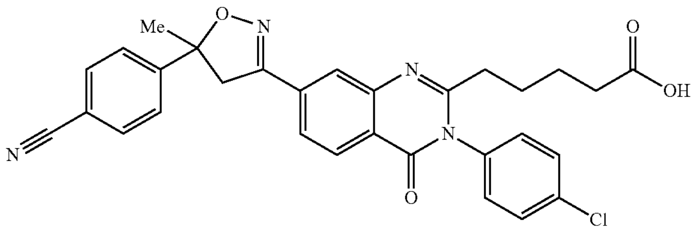 [SMILES: CC1(c2ccc(C#N)cc2)CC(c2ccc3c(=O)n(-c4ccc(Cl)cc4)c(CCCCC(=O)O)nc3c2)=NO1] | 541 |
| 114 | Enantiomer 1 | 525 |
| 115 | Enantiomer 2 | 525 |
| 116 | 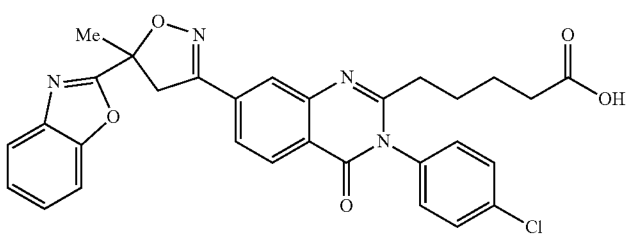 [SMILES: CC1(c2nc3ccccc3o2)CC(c2ccc3c(=O)n(-c4ccc(Cl)cc4)c(CCCCC(=O)O)nc3c2)=NO1] | 557 |
| 117 | 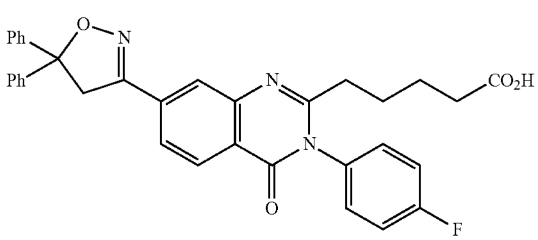 [SMILES: O=C(O)CCCCc1nc2cc(C3=NOC(c4ccccc4)(c4ccccc4)C3)ccc2c(=O)n1-c1ccc(F)cc1] | 562 |
| 118 | Enantiomer 1 | 525 |

| Cpd | Structure | MS (M + H+) |
|---|---|---|
| 119 | 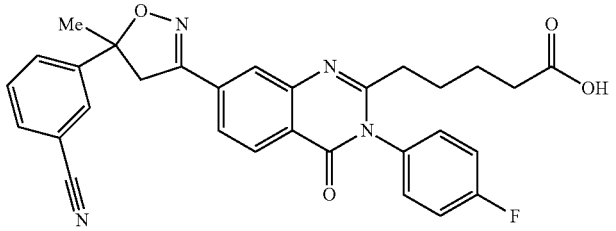<br>Enantiomer 2 | 525 |
| 120 | 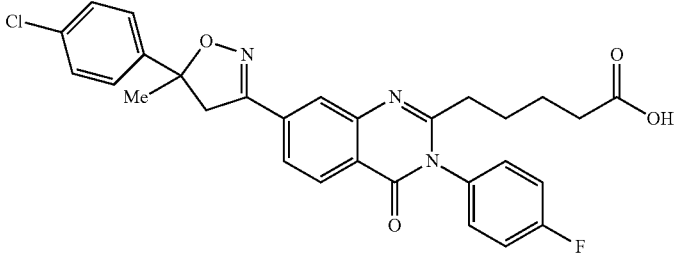<br>Enantiomer 1 | 534 |
| 121 | 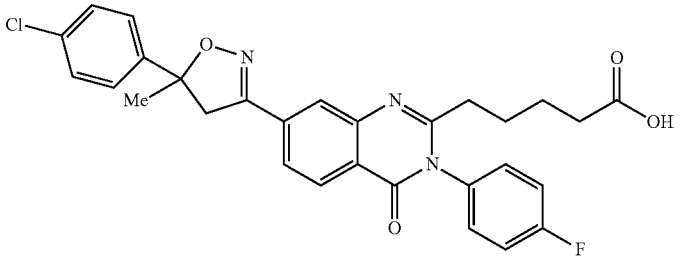<br>Enantiomer 2 | 534 |
| 122 | 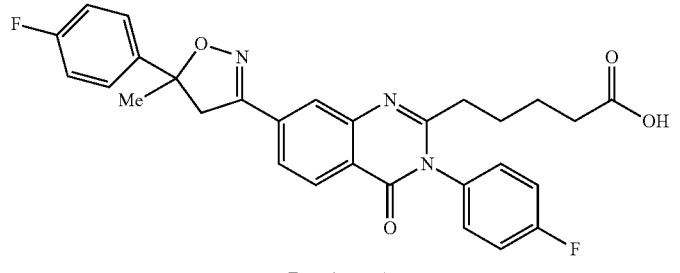 [SMILES: CC1(c2ccc(F)c(F)c2)CC(c2ccc3c(=O)n(-c4ccc(F)cc4)c(CCCCC(=O)O)nc3c2)=NO1]<br>Enantiomer 1 | 518 |
| 123 | 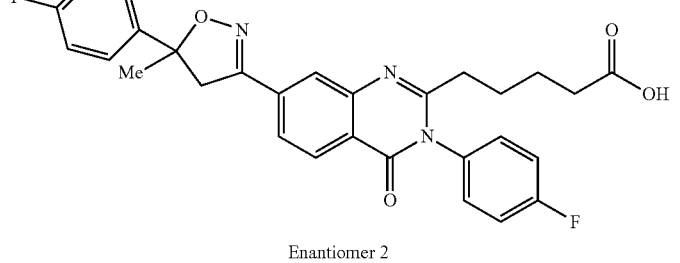<br>Enantiomer 2 | 518 |

-continued
| Cpd | Structure | MS (M + H+) |
|---|---|---|
| 124 | 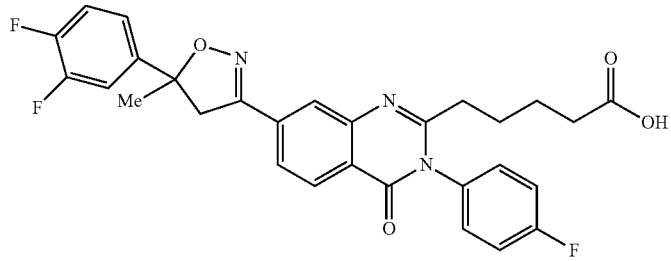 | 536 |
| 125 | 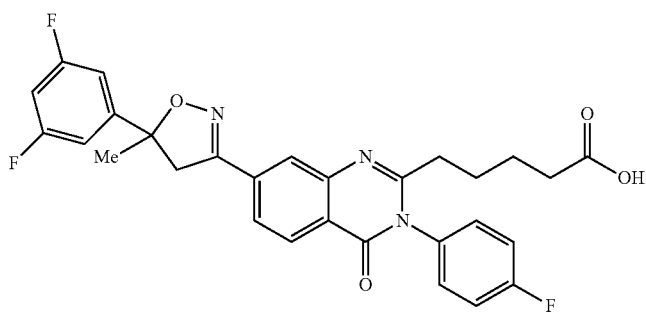  Enantiomer 1 | 536 |
| 126 | 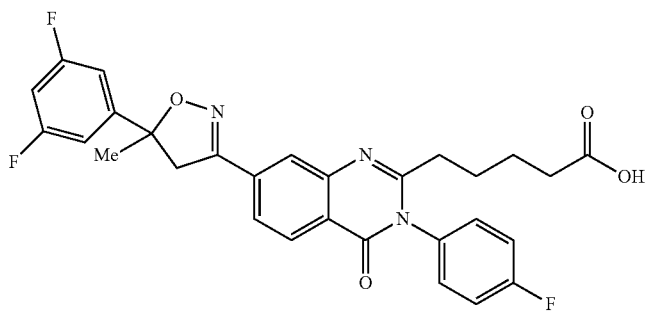  Enantiomer 2 | 536 |
| 127 | 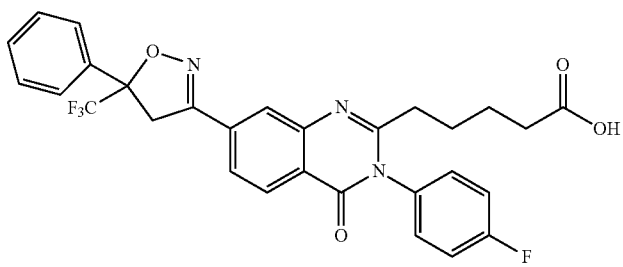 [SMILES: O=C(O)CCCCc1nc2cc(C3=NOC(c4ccccc4)(C(F)(F)F)C3)ccc2c(=O)n1-c1ccc(F)cc1] | 554 |
| 128 | 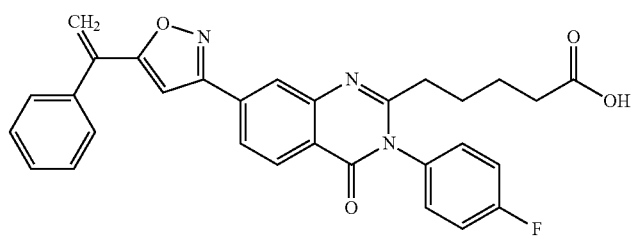 [SMILES: C=C(c1ccccc1)c1cc(-c2ccc3c(=O)n(-c4ccc(F)cc4)c(CCCCC(=O)O)nc3c2)no1] | 510 |

| Cpd | Structure | MS (M + H⁺) |
|-----|-----------|-------------|
| 129 | 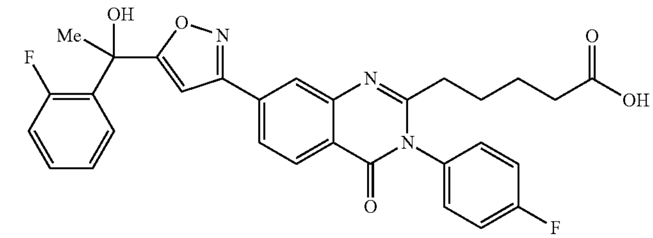 [SMILES: CC(O)(c1cc(-c2ccc3c(=O)n(-c4ccc(F)cc4)c(CCCCC(=O)O)nc3c2)no1)c1ccccc1F] | 546 |
| 130 | 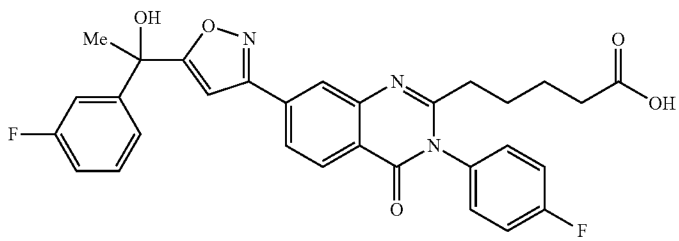 [SMILES: CC(O)(c1cccc(F)c1)c1cc(-c2ccc3c(=O)n(-c4ccc(F)cc4)c(CCCCC(=O)O)nc3c2)no1] | 546 |
| 131 | 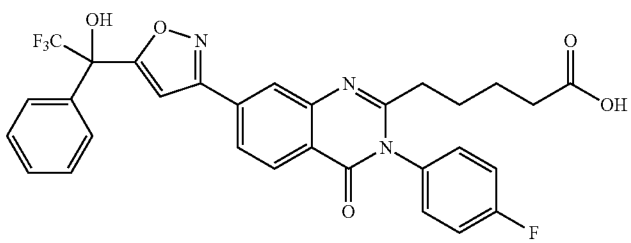 [SMILES: O=C(O)CCCCc1nc2cc(-c3cc(C(O)(c4ccccc4)C(F)(F)F)on3)ccc2c(=O)n1-c1ccc(F)cc1] | 582 |
| 132 | 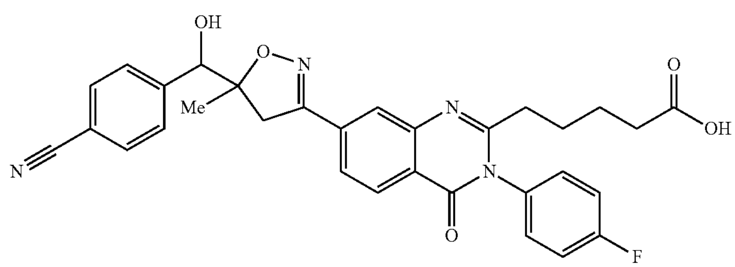 [SMILES: CC1(C(O)c2ccc(C#N)cc2)CC(c2ccc3c(=O)n(-c4ccc(F)cc4)c(CCCCC(=O)O)nc3c2)=NO1] | 555 |
| 133 | 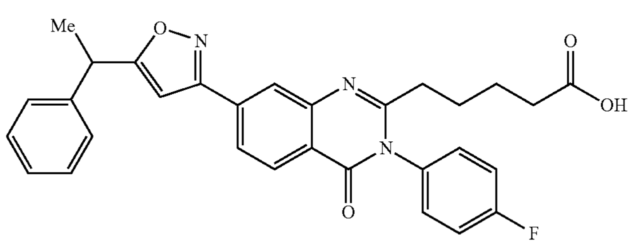 [SMILES: CC(c1ccccc1)c1cc(-c2ccc3c(=O)n(-c4ccc(F)cc4)c(CCCCC(=O)O)nc3c2)no1] | 512 |
| 134 | 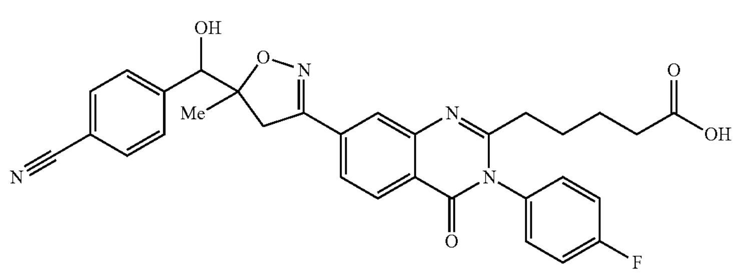 [SMILES: CC1(C(O)c2ccc(C#N)cc2)CC(c2ccc3c(=O)n(-c4ccc(F)cc4)c(CCCCC(=O)O)nc3c2)=NO1] | 555 |

-continued
| Cpd | Structure | MS (M + H⁺) |
|---|---|---|
| 135 | 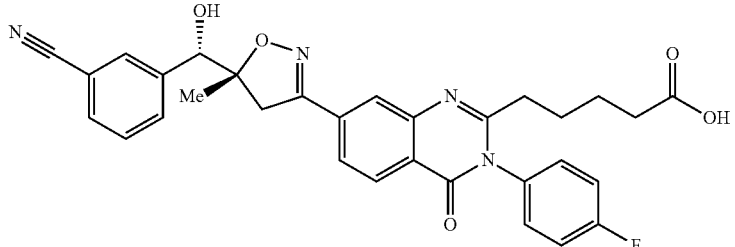 | 555 |
| 136 | 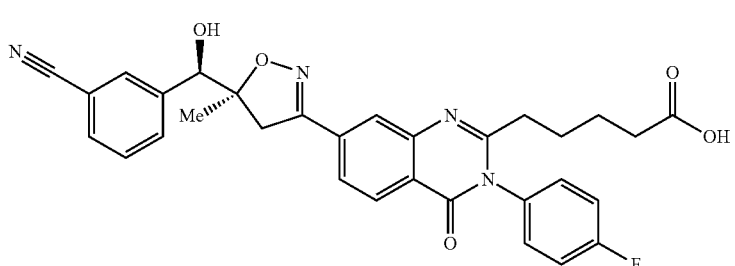 | 555 |
| 137 | 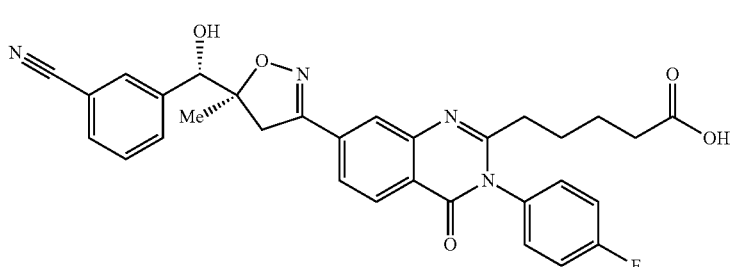 | 555 |
| 138 | 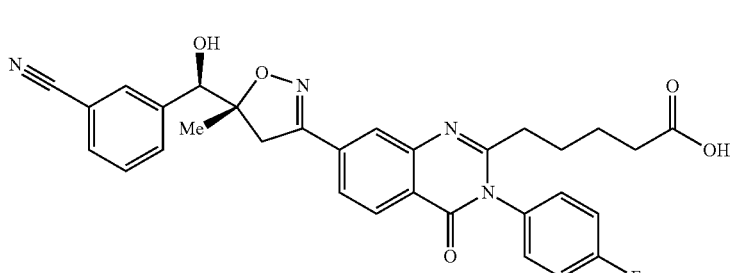 | 555 |
| 139 | 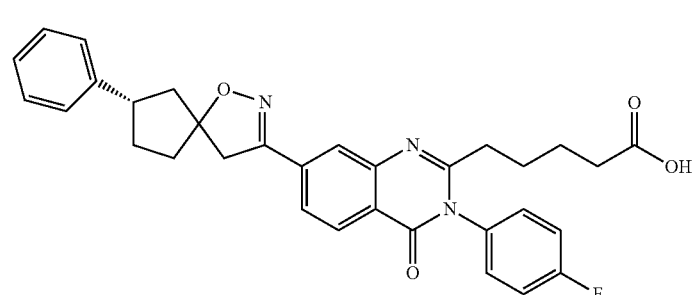<br>Stereoisomer 1 | 540 |

-continued
| Cpd | Structure | MS (M + H⁺) |
|---|---|---|
| 140 | 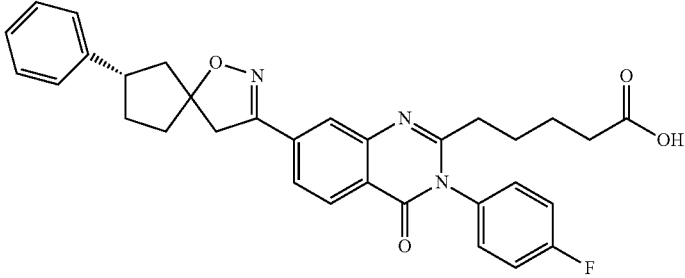 Stereoisomer 2 | 540 |
| 141 | 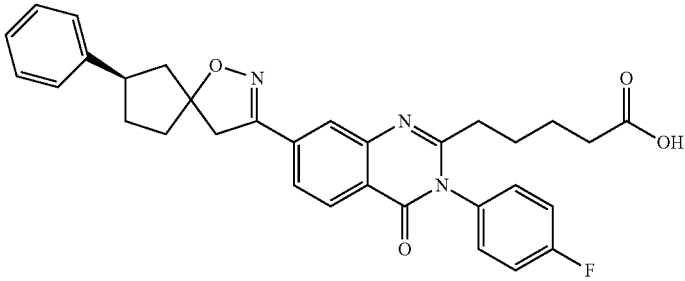 Stereoisomer 1 | 540 |
| 142 | 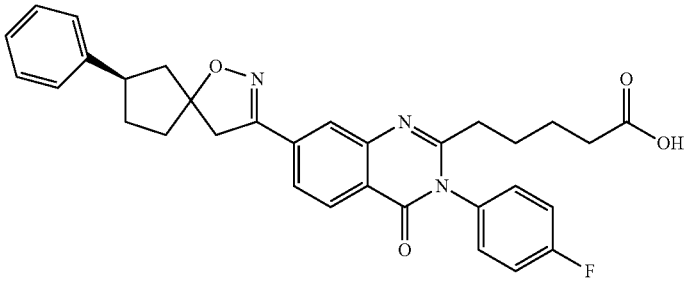 Stereoisomer 2 | 540 |
| 143 | 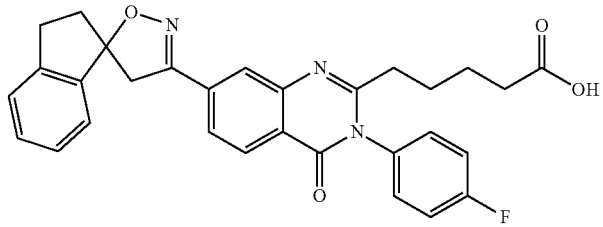 [SMILES: O=C(O)CCCCc1nc2cc(C3=NOC4(CCc5ccccc54)C3)ccc2c(=O)n1-c1ccc(F)cc1] | 512 |
| 144 | 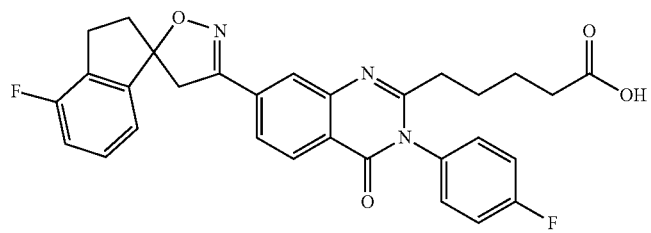 [SMILES: O=C(O)CCCCc1nc2cc(C3=NOC4(CCc5c(F)cccc54)C3)ccc2c(=O)n1-c1ccc(F)cc1] | 530 |

-continued

| Cpd | Structure | MS (M + H⁺) |
|---|---|---|
| 145 | 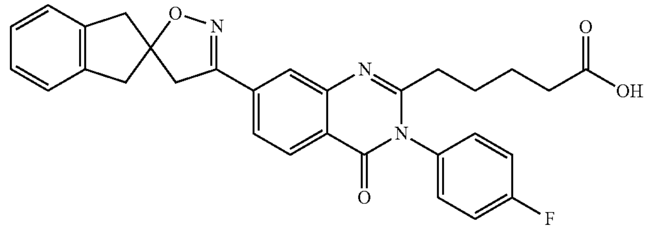 [SMILES: O=C(O)CCCCc1nc2cc(C3=NOC4(C3)Cc3ccccc3C4)ccc2c(=O)n1-c1ccc(F)cc1] | 512 |
| 146 | 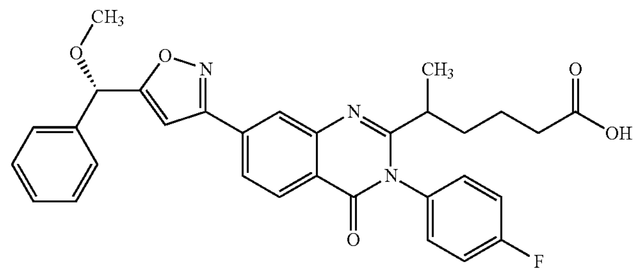 [SMILES: CO[C@@H](c1ccccc1)c1cc(-c2ccc3c(=O)n(-c4ccc(F)cc4)c(C(C)CCCC(=O)O)nc3c2)no1] | 542 |
| 147 | 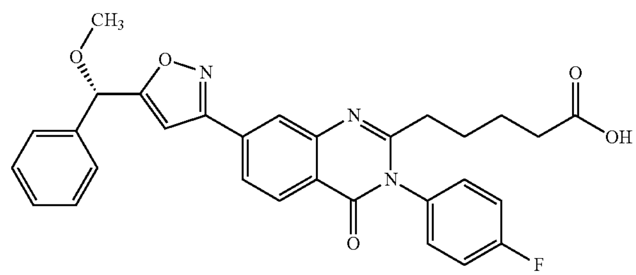 [SMILES: CO[C@@H](c1ccccc1)c1cc(-c2ccc3c(=O)n(-c4ccc(F)cc4)c(CCCCC(=O)O)nc3c2)no1] | 528 |
| 148 | 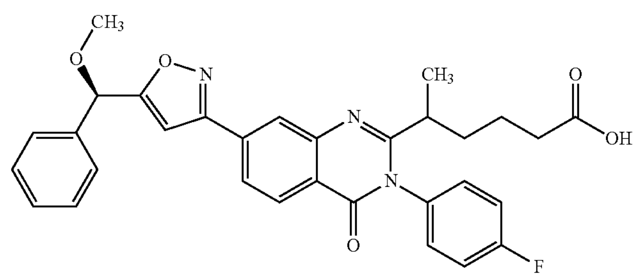 [SMILES: CO[C@H](c1ccccc1)c1cc(-c2ccc3c(=O)n(-c4ccc(F)cc4)c(C(C)CCCC(=O)O)nc3c2)no1] | 542 |
| 149 | 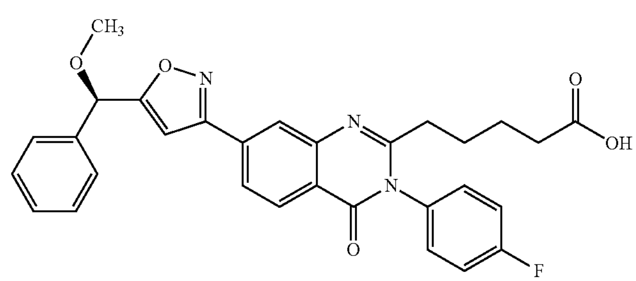 [SMILES: CO[C@H](c1ccccc1)c1cc(-c2ccc3c(=O)n(-c4ccc(F)cc4)c(CCCCC(=O)O)nc3c2)no1] | 528 |
| 150 | 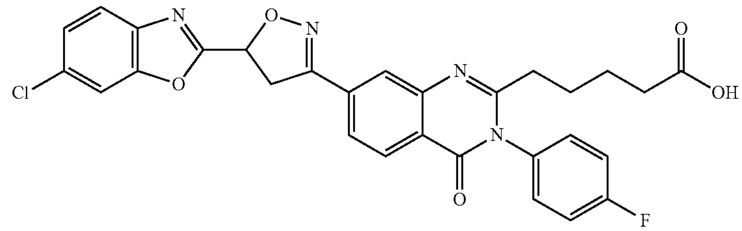 [SMILES: O=C(O)CCCCc1nc2cc(C3=NOC(c4nc5ccc(Cl)cc5o4)C3)ccc2c(=O)n1-c1ccc(F)cc1] | 561 |

-continued
| Cpd | Structure | MS (M + H+) |
|---|---|---|
| 151 | 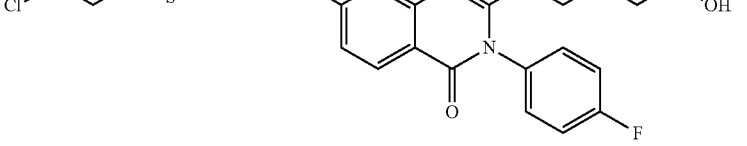 | 577 |
| 152 | 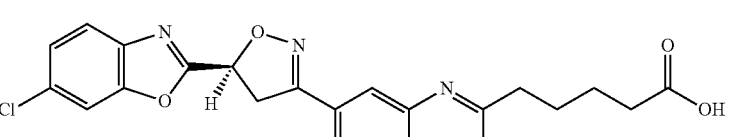 | 561 |
| 153 | 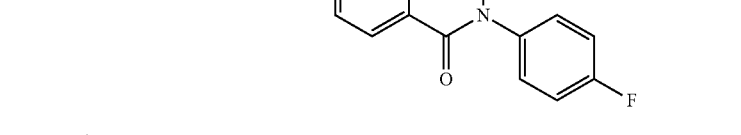 | 561 |
| 154 | 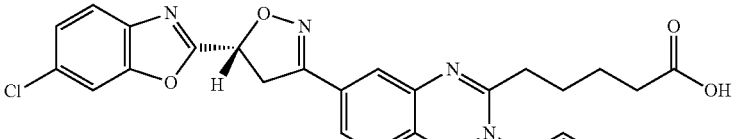 | 577 |
| 155 | 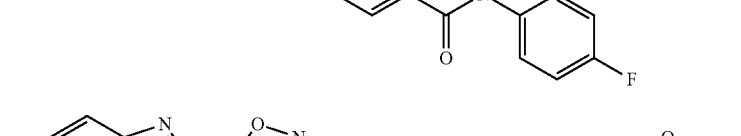 | 577 |
| 156 | 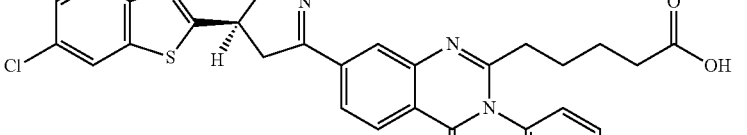 | 528 |

| Cpd | Structure | MS (M + H⁺) |
|---|---|---|
| 157 | 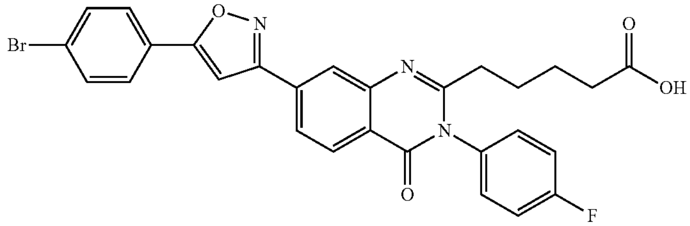 [SMILES: O=C(O)CCCCc1nc2cc(-c3cc(-c4ccc(Br)cc4)on3)ccc2c(=O)n1-c1ccc(F)cc1] | 563 |
| 158 | 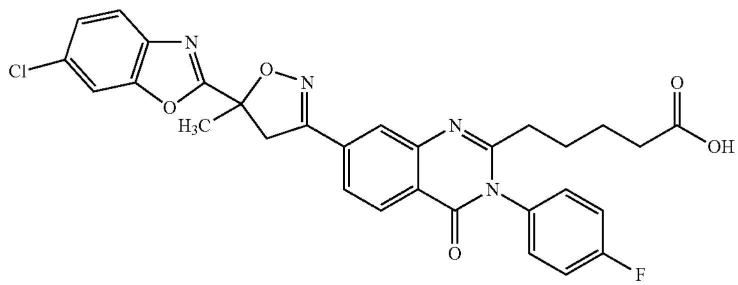 [SMILES: CC1(c2nc3ccc(Cl)cc3o2)CC(c2ccc3c(=O)n(-c4ccc(F)cc4)c(CCCCC(=O)O)nc3c2)=NO1] | 575 |
| 159 | 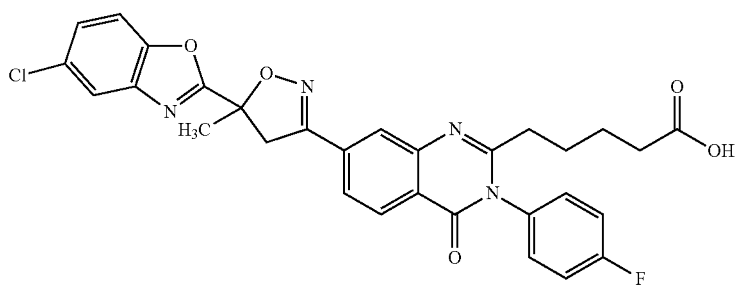 [SMILES: CC1(c2nc3cc(Cl)ccc3o2)CC(c2ccc3c(=O)n(-c4ccc(F)cc4)c(CCCCC(=O)O)nc3c2)=NO1] | 575 |
| 160 | 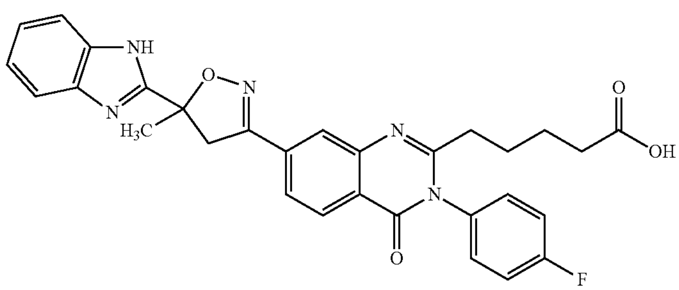 [SMILES: CC1(c2nc3ccccc3[nH]2)CC(c2ccc3c(=O)n(-c4ccc(F)cc4)c(CCCCC(=O)O)nc3c2)=NO1] | 540 |
| 161 | 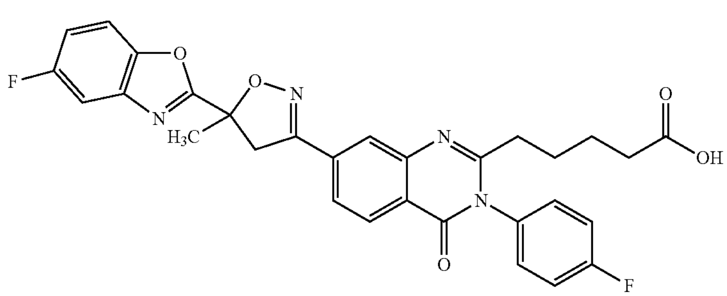 [SMILES: CC1(c2nc3cc(F)ccc3o2)CC(c2ccc3c(=O)n(-c4ccc(F)cc4)c(CCCCC(=O)O)nc3c2)=NO1] | 559 |

-continued

| Cpd | Structure | MS (M + H⁺) |
|---|---|---|
| 162 | 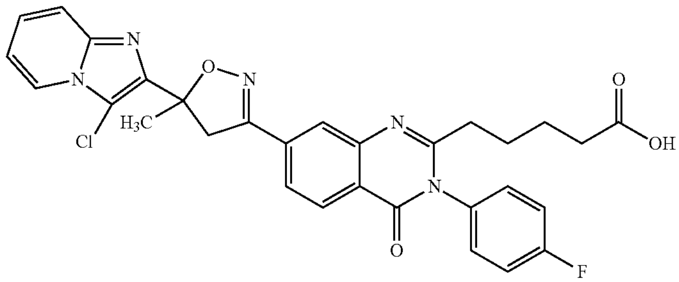 [SMILES: CC1(c2nc3ccccn3c2Cl)CC(c2ccc3c(=O)n(-c4ccc(F)cc4)c(CCCCC(=O)O)nc3c2)=NO1] | 576 |
| 163 | 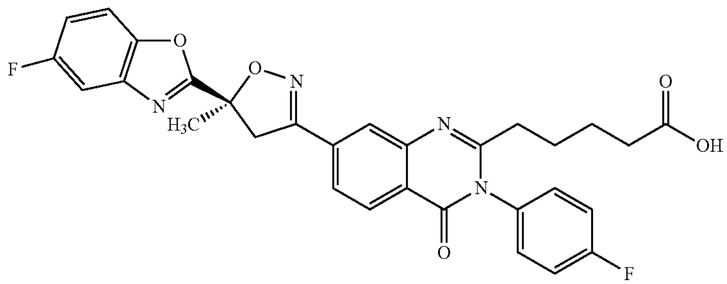 [SMILES: C[C@@]1(c2nc3cc(F)ccc3o2)CC(c2ccc3c(=O)n(-c4ccc(F)cc4)c(CCCCC(=O)O)nc3c2)=NO1] | 559 |
| 164 | 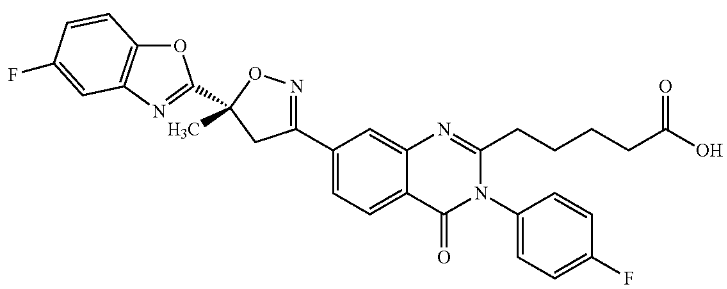 [SMILES: C[C@]1(c2nc3cc(F)ccc3o2)CC(c2ccc3c(=O)n(-c4ccc(F)cc4)c(CCCCC(=O)O)nc3c2)=NO1] | 559 |
| 165 | 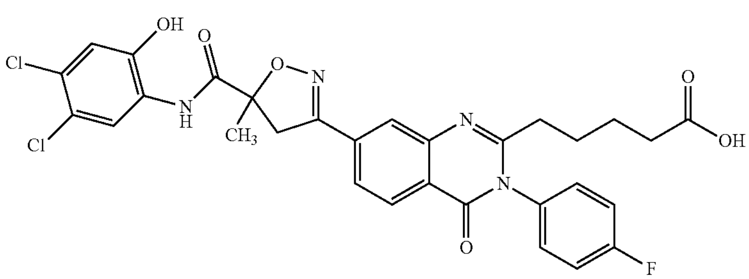 [SMILES: CC1(C(=O)Nc2cc(Cl)c(Cl)cc2O)CC(c2ccc3c(=O)n(-c4ccc(F)cc4)c(CCCCC(=O)O)nc3c2)=NO1] | 629 |
| 166 | 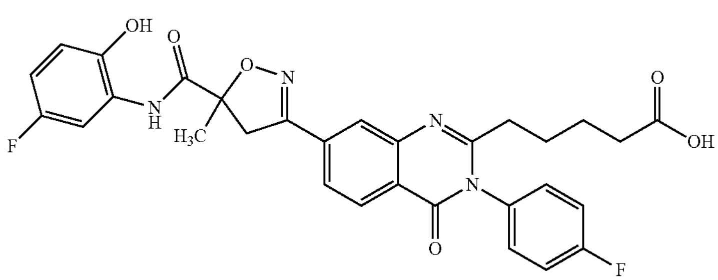 [SMILES: CC1(C(=O)Nc2cc(F)ccc2O)CC(c2ccc3c(=O)n(-c4ccc(F)cc4)c(CCCCC(=O)O)nc3c2)=NO1] | 577 |

-continued
| Cpd | Structure | MS (M + H+) |
|---|---|---|
| 167 | 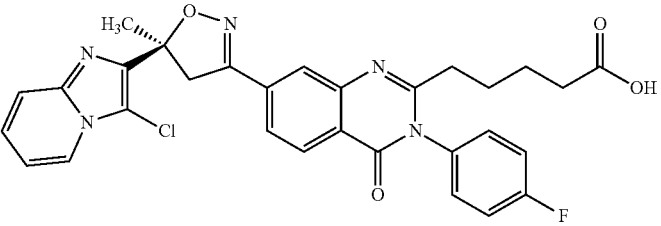 [SMILES: C[C@@]1(c2nc3ccccn3c2Cl)CC(c2ccc3c(=O)n(-c4ccc(F)cc4)c(CCCCC(=O)O)nc3c2)=NO1] | 576 |
| 168 | 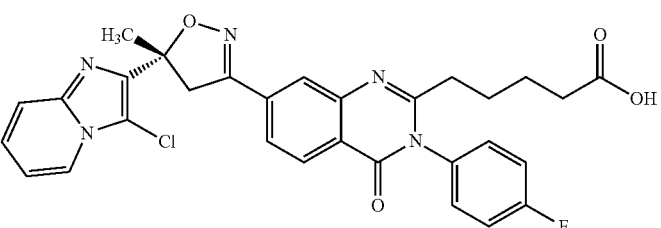 | 576 |
| 169 | 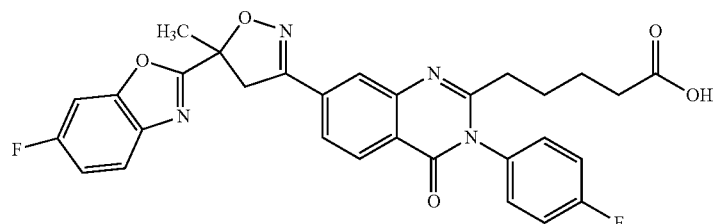 | 559 |
| 170 | 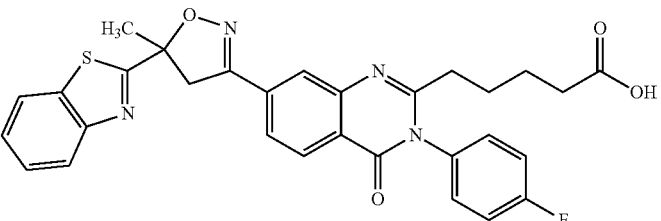 | 557 |
| 171 | 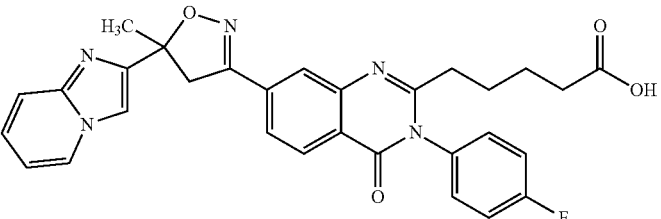 | 540 |
| 172 | 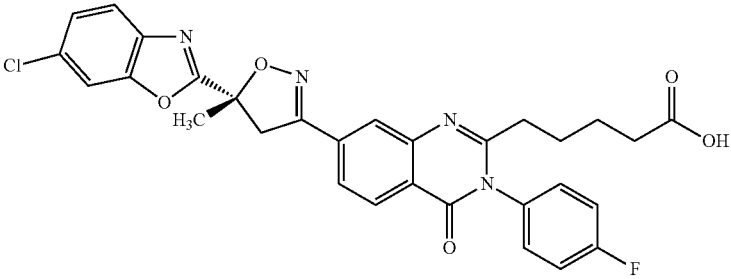 [SMILES: C[C@]1(c2nc3ccc(Cl)cc3o2)CC(c2ccc3c(=O)n(-c4ccc(F)cc4)c(CCCCC(=O)O)nc3c2)=NO1] | 575 |

-continued

| Cpd | Structure | MS (M + H+) |
|---|---|---|
| 173 | 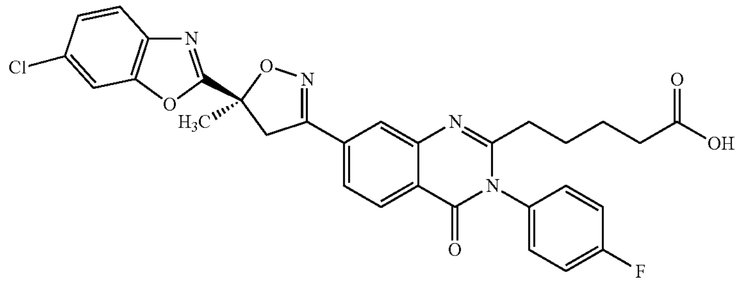 [SMILES: C[C@@]1(c2nc3ccc(Cl)cc3o2)CC(c2ccc3c(=O)n(-c4ccc(F)cc4)c(CCCCC(=O)O)nc3c2)=NO1] | 575 |
| 174 | 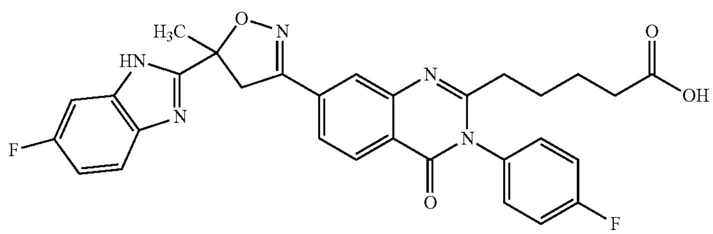 [SMILES: CC1(c2nc3ccc(F)cc3[nH]2)CC(c2ccc3c(=O)n(-c4ccc(F)cc4)c(CCCCC(=O)O)nc3c2)=NO1] | 558 |
| 175 | 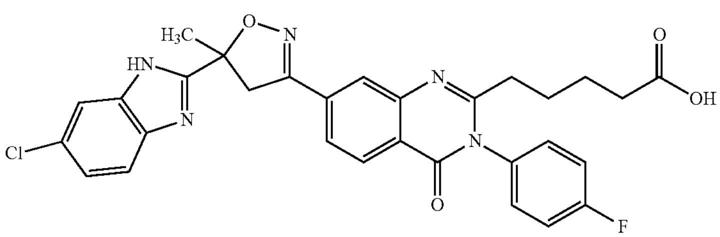 [SMILES: CC1(c2nc3ccc(Cl)cc3[nH]2)CC(c2ccc3c(=O)n(-c4ccc(F)cc4)c(CCCCC(=O)O)nc3c2)=NO1] | 575 |
| 176 | 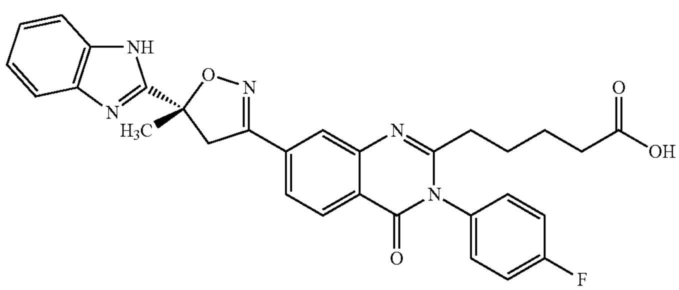 [SMILES: C[C@]1(c2nc3ccccc3[nH]2)CC(c2ccc3c(=O)n(-c4ccc(F)cc4)c(CCCCC(=O)O)nc3c2)=NO1] | 540 |
| 177 | 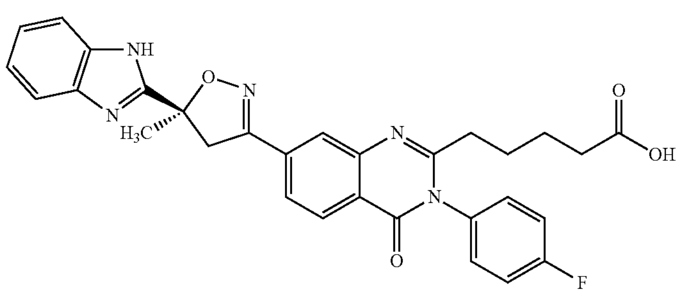 [SMILES: C[C@@]1(c2nc3ccccc3[nH]2)CC(c2ccc3c(=O)n(-c4ccc(F)cc4)c(CCCCC(=O)O)nc3c2)=NO1] | 540 |
| 178 | 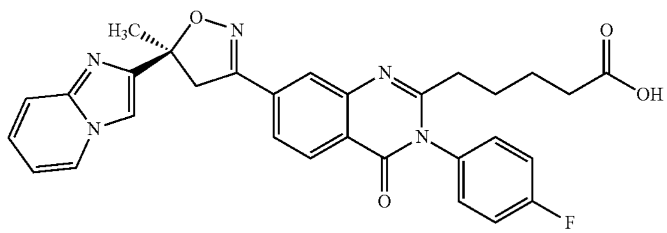 [SMILES: C[C@@]1(c2cn3ccccc3n2)CC(c2ccc3c(=O)n(-c4ccc(F)cc4)c(CCCCC(=O)O)nc3c2)=NO1] | 540 |

-continued

| Cpd | Structure | MS (M + H⁺) |
|---|---|---|
| 179 | 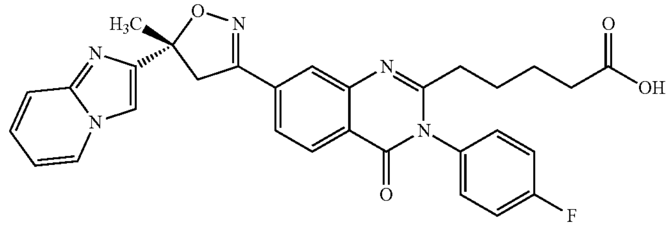 [SMILES: C[C@]1(c2cn3ccccc3n2)CC(c2ccc3c(=O)n(-c4ccc(F)cc4)c(CCCCC(=O)O)nc3c2)=NO1] | 540 |
| 180 | 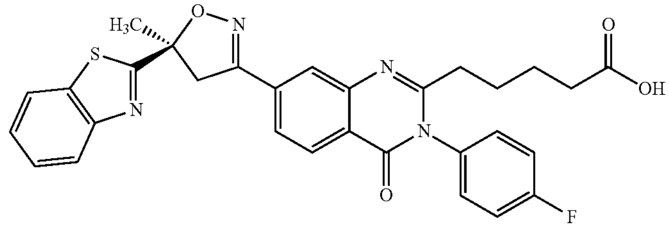 [SMILES: C[C@@]1(c2nc3ccccc3s2)CC(c2ccc3c(=O)n(-c4ccc(F)cc4)c(CCCCC(=O)O)nc3c2)=NO1] | 557 |
| 181 | 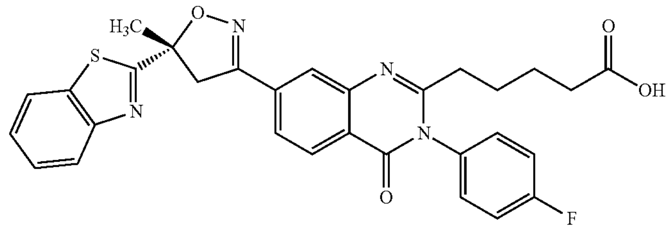 [SMILES: C[C@]1(c2nc3ccccc3s2)CC(c2ccc3c(=O)n(-c4ccc(F)cc4)c(CCCCC(=O)O)nc3c2)=NO1] | 557 |
| 182 | 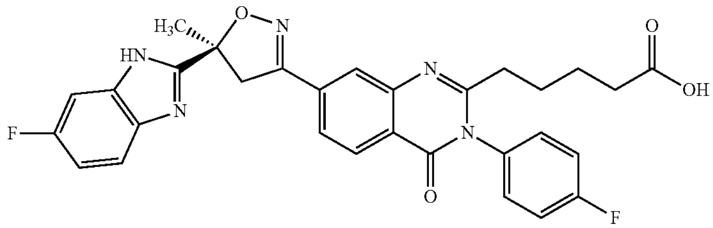 [SMILES: C[C@@]1(c2nc3ccc(F)cc3[nH]2)CC(c2ccc3c(=O)n(-c4ccc(F)cc4)c(CCCCC(=O)O)nc3c2)=NO1] | 558 |
| 183 | 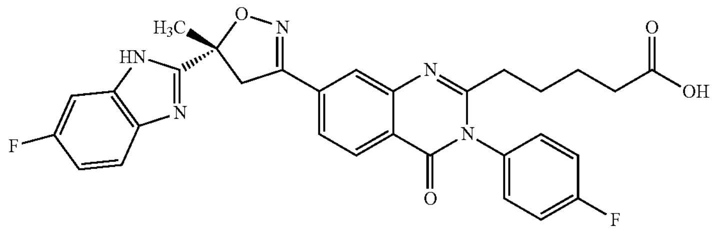 [SMILES: C[C@]1(c2nc3ccc(F)cc3[nH]2)CC(c2ccc3c(=O)n(-c4ccc(F)cc4)c(CCCCC(=O)O)nc3c2)=NO1] | 558 |
| 184 | 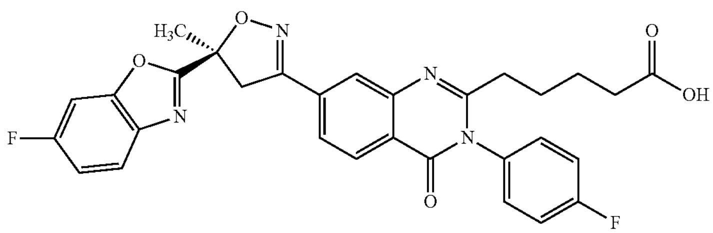 [SMILES: C[C@@]1(c2nc3ccc(F)cc3o2)CC(c2ccc3c(=O)n(-c4ccc(F)cc4)c(CCCCC(=O)O)nc3c2)=NO1] | 559 |

| Cpd | Structure | MS (M + H⁺) |
|---|---|---|
| 185 | 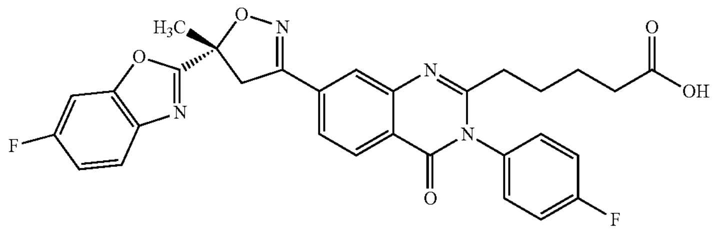 [SMILES: C[C@]1(c2nc3ccc(F)cc3o2)CC(c2ccc3c(=O)n(-c4ccc(F)cc4)c(CCCCC(=O)O)nc3c2)=NO1] | 559 |
| 186 | 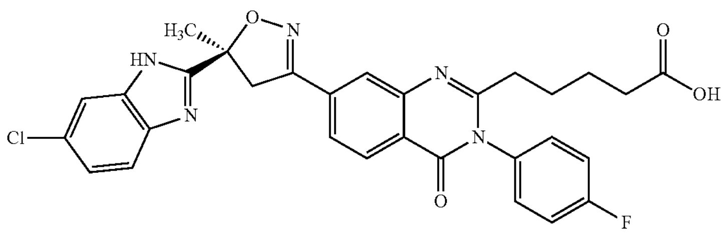 [SMILES: C[C@@]1(c2nc3ccc(Cl)cc3[nH]2)CC(c2ccc3c(=O)n(-c4ccc(F)cc4)c(CCCCC(=O)O)nc3c2)=NO1] | 575 |
| 187 | 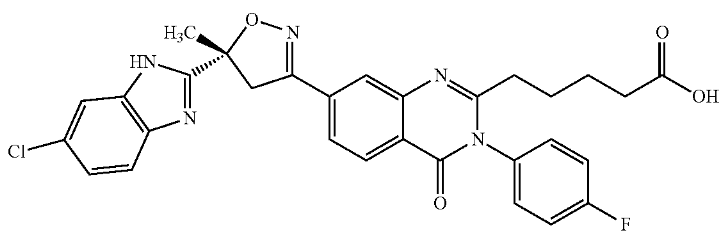 [SMILES: C[C@]1(c2nc3ccc(Cl)cc3[nH]2)CC(c2ccc3c(=O)n(-c4ccc(F)cc4)c(CCCCC(=O)O)nc3c2)=NO1] | 575 |
| 188 | 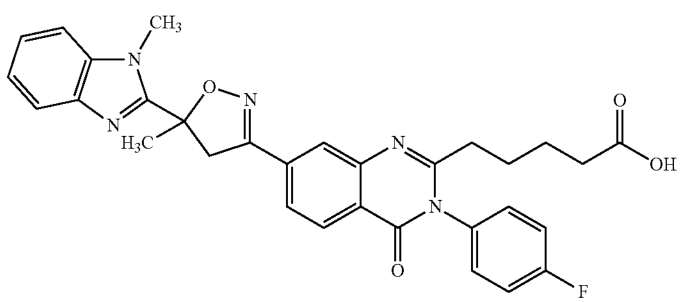 [SMILES: Cn1c(C2(C)CC(c3ccc4c(=O)n(-c5ccc(F)cc5)c(CCCCC(=O)O)nc4c3)=NO2)nc2ccccc21] | 554 |
| 189 | 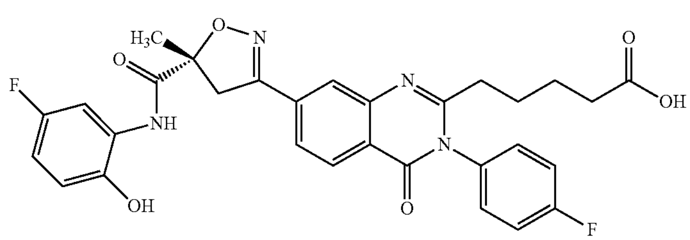 [SMILES: C[C@]1(C(=O)Nc2cc(F)ccc2O)CC(c2ccc3c(=O)n(-c4ccc(F)cc4)c(CCCCC(=O)O)nc3c2)=NO1] | 577 |
| 190 | 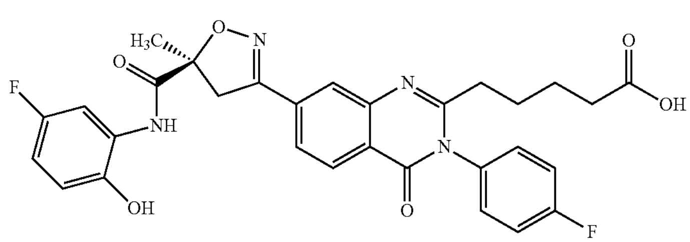 [SMILES: C[C@@]1(C(=O)Nc2cc(F)ccc2O)CC(c2ccc3c(=O)n(-c4ccc(F)cc4)c(CCCCC(=O)O)nc3c2)=NO1] | 577 |

| Cpd | Structure | MS (M + H⁺) |
|---|---|---|
| 191 | 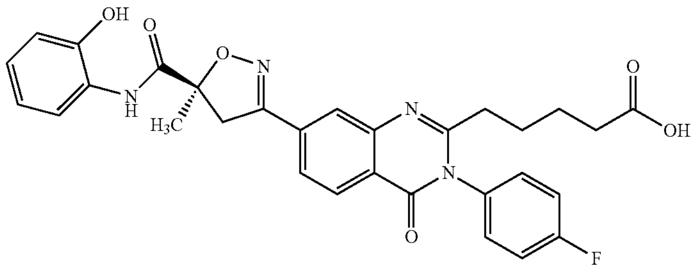 [SMILES: C[C@@]1(C(=O)Nc2ccccc2O)CC(c2ccc3c(=O)n(-c4ccc(F)cc4)c(CCCCC(=O)O)nc3c2)=NO1] | 559 |
| 192 | 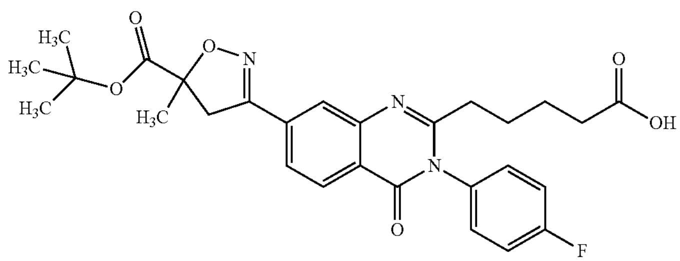 [SMILES: CC(C)(C)OC(=O)C1(C)CC(c2ccc3c(=O)n(-c4ccc(F)cc4)c(CCCCC(=O)O)nc3c2)=NO1] | 524 |
| 193 | 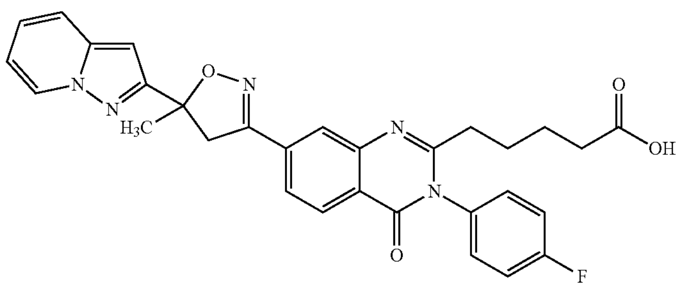 [SMILES: CC1(c2cc3ccccn3n2)CC(c2ccc3c(=O)n(-c4ccc(F)cc4)c(CCCCC(=O)O)nc3c2)=NO1] | 540 |
| 194 | 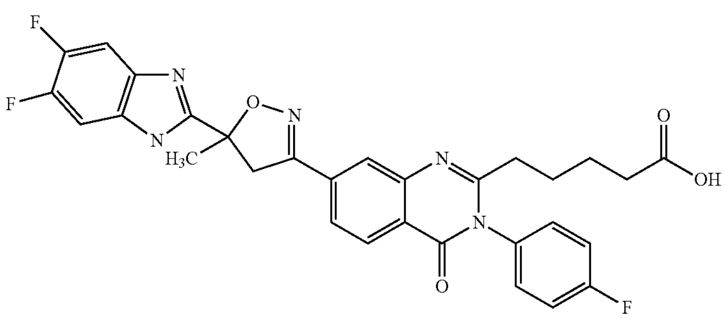 [SMILES: CC1(c2nc3cc(F)c(F)cc3[nH]2)CC(c2ccc3c(=O)n(-c4ccc(F)cc4)c(CCCCC(=O)O)nc3c2)=NO1] | 576 |
| 195 | 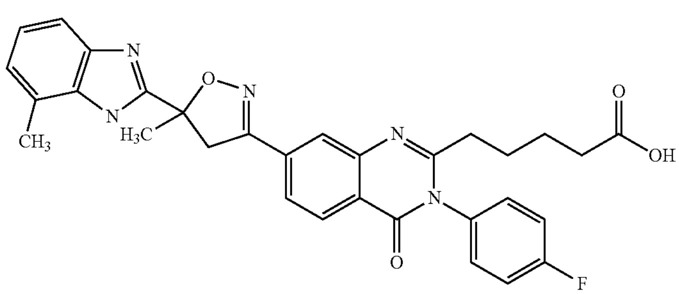 [SMILES: Cc1cccc2nc(C3(C)CC(c4ccc5c(=O)n(-c6ccc(F)cc6)c(CCCCC(=O)O)nc5c4)=NO3)[nH]c12] | 554 |

-continued
| Cpd | Structure | MS (M + H+) |
|---|---|---|
| 196 | 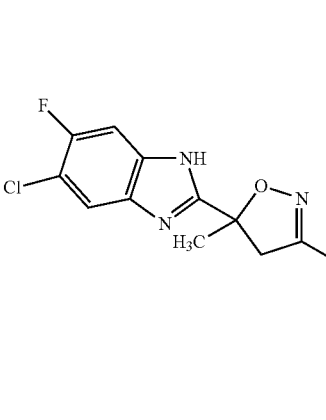 | 608 |
| 197 | 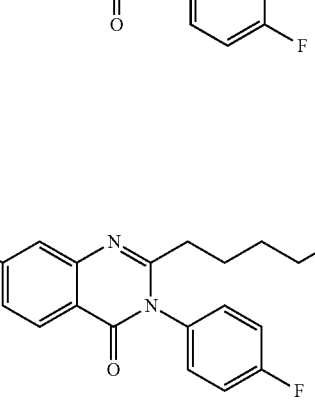 | 592 |
| 198 | 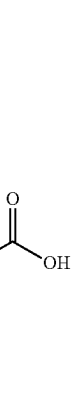 | 576 |
| 199 | 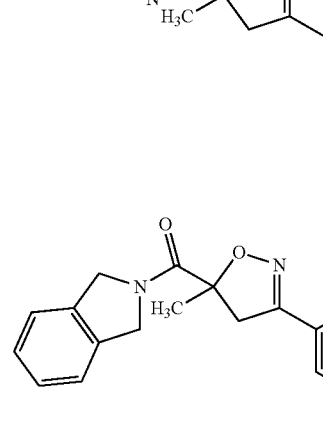 | 569 |
| 200 | 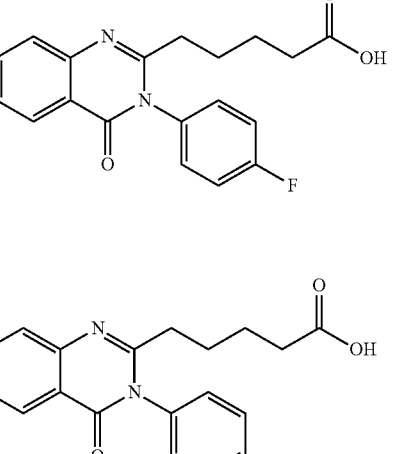 | 468 |

| Cpd | Structure | MS (M + H+) |
|---|---|---|
| 201 | 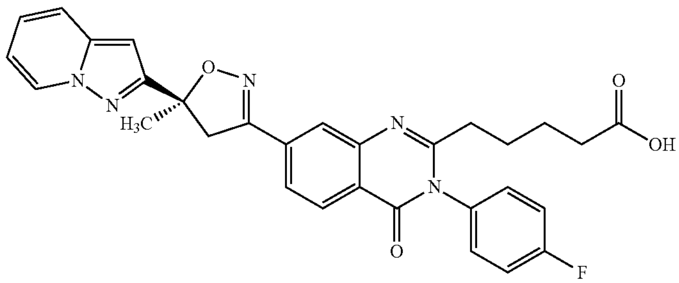 [SMILES: C[C@@]1(c2cc3ccccn3n2)CC(c2ccc3c(=O)n(-c4ccc(F)cc4)c(CCCCC(=O)O)nc3c2)=NO1] | 540 |
| 202 | 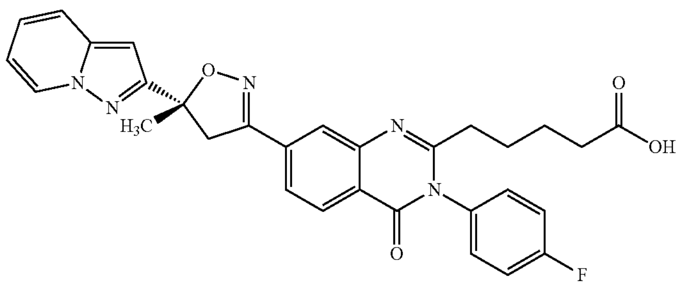 [SMILES: C[C@]1(c2cc3ccccn3n2)CC(c2ccc3c(=O)n(-c4ccc(F)cc4)c(CCCCC(=O)O)nc3c2)=NO1] | 540 |
| 203 | 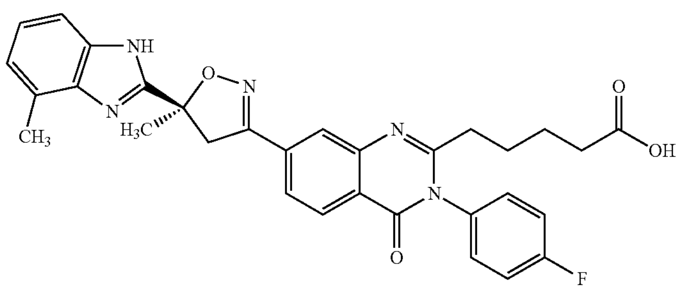 [SMILES: Cc1cccc2[nH]c([C@]3(C)CC(c4ccc5c(=O)n(-c6ccc(F)cc6)c(CCCCC(=O)O)nc5c4)=NO3)nc12] | 554 |
| 204 | 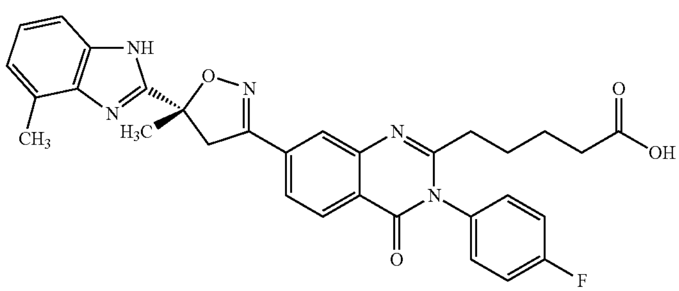 [SMILES: Cc1cccc2[nH]c([C@@]3(C)CC(c4ccc5c(=O)n(-c6ccc(F)cc6)c(CCCCC(=O)O)nc5c4)=NO3)nc12] | 554 |
| 205 | 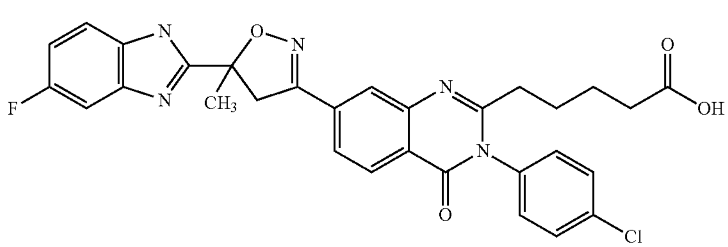 [SMILES: CC1(c2nc3cc(F)ccc3[nH]2)CC(c2ccc3c(=O)n(-c4ccc(Cl)cc4)c(CCCCC(=O)O)nc3c2)=NO1] | 574 |

-continued

| Cpd | Structure | MS (M + H⁺) |
|-----|-----------|-------------|
| 206 | 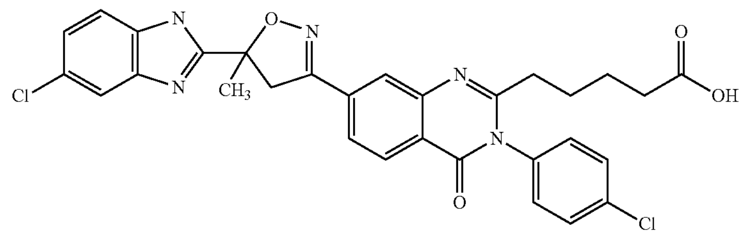 [SMILES: CC1(c2nc3cc(Cl)ccc3[nH]2)CC(c2ccc3c(=O)n(-c4ccc(Cl)cc4)c(CCCCC(=O)O)nc3c2)=NO1] | 592 |
| 207 | 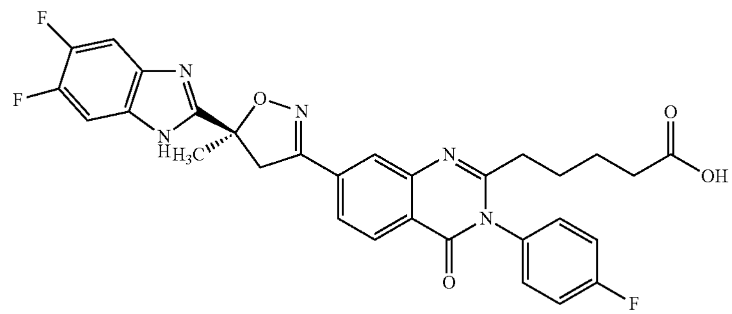 | 577 |
| 208 | 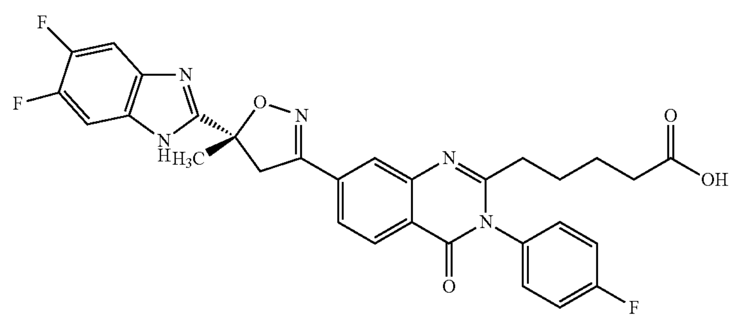 | 577 |
| 209 | 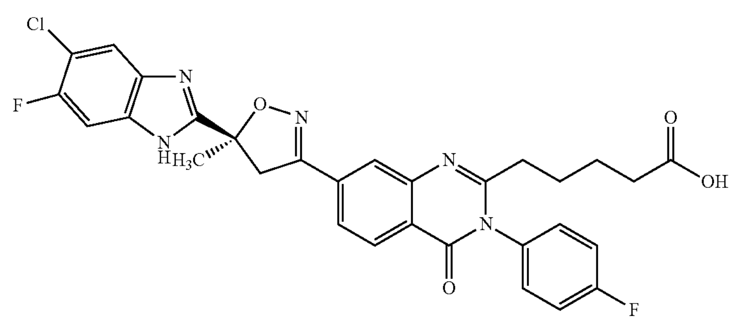 [SMILES: C[C@@]1(c2nc3cc(F)c(F)cc3[nH]2)CC(c2ccc3c(=O)n(-c4ccc(F)cc4)c(CCCCC(=O)O)nc3c2)=NO1] | 592 |
| 210 | 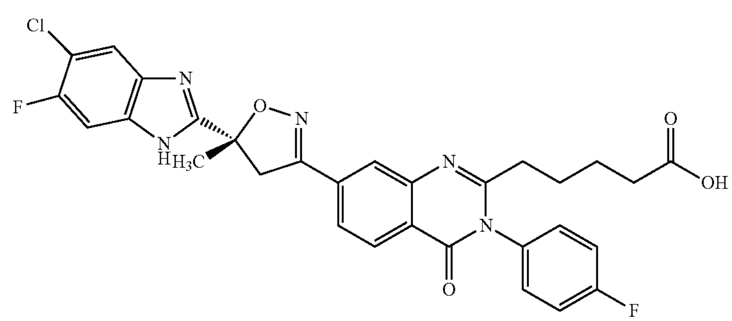 [SMILES: C[C@]1(c2nc3cc(Cl)c(F)cc3[nH]2)CC(c2ccc3c(=O)n(-c4ccc(F)cc4)c(CCCCC(=O)O)nc3c2)=NO1] | 592 |

| Cpd | Structure | MS (M + H⁺) |
|---|---|---|
| 211 | 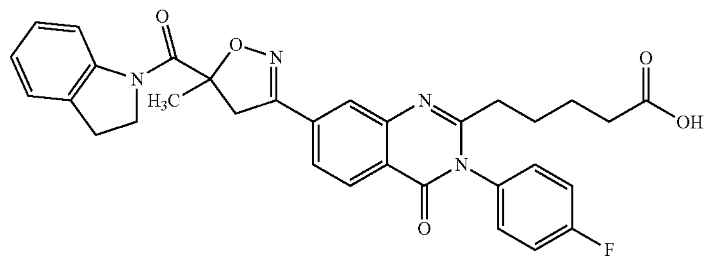 [SMILES: CC1(C(=O)N2CCc3ccccc32)CC(c2ccc3c(=O)n(-c4ccc(F)cc4)c(CCCCC(=O)O)nc3c2)=NO1] | 569 |
| 212 | 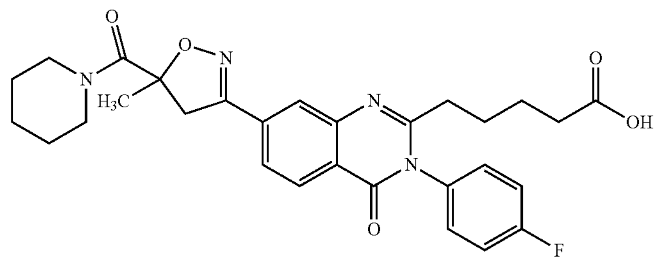 [SMILES: CC1(C(=O)N2CCCCC2)CC(c2ccc3c(=O)n(-c4ccc(F)cc4)c(CCCCC(=O)O)nc3c2)=NO1] | 535 |
| 213 | 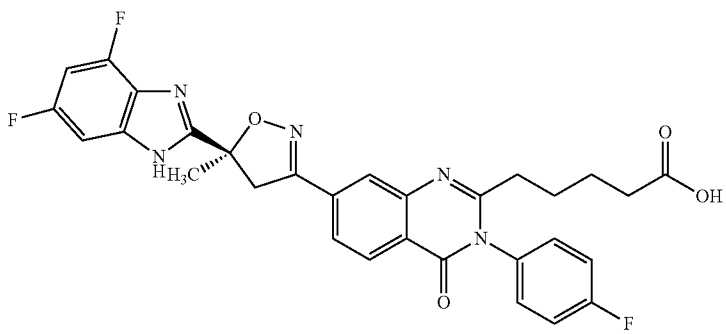 [SMILES: C[C@@]1(c2nc3c(F)cc(F)cc3[nH]2)CC(c2ccc3c(=O)n(-c4ccc(F)cc4)c(CCCCC(=O)O)nc3c2)=NO1] | 576 |
| 214 | 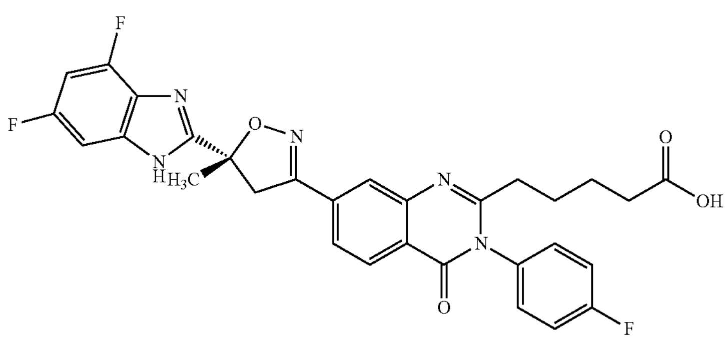 [SMILES: C[C@]1(c2nc3c(F)cc(F)cc3[nH]2)CC(c2ccc3c(=O)n(-c4ccc(F)cc4)c(CCCCC(=O)O)nc3c2)=NO1] | 576 |
| 215 | 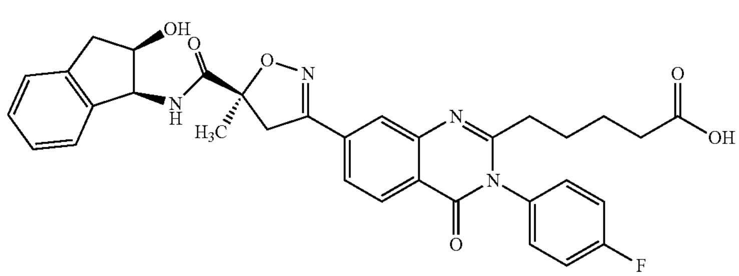 [SMILES: C[C@@]1(C(=O)N[C@H]2c3ccccc3C[C@H]2O)CC(c2ccc3c(=O)n(-c4ccc(F)cc4)c(CCCCC(=O)O)nc3c2)=NO1] | 599 |

-continued

| Cpd | Structure | MS (M + H⁺) |
|---|---|---|
| 216 | 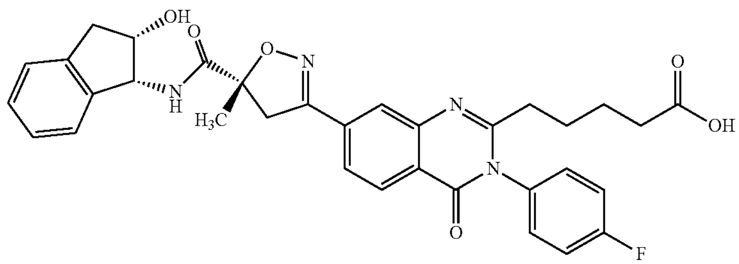 [SMILES: C[C@]1(C(=O)N[C@@H]2c3ccccc3C[C@@H]2O)CC(c2ccc3c(=O)n(-c4ccc(F)cc4)c(CCCCC(=O)O)nc3c2)=NO1] | 599 |
| 217 | 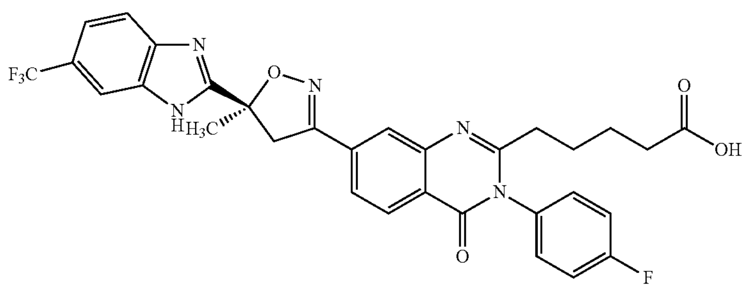 [SMILES: C[C@@]1(c2nc3ccc(C(F)(F)F)cc3[nH]2)CC(c2ccc3c(=O)n(-c4ccc(F)cc4)c(CCCCC(=O)O)nc3c2)=NO1] | 608 |
| 218 | 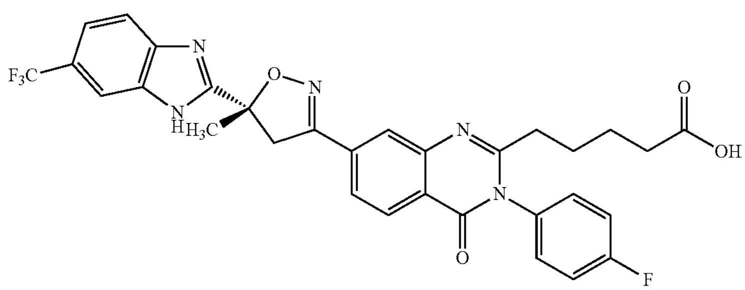 [SMILES: C[C@]1(c2nc3ccc(C(F)(F)F)cc3[nH]2)CC(c2ccc3c(=O)n(-c4ccc(F)cc4)c(CCCCC(=O)O)nc3c2)=NO1] | 608 |
| 219 | 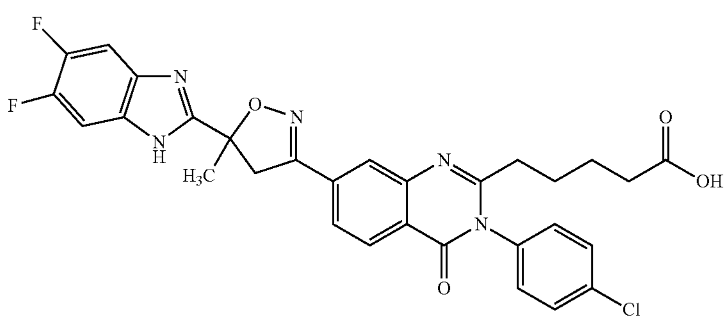 [SMILES: CC1(c2nc3cc(F)c(F)cc3[nH]2)CC(c2ccc3c(=O)n(-c4ccc(Cl)cc4)c(CCCCC(=O)O)nc3c2)=NO1] | 592 |
| 220 | 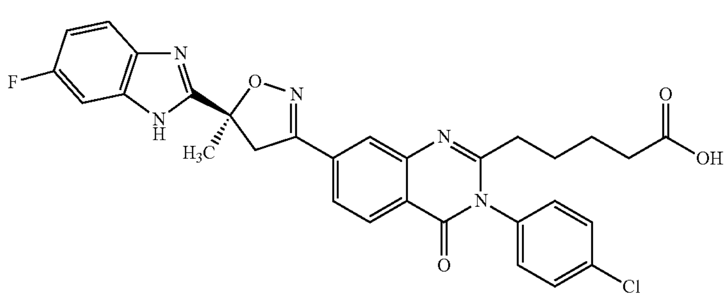 [SMILES: C[C@@]1(c2nc3ccc(F)cc3[nH]2)CC(c2ccc3c(=O)n(-c4ccc(Cl)cc4)c(CCCCC(=O)O)nc3c2)=NO1] | 574 |

-continued

| Cpd | Structure | MS (M + H⁺) |
|---|---|---|
| 221 | 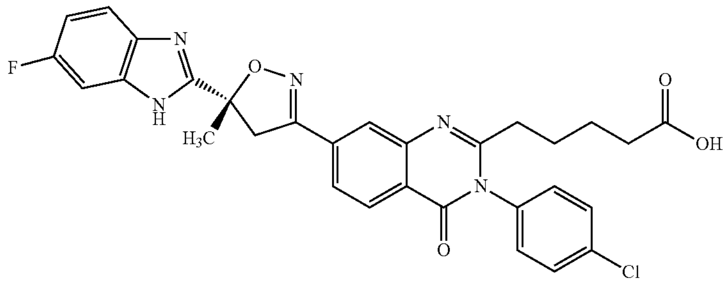 [SMILES: C[C@]1(c2nc3ccc(F)cc3[nH]2)CC(c2ccc3c(=O)n(-c4ccc(Cl)cc4)c(CCCCC(=O)O)nc3c2)=NO1] | 574 |
| 222 | 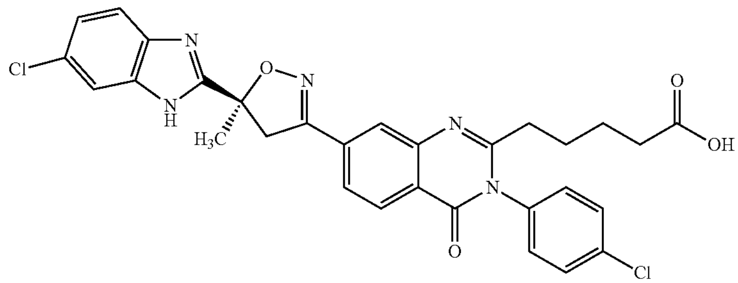 [SMILES: C[C@@]1(c2nc3ccc(Cl)cc3[nH]2)CC(c2ccc3c(=O)n(-c4ccc(Cl)cc4)c(CCCCC(=O)O)nc3c2)=NO1] | 592 |
| 223 | 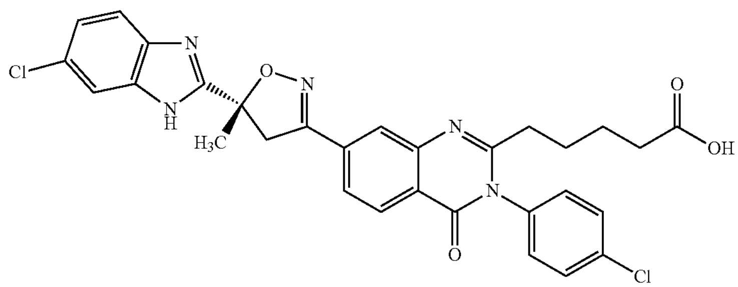 [SMILES: C[C@]1(c2nc3ccc(Cl)cc3[nH]2)CC(c2ccc3c(=O)n(-c4ccc(Cl)cc4)c(CCCCC(=O)O)nc3c2)=NO1] | 592 |
| 224 | 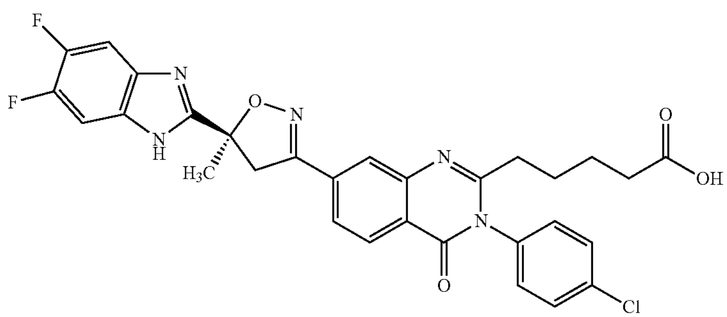 [SMILES: C[C@@]1(c2nc3cc(F)c(F)cc3[nH]2)CC(c2ccc3c(=O)n(-c4ccc(Cl)cc4)c(CCCCC(=O)O)nc3c2)=NO1] | 592 |
| 225 | 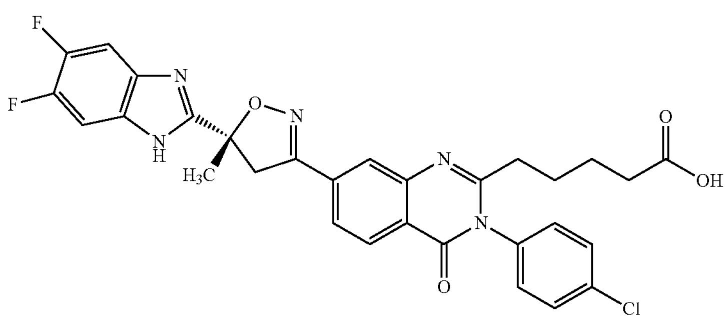 [SMILES: C[C@]1(c2nc3cc(F)c(F)cc3[nH]2)CC(c2ccc3c(=O)n(-c4ccc(Cl)cc4)c(CCCCC(=O)O)nc3c2)=NO1] | 592 |

-continued

| Cpd | Structure | MS (M + H⁺) |
|---|---|---|
| 226 | 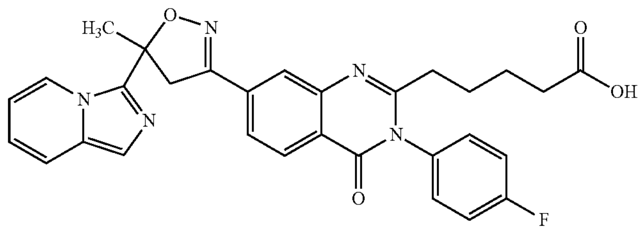 [SMILES: CC1(c2ncc3ccccn23)CC(c2ccc3c(=O)n(-c4ccc(F)cc4)c(CCCCC(=O)O)nc3c2)=NO1] | 540 |
| 227 | 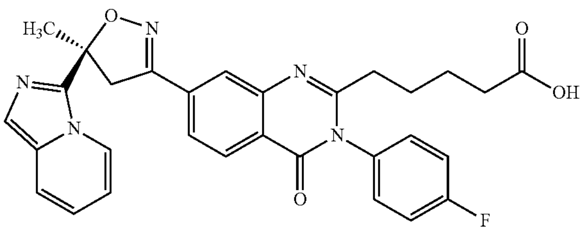 [SMILES: C[C@@]1(c2ncc3ccccn23)CC(c2ccc3c(=O)n(-c4ccc(F)cc4)c(CCCCC(=O)O)nc3c2)=NO1] | 540 |
| 228 | 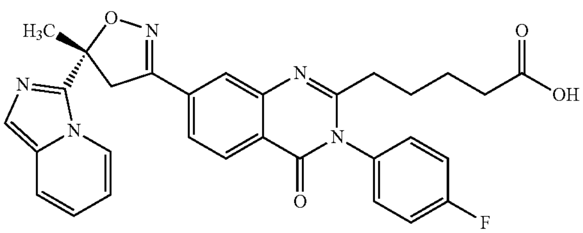 [SMILES: C[C@]1(c2ncc3ccccn23)CC(c2ccc3c(=O)n(-c4ccc(F)cc4)c(CCCCC(=O)O)nc3c2)=NO1] | 540 |
| 229 | 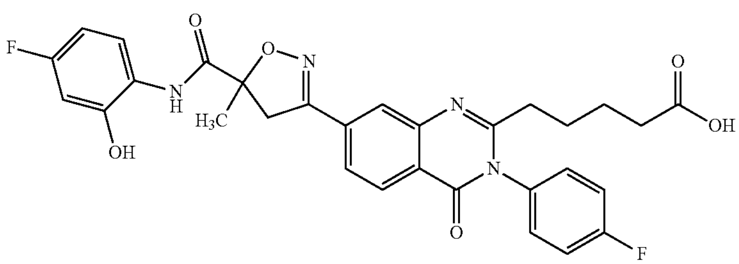 [SMILES: CC1(C(=O)Nc2ccc(F)cc2O)CC(c2ccc3c(=O)n(-c4ccc(F)cc4)c(CCCCC(=O)O)nc3c2)=NO1] | 577 |
| 230 | 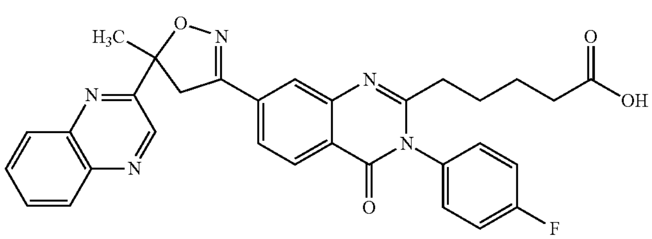 [SMILES: CC1(c2cnc3ccccc3n2)CC(c2ccc3c(=O)n(-c4ccc(F)cc4)c(CCCCC(=O)O)nc3c2)=NO1] | 552 |
| 231 | 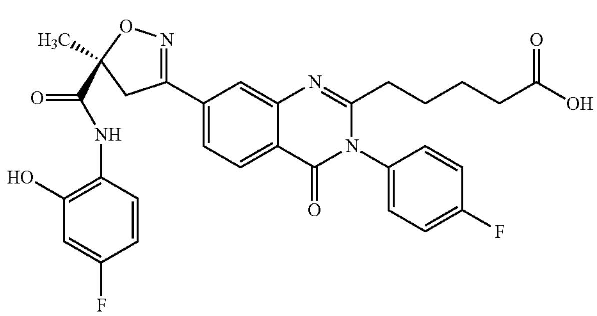 [SMILES: C[C@@]1(C(=O)Nc2ccc(F)cc2O)CC(c2ccc3c(=O)n(-c4ccc(F)cc4)c(CCCCC(=O)O)nc3c2)=NO1] | 577 |

| Cpd | Structure | MS (M + H+) |
|---|---|---|
| 232 | 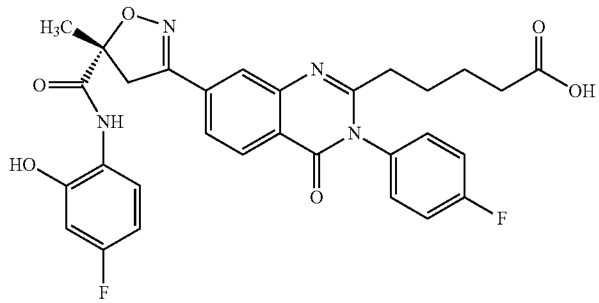 [SMILES: C[C@]1(C(=O)Nc2ccc(F)cc2O)CC(c2ccc3c(=O)n(-c4ccc(F)cc4)c(CCCCC(=O)O)nc3c2)=NO1] | 577 |
| 233 | 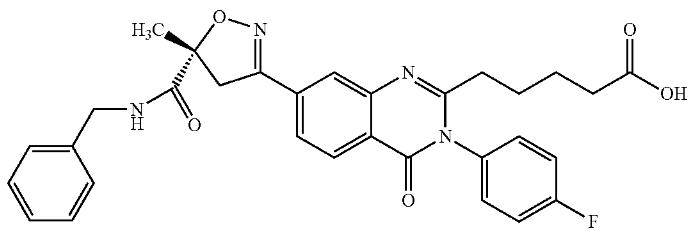 [SMILES: C[C@]1(C(=O)NCc2ccccc2)CC(c2ccc3c(=O)n(-c4ccc(F)cc4)c(CCCCC(=O)O)nc3c2)=NO1] | 557 |
| 234 | 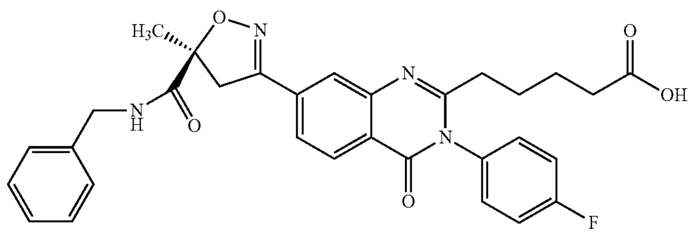 [SMILES: C[C@@]1(C(=O)NCc2ccccc2)CC(c2ccc3c(=O)n(-c4ccc(F)cc4)c(CCCCC(=O)O)nc3c2)=NO1] | 557 |
| 235 | 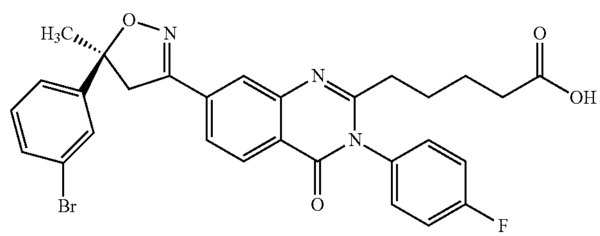 [SMILES: C[C@@]1(c2cccc(Br)c2)CC(c2ccc3c(=O)n(-c4ccc(F)cc4)c(CCCCC(=O)O)nc3c2)=NO1] | 580 |
| 236 | 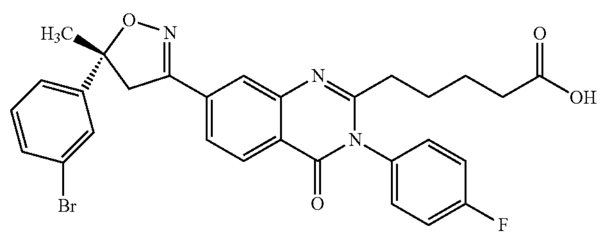 [SMILES: C[C@]1(c2cccc(Br)c2)CC(c2ccc3c(=O)n(-c4ccc(F)cc4)c(CCCCC(=O)O)nc3c2)=NO1] | 580 |
| 237 | 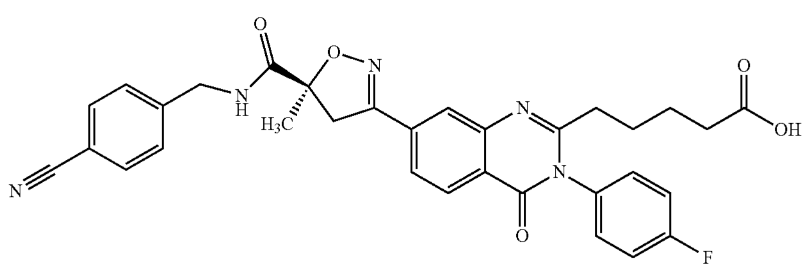 [SMILES: C[C@@]1(C(=O)NCc2ccc(C#N)cc2)CC(c2ccc3c(=O)n(-c4ccc(F)cc4)c(CCCCC(=O)O)nc3c2)=NO1] | 583 |

-continued
| Cpd | Structure | MS (M + H+) |
|---|---|---|
| 238 | 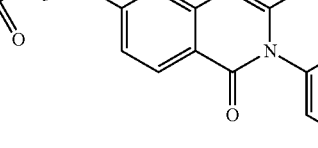 | 569 |
| 239 | 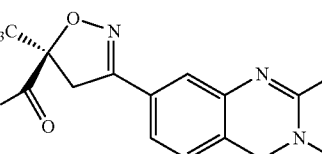 | 598 |
| 240 | 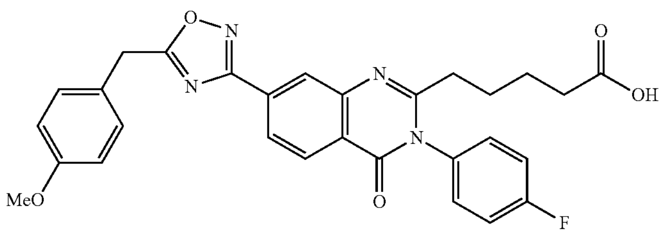 [SMILES: COc1ccc(Cc2nc(-c3ccc4c(=O)n(-c5ccc(F)cc5)c(CCCCC(=O)O)nc4c3)no2)cc1] | 529 |
| 241 | 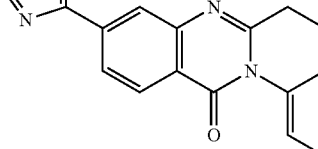 | 531 |
| 242 | 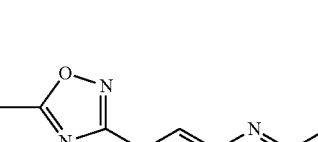 | 525 |
| 243 | 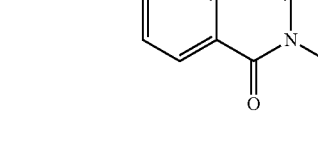 | 524 |

| Cpd | Structure | MS (M + H⁺) |
|---|---|---|
| 244 | Enantiomer 1 | 539 |
| 245 | Enantiomer 2 | 539 |
| 246 | Enantiomer 1 | 539 |
| 247 | Enantiomer 2 | 539 |
| 248 | 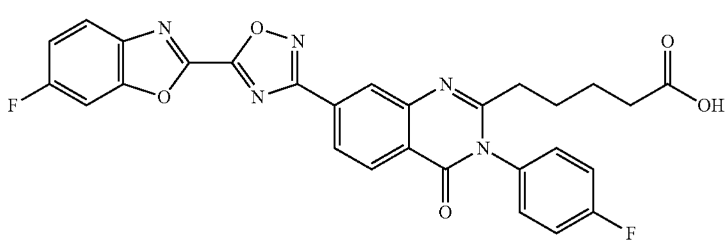 [SMILES: O=C(O)CCCCc1nc2cc(-c3noc(-c4nc5ccc(F)cc5o4)n3)ccc2c(=O)n1-c1ccc(F)cc1] | 544 |

-continued

| Cpd | Structure | MS (M + H⁺) |
|---|---|---|
| 249 | 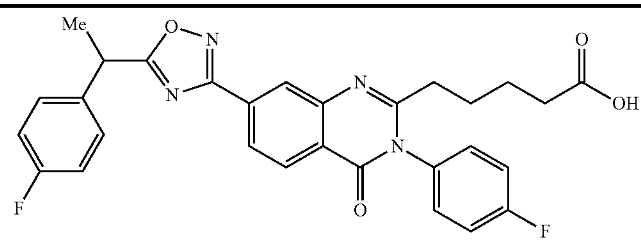 | 531 |
| 250 | 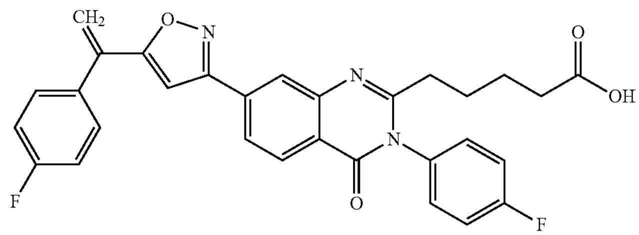 [SMILES: C=C(c1ccc(F)cc1)c1cc(-c2ccc3c(=O)n(-c4ccc(F)cc4)c(CCCCC(=O)O)nc3c2)no1] | 528 |
| 251 | 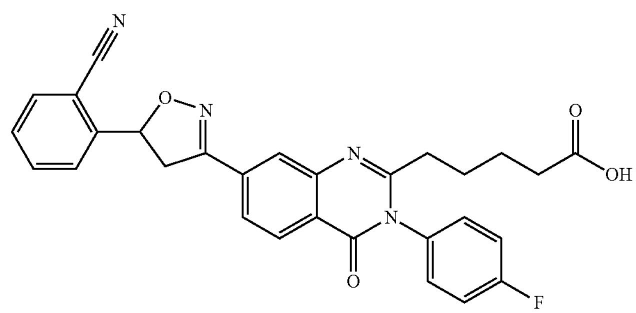 [SMILES: N#Cc1ccccc1C1CC(c2ccc3c(=O)n(-c4ccc(F)cc4)c(CCCCC(=O)O)nc3c2)=NO1] | 511 |
| 252 | 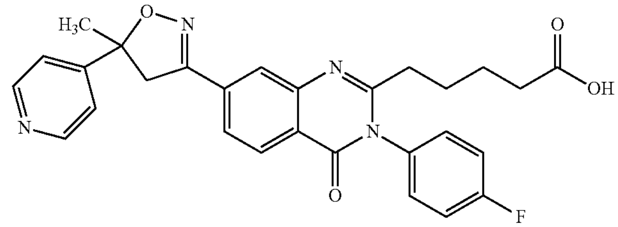 [SMILES: CC1(c2ccncc2)CC(c2ccc3c(=O)n(-c4ccc(F)cc4)c(CCCCC(=O)O)nc3c2)=NO1] | 501 |
| 253 | 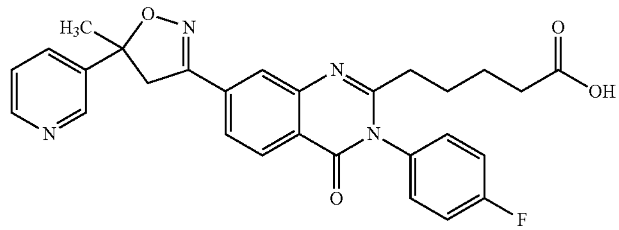 [SMILES: CC1(c2cccnc2)CC(c2ccc3c(=O)n(-c4ccc(F)cc4)c(CCCCC(=O)O)nc3c2)=NO1] | 501 |
| 254 | 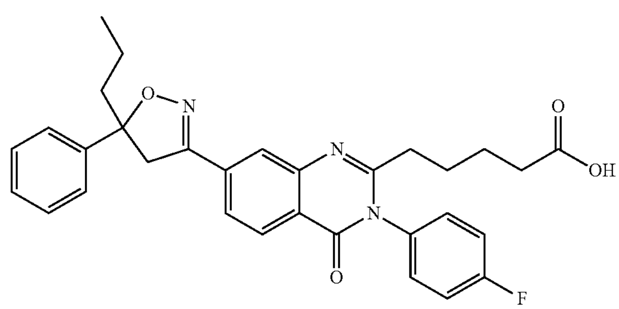 [SMILES: CCCC1(c2ccccc2)CC(c2ccc3c(=O)n(-c4ccc(F)cc4)c(CCCCC(=O)O)nc3c2)=NO1] | 528 |

-continued

| Cpd | Structure | MS (M + H⁺) |
|---|---|---|
| 255 | 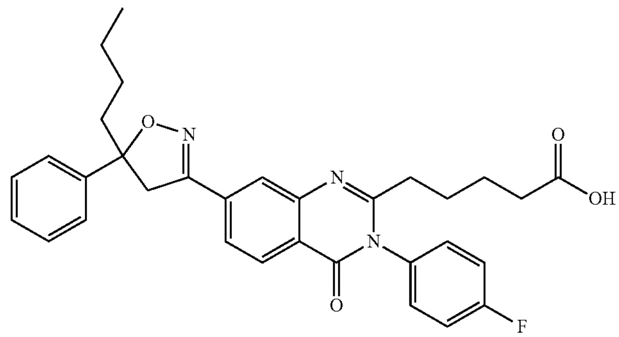 [SMILES: CCCCC1(c2ccccc2)CC(c2ccc3c(=O)n(-c4ccc(F)cc4)c(CCCCC(=O)O)nc3c2)=NO1] | 542 |
| 256 | 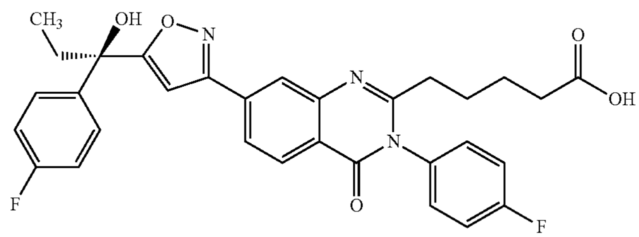 [SMILES: CC[C@@](O)(c1ccc(F)cc1)c1cc(-c2ccc3c(=O)n(-c4ccc(F)cc4)c(CCCCC(=O)O)nc3c2)no1] | 560 |
| 257 | 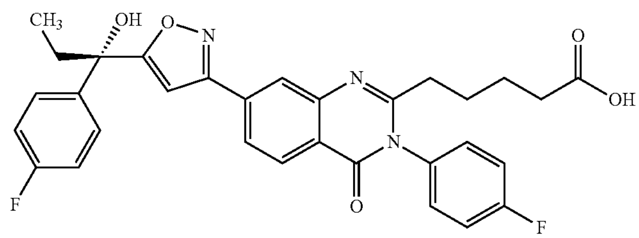 [SMILES: CC[C@](O)(c1ccc(F)cc1)c1cc(-c2ccc3c(=O)n(-c4ccc(F)cc4)c(CCCCC(=O)O)nc3c2)no1] | 560 |
| 258 | 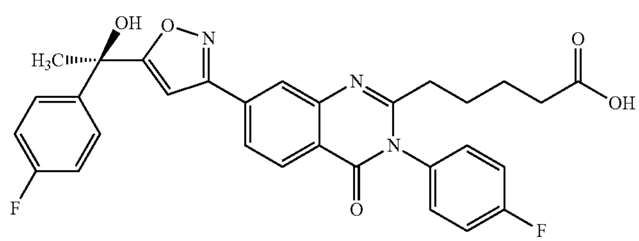 [SMILES: C[C@@](O)(c1ccc(F)cc1)c1cc(-c2ccc3c(=O)n(-c4ccc(F)cc4)c(CCCCC(=O)O)nc3c2)no1] | 546 |
| 259 | 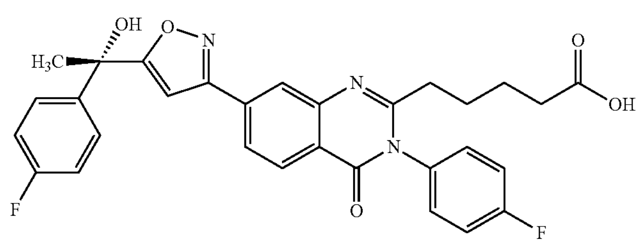 [SMILES: C[C@](O)(c1ccc(F)cc1)c1cc(-c2ccc3c(=O)n(-c4ccc(F)cc4)c(CCCCC(=O)O)nc3c2)no1] | 546 |
| 260 | 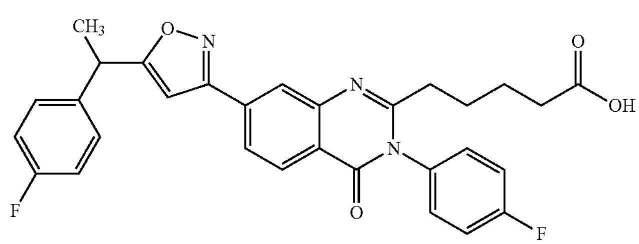 | 530 |

-continued

| Cpd | Structure | MS (M + H⁺) |
|---|---|---|
| 261 | 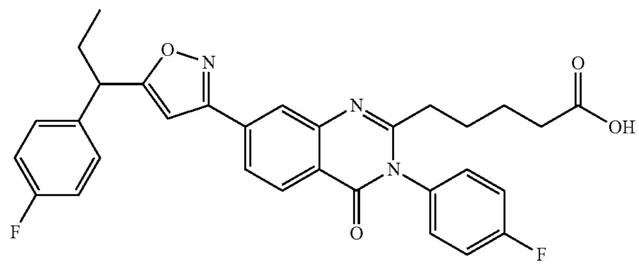 [SMILES: CCC(c1ccc(F)cc1)c1cc(-c2ccc3c(=O)n(-c4ccc(F)cc4)c(CCCCC(=O)O)nc3c2)no1] | 544 |
| 262 | 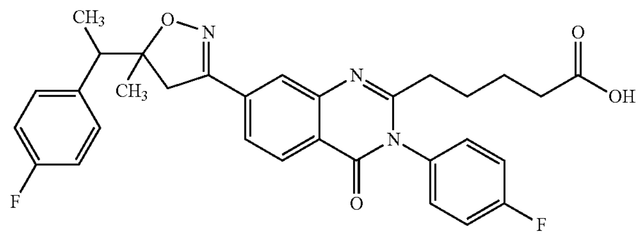 [SMILES: CC(c1ccc(F)cc1)C1(C)CC(c2ccc3c(=O)n(-c4ccc(F)cc4)c(CCCCC(=O)O)nc3c2)=NO1] | 546 |
| 263 | 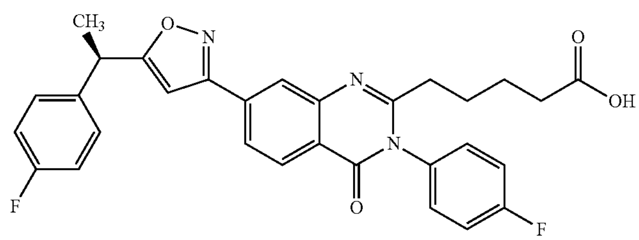 | 530 |
| 264 | 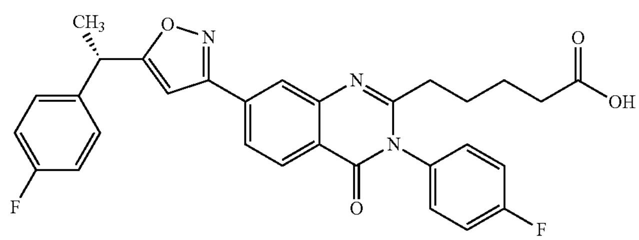 | 530 |
| 265 | 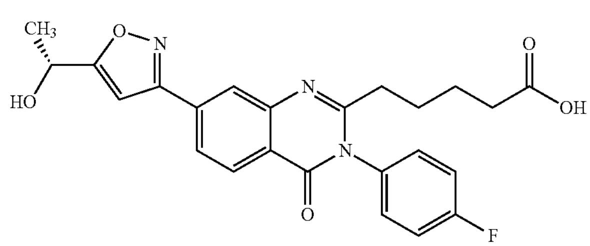 [SMILES: C[C@@H](O)c1cc(-c2ccc3c(=O)n(-c4ccc(F)cc4)c(CCCCC(=O)O)nc3c2)no1] | 452 |
| 266 | 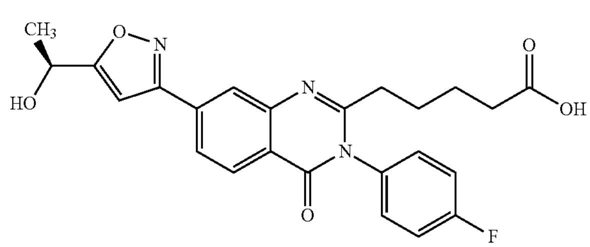 [SMILES: C[C@H](O)c1cc(-c2ccc3c(=O)n(-c4ccc(F)cc4)c(CCCCC(=O)O)nc3c2)no1] | 452 |

-continued

| Cpd | Structure | MS (M + H⁺) |
|---|---|---|
| 267 | 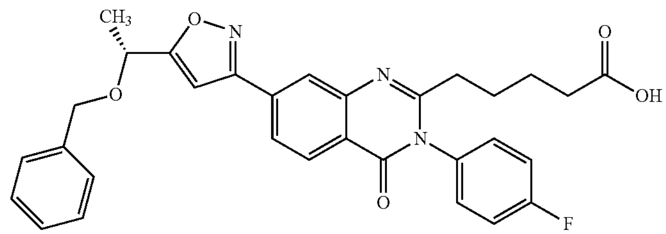 [SMILES: C[C@@H](OCc1ccccc1)c1cc(-c2ccc3c(=O)n(-c4ccc(F)cc4)c(CCCCC(=O)O)nc3c2)no1] | 542 |
| 268 | 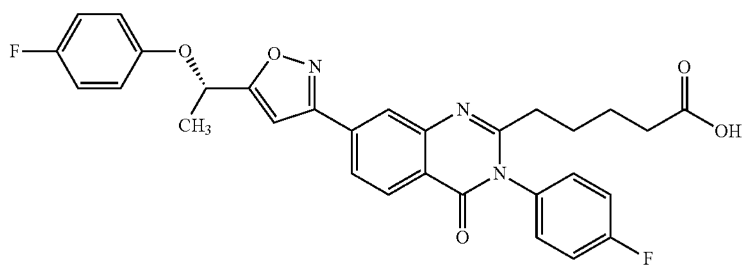 [SMILES: C[C@H](Oc1ccc(F)cc1)c1cc(-c2ccc3c(=O)n(-c4ccc(F)cc4)c(CCCCC(=O)O)nc3c2)no1] | 546 |
| 269 | 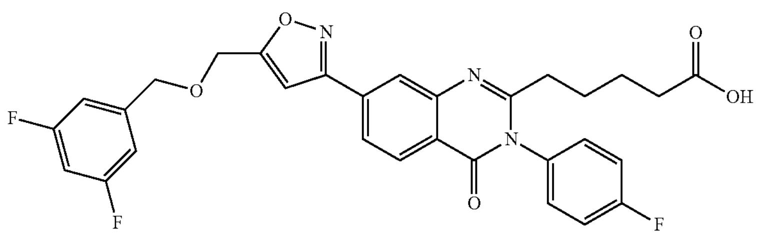 [SMILES: O=C(O)CCCCc1nc2cc(-c3cc(COCc4cc(F)cc(F)c4)on3)ccc2c(=O)n1-c1ccc(F)cc1] | 564 |
| 270 | 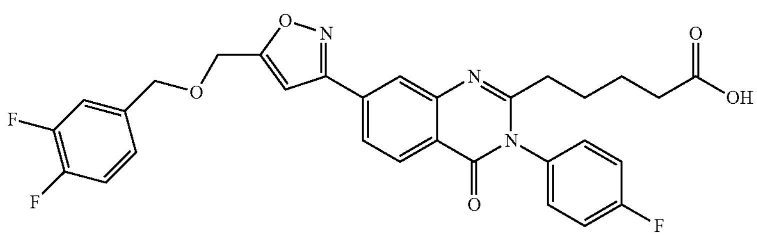 [SMILES: O=C(O)CCCCc1nc2cc(-c3cc(COCc4ccc(F)c(F)c4)on3)ccc2c(=O)n1-c1ccc(F)cc1] | 564 |
| 271 | 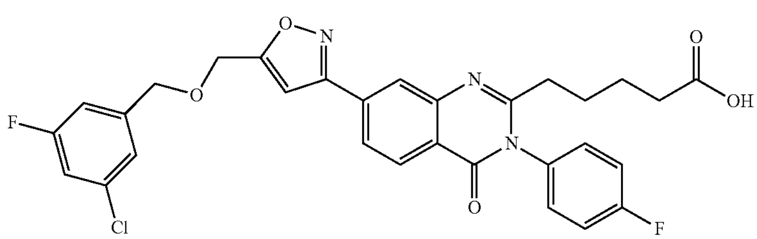 | 580 |
| 272 | 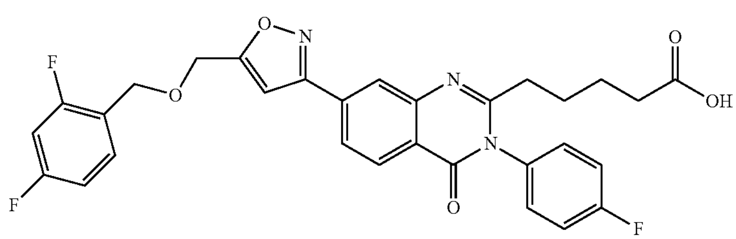 [SMILES: O=C(O)CCCCc1nc2cc(-c3cc(COCc4ccc(F)cc4F)on3)ccc2c(=O)n1-c1ccc(F)cc1] | 564 |

-continued

| Cpd | Structure | MS (M + H⁺) |
|---|---|---|
| 273 | 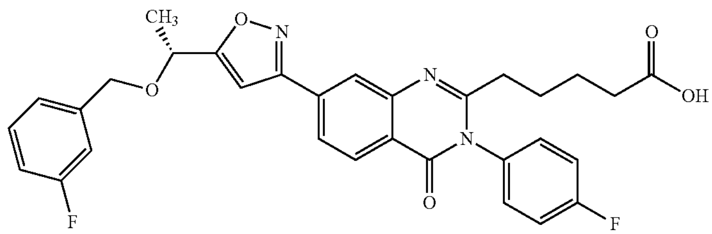 [SMILES: C[C@@H](OCc1cccc(F)c1)c1cc(-c2ccc3c(=O)n(-c4ccc(F)cc4)c(CCCCC(=O)O)nc3c2)no1] | 560 |
| 274 | 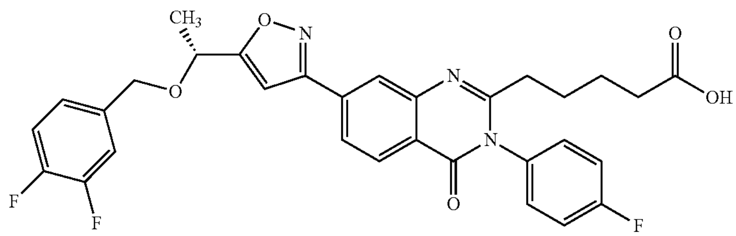 [SMILES: C[C@@H](OCc1ccc(F)c(F)c1)c1cc(-c2ccc3c(=O)n(-c4ccc(F)cc4)c(CCCCC(=O)O)nc3c2)no1] | 578 |
| 275 | 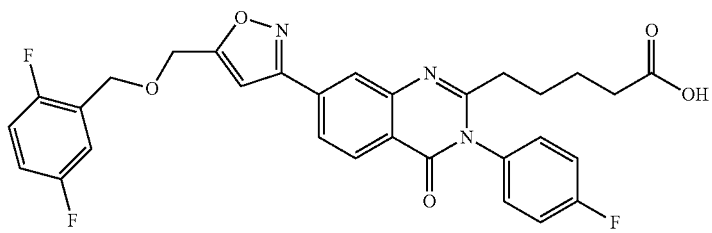 [SMILES: O=C(O)CCCCc1nc2cc(-c3cc(COCc4cc(F)ccc4F)on3)ccc2c(=O)n1-c1ccc(F)cc1] | 564 |
| 276 | 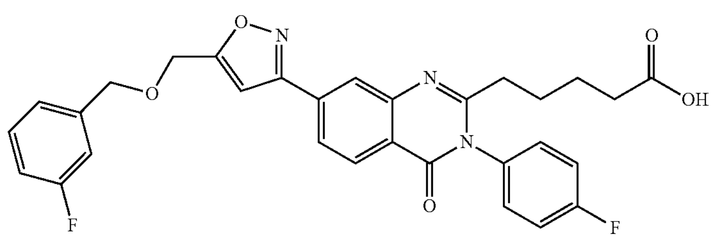 | 546 |
| 277 | 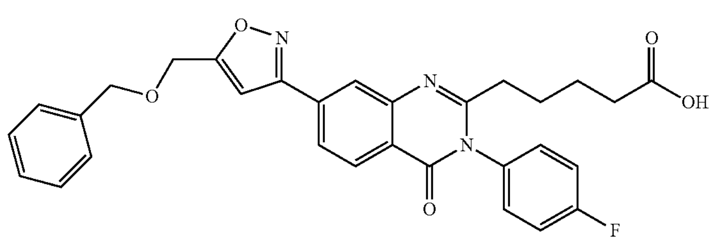 [SMILES: O=C(O)CCCCc1nc2cc(-c3cc(COCc4ccccc4)on3)ccc2c(=O)n1-c1ccc(F)cc1] | 528 |
| 278 | 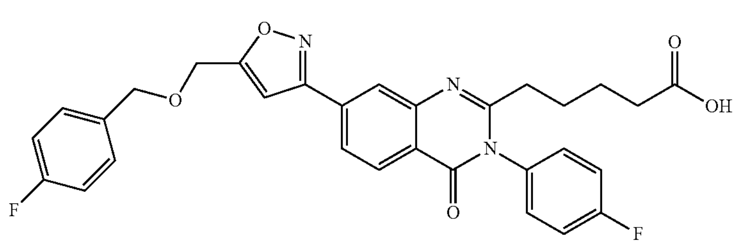 [SMILES: O=C(O)CCCCc1nc2cc(-c3cc(COCc4ccc(F)cc4)on3)ccc2c(=O)n1-c1ccc(F)cc1] | 546 |

-continued

| Cpd | Structure | MS (M + H⁺) |
|---|---|---|
| 279 | 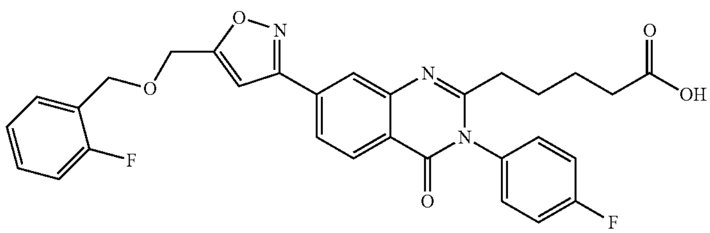 [SMILES: O=C(O)CCCCc1nc2cc(-c3cc(COCc4ccccc4F)on3)ccc2c(=O)n1-c1ccc(F)cc1] | 546 |
| 280 | 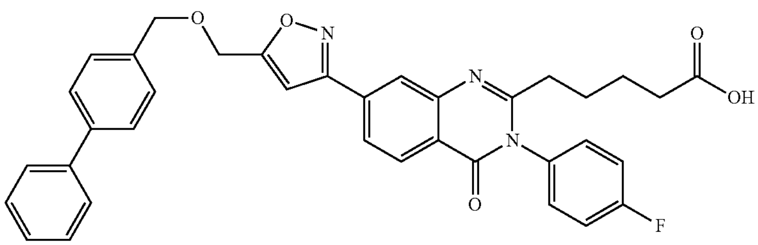 [SMILES: O=C(O)CCCCc1nc2cc(-c3cc(COCc4ccc(-c5ccccc5)cc4)on3)ccc2c(=O)n1-c1ccc(F)cc1] | 604 |
| 281 | 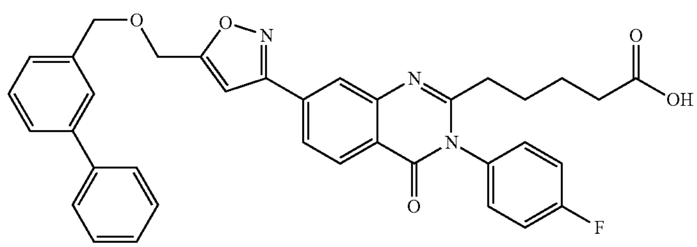 [SMILES: O=C(O)CCCCc1nc2cc(-c3cc(COCc4cccc(-c5ccccc5)c4)on3)ccc2c(=O)n1-c1ccc(F)cc1] | 604 |
| 282 | 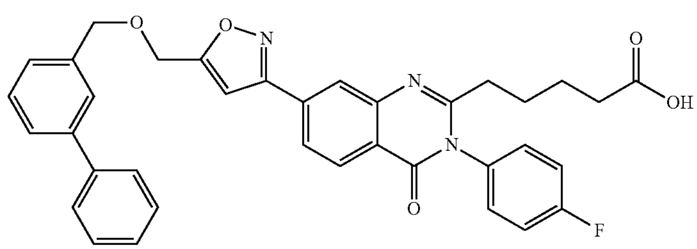 [SMILES: O=C(O)CCCCc1nc2cc(-c3cc(COCc4cccc(-c5ccccc5)c4)on3)ccc2c(=O)n1-c1ccc(F)cc1] | 604 |
| 283 | 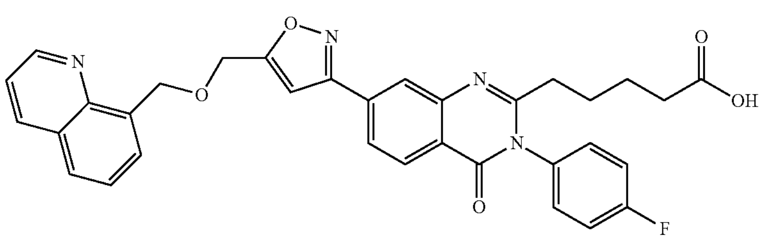 [SMILES: O=C(O)CCCCc1nc2cc(-c3cc(COCc4cccc5cccnc45)on3)ccc2c(=O)n1-c1ccc(F)cc1] | 579 |
| 284 | 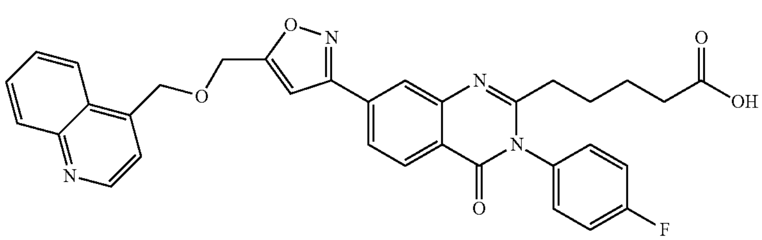 | 579 |

| Cpd | Structure | MS (M + H⁺) |
|---|---|---|
| 285 | 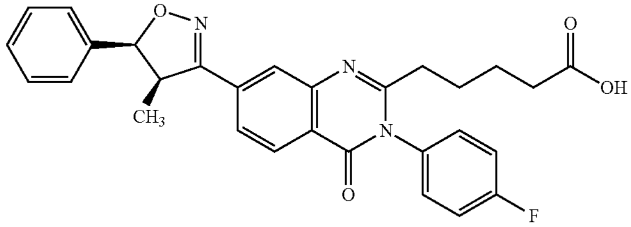 [SMILES: C[C@@H]1C(c2ccc3c(=O)n(-c4ccc(F)cc4)c(CCCCC(=O)O)nc3c2)=NO[C@@H]1c1ccccc1] | 500 |
| 286 | 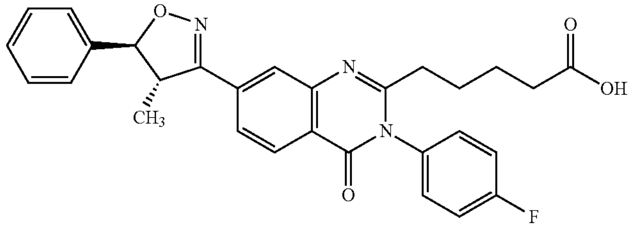 [SMILES: C[C@H]1C(c2ccc3c(=O)n(-c4ccc(F)cc4)c(CCCCC(=O)O)nc3c2)=NO[C@@H]1c1ccccc1] | 500 |
| 287 | 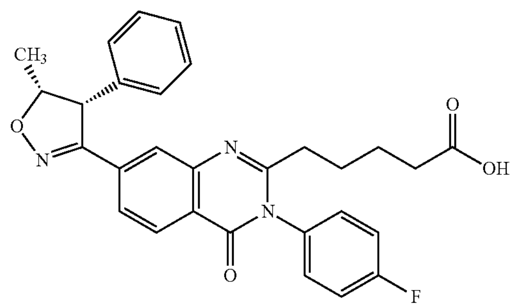 [SMILES: C[C@H]1ON=C(c2ccc3c(=O)n(-c4ccc(F)cc4)c(CCCCC(=O)O)nc3c2)[C@H]1c1ccccc1] | 500 |
| 288 | 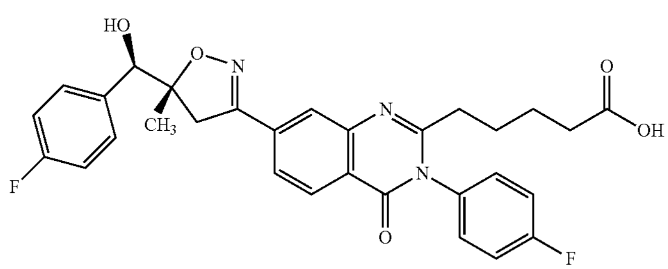 [SMILES: C[C@]1([C@H](O)c2ccc(F)cc2)CC(c2ccc3c(=O)n(-c4ccc(F)cc4)c(CCCCC(=O)O)nc3c2)=NO1] | 548 |
| 289 | 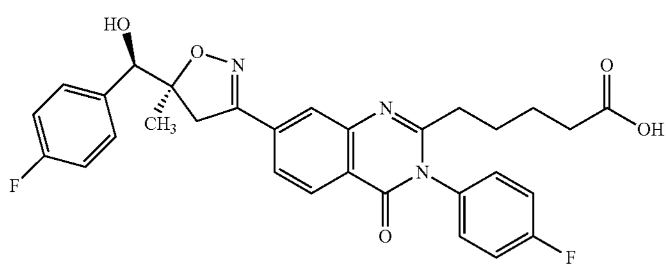 [SMILES: C[C@@]1([C@H](O)c2ccc(F)cc2)CC(c2ccc3c(=O)n(-c4ccc(F)cc4)c(CCCCC(=O)O)nc3c2)=NO1] | 548 |
| 290 | 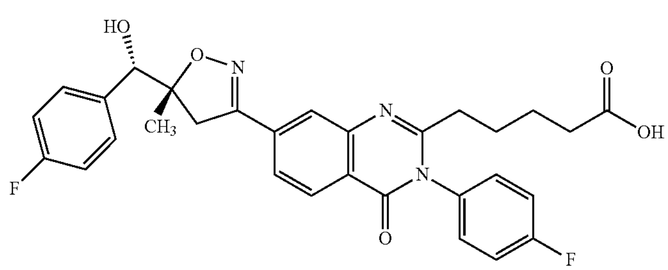 [SMILES: C[C@]1([C@@H](O)c2ccc(F)cc2)CC(c2ccc3c(=O)n(-c4ccc(F)cc4)c(CCCCC(=O)O)nc3c2)=NO1] | 548 |

| Cpd | Structure | MS (M + H⁺) |
|---|---|---|
| 291 | (structure shown) | 548 |
| 292 | (structure shown) | 532 |
| 293 | (structure shown) | 532 |

BIOLOGICAL ASSAYS

Radioligand Binding Assay.

Radioligand binding assays were performed at room temperature in 50 mM Tris-HCl pH 7.4, 1 mM EDTA containing 2 mM $MnCl_2$ and 3.0 nM [$^3$H]PGD$_2$ (NEN, 171 Ci mmol$^{-1}$), in a final volume of 0.2 mL. Competing ligands were diluted in dimethylsulfoxide (Me$_2$SO) that was kept constant at 1% (v/v) of the final incubation volume. The reaction was initiated by the addition of 8-20 µg of membrane protein prepared from a HEK-hCRTH2 cell line. Total and non-specific binding were determined in the absence and the presence of 10 WI PGD$_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted (0.3% polyethyleneimine) 96-well printed filtermate (Wallac) using a Tomtec harvester. After washing with cold buffer, the filter was dried for 2 minutes in microwave, and Meltilex Scintillator sheet (Wallac) was melted on for 2 min. The radioactivity was measured with Betaplate model 1205 (Wallac). The Ki (in nM) values for representative compounds of the present invention are as follows:

For the purposes of this invention, a compound preferentially binds the CRTH2 receptor with a $K_i$<50 nM, and preferentially <10 nM. The Ki (in nM) values for representative compounds of the present invention are as follows:

$K_i$≤100 nM and >50 nM: Example 190.

$K_i$≤50 nM and >10 nM: Examples 1K, 5i, 5J, 5K, 5Q, 8C, 14, 14C, 15, 15E, 15G, 15H, 15U, 15V, 15W, 18, 20B, 21C, 22C, 24L, 24M, 24R, 25H, 25K, 26C, 26D, 26G, 26i, 26K, 26L, 28D, 32, 35G, 39, 39E, 39G, 39H, 39I, 40, 42G, 44, 104, 109, 110, 117, 118, 126, 127, 131, 132, 134, 138, 143, 144, 146, 152, 156, 157, 164, 165, 183, 185, 200, 202, 207, 210, 212, 216, 225, 226, 227, 230, 234, 236, 237, 238, 239, 243, 245, 247, 248, 249, 258, 259, 265, 267, 274, 277, 278, 280, 281, 283, 284, 288, 291, 292, and 293.

$K_i$≤10 nM: Examples 5M, 5N, 8D, 9, 13, 15F, 15i, 15J, 15K, 15L, 15M, 15N, 15o, 15P, 15Q, 15T, 15X, 15Y, 15Z, 17, 17B, 17B, 19, 19D, 20, 21, 21D, 21E, 24, 24F, 24G, 24H, 24i, 24J, 24N, 24o, 24P, 24Q, 25, 25C, 25D, 25E, 25F, 25G, 25i, 25J, 25L, 25M, 26, 26E, 26F, 26J, 26M, 28, 28E, 29, 33, 35, 36, 37, 37E, 39F, 39J, 39K, 39L, 41, 42, 42E, 42F, 43, 43D, 100, 101, 102, 103, 105, 106, 107, 108, 111, 112, 113, 114, 115, 116, 119, 120, 121, 122, 123, 124, 125, 128, 129, 130, 133, 136, 137, 139, 140, 141, 142, 145, 147, 148, 149, 150, 151, 153, 154, 155, 158, 159, 160, 161, 162, 163, 166, 167, 169, 170, 171, 172, 174, 175, 176, 178, 180, 181, 182, 184, 186, 189, 191, 192, 193, 194, 195, 196, 197, 198, 199, 201, 203, 205, 206, 208, 209, 211, 213, 215, 217, 219, 220, 222, 224, 229, 231, 235, 240, 241, 242, 244, 246, 250, 251, 252, 253, 254, 255, 256, 257, 260, 261, 262, 263, 264, 268, 269, 270, 271, 272, 273, 275, 276, 279, 282, 285, 286, 287, 289, and 290.

Representative compounds of the invention had the Ki values specified in parentheses immediately following the compound number in the above-described assay: 14 (17.2 nM), 19D (1.2 nM), 24M (40.5 nM), 25 (1.0 nM), 26 (7.4 nM), 32 (22.1 nM), 35 (1.9 nM), 35G (19.6 nM), 44 (32.6 nM), 184 (5.7 nM), 190 (96.2 nM) and 207 (17.0 nM).

i[cAMP] measurements.

HEK-hCRTH2 cells were grown to 80-90% confluency. On the day of the assay, the cells were washed with PBS, incubated for 2 min in cell dissociation buffer, harvested by centrifugation at 300 g for 7 min at room temperature and resuspended at 1.25e10⁶ cells in Hanks' balanced salt solution containing 20 mM HEPES pH 7.4 and 0.75 mM IBMX (HBSS/HEPES/IBMX). The assay was performed in 384-plate format with 0.01 mL HBSS/HEPES/IBMX per well containing 12 500 cells and 70 to 75 nl of the test compound and DK-PGD2 at various concentrations. Following a 0 to 10 to min pre-incubation of the cells with the test compound at 37° C., 0.005 mL of 30 uM Forskolin dilute in HBSS 20 mM Hepes, was added at a respectively final concentration of 10 uM to initiate the reaction. After 10 to 60 min incubation at room temp or 37° C., the cAMP content was quantified using the cAMP XS+ HitHunter chemiluminescence assay. (GE Healthcare 90-0075). % inhibition was calculated using the Forskolin and EC85 DK-PGD2 controls.

β-Arrestin Assay:

CHO-K1 cells obtained from DiscoverX are stably transfected with human CRTH2 (propagation medium: F-12, 10% FBS, 300 ug/mL hygB and 800 ug/mL G418). Cells are grown in T175 cm² flask. While in log phase, cells are collected via 0.05% trypsin treatment. Triturated cells are filtered and 40 uL (10K cells) are plated per well in a 384-well white clear bottom plate and incubated O/N. Cell plate is emptied via inversion and blotted dry. Each well is filled with 35 uL of HBSS (with Ca++ and Mg++) and incubated for 5 min. Compounds are added in volumes of 5 uL and plate is gently shaken for 2 min. followed by an incubation at 37° C. for 20 min. All compounds and controls are diluted in HBSS assay buffer (with Ca++ and Mg++) with final concentration range of 10-5M to 3×10-11M, 11 point Dose response curves. Final DMSO % is ≤0.3%. Agonist Assay: 5 ul/well of compound is added into cell plate and left to incubate at 37° C. for 90 min. Antagonist Assay: 5 ul/well of compounds were added into cell plate. Incubate 30 minutes @ 37° C. Stimulate cells with 5 ul/well of PGD₂ [100 nM] final. Incubate plate for 60 minutes @ 37° C. Resulting signal is detected via Discoverx PathHunter Detection Kit. Total of 12 ul/well is added to each well, plate is covered and incubated for 60 min. with gentle shaking. Chemiluminescent detection is done by SpectraMax plate reader.

Eosinophil Shape Change Assay in Human Whole Blood:

Blood was collected in vacutainers containing EDTA. The antagonist was added to blood and incubated for 10 min at room temperature. DK-PGD₂ (13,14-dihydro-15-keto prostaglandin D₂) was then added to blood for 4 min at 37° C. in a running water bath. Blood cells were then fixed in presence of cold 0.25% (v/v) paraformaldehyde prepared in 75% (v/v) PBS for 1 min on ice. 175 μL of fixed blood was transferred into 870 μL of cold 155 mM NH₄Cl lysis solution and incubated at 4° C. for at least 40 min. The solution was then centrifuged at 430 g for 5 min and the supernatant was discarded. Centrifuged cells were analyzed with a FACs Calibur flow cytometer (Becton Dickinson). Flow cytometry raw data were analyzed with FlowJo software by isolating the eosinophils from the neutrophils based on their high autofluorescence and determining the percent of total eosinophils with increased FSC-H value. Maximum (100%) and minimum (0%) shape change were determined in the presence of 10 μM DK-PGD₂ and PBS, respectively. A dose response curve with DK-PGD₂ was performed with every assay to determine the EC₅₀ for each blood donor. Compounds were tested in 10-dose titration curves in the presence of 30 nM DK-PGD₂ to determine an antagonist IC₅₀.

Compounds of the present invention are selective for the CRTH2 receptor over the DP receptor. Assays on the DP, as well as other prostanoid, receptors are described in WO2003/06220.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound for the formula:

Formula I

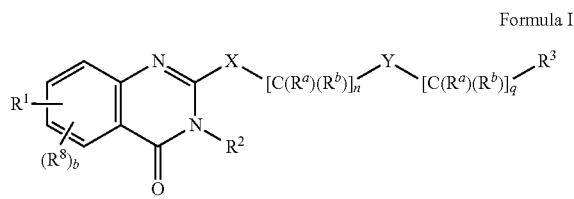

or a pharmaceutically acceptable salt thereof wherein:
X is a bond or —S(O)$_m$—;
Y is selected from the group consisting of:
  a) a bond, —O—, —NH—, —N(R⁹)— or —N(COR⁹)—;

b)
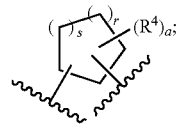

c)
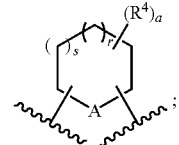

d)
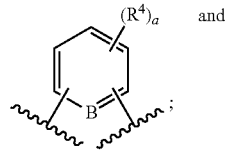 and e)
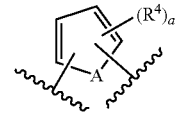

where
  A is —O—, —S— or N(R)—;
  B is —C— or —N—;
  a is 0, 1, 2, or 3;
  r is 0, 1 or 2;
  s is 0, 1 or 2;
R is H, alkyl or haloalkyl;
R$^a$ is independently H, halo, alkyl or haloalkyl;
R$^b$ is independently H, halo, alkyl or haloalkyl;
R¹ is heteroaryl, heterocyclyl or heterocyclenyl;
R² is aryl, heteroaryl, alkyl or heterocyclyl;

R³ is —C(O)OH or —N(H)—SO₂—Rᶜ;
where:
Rᶜ is alkyl, haloalkyl, cycloalkyl, aryl or heteroaryl;
R⁴ is independently selected from the group consisting of alkyl, —OH, halo, alkoxy, haloalkoxy, —CN and haloalkyl;
R⁸ is independently selected from the group consisting of —CN, halo, alkyl, haloalkyl, alkoxy, haloalkoxy and cycloalkyl;
R⁹ is alkyl, haloalkyl, alkoxy, haloalkoxy or cycloalkyl;
and wherein:
i) the heteroaryl, heterocyclyl or heterocyclenyl group in R¹; and
ii) each of the aryl, heteroaryl, alkyl or heterocyclyl groups of R²; are independently unsubstituted or substituted by 1 to 5 R⁵ groups independently selected from the group consisting of alkyl, alkenyl, alkynyl, cycloalkyl, cycloalkenyl, heterocyclyl, heterocyclenyl, aryl, heteroaryl, halo, —CN, —SF₅, —OSF₅, —NO₂, —CH₂OSi(R¹⁴)(R¹⁵)(R¹⁶, —OR¹⁴, —C(O)R¹⁴, —C(O)OR¹⁴, —O—C(O)—R¹⁴, —O—C(O)N(R¹⁴)(R¹⁵), —C(O)N(R¹⁴)(R¹⁵), —S(O)ₘR¹⁴, —S(O)ₚN(R¹⁴)(R¹⁵), —C(=NOR¹⁴)R¹⁵, —N(R¹⁴)(R¹⁵), —N(R¹⁴)C(O)R¹⁵, —N(R¹⁴)S(O)ₚR¹⁵, —N(R¹⁴)S(O)ₚN(R¹⁵)(R¹⁶), —N(R¹⁴)C(O)N(R¹⁵)(R¹⁶) and —N(R¹⁴)C(O)OR¹⁶;
or when a position is disubstituted by two R⁵ groups, the two R⁵ groups can form a cycloalkyl or heterocyclyl ring that is unsubstituted or is substituted by 1 to 5 R⁶ groups;
and wherein:
each of the alkyl, alkenyl, alkynyl, cycloalkyl, cycloalkenyl, heterocyclyl, heterocyclenyl, aryl, heteroaryl groups in R⁵ are independently unsubstituted or substituted by 1 to 5 R⁶ groups independently selected from the group consisting of alkyl, alkenyl, alkynyl, cycloalkyl, cycloalkenyl, heterocyclyl, heterocyclenyl, aryl, heteroaryl, halo, —CN, —SF₅, —OSF₅, —NO₂, —CH₂OSi(R¹⁴)(R¹⁵)(R¹⁶), —OR¹⁴, —C(O)R¹⁴, —C(O)OR¹⁴, —O—C(O)—R¹⁴, —O—C(O)—N(R¹⁴)(R¹⁵), —C(O)N(R¹⁴)(R¹⁵), —S(O)ₘR¹⁴, —S(O)ₚN(R¹⁴)(R¹⁵), —C(=NOR¹⁴)R¹⁵, —N(R¹⁴)(R¹⁵), —N(R¹⁴)C(O)R¹⁵; —N(R¹⁴)S(O)ₚR¹⁵, —N(R¹⁴)S(O)ₚN(R¹⁵)(R¹⁶), —N(R¹⁴)C(O)N(R¹⁵)(R¹⁶); —N(R¹⁴)C(O)OR¹⁶ and —N(R¹⁴)C(O)R¹⁶; and
wherein each of the alkyl, alkenyl, alkynyl, cycloalkyl, cycloalkenyl, heterocyclyl, heterocyclenyl, aryl, heteroaryl groups in R⁶ are independently unsubstituted or substituted by 1 to 5 R⁷ groups independently selected from the group consisting of alkyl, alkenyl, alkynyl, cycloalkyl, cycloalkenyl, heterocyclyl, heterocyclenyl, aryl, heteroaryl, halo, —CN, —SF₅, —OSF₅, —NO₂, —CH₂OSi(R¹⁴)(R¹⁵)(R¹⁶), —OR¹⁴, —C(O)R¹⁴, —C(O)OR¹⁴, —O—C(O)—R¹⁴, —O—C(O)—N(R¹⁴)(R¹⁵), —C(O)N(R¹⁴)(R¹⁵), —S(O)ₘR¹⁴, —S(O)ₚN(R¹⁴)(R¹⁵), —C(=NOR¹⁴)R¹⁵, —N(R¹⁴)(R¹⁵), —N(R¹⁴)C(O)R¹⁵, —N(R¹⁴)S(O)ₚR¹⁵, —N(R¹⁴)S(O)ₚN(R¹⁵)(R¹⁶), —N(R¹⁴)C(O)N(R¹⁵)(R¹⁶), —N(R¹⁴)C(O)OR¹⁶ and —N(R¹⁴)C(O)R¹⁶;
wherein:
R¹⁴, R¹⁵ and R¹⁶ are independently selected from the group consisting of H, alkyl, alkenyl, alkynyl, cycloalkyl, cycloalkenyl, heterocyclyl, heterocyclenyl, aryl, heteroaryl, R¹⁷-alkyl, R¹⁷-alkenyl, R¹⁷-alkynyl, R¹⁷-cycloalkyl, R¹⁷-cycloalkenyl, R¹⁷-heterocyclyl, R¹⁷-heterocyclenyl, R¹⁷-aryl, and R¹⁷-heteroaryl;

R¹⁷ is 1-5 substituents independently selected from the group consisting of alkyl, alkenyl, alkynyl, cycloalkyl, cycloalkenyl, heterocyclyl, heterocyclenyl, aryl, halo-substituted aryl, nitrile-substituted aryl, phenyl-substituted aryl, heteroaryl, halo, —CN, —SF₅, —OSF₅, —NO₂, heteroaryl, haloalkyl, —C(O)R¹⁸, —C(O)OH, —C(O)OR¹⁸, —C(O)NHR¹⁹, —C(O)NH₂, —C(O)N(R¹⁸)(R¹⁹), —S(O)ₘR¹⁸, —S(O)ₚNH₂, —S(O)NHₚ(alkyl), —S(O)ₚN(alkyl)(alkyl), —S(O)ₚNH(aryl), —S(O)₂NHR¹⁹, —S(O)₂NH(heterocycloalkyl), —S(O)₂N(alkyl)(aryl), haloalkoxy, —OH, —OR¹⁹, —O-heterocycloalkyl, —O-cycloalkylalkyl, —O-heterocyclylalkyl, —NH₂, —NHR¹⁹, —N(alkyl)₂, —N(arylalkyl)₂, —N(arylalkyl)-(heteroarylalkyl), —NHC(O)R¹⁹, —NHC(O)NH₂, —NHC(O)NH(alkyl), —NHC(O)N(alkyl)(alkyl), —N(alkyl)C(O)NH(alkyl), —N(alkyl)C(O)N(alkyl)(alkyl), —NHS(O)₂R²¹, —NHS(O)₂NH(alkyl), —NHS(O)₂N(alkyl)(alkyl), —N(alkyl)S(O)₂NH(alkyl) and —N(alkyl)S(O)₂N(alkyl)(alkyl);

R¹⁸ is alkyl, cycloalkyl, aryl, arylalkyl or heteroarylalkyl;

R¹⁹ is alkyl, cycloalkyl, aryl, halo substituted aryl, arylalkyl, heteroaryl or heteroarylalkyl;

R²¹ is alkyl, cycloalkyl, aryl, halo substituted aryl, arylalkyl, heteroaryl or heteroarylalkyl;

b is 0, 1 or 2;

n is an integer from 1 to 5;

m is independently an integer from 0 to 2;

p is an integer from 1 to 2;

q is an integer from 0 to 5;

wherein each heteroaryl is independently an aromatic monocyclic or bicyclic ring system comprising 5 to 14 ring atoms, wherein one or more of the ring atoms is nitrogen, oxygen, or sulfur, each heterocyclyl is independently a non-aromatic saturated monocyclic or multicyclic ring system comprising 3 to 12 ring atoms, wherein one or more of the ring atoms is nitrogen, oxygen, or sulfur; and each heterocyclenyl is independently a non-aromatic monocyclic or multicyclic ring system comprising 3 to 10 ring atoms, wherein one or more of the ring atoms is nitrogen, oxygen, or sulfur; and wherein the heterocyclenyl contains at least one carbon-carbon double bond or carbon-nitrogen double bond.

2. The compound according to claim 1 which has the formula:

Formula II

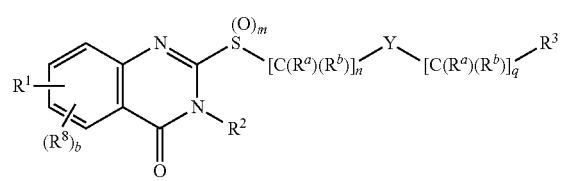

or a pharmaceutically acceptable salt thereof wherein:
Y is selected from the group consisting of:
a) a bond;

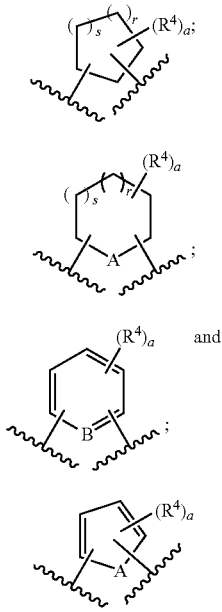

b)

c)

d) and e)

where
A is —O—, —S— or N(R)—;
B is —C— or —N—;
a is 0, 1, 2, or 3;
r is 0, 1 or 2;
s is 0, 1 or 2;
R is H, alkyl or haloalkyl;
$R^a$ is independently H, halo, alkyl or haloalkyl
$R^b$ is independently H, halo, alkyl or haloalkyl;
$R^1$ is heteroaryl, heterocyclyl or heterocyclenyl;
$R^2$ is aryl, heteroaryl, alkyl or heterocyclyl;
$R^3$ is —C(O)OH or —N(H)—SO$_2$—$R^c$;
where:
$R^c$ is alkyl, haloalkyl, cycloalkyl, aryl or heteroaryl;
$R^4$ is independently selected from the group consisting of alkyl, —OH, halo, alkoxy, haloalkoxy, —CN and haloalkyl;
$R^8$ is independently selected from the group consisting of —CN, halo, alkyl, haloalkyl, alkoxy, haloalkoxy and cycloalkyl;
and wherein:
i) the heteroaryl heterocyclyl or heterocyclenyl group in $R^1$; and
ii) each of the aryl, heteroaryl, alkyl or heterocyclyl groups of $R^2$; are independently unsubstituted or substituted by 1 to 5 $R^5$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$) and —N(R$^{14}$)C(O)OR$^{16}$;

or when a position is disubstituted by two $R^5$ groups, the two $R^5$ groups can form a cycloalkyl or heterocyclyl ring that is unsubstituted or is substituted by 1 to 5 $R^6$ groups
and wherein:
each of the alkyl, alkenyl, alkynyl, cycloalkyl, cycloalkenyl, heterocyclyl, heterocyclenyl, aryl, heteroaryl groups in $R^5$ are independently unsubstituted or substituted by 1 to 5 $R^6$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$); —N(R$^{14}$)C(O)OR$^{16}$ and —N(R$^{14}$)C(O)R$^{16}$; and
wherein each of the alkyl, alkenyl, alkynyl, cycloalkyl, cycloalkenyl, heterocyclyl, heterocyclenyl, aryl, heteroaryl groups in $R^6$ are independently unsubstituted or substituted by 1 to 5 $R^7$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$); —N(R$^{14}$)C(O)OR$^{16}$ and —N(R$^{14}$)C(O)R$^{16}$;
wherein:
$R^{14}$, $R^{15}$ and $R^{16}$ are independently selected from the group consisting of H, alkyl, alkenyl, alkynyl, cycloalkyl, cycloalkenyl, heterocyclyl, heterocyclenyl, aryl, heteroaryl, $R^{17}$-alkyl, $R^{17}$-alkenyl, $R^{17}$-alkynyl, $R^{17}$-cycloalkyl, $R^{17}$-cycloalkenyl, $R^{17}$-heterocyclyl, $R^{17}$-heterocyclenyl, $R^{17}$-aryl, and $R^{17}$-heteroaryl;
$R^{17}$ is 1-5 substituents independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, heteroaryl, haloalkyl, —C(O)R$^{18}$, —C(O)OH, —C(O)OR$^{18}$, —C(O)NHR$^{19}$, —C(O)NH$_2$, —C(O)N(R$^{18}$)(R$^{19}$), —S(O)$_m$R$^{18}$, —S(O)$_p$NH$_2$, —S(O)NH$_p$(alkyl), —S(O)$_p$N(alkyl)(alkyl), —S(O)$_p$NH(aryl), —S(O)$_2$NHR$^{19}$, —S(O)$_2$NH(heterocycloalkyl), —S(O)$_2$N(alkyl)(aryl), haloalkoxy, —OH, —OR$^{19}$, —O-heterocycloalkyl, —O-cycloalkylalkyl, —O-heterocyclylalkyl, —NH$_2$, —NHR$^{19}$, —N(alkyl)$_2$, —N(arylalkyl)$_2$, —N(arylalkyl)-(heteroarylalkyl), —NHC(O)R$^{19}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{21}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);
$R^{18}$ is alkyl, cycloalkyl, aryl, arylalkyl or heteroarylalkyl;
$R^{19}$ is alkyl, cycloalkyl, aryl, halo substituted aryl, arylalkyl, heteroaryl or heteroarylalkyl;
$R^{21}$ is alkyl, cycloalkyl, aryl, halo substituted aryl, arylalkyl, heteroaryl or heteroarylalkyl;
b is 0, 1 or 2;
n is an integer from 1 to 5;
m is independently an integer from 0 to 2;
p is an integer from 1 to 2; and
q is an integer from 0 to 5.

3. The compound of claim 1 which has the formula:

Formula III

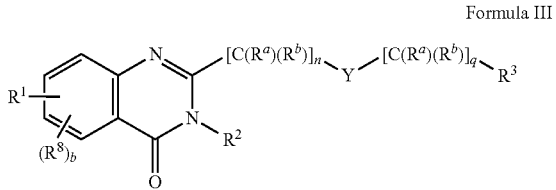

or a pharmaceutically acceptable salt thereof
wherein:
Y is selected from the group consisting of:
a) a bond;

b)
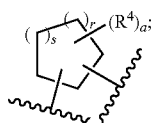

c)
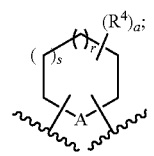

d)
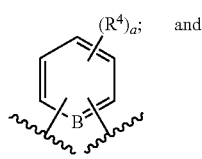 and e)
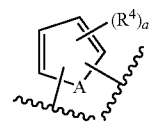

where
A is —O—, —S— or N(R)—;
B is —C— or —N—;
a is 0, 1, 2, or 3;
r is 0, 1 or 2; and
s is 0, 1 or 2;
R is H, alkyl or haloalkyl;
$R^a$ is independently H, halo, alkyl or haloalkyl
$R^b$ is independently H, halo, alkyl or haloalkyl;
$R^1$ is heteroaryl, heterocyclyl or heterocyclenyl;
$R^2$ is aryl, heteroaryl, alkyl or heterocyclyl;
$R^3$ is —C(O)OH or —N(H)—SO$_2$—$R^c$;
where:
$R^c$ is alkyl, haloalkyl, cycloalkyl, aryl or heteroaryl;
$R^4$ is independently selected from the group consisting of alkyl, —OH, halo, alkoxy, haloalkoxy, —CN and haloalkyl;
$R^8$ is independently selected from the group consisting of —CN, halo, alkyl, haloalkyl, alkoxy, haloalkoxy and cycloalkyl;

and wherein:
i) the heteroaryl, heterocyclyl or heterocyclenyl group in $R^1$; and
ii) each of the aryl, heteroaryl, alkyl or heterocyclyl groups of $R^2$; are independently unsubstituted or substituted by 1 to 5 $R^5$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$) and —N(R$^{14}$)C(O)OR$^{16}$;
or when a position is disubstituted by two $R^5$ groups, the two $R^5$ groups can form a cycloalkyl or heterocyclyl ring that is unsubstituted or is substituted by 1 to 5 $R^6$ groups
and wherein:
each of the alkyl, alkenyl, alkynyl, cycloalkyl, cycloalkenyl, heterocyclyl, heterocyclenyl, aryl, heteroaryl groups in $R^5$ are independently unsubstituted or substituted by 1 to 5 $R^6$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$); —N(R$^{14}$)C(O)OR$^{16}$ and —N(R$^{14}$)C(O)R$^{16}$; and
wherein each of the alkyl, alkenyl, alkynyl, cycloalkyl, cycloalkenyl, heterocyclyl, heterocyclenyl, aryl, heteroaryl groups in $R^6$ are independently unsubstituted or substituted by 1 to 5 $R^7$ groups independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, —CH$_2$OSi(R$^{14}$)(R$^{15}$)(R$^{16}$), —OR$^{14}$, —C(O)R$^{14}$, —C(O)OR$^{14}$, —O—C(O)—R$^{14}$, —O—C(O)—N(R$^{14}$)(R$^{15}$), —C(O)N(R$^{14}$)(R$^{15}$), —S(O)$_m$R$^{14}$, —S(O)$_p$N(R$^{14}$)(R$^{15}$), —C(=NOR$^{14}$)R$^{15}$, —N(R$^{14}$)(R$^{15}$), —N(R$^{14}$)C(O)R$^{15}$, —N(R$^{14}$)S(O)$_p$R$^{15}$, —N(R$^{14}$)S(O)$_p$N(R$^{15}$)(R$^{16}$), —N(R$^{14}$)C(O)N(R$^{15}$)(R$^{16}$); —N(R$^{14}$)C(O)OR$^{16}$ and —N(R$^{14}$)C(O)R$^{16}$;
wherein:
$R^{14}$, $R^{15}$ and $R^{16}$ are independently selected from the group consisting of H, alkyl, alkenyl, alkynyl, cycloalkyl, cycloalkenyl, heterocyclyl, heterocyclenyl, aryl, heteroaryl, $R^{17}$-alkyl, $R^{17}$-alkenyl, $R^{17}$-alkynyl, $R^{17}$-cycloalkyl, $R^{17}$-cycloalkenyl, $R^{17}$-heterocyclyl, $R^{17}$-heterocyclenyl, $R^{17}$-aryl, and $R^{17}$-heteroaryl;
$R^{17}$ is 1-5 substituents independently selected from the group consisting of alkyl, alkenyl, alkynyl, cycloalkyl, cycloalkenyl, heterocyclyl, heterocyclenyl, aryl, heteroaryl, halo, —CN, —SF$_5$, —OSF$_5$, —NO$_2$, heteroaryl, haloalkyl, —C(O)R$^{18}$, —C(O)OH, —C(O)OR$^{18}$, —C(O)NHR$^{19}$, —C(O)NH$_2$, —C(O)N(R$^{18}$)(R$^{19}$), —S(O)$_m$R$^{18}$, —S(O)$_p$NH$_2$, —S(O)NH$_p$(alkyl), —S(O)$_p$N(alkyl)(alkyl), —S(O)$_p$NH(aryl), —S(O)$_2$NHR$^{19}$, —S(O)$_2$NH(heterocycloalkyl), —S(O)$_2$N(alkyl)(aryl), haloalkoxy, —OH, —OR$^{19}$, —O-heterocycloalkyl, —O-cycloalkylalkyl, —O-heterocyclylalkyl, —NH$_2$, —NHR$^{19}$, —N(alkyl)$_2$, —N(arylalkyl)$_2$, —N(arylalkyl)-(heteroarylalkyl), —NHC(O)R$^{19}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{21}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

R$^{18}$ is alkyl, cycloalkyl, aryl, arylalkyl or heteroarylalkyl;

R$^{19}$ is alkyl, cycloalkyl, aryl, halo substituted aryl, arylalkyl, heteroaryl or heteroarylalkyl;

R$^{21}$ is alkyl, cycloalkyl, aryl, halo substituted aryl, arylalkyl, heteroaryl or heteroarylalkyl;

b is 0, 1 or 2 n is an integer from 1 to 5;

m is independently an integer from 0 to 2;

p is an integer from 1 to 2; and q is an integer from 0 to 5.

4. The compound of claim 2, which has the structural formula:

Formula IV or a pharmaceutically acceptable salt thereof wherein:

R$^1$ is heteroaryl or R$^5$-heteroaryl, wherein the heteroaryl ring is a ring selected from the group consisting of thiazole, oxazole, imidazole, 1,2-diazole, triazole, pyridine, pyrimidine, thiophene and furan, isooxazole, isothiazole and oxadiazole;

R$^5$ is 1 to 5 substituents independently selected from the group consisting of —C$_1$-C$_5$-alkyl, halogen, —C$_1$-C$_5$-haloalkyl, —C$_1$-C$_5$-alkoxy, —C$_1$-C$_5$, haloalkoxy, aryl, R$^6$-aryl, —C$_1$-C$_5$alkyl-aryl and —C$_1$-C$_5$-alkyl-aryl-R$^7$ R$^6$ is 1 to 5 substituents independently selected from the group consisting of —C$_1$-C$_5$-alkyl, halogen, —CN, —C$_1$-C$_5$-haloalkyl, —OH or —C$_1$-C$_5$-alkoxy and —S(O)$_2$alkyl;

R$^7$ is 1 to 5 substituents independently selected from the group consisting of —C$_1$-C$_5$-alkyl, halogen, —CN, —C$_1$-C$_5$-haloalkyl, —OH or —C$_1$-C$_5$-alkoxy and —S(O)$_2$alkyl;

Z is halogen; and n is 1 or 2.

5. The compound of claim 3, which has the formula:

Formula V or a pharmaceutically acceptable salt thereof wherein:

R$^1$ is heteroaryl or R$^5$-heteroaryl, wherein the heteroaryl ring is a ring selected from the group consisting of thiazole, oxazole, imidazole, 1,2-diazole, triazole, pyridine, pyrimidine, thiophene, furan, isooxazole, isothiazole and oxadiazole;

R$^5$ is 1 to 5 substituents independently selected from the group consisting of —C$_1$-C$_5$-alkyl, halogen, —C$_1$-C$_5$-haloalkyl, C$_1$-C$_5$-alkoxy, —C$_1$-C$_5$-haloalkoxy, aryl, R$^6$-aryl —C$_1$-C$_5$-alkyl-aryl and —C$_1$-C$_5$alkyl-aryl-R$^7$ R$^6$ is 1 to 5 substituents independently selected from the group consisting of —C$_1$-C$_5$-alkyl, halogen, —CN, —C$_1$-C$_5$-haloalkyl, —OH or —C$_1$-C$_5$-alkoxy and —S(O)$_2$alkyl;

R$^7$ is 1 to 5 substituents independently selected from the group consisting of —C$_1$-C$_5$-alkyl, halogen, —CN, —C$_1$-C$_5$-haloalkyl, —OH or —C$_1$-C$_5$-alkoxy and —S(O)$_2$alkyl;

Z is halogen; and n is 3 or 4.

6. The compound of claim 3, which has the formula:

Formula V or a pharmaceutically acceptable salt thereof wherein:

R$^5$-heterocyclenyl, wherein the heterocyclenyl ring is a ring selected from the group consisting of 4,5-dihydroisoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, and dihydrothiopyranyl;

R$^5$ is 1 to 5 substituents independently selected from the group consisting of —C$_1$-C$_5$-alkyl, halogen, —C$_1$-C$_5$-haloalkyl, —C$_1$-C$_5$-alkoxy, —C$_1$-C$_5$-haloalkoxy, aryl, R$^6$-aryl, —C$_1$-C$_5$-alkyl-aryl and —C$_1$-C$_5$-alkyl-aryl-R$^7$ R$^6$ is 1 to 5 substituents independently selected from the group consisting of —C$_1$-C$_5$-alkyl, halogen, —CN, —C$_1$-C$_5$-haloalkyl, —OH, —C$_1$-C$_5$-alkoxy and —S(O)$_2$alkyl;

R$^7$ is 1 to 5 substituents independently selected from the group consisting of —C$_1$-C$_5$-alkyl, halogen, —CN, —C$_1$-C$_5$-haloalkyl, —OH and —C$_1$-C$_5$-alkoxy and —S(O)$_2$alkyl;

Z is halogen; and n is 3 or 4.

7. The compound of claim 1, which has the formula:

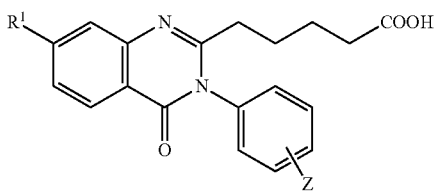

Formula VI or a pharmaceutically acceptable salt thereof,
wherein:
  Z is a H or a halogen;
  $R^1$ is $R^5$-heterocyclenyl, wherein the heterocyclenyl ring is a ring selected from the group consisting of 4,5-dihydroisoxazole, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, 7-oxabicyclo[2.2.1]heptenyl, dihydrothiophenyl, and dihydrothiopyranyl;
  $R^5$ is 1 to 2 substituents independently selected from the group consisting of —$C_1$-$C_5$-alkyl, —$C_1$-$C_5$-haloalkyl, $C_1$-$C_5$- alkoxy, —$C_1$-$C_5$-haloalkoxy, aryl, $R^6$-aryl, —$C_1$-$C_5$, alkyl-aryl-$R^7$, heteroaryl and $R^6$-heteroaryl: and
  where $R^6$ and $R^7$ at each occurrence independently are —$C_1$-$C_5$-alkyl, halogen, —CN, —$C_1$-$C_5$-haloalkyl, —OH, —$C_1$-$C_5$-alkoxy or —$S(O)_2$—$C_1$-$C_5$-alkyl.

8. The compound of claim 1, which has the formula:

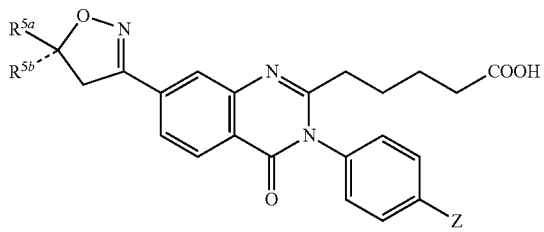

Formula VII or a pharmaceutically acceptable salt thereof,
wherein:
  Z is H, Cl or F;
  $R^{5a}$ is phenyl, benzoxazole, benzothiazole, benzimidazole, imidazo[1,2-a]pyridine, pyrazolo[1,5-a]pyridine, and quinoxaline;
  wherein $R^{5a}$ is unsubstituted or substituted by 1 to 2 $R^6$ groups independently selected from the group consisting of $C_1$-$C_3$-alkyl, halo, $CF_3$, and —CN; and
  wherein $R^{5b}$ is absent or present, and if present, is $CH_3$.

9. The compound of claim 1, which has the formula:

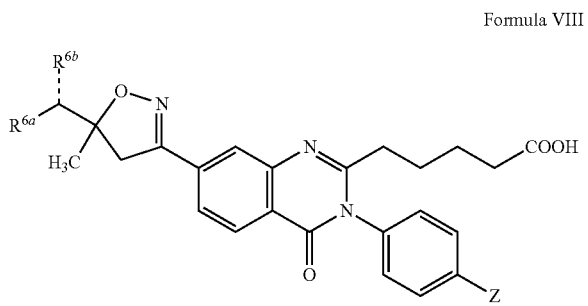

Formula VIII or a pharmaceutically acceptable salt thereof,
wherein:
  Z is H, Cl or F and
  $R^{6a}$ is phenyl, wherein the phenyl of $R^{6a}$ is unsubstituted or substituted by 1 to 2 $R^7$ groups independently selected from the group consisting of halo, $C_1$-$C_3$ alkyl, and —CN; and
  wherein $R^{6b}$ is absent or present, and, if present, is selected from the group consisting of —$CH_3$ and —OH.

10. The compound of claim 1, which has the formula:

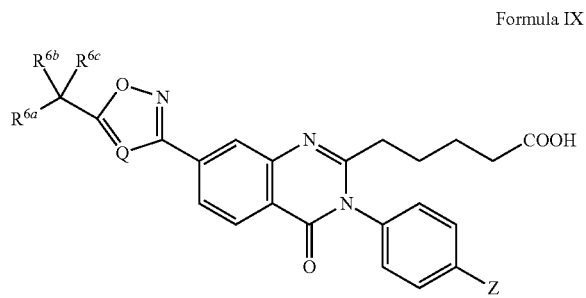

Formula IX or a pharmaceutically acceptable salt thereof,
wherein:
  Z is H, Cl or F;
  Q is C(H) or N;
  $R^{6a}$ is selected from the group consisting of:
    (a) -M-E; and
    (b) -E;
    wherein M is selected from the group consisting of —N(H)S(O)—, —N(H)C(O)—, —S—, —S(O)—, —S—, and —$OCH_2$—;
    E is selected from the group consisting of:
      (i) $C_1$-$C_3$-alkyl;
      (ii) —O—($C_1$-$C_4$-alkyl);
      (iii) an aryl selected from the group consisting of phenyl and napthalene;
      (iv) a heteroaryl selected from the group consisting of quinoline, quinoxaline, and benzimidazole; and
      (v) 2,3-dihydroindole;
      wherein said aryl or heteroaryl of E is unsubstituted or substituted by 1 to 3 moieties selected from the group consisting of $C_1$-$C_6$-alkyl, halo, $CF_3$, $OCF_3$, CN, $OCH_3$, and phenyl;
  $R^{6b}$ is H, OH, or $OCH_3$; and
  $R^{6c}$ is H, $C_1$-$C_3$-alkyl, or $CF_3$;
  or alternatively, $R^{6b}$ and $R^{6c}$ together with the carbon atom to which they are attached form —C(O)— or —C(=$CH_2$)—.

11. The compound according to claim 1 or a pharmaceutically acceptable salt thereof which is selected from the group consisting of:
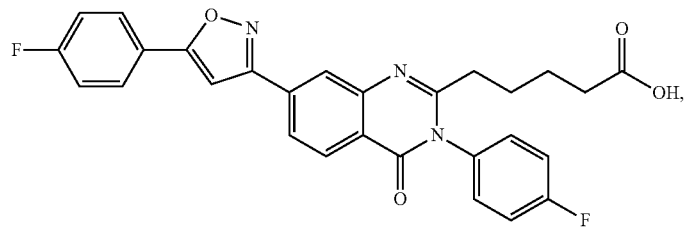
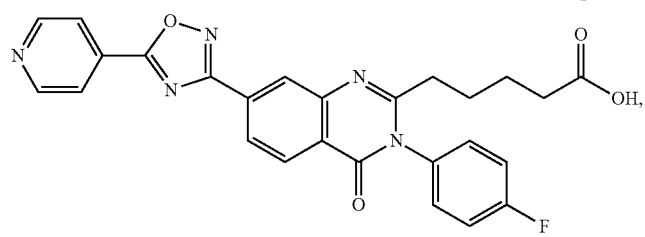
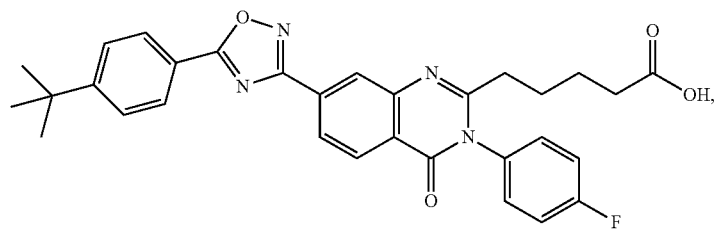
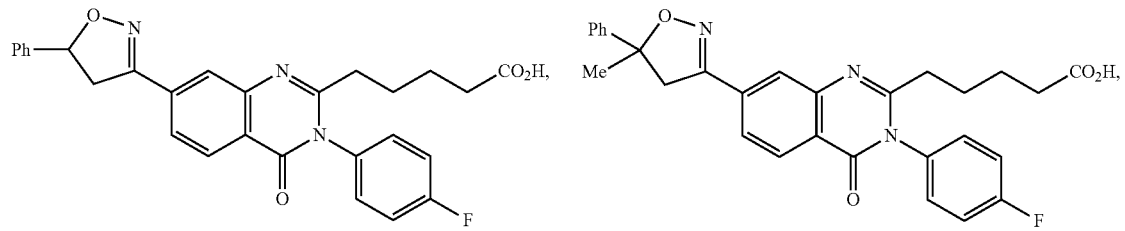
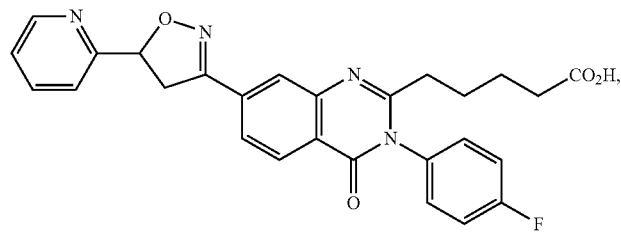
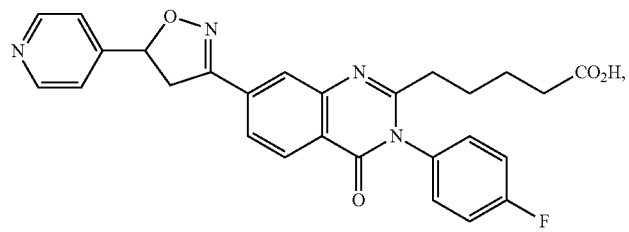
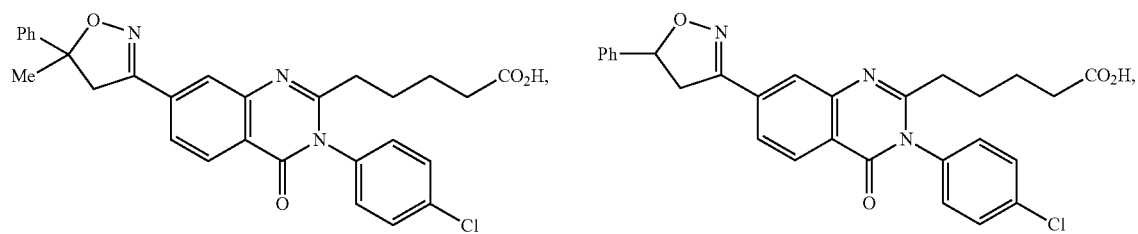

-continued
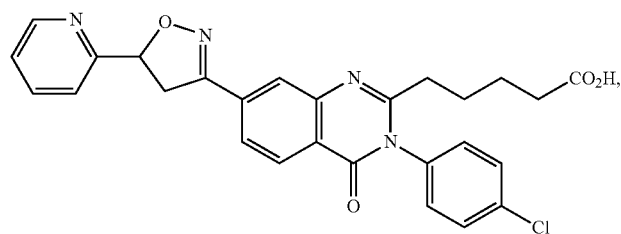
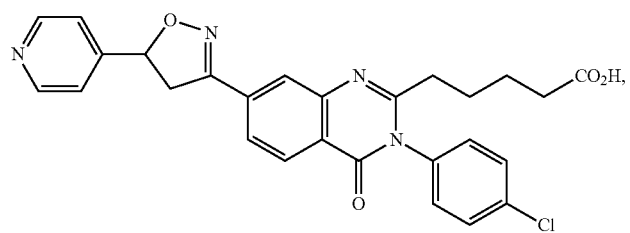
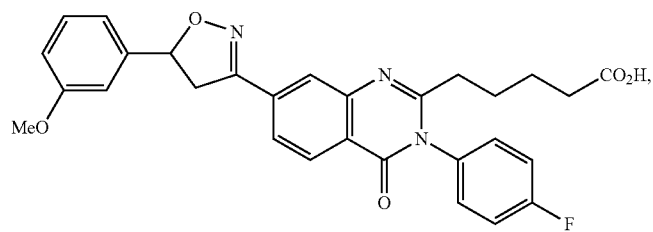
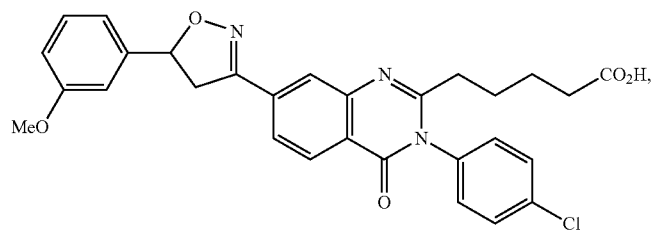
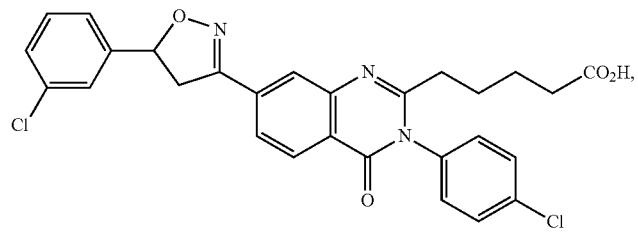
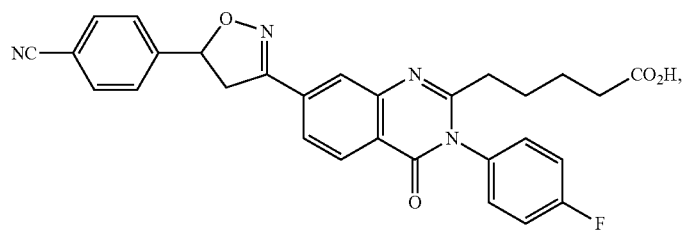
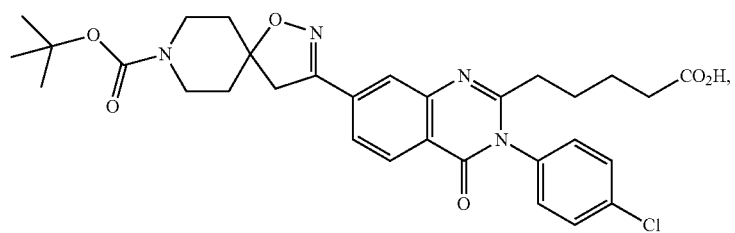

-continued
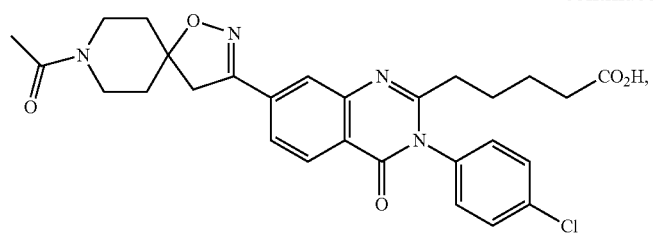
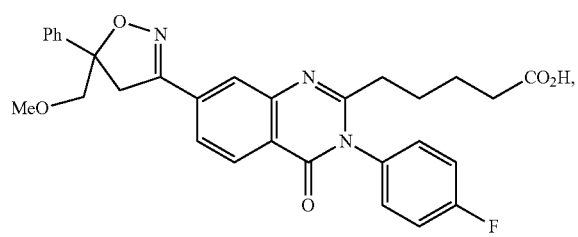
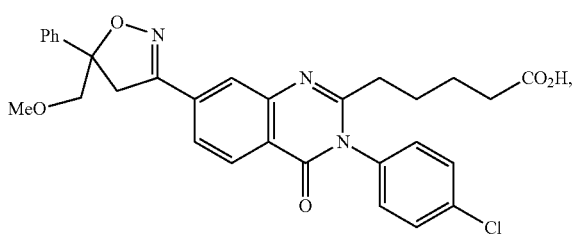
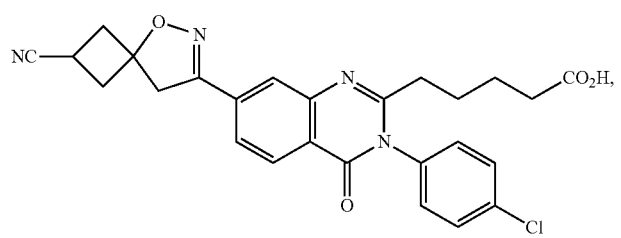
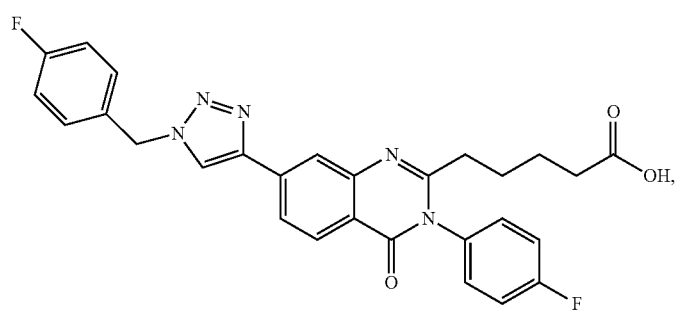
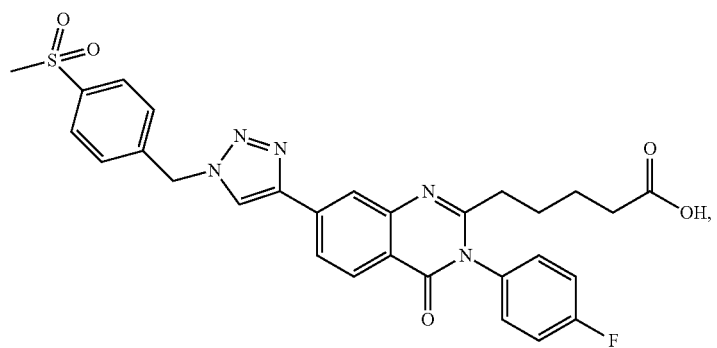
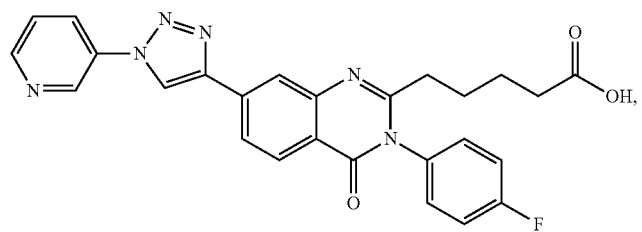

-continued
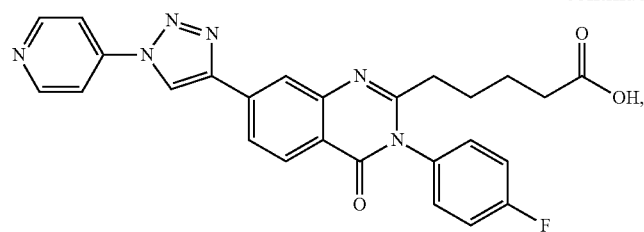
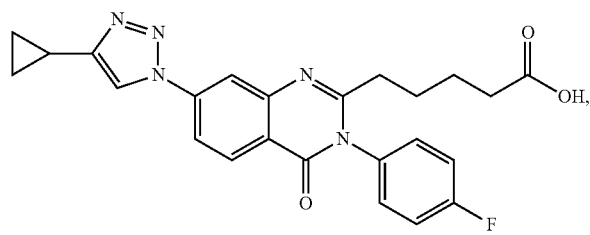
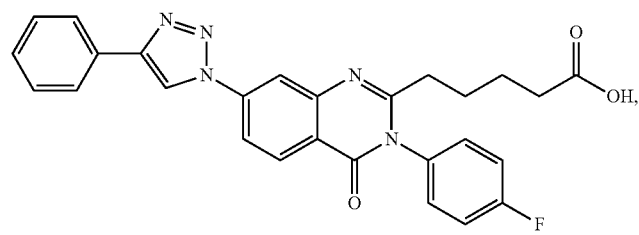
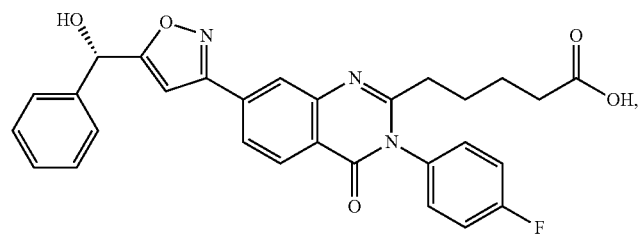
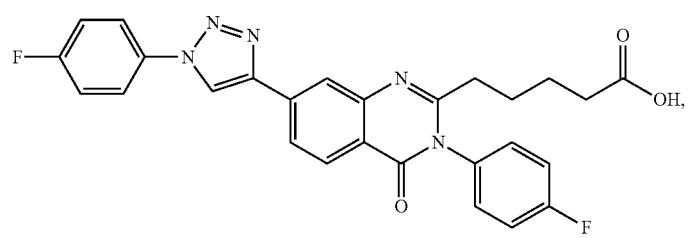
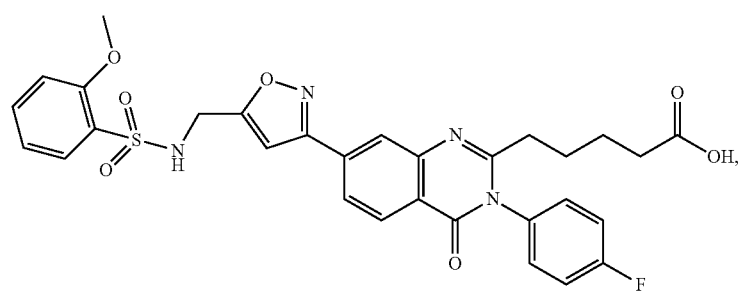
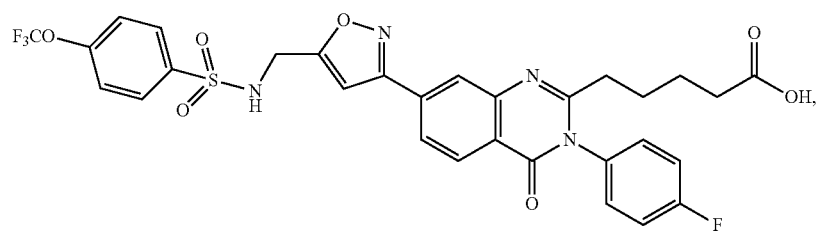

-continued
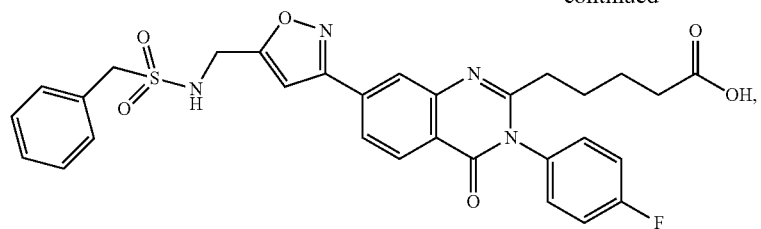
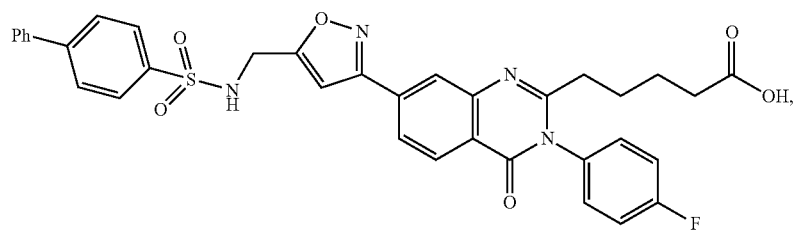
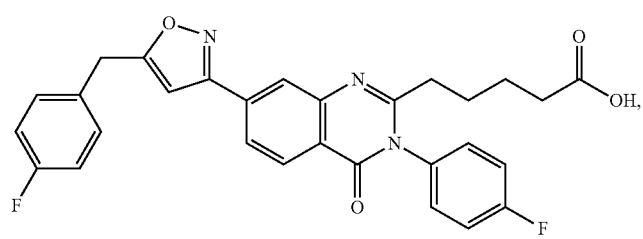
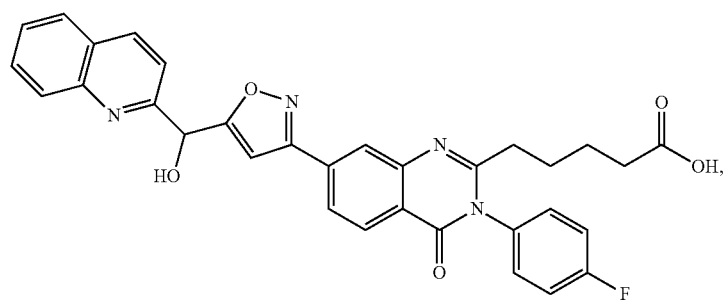
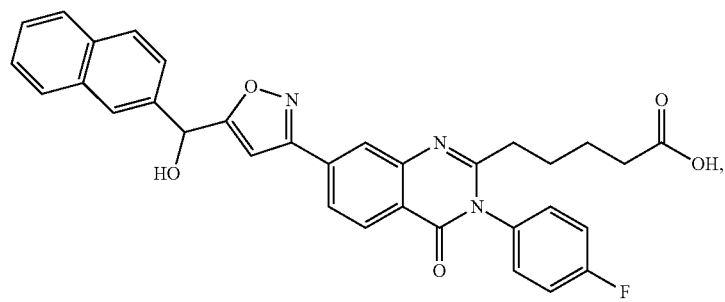
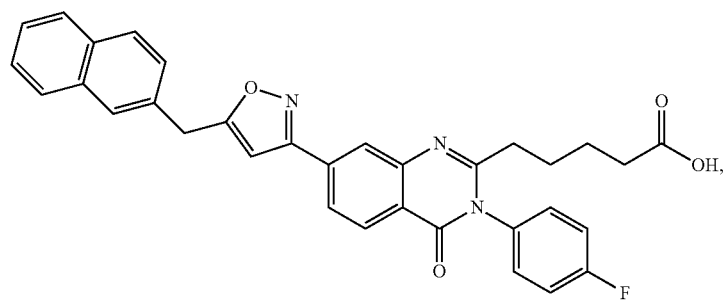

-continued
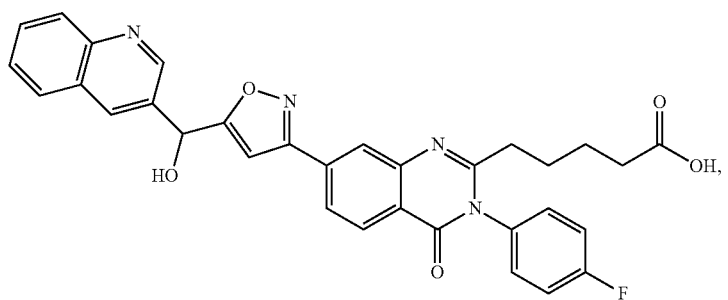
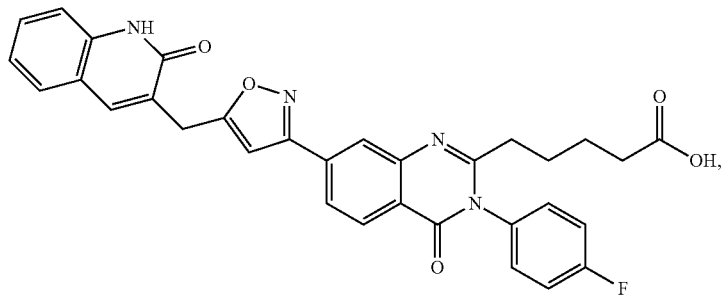
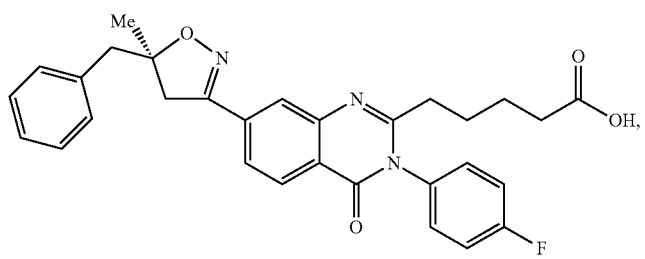
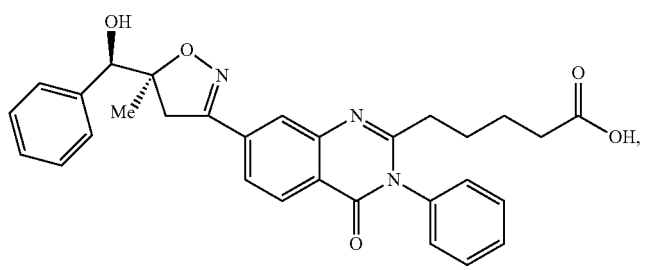
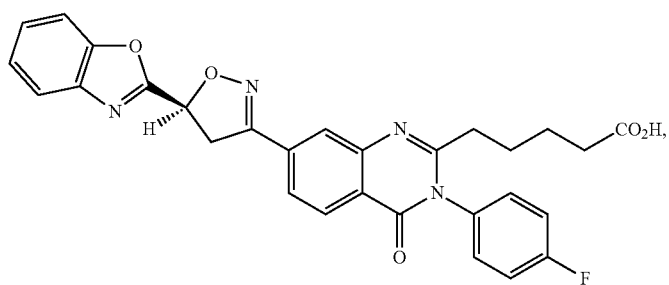
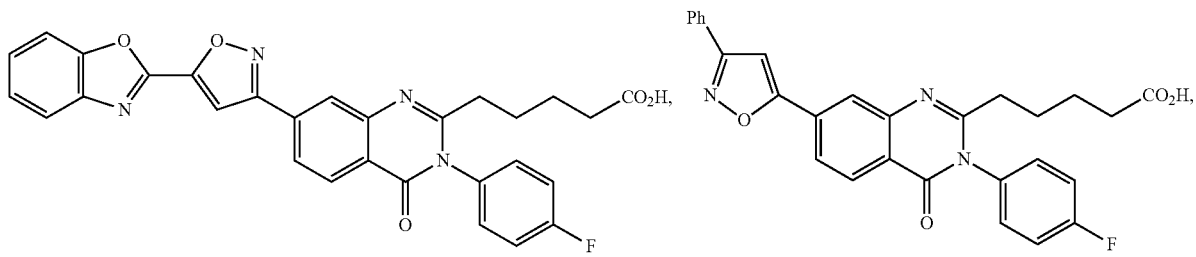

-continued
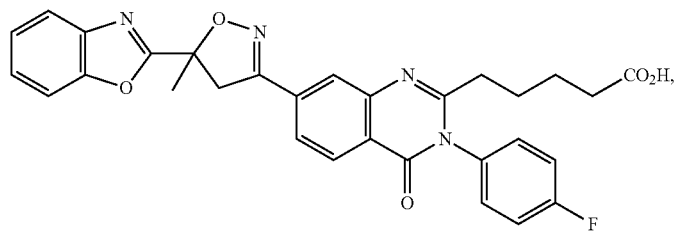
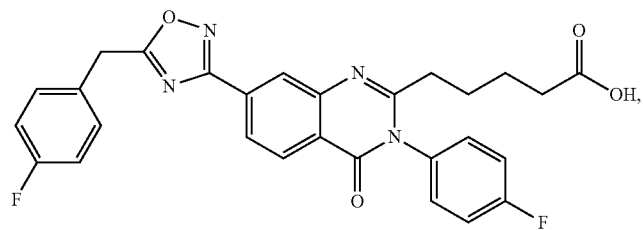
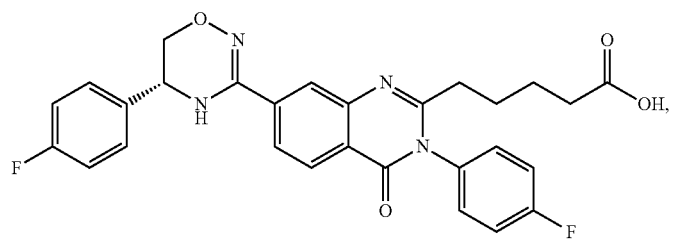
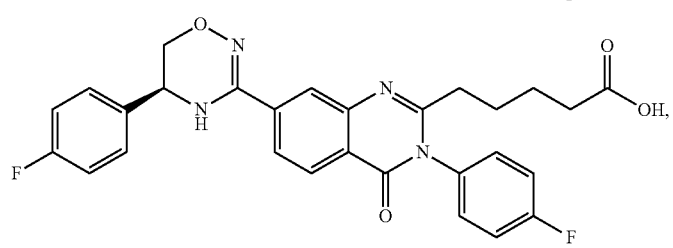
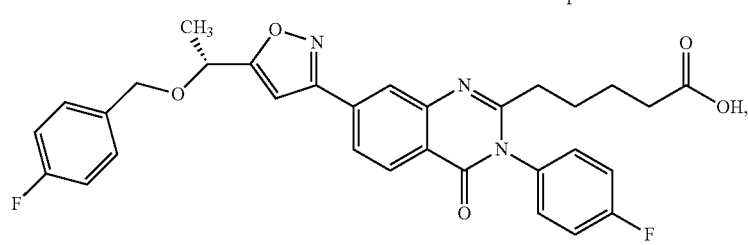
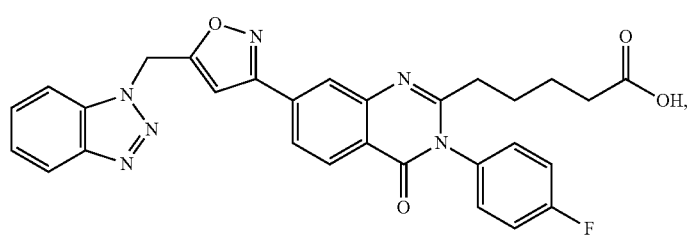
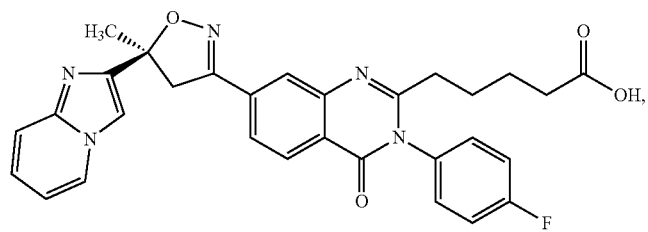

-continued
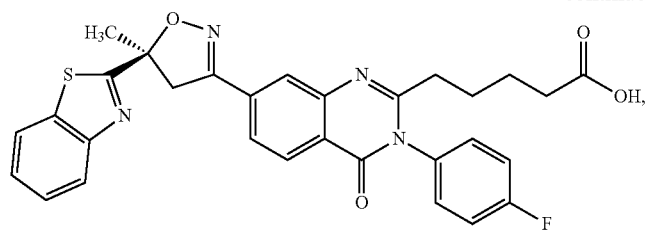
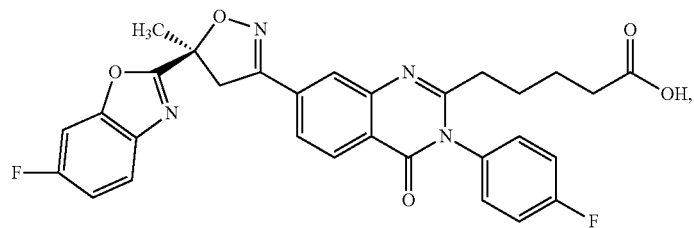
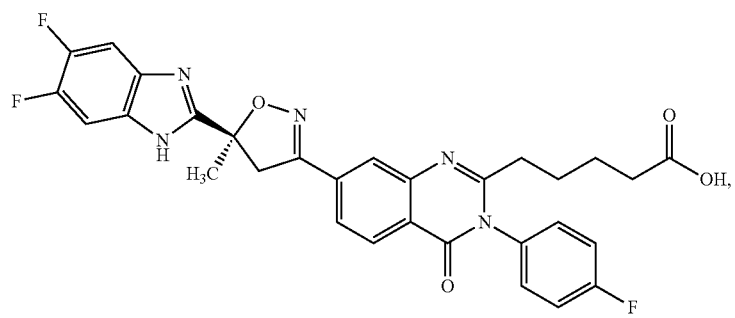
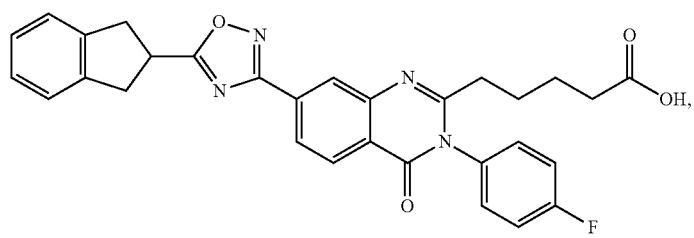
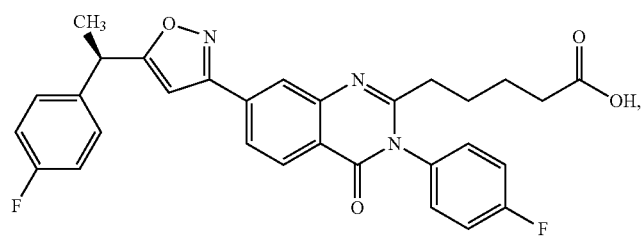
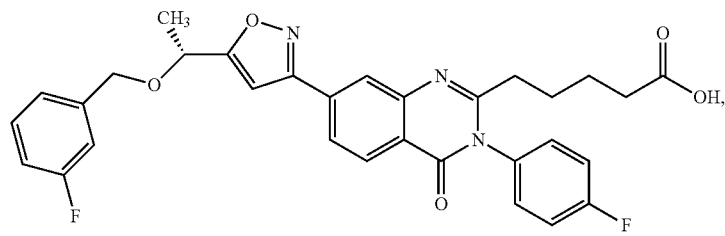
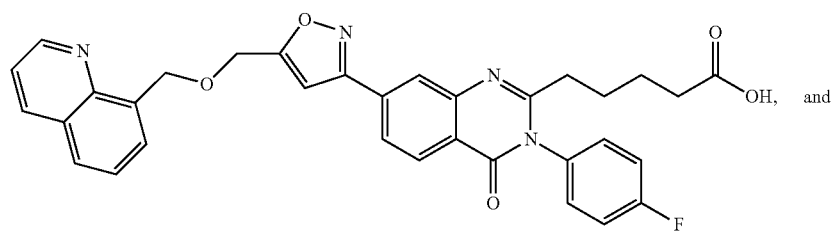 and -continued

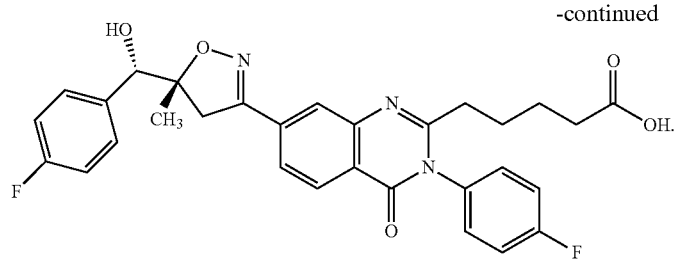

12. A pharmaceutical composition comprising an effective amount of a compound of Formula I according to claim 1 or a pharmaceutically acceptable salt thereof and a pharmaceutically acceptable carrier.

13. The pharmaceutical composition according to claim 12 which further comprises an effective amount of a leukotriene antagonist selected from the group consisting of montelukast, zafirlukast, and pranlukast.

14. A method for treating asthma, or allergic rhinitis, comprising administering an effective amount of the compound of claim 1 or a pharmaceutically acceptable salt thereof to a mammal in need of such treatment.

15. The compound of claim 1 which is

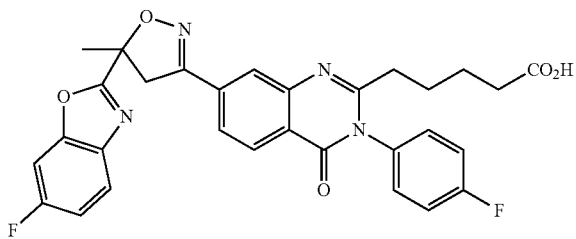 [SMILES: CC1(c2nc3ccc(F)cc3o2)CC(c2ccc3c(=O)n(-c4ccc(F)cc4)c(CCCCC(=O)O)nc3c2)=NO1]

or a pharmaceutically acceptable salt thereof.

16. The method of claim 14, wherein the mammal is in need of treatment for asthma.

* * * * *